US006506384B1

(12) United States Patent
Laal et al.

(10) Patent No.: US 6,506,384 B1
(45) Date of Patent: Jan. 14, 2003

(54) EARLY DETECTION OF MYCOBACTERIAL DISEASE

(75) Inventors: Suman Laal, Croton-on-Hudson, NY (US); Susan Zolla-Pazner, New York, NY (US); John T. Belisle, Fort Collins, CO (US)

(73) Assignees: New York University, New York, NY (US); Colorado State University Research Foundation, Fort Collins, CO (US)

( * ) Notice: Subject to any disclaimer, the term of this patent is extended or adjusted under 35 U.S.C. 154(b) by 0 days.

(21) Appl. No.: 09/396,347

(22) Filed: Sep. 14, 1999

Related U.S. Application Data

(63) Continuation-in-part of application No. 09/001,984, filed on Dec. 31, 1997, now Pat. No. 6,245,331.

(51) Int. Cl.[7] .............................................. A61K 39/40
(52) U.S. Cl. ...................... 424/168.1; 424/9.1; 424/9.2; 424/130.1; 424/164.1; 424/184.1; 424/185.1; 424/234.1; 424/248.1; 424/278.1; 435/7.1; 435/7.2; 530/300; 530/350
(58) Field of Search ........................ 424/9.1, 9.2, 130.1, 424/164.1, 168.1, 184.1, 185.1, 234.1, 248.1, 278.1; 435/7.1, 7.2; 530/700, 750

(56) References Cited

U.S. PATENT DOCUMENTS 5,330,754 A 7/1994 Kapoor et al.

OTHER PUBLICATIONS

Eduardo, S.D., et al, "An ELISA for the Serodiagnosis of Tuberculosis Using a 30,000–Da Native Antigen of *Mycobacterium tuberculosis*," Journal of Infectious Disease (1990) 162:928–931.

McDonough, J.A., et al., "Microplate and dot immunoassays for the serodiagnosis of tuberculosis," J Lab Clin Med (1992) 120:318–22.

Bassey, E.O.E., et al., "Candidate antigens for improved serodiagnosis of tuberculosis," Tubercle and Lung Disease (1996) 77:136–145.

Young, D.B., et al., "Mycobacterial protein antigens: acompilation," Molecular Microbiology (1992) 6(2):133–145.

*Primary Examiner*—Rodney P Swartz
(74) *Attorney, Agent, or Firm*—Shmeul Livnat; Venable, Baetjer, Howard & Civiletti

(57) ABSTRACT

A number of protein and glycoprotein antigens secreted by *Mycobacterium. tuberculosis* (Mt) have been identified as "early" Mt antigens on the basis early antibodies present in subjects infected with Mt prior to the development of detectable clinical disease. These early Mt antigens, in particular an 88 kDa secreted protein having a pI of about 5.2 and the sequence of SEQ ID NO:106, which is present in Mt lipoarabinomannan-free culture filtrate, a protein characterized as Mt antigen 85C; a protein characterized as Mt antigen MPT51, a glycoprotein characterized as Mt antigen MPT32; and a 49 kDa protein having a pI of about 5.1, are useful in immunoassay methods for early, rapid detection of TB in a subject. Preferred immunoassays detect the antibodies in the subject's urine. Also provided are antigenic compositions, kits and methods to useful for detecting an early Mt antigen, an early Mt antibody, and immune complexes thereof. For the first time, a surrogate marker is available for inexpensive screening of individuals at heightened risk for developing advanced TB, in particular HIV-1 infected subjects and other immunocompromised individuals.

40 Claims, 39 Drawing Sheets mAb IT-57 mAb IT-42

Anti-catalase polyclonal Ab

TB Serum

AMINO ACID SEQUENCE OF 88 kDA protein (early Mt antigen)

```
  1   mtdrvsvgnl riarvlydfv nnealpgtdi dpdsfwagvd kvvadltpqn qallnardel
 61   qaqidkwhrr rviepidmda yrqflteigy llpepddfti ttsgvdaeit ttagpqlvvp
121   vlnarfalna anarwgslyd alygtdvipe tdgaekgpty nkvrgdkvia yarkflddsv
181   plssgsfgda tgftvqdgql vvalpdkstg lanpgqfagy tgaaesptsv llinhglhie
241   ilidpesqvg ttdragvkdv ilesaittim dfedsvaavd aadkvlgyrn wlglnkgdla
301   aavdkdgtaf lrvlnrdrny tapgggqftl pgrslmfvrn vghlmtndai vdtdgsevfe
361   gimdalftgl iaihglkasd vngplinsrt gsiyivkpkm hgpaevaftc elfsrvedvl
421   glpqntmkig imdeerrttv nlkacikaaa drvvfintgf ldrtgdeiht smeagpmvrk
481   gtmksqpwil ayedhnvdag laagfsgraq vgkgmwtmte lmadmvetki aqpragasta
541   wvpsptaatl halhyhqvdv aavqqglagk rratieqllt iplakelawa pdeireevdn
601   ncqsilgyvv rwvdqgvgcs kvpdihdval medratlris sqllanwlrh gvitsadvra
661   slermaplvd rqnagdvayr pmapnfddsi aflaaqelil sgaqqpngyt epilhrrrre
721   fkaraaekpa psdragddaa r
```

Reference Information

LOCUS        CAB01465  741 aa      BCT      17-JUN-1998
DEFINITION   glcB.
ACCESSION    CAB01465
PID          g1483534
VERSION      CAB01465.1  GI:1483534
DBSOURCE     embl locus MTCY1A11, accession Z78020.1
ORGANISM     *Mycobacterium tuberculosis*
REFERENCE    1 (residues 1 to 741)
AUTHORS      Cole,S.T., Brosch,R., Parkhill,J., *et al.*,
TITLE        Deciphering the biology of Mycobacterium tuberculosis from the complete genome sequence
JOURNAL      Nature 393 (6685), 537-544 (1998)
FEATURES     Location/Qualifiers
Source       1..741   /organism="Mycobacterium tuberculosis"
                      /strain="H37Rv"
                      /db_xref="taxon:1773"
                      /clone="Y1A11"
Protein      1..741   /product="glcB"
CDS          1..741
                      /gene="glcB"
                      /note="Rv1837c, (MTCY1A11.06), glcB, malate synthase,len:741, highly similar to eg MASY_CORGL P42450 malate synthase(738 aa) FASTA scores, opt: 2961, z-score: 3491.7, E(): 0,(61.3% identity in 724 aa overlap))"
                      /db_xref="SWISS-PROT:Q50596"
                      /coded_by="complement(Z78020.1:28404..30629)"
                      /transl_table=11

Fig. 33

```
                         SEQUENCE LISTING

<160> NUMBER OF SEQ ID NOS: 106

<210> SEQ ID NO 1
<211> LENGTH: 39
<212> TYPE: PRT
<213> ORGANISM: Mycobacterium tuberculosis strain H37Rv

<400> SEQUENCE: 1

Phe Ser Arg Pro Gly Leu Pro Val Glu Tyr Leu Gln Val Pro Ser Pro
  1               5                  10                  15

Ser Met Gly Arg Asp Ile Lys Val Gln Phe Gln Ser Gly Gly Ala Asn
             20                  25                  30

Ser Pro Ala Leu Tyr Leu Leu
         35

<210> SEQ ID NO 2
<211> LENGTH: 39
<212> TYPE: PRT
<213> ORGANISM: Mycobacterium tuberculosis strain H37Rv

<400> SEQUENCE: 2
```

-continued

```
Phe Ser Arg Pro Gly Leu Pro Val Glu Tyr Leu Gln Val Pro Ser Pro
  1               5                  10                  15

Ser Met Gly Arg Asp Ile Lys Val Gln Phe Gln Ser Gly Gly Asn Asn
             20                  25                  30

Ser Pro Ala Val Tyr Leu Leu
         35

<210> SEQ ID NO 3
<211> LENGTH: 37
<212> TYPE: PRT
<213> ORGANISM: Mycobacterium tuberculosis strain H37Rv

<400> SEQUENCE: 3

Phe Ser Arg Pro Gly Leu Pro Val Glu Tyr Leu Gln Val Pro Ser Ala
  1               5                  10                  15

Ser Met Gly Arg Asp Ile Lys Val Gln Phe Gln Gly Gly Gly Pro His
             20                  25                  30

Ala Val Tyr Leu Leu
         35

<210> SEQ ID NO 4
<211> LENGTH: 32
<212> TYPE: PRT
<213> ORGANISM: Mycobacterium tuberculosis strain H37Rv

<400> SEQUENCE: 4

Ala Pro Tyr Glu Asn Leu Met Tyr Pro Ser Pro Ser Met Gly Arg Asp
  1               5                  10                  15

Lys Pro Val Ala Phe Leu Ala Gly Gly Pro His Ala Val Tyr Leu Leu
             20                  25                  30

<210> SEQ ID NO 5
<211> LENGTH: 12
<212> TYPE: PRT
<213> ORGANISM: Mycobacterium tuberculosis strain H37Rv

<400> SEQUENCE: 5

Asp Pro Glu Pro Ala Pro Pro Val Pro Thr Thr Ala
  1               5                  10

<210> SEQ ID NO 6
<211> LENGTH: 26
<212> TYPE: PRT
<213> ORGANISM: Mycobacterium tuberculosis strain H37Rv

<400> SEQUENCE: 6

Ala Pro Tyr Glu Leu Asn Ile Thr Ser Ala Thr Tyr Gln Ser Ala Ile
  1               5                  10                  15

Pro Pro Arg Gly Thr Gln Ala Val Val Leu
             20                  25

<210> SEQ ID NO 7
<211> LENGTH: 11
<212> TYPE: PRT
<213> ORGANISM: Mycobacterium tuberculosis strain H37Rv
<220> FEATURE:
<221> NAME/KEY: MISC_FEATURE
<222> LOCATION: (1)..(1)
<223> OTHER INFORMATION: Xaa can be any amino acid

<400> SEQUENCE: 7

Xaa Pro Val Ala Pro Pro Pro Pro Ala Ala Ala
  1               5                  10

```
<210> SEQ ID NO 8
<211> LENGTH: 13
<212> TYPE: PRT
<213> ORGANISM: Mycobacterium tuberculosis strain H37Rv
<220> FEATURE:
<221> NAME/KEY: MISC_FEATURE
<222> LOCATION: (9)..(9)
<223> OTHER INFORMATION: Xaa can be any amino acid

<400> SEQUENCE: 8

Gly Glu Val Ala Pro Thr Pro Thr Xaa Pro Thr Pro Gln
  1               5                  10

<210> SEQ ID NO 9
<211> LENGTH: 13
<212> TYPE: PRT
<213> ORGANISM: Mycobacterium tuberculosis strain H37Rv

<400> SEQUENCE: 9

Gly Glu Val Ala Pro Thr Pro Thr Thr Pro Thr Pro Gln
  1               5                  10

<210> SEQ ID NO 10
<211> LENGTH: 7
<212> TYPE: PRT
<213> ORGANISM: Mycobacterium tuberculosis strain H37Rv
<220> FEATURE:
<221> NAME/KEY: MISC_FEATURE
<222> LOCATION: (6)..(6)
<223> OTHER INFORMATION: Xaa can be any amino acid

<400> SEQUENCE: 10

Ala Ser Pro Pro Ser Xaa Ala
  1               5

<210> SEQ ID NO 11
<211> LENGTH: 35
<212> TYPE: PRT
<213> ORGANISM: Mycobacterium tuberculosis strain H37Rv

<400> SEQUENCE: 11

Val Ala Pro Pro Pro Ala Pro Ala Pro Ala Pro Ala Glu Pro Ala Pro
  1               5                  10                  15

Ala Pro Ala Pro Ala Gly Glu Val Ala Pro Thr Pro Thr Thr Pro Thr
                 20                  25                  30

Pro Gln Arg
         35

<210> SEQ ID NO 12
<211> LENGTH: 7
<212> TYPE: PRT
<213> ORGANISM: Mycobacterium tuberculosis strain H37Rv
<220> FEATURE:
<221> NAME/KEY: MISC_FEATURE
<222> LOCATION: (6)..(6)
<223> OTHER INFORMATION: Xaa can be any amino acid

<400> SEQUENCE: 12

Ala Ser Pro Pro Ser Xaa Ala
  1               5

<210> SEQ ID NO 13
<211> LENGTH: 10
<212> TYPE: PRT
<213> ORGANISM: Mycobacterium tuberculosis strain H37Rv
```

```
<400> SEQUENCE: 13

Asn Asn Pro Val Asp Lys Gly Ala Ala Lys
  1               5                  10

<210> SEQ ID NO 14
<211> LENGTH: 6
<212> TYPE: PRT
<213> ORGANISM: Mycobacterium tuberculosis strain H37Rv

<400> SEQUENCE: 14

Asp Thr Arg Ile Val Leu
  1               5

<210> SEQ ID NO 15
<211> LENGTH: 7
<212> TYPE: PRT
<213> ORGANISM: Mycobacterium tuberculosis strain H37Rv

<400> SEQUENCE: 15

Ala Ala Pro Pro Ala Pro Ala
  1               5

<210> SEQ ID NO 16
<211> LENGTH: 9
<212> TYPE: PRT
<213> ORGANISM: Mycobacterium tuberculosis strain H37Rv

<400> SEQUENCE: 16

Gly Trp Val Glu Ser Asp Ala Ala His
  1               5

<210> SEQ ID NO 17
<211> LENGTH: 9
<212> TYPE: PRT
<213> ORGANISM: Mycobacterium tuberculosis strain H37Rv
<220> FEATURE:
<221> NAME/KEY: MISC_FEATURE
<222> LOCATION: (1)..(1)
<223> OTHER INFORMATION: Xaa can be any amino acid

<400> SEQUENCE: 17

Xaa Pro Val Ala Pro Pro Pro Ala
  1               5

<210> SEQ ID NO 18
<211> LENGTH: 11
<212> TYPE: PRT
<213> ORGANISM: Mycobacterium tuberculosis strain H37Rv

<400> SEQUENCE: 18

Thr Asp Ser Lys Ala Ala Ala Arg Leu Gly Ser
  1               5                  10

<210> SEQ ID NO 19
<211> LENGTH: 16
<212> TYPE: PRT
<213> ORGANISM: Mycobacterium tuberculosis strain H37Rv

<400> SEQUENCE: 19

Gly Ser Ala Leu Leu Ala Lys Thr Thr Gly Asp Pro Pro Phe Pro Gly
  1               5                  10                  15

<210> SEQ ID NO 20
<211> LENGTH: 13
```

-continued

```
<212> TYPE: PRT
<213> ORGANISM: Mycobacterium tuberculosis strain H37Rv
<220> FEATURE:
<221> NAME/KEY: MISC_FEATURE
<222> LOCATION: (9)..(9)
<223> OTHER INFORMATION: Xaa at posiiton 9 can be any amino acid

<400> SEQUENCE: 20

Gly Glu Val Ala Pro Thr Pro Thr Xaa Pro Thr Pro Gln
 1               5                  10

<210> SEQ ID NO 21
<211> LENGTH: 5
<212> TYPE: PRT
<213> ORGANISM: Mycobacterium tuberculosis strain H37Rv

<400> SEQUENCE: 21

Leu Pro Ala Gly Trp
 1               5

<210> SEQ ID NO 22
<211> LENGTH: 5
<212> TYPE: PRT
<213> ORGANISM: Mycobacterium tuberculosis strain H37Rv

<400> SEQUENCE: 22

Ile Val Leu Gly Arg
 1               5

<210> SEQ ID NO 23
<211> LENGTH: 11
<212> TYPE: PRT
<213> ORGANISM: Mycobacterium tuberculosis strain H37Rv
<220> FEATURE:
<221> NAME/KEY: MISC_FEATURE
<222> LOCATION: (1)..(1)
<223> OTHER INFORMATION: Xaa can be any amino acid

<400> SEQUENCE: 23

Xaa Pro Val Ala Pro Pro Pro Ala Ala Ala
 1               5                  10

<210> SEQ ID NO 24
<211> LENGTH: 5
<212> TYPE: PRT
<213> ORGANISM: Mycobacterium tuberculosis strain H37Rv

<400> SEQUENCE: 24

Tyr Tyr Glu Val Lys
 1               5

<210> SEQ ID NO 25
<211> LENGTH: 13
<212> TYPE: PRT
<213> ORGANISM: Mycobacterium tuberculosis strain H37Rv

<400> SEQUENCE: 25

Gly Glu Val Ala Pro Thr Pro Thr Thr Pro Thr Pro Gln
 1               5                  10

<210> SEQ ID NO 26
<211> LENGTH: 11
<212> TYPE: PRT
<213> ORGANISM: Mycobacterium tuberculosis strain H37Rv

<400> SEQUENCE: 26
```

-continued

```
Ala Ala Asn Thr Pro Asn Ala Gln Pro Gly Asp
 1               5                  10

<210> SEQ ID NO 27
<211> LENGTH: 13
<212> TYPE: PRT
<213> ORGANISM: Mycobacterium tuberculosis strain H37Rv

<400> SEQUENCE: 27

Leu Asp Ala Asn Gly Val Ser Gly Ser Ala Ser Tyr Tyr
 1               5                  10

<210> SEQ ID NO 28
<211> LENGTH: 13
<212> TYPE: PRT
<213> ORGANISM: Mycobacterium tuberculosis strain H37Rv

<400> SEQUENCE: 28

Glu Val Lys Phe Ser Asp Pro Ser Lys Pro Asn Gly Gln
 1               5                  10

<210> SEQ ID NO 29
<211> LENGTH: 12
<212> TYPE: PRT
<213> ORGANISM: Mycobacterium tuberculosis strain H37Rv
<220> FEATURE:
<221> NAME/KEY: MISC_FEATURE
<222> LOCATION: (10)..(10)
<223> OTHER INFORMATION: Xaa can be any amino acid

<400> SEQUENCE: 29

Asp Pro Glu Pro Ala Pro Pro Val Pro Xaa Thr Ala
 1               5                  10

<210> SEQ ID NO 30
<211> LENGTH: 8
<212> TYPE: PRT
<213> ORGANISM: Mycobacterium tuberculosis strain H37Rv

<400> SEQUENCE: 30

Thr Gly Val Ile Gly Ser Pro Ala
 1               5

<210> SEQ ID NO 31
<211> LENGTH: 16
<212> TYPE: PRT
<213> ORGANISM: Mycobacterium tuberculosis strain H37Rv

<400> SEQUENCE: 31

Phe Val Val Trp Leu Gly Thr Ala Asn Asn Pro Val Asp Lys Gly Ala
 1               5                  10                  15

<210> SEQ ID NO 32
<211> LENGTH: 13
<212> TYPE: PRT
<213> ORGANISM: Mycobacterium tuberculosis strain H37Rv

<400> SEQUENCE: 32

Gly Arg Leu Asp Gln Lys Leu Tyr Ala Ser Ala Glu Ala
 1               5                  10

<210> SEQ ID NO 33
<211> LENGTH: 8
<212> TYPE: PRT
<213> ORGANISM: Mycobacterium tuberculosis strain H37Rv
```

```
<400> SEQUENCE: 33

Tyr Met Pro Tyr Pro Gly Thr Arg
 1               5

<210> SEQ ID NO 34
<211> LENGTH: 10
<212> TYPE: PRT
<213> ORGANISM: Mycobacterium tuberculosis strain H37Rv

<400> SEQUENCE: 34

Pro Asn Ala Pro Pro Pro Val Ile Ala
 1               5                   10

<210> SEQ ID NO 35
<211> LENGTH: 6
<212> TYPE: PRT
<213> ORGANISM: Mycobacterium tuberculosis strain H37Rv

<400> SEQUENCE: 35

Gln Glu Thr Val Ser Leu
 1               5

<210> SEQ ID NO 36
<211> LENGTH: 18
<212> TYPE: PRT
<213> ORGANISM: Mycobacterium tuberculosis strain H37Rv

<400> SEQUENCE: 36

Val Ile Gly Ser Pro Ala Ala Asn Ala Pro Asp Ala Gly Pro Pro Gln
 1               5                   10                  15

Arg Trp

<210> SEQ ID NO 37
<211> LENGTH: 6
<212> TYPE: PRT
<213> ORGANISM: Mycobacterium tuberculosis strain H37Rv

<400> SEQUENCE: 37

Gly Gly Phe Ser Phe Ala
 1               5

<210> SEQ ID NO 38
<211> LENGTH: 7
<212> TYPE: PRT
<213> ORGANISM: Mycobacterium tuberculosis strain H37Rv

<400> SEQUENCE: 38

Ala Glu Ser Ile Arg Pro Leu
 1               5

<210> SEQ ID NO 39
<211> LENGTH: 9
<212> TYPE: PRT
<213> ORGANISM: Mycobacterium tuberculosis strain H37Rv

<400> SEQUENCE: 39

Asn Gly Val Ser Gly Ser Ala Ser Tyr
 1               5

<210> SEQ ID NO 40
<211> LENGTH: 5
<212> TYPE: PRT
<213> ORGANISM: Mycobacterium tuberculosis strain H37Rv
```

```
-continued

<400> SEQUENCE: 40

Ile Val Leu Gly Arg
  1               5

<210> SEQ ID NO 41
<211> LENGTH: 19
<212> TYPE: PRT
<213> ORGANISM: Mycobacterium tuberculosis strain H37Rv

<400> SEQUENCE: 41

Thr Gly Val Ile Gly Ser Pro Ala Ala Asn Ala Pro Asp Ala Gly Pro
  1               5                  10                  15

Pro Gln Arg

<210> SEQ ID NO 42
<211> LENGTH: 35
<212> TYPE: PRT
<213> ORGANISM: Mycobacterium tuberculosis strain H37Rv

<400> SEQUENCE: 42

Val Ala Pro Pro Pro Ala Pro Ala Pro Ala Pro Ala Glu Pro Ala Pro
  1               5                  10                  15

Ala Pro Ala Pro Ala Gly Glu Val Ala Pro Thr Pro Thr Thr Pro Thr
                 20                  25                  30

Pro Gln Arg
         35

<210> SEQ ID NO 43
<211> LENGTH: 19
<212> TYPE: PRT
<213> ORGANISM: Mycobacterium tuberculosis strain H37Rv

<400> SEQUENCE: 43

Thr Thr Gly Asp Pro Pro Phe Pro Gly Gln Pro Pro Val Ala Asn
  1               5                  10                  15

Asp Thr Arg

<210> SEQ ID NO 44
<211> LENGTH: 13
<212> TYPE: PRT
<213> ORGANISM: Mycobacterium tuberculosis strain H37Rv

<400> SEQUENCE: 44

Ala Ser Ala Glu Ala Thr Asp Ser Lys Ala Ala Ala Arg
  1               5                  10

<210> SEQ ID NO 45
<211> LENGTH: 9
<212> TYPE: PRT
<213> ORGANISM: Mycobacterium tuberculosis strain H37Rv

<400> SEQUENCE: 45

Ile Val Leu Gly Arg Leu Asp Gln Lys
  1               5

<210> SEQ ID NO 46
<211> LENGTH: 8
<212> TYPE: PRT
<213> ORGANISM: Mycobacterium tuberculosis strain H37Rv

<400> SEQUENCE: 46

Ile Asp Asn Pro Val Gly Gly Phe
```

-continued

<210> SEQ ID NO 47
<211> LENGTH: 20
<212> TYPE: PRT
<213> ORGANISM: Mycobacterium tuberculosis strain H37Rv

<400> SEQUENCE: 47

Thr Gly Val Ile Gly Ser Pro Ala Ala Asn Ala Pro Asp Ala Gly Pro
 1               5                  10                  15

Pro Gln Arg Trp
            20

<210> SEQ ID NO 48
<211> LENGTH: 15
<212> TYPE: PRT
<213> ORGANISM: Mycobacterium tuberculosis strain H37Rv

<400> SEQUENCE: 48

Glu Val Lys Phe Ser Asp Pro Ser Lys Pro Asn Gly Gln Ile Trp
 1               5                  10                  15

<210> SEQ ID NO 49
<211> LENGTH: 19
<212> TYPE: PRT
<213> ORGANISM: Mycobacterium tuberculosis strain H37Rv

<400> SEQUENCE: 49

Leu Gly Thr Ala Asn Asn Pro Val Asp Lys Gly Ala Ala Lys Ala Leu
 1               5                  10                  15

Ala Glu Ser

<210> SEQ ID NO 50
<211> LENGTH: 14
<212> TYPE: PRT
<213> ORGANISM: Mycobacterium tuberculosis strain H37Rv

<400> SEQUENCE: 50

Ile Arg Pro Leu Val Glu Ser Asp Ala Ala His Phe Asp Tyr
 1               5                  10

<210> SEQ ID NO 51
<211> LENGTH: 8
<212> TYPE: PRT
<213> ORGANISM: Mycobacterium tuberculosis strain H37Rv

<400> SEQUENCE: 51

Ser Phe Ala Leu Pro Ala Gly Trp
 1               5

<210> SEQ ID NO 52
<211> LENGTH: 23
<212> TYPE: PRT
<213> ORGANISM: Mycobacterium tuberculosis strain H37Rv

<400> SEQUENCE: 52

Ala Leu Pro Ala Gly Trp Val Glu Ser Asp Ala Ala His Phe Asp Tyr
 1               5                  10                  15

Gly Ser Ala Leu Leu Ala Lys
            20

<210> SEQ ID NO 53
<211> LENGTH: 7

```
<212> TYPE: PRT
<213> ORGANISM: Mycobacterium tuberculosis strain H37Rv

<400> SEQUENCE: 53

Glu Thr Val Ser Leu Asp Ala
 1               5

<210> SEQ ID NO 54
<211> LENGTH: 7
<212> TYPE: PRT
<213> ORGANISM: Mycobacterium tuberculosis strain H37Rv

<400> SEQUENCE: 54

Ala Ser Pro Pro Ser Thr Ala
 1               5

<210> SEQ ID NO 55
<211> LENGTH: 11
<212> TYPE: PRT
<213> ORGANISM: Mycobacterium tuberculosis strain H37Rv

<400> SEQUENCE: 55

Thr Pro Val Ala Pro Pro Pro Ala Ala Ala
 1               5                  10

<210> SEQ ID NO 56
<211> LENGTH: 12
<212> TYPE: PRT
<213> ORGANISM: Mycobacterium tuberculosis strain H37Rv
<220> FEATURE:
<221> NAME/KEY: MISC_FEATURE
<222> LOCATION: (9)..(9)
<223> OTHER INFORMATION: Xaa is Asp or Gly

<400> SEQUENCE: 56

Ala Pro Pro Ser Cys Ala Gly Leu Xaa Cys Thr Val
 1               5                  10

<210> SEQ ID NO 57
<211> LENGTH: 7
<212> TYPE: PRT
<213> ORGANISM: Mycobacterium tuberculosis strain H37Rv
<220> FEATURE:
<221> NAME/KEY: MISC_FEATURE
<222> LOCATION: (1)..(1)
<223> OTHER INFORMATION: Xaa at position 1 can be any amino acid
<220> FEATURE:
<221> NAME/KEY: MISC_FEATURE
<222> LOCATION: (2)..(2)
<223> OTHER INFORMATION: Xaa can be any amino acid
<220> FEATURE:
<221> NAME/KEY: MISC_FEATURE
<222> LOCATION: (5)..(5)
<223> OTHER INFORMATION: Xaa can be any amino acid

<400> SEQUENCE: 57

Xaa Xaa Ala Val Xaa Val Thr
 1               5

<210> SEQ ID NO 58
<211> LENGTH: 16
<212> TYPE: PRT
<213> ORGANISM: Mycobacterium tuberculosis strain H37Rv

<400> SEQUENCE: 58

Phe Ser Arg Pro Gly Leu Pro Val Glu Tyr Leu Gln Val Pro Ser Pro
 1               5                  10                  15
```

```
<210> SEQ ID NO 59
<211> LENGTH: 21
<212> TYPE: PRT
<213> ORGANISM: Mycobacterium tuberculosis strain H37Rv

<400> SEQUENCE: 59

Thr Glu Lys Thr Pro Asp Asp Val Phe Lys Leu Ala Asp Asp Glu Lys
 1               5                  10                  15

Val Glu Tyr Val Asp
            20

<210> SEQ ID NO 60
<211> LENGTH: 15
<212> TYPE: PRT
<213> ORGANISM: Mycobacterium tuberculosis strain H37Rv
<220> FEATURE:
<221> NAME/KEY: MISC_FEATURE
<222> LOCATION: (1)..(1)(
<223> OTHER INFORMATION: Xaa can be any amino acid
<220> FEATURE:
<221> NAME/KEY: MISC_FEATURE
<222> LOCATION: (4)..(4)
<223> OTHER INFORMATION: Xaa is Met or Leu
<220> FEATURE:
<221> NAME/KEY: MISC_FEATURE
<222> LOCATION: (6)..(6)
<223> OTHER INFORMATION: Xaa can be any amino acid
<220> FEATURE:
<221> NAME/KEY: MISC_FEATURE
<222> LOCATION: (9)..(9)
<223> OTHER INFORMATION: Xaa can be any amino acid
<220> FEATURE:
<221> NAME/KEY: MISC_FEATURE
<222> LOCATION: (11)..(11)
<223> OTHER INFORMATION: Xaa can be any amino acid
<220> FEATURE:
<221> NAME/KEY: MISC_FEATURE
<222> LOCATION: (12)..(12)
<223> OTHER INFORMATION: Xaa can be any amino acid

<400> SEQUENCE: 60

Xaa Pro Val Xaa Val Xaa Pro Gly Xaa Glu Xaa Xaa Gln Asp Asn
 1               5                  10                  15

<210> SEQ ID NO 61
<211> LENGTH: 12
<212> TYPE: PRT
<213> ORGANISM: Mycobacterium tuberculosis strain H37Rv
<220> FEATURE:
<221> NAME/KEY: MISC_FEATURE
<222> LOCATION: (1)..(1)
<223> OTHER INFORMATION: Xaa at posiiton 1 can be any amino acid

<400> SEQUENCE: 61

Xaa Val Tyr Asp Val Ile Met Leu Thr Ala Gly Pro
 1               5                  10

<210> SEQ ID NO 62
<211> LENGTH: 9
<212> TYPE: PRT
<213> ORGANISM: Mycobacterium tuberculosis strain H37Rv
<220> FEATURE:
<221> NAME/KEY: MISC_FEATURE
<222> LOCATION: (8)..(8)
<223> OTHER INFORMATION: Xaa at posiiton 8 can be any amino acid

<400> SEQUENCE: 62

Ala Pro Tyr Glu Asn Leu Met Xaa Pro
 1               5
```

```
<210> SEQ ID NO 63
<211> LENGTH: 10
<212> TYPE: PRT
<213> ORGANISM: Mycobacterium tuberculosis strain H37Rv
<220> FEATURE:
<221> NAME/KEY: MISC_FEATURE
<222> LOCATION: (1)..(1)
<223> OTHER INFORMATION: Xaa is Lys or Asn
<220> FEATURE:
<221> NAME/KEY: MISC_FEATURE
<222> LOCATION: (6)..(6)
<223> OTHER INFORMATION: Xaa at position 6 cn be any amino acid
<220> FEATURE:
<221> NAME/KEY: MISC_FEATURE
<222> LOCATION: (8)..(8)
<223> OTHER INFORMATION: Xaa can be any amino acid

<400> SEQUENCE: 63

Xaa Val Ile Arg Ile Xaa Gly Xaa Thr Asp
 1               5                  10

<210> SEQ ID NO 64
<211> LENGTH: 15
<212> TYPE: PRT
<213> ORGANISM: Mycobacterium tuberculosis strain H37Rv

<400> SEQUENCE: 64

Phe Ala Pro Leu Asn Ser Trp Pro Asp Asn Ala Ser Leu Asp Lys
 1               5                  10                  15

<210> SEQ ID NO 65
<211> LENGTH: 9
<212> TYPE: PRT
<213> ORGANISM: Mycobacterium tuberculosis strain H37Rv

<400> SEQUENCE: 65

Glu Ala Thr Trp Leu Gly Asp Glu Arg
 1               5

<210> SEQ ID NO 66
<211> LENGTH: 17
<212> TYPE: PRT
<213> ORGANISM: Mycobacterium tuberculosis strain H37Rv

<400> SEQUENCE: 66

Asp Ala Ile Thr Ser Gly Ile Glu Val Val Trp Thr Asn Thr Pro Thr
 1               5                  10                  15

Lys

<210> SEQ ID NO 67
<211> LENGTH: 11
<212> TYPE: PRT
<213> ORGANISM: Mycobacterium tuberculosis strain H37Rv

<400> SEQUENCE: 67

Ser Pro Ala Gly Ala Trp Gln Tyr Thr Ala Lys
 1               5                  10

<210> SEQ ID NO 68
<211> LENGTH: 17
<212> TYPE: PRT
<213> ORGANISM: Mycobacterium tuberculosis strain H37Rv

<400> SEQUENCE: 68

Asp Gly Ala Gly Ala Gly Thr Ile Pro Asp Pro Phe Gly Gly Pro Gly
 1               5                  10                  15
```

Arg

<210> SEQ ID NO 69
<211> LENGTH: 15
<212> TYPE: PRT
<213> ORGANISM: Mycobacterium tuberculosis strain H37Rv

<400> SEQUENCE: 69

Arg Trp Leu Glu His Pro Glu Leu Ala Asp Glu Phe Ala Lys
 1               5                  10                  15

<210> SEQ ID NO 70
<211> LENGTH: 18
<212> TYPE: PRT
<213> ORGANISM: Mycobacterium tuberculosis strain H37Rv

<400> SEQUENCE: 70

Thr Leu Glu Glu Ile Gln Glu Ser Phe Asn Ser Ala Ala Pro Gly Asn
 1               5                  10                  15

Ile Lys

<210> SEQ ID NO 71
<211> LENGTH: 13
<212> TYPE: PRT
<213> ORGANISM: Mycobacterium tuberculosis strain H37Rv

<400> SEQUENCE: 71

Ala Gly His Asn Ile Thr Val Pro Phe Thr Pro Gly Arg
 1               5                  10

<210> SEQ ID NO 72
<211> LENGTH: 19
<212> TYPE: PRT
<213> ORGANISM: Mycobacterium tuberculosis strain H37Rv

<400> SEQUENCE: 72

Thr Asp Ala Ser Gln Glu Gln Thr Asp Val Glu Ser Phe Ala Val Leu
 1               5                  10                  15

Glu Pro Lys

<210> SEQ ID NO 73
<211> LENGTH: 13
<212> TYPE: PRT
<213> ORGANISM: Mycobacterium tuberculosis strain H37Rv

<400> SEQUENCE: 73

Gly Asn Pro Leu Pro Ala Glu Tyr Met Leu Leu Asp Lys
 1               5                  10

<210> SEQ ID NO 74
<211> LENGTH: 19
<212> TYPE: PRT
<213> ORGANISM: Mycobacterium tuberculosis strain H37Rv

<400> SEQUENCE: 74

Ala Asn Leu Leu Thr Leu Ser Ala Pro Glu Met Thr Val Leu Val Gly
 1               5                  10                  15

Gly Leu Arg

<210> SEQ ID NO 75
<211> LENGTH: 12
<212> TYPE: PRT

<213> ORGANISM: Mycobacterium tuberculosis strain H37Rv

<400> SEQUENCE: 75

Val Asp Leu Val Phe Gly Ser Asn Ser Glu Leu Arg
 1               5                  10

<210> SEQ ID NO 76
<211> LENGTH: 15
<212> TYPE: PRT
<213> ORGANISM: Mycobacterium tuberculosis strain H37Rv

<400> SEQUENCE: 76

Ala Leu Val Glu Val Tyr Gly Ala Asp Ala Gln Pro Lys Phe
 1               5                  10                  15

<210> SEQ ID NO 77
<211> LENGTH: 10
<212> TYPE: PRT
<213> ORGANISM: Mycobacterium tuberculosis strain H37Rv

<400> SEQUENCE: 77

Thr Glu Gln Gln Trp Asp Phe Ala Gly Ile
 1               5                  10

<210> SEQ ID NO 78
<211> LENGTH: 10
<212> TYPE: PRT
<213> ORGANISM: Mycobacterium tuberculosis strain H37Rv

<400> SEQUENCE: 78

Asp Pro Ala Pro Ala Pro Pro Val Pro Thr
 1               5                  10

<210> SEQ ID NO 79
<211> LENGTH: 5
<212> TYPE: PRT
<213> ORGANISM: Mycobacterium tuberculosis strain H37Rv

<400> SEQUENCE: 79

Asp Glu Cys Ile Gln
 1               5

<210> SEQ ID NO 80
<211> LENGTH: 5
<212> TYPE: PRT
<213> ORGANISM: Mycobacterium tuberculosis strain H37Rv

<400> SEQUENCE: 80

Arg Ile Lys Ile Phe
 1               5

<210> SEQ ID NO 81
<211> LENGTH: 13
<212> TYPE: PRT
<213> ORGANISM: Mycobacterium tuberculosis strain H37Rv

<400> SEQUENCE: 81

Ala Tyr Pro Ile Thr Gly Lys Leu Gly Ser Glu Leu Thr
 1               5                  10

<210> SEQ ID NO 82
<211> LENGTH: 10
<212> TYPE: PRT
<213> ORGANISM: Mycobacterium tuberculosis strain H37Rv

```
<400> SEQUENCE: 82

Met Ala Lys Val Asn Ile Lys Pro Leu Glu
 1               5                  10

<210> SEQ ID NO 83
<211> LENGTH: 10
<212> TYPE: PRT
<213> ORGANISM: Mycobacterium tuberculosis strain H37Rv

<400> SEQUENCE: 83

Cys Gly Ser Lys Pro Pro Ser Pro Glu Thr
 1               5                  10

<210> SEQ ID NO 84
<211> LENGTH: 10
<212> TYPE: PRT
<213> ORGANISM: Mycobacterium tuberculosis strain H37Rv

<400> SEQUENCE: 84

Cys Gly Ser Lys Pro Pro Ser Pro Glu Thr
 1               5                  10

<210> SEQ ID NO 85
<211> LENGTH: 5
<212> TYPE: PRT
<213> ORGANISM: Mycobacterium tuberculosis strain H37Rv

<400> SEQUENCE: 85

Arg Asp Ser Glu Lys
 1               5

<210> SEQ ID NO 86
<211> LENGTH: 10
<212> TYPE: PRT
<213> ORGANISM: Mycobacterium tuberculosis strain H37Rv

<400> SEQUENCE: 86

Met Ala Arg Ala Val Gly Ile Asp Leu Gly
 1               5                  10

<210> SEQ ID NO 87
<211> LENGTH: 10
<212> TYPE: PRT
<213> ORGANISM: Mycobacterium tuberculosis strain H37Rv

<400> SEQUENCE: 87

Cys Gly Ser Lys Pro Pro Ser Pro Glu Thr
 1               5                  10

<210> SEQ ID NO 88
<211> LENGTH: 12
<212> TYPE: PRT
<213> ORGANISM: Mycobacterium tuberculosis strain H37Rv
<220> FEATURE:
<221> NAME/KEY: MISC_FEATURE
<222> LOCATION: (9)..(9)
<223> OTHER INFORMATION: Xaa is Asp or Gly

<400> SEQUENCE: 88

Ala Pro Pro Ser Cys Ala Gly Leu Xaa Cys Thr Val
 1               5                  10

<210> SEQ ID NO 89
<211> LENGTH: 9
<212> TYPE: PRT
```

```
<213> ORGANISM: Mycobacterium tuberculosis strain H37Rv

<400> SEQUENCE: 89

Cys Ser Ser Asn Lys Ser Thr Thr Gly
 1               5

<210> SEQ ID NO 90
<211> LENGTH: 10
<212> TYPE: PRT
<213> ORGANISM: Mycobacterium tuberculosis strain H37Rv

<400> SEQUENCE: 90

Met Ala Arg Ala Val Gly Ile Asp Leu Gly
 1               5                  10

<210> SEQ ID NO 91
<211> LENGTH: 7
<212> TYPE: PRT
<213> ORGANISM: Mycobacterium tuberculosis strain H37Rv
<220> FEATURE:
<221> NAME/KEY: MISC_FEATURE
<222> LOCATION: (1)..(1)
<223> OTHER INFORMATION: Xaa can be any amino acid
<220> FEATURE:
<221> NAME/KEY: MISC_FEATURE
<222> LOCATION: (2)..(2)
<223> OTHER INFORMATION: Xaa can be any amino acid
<220> FEATURE:
<221> NAME/KEY: MISC_FEATURE
<222> LOCATION: (5)..(5)
<223> OTHER INFORMATION: Xaa can be any amino acid

<400> SEQUENCE: 91

Xaa Xaa Ala Val Xaa Val Thr
 1               5

<210> SEQ ID NO 92
<211> LENGTH: 10
<212> TYPE: PRT
<213> ORGANISM: Mycobacterium tuberculosis strain H37Rv

<400> SEQUENCE: 92

Phe Ser Arg Pro Gly Leu Pro Val Glu Tyr
 1               5                  10

<210> SEQ ID NO 93
<211> LENGTH: 10
<212> TYPE: PRT
<213> ORGANISM: Mycobacterium tuberculosis strain H37Rv
<220> FEATURE:
<221> NAME/KEY: MISC_FEATURE
<222> LOCATION: (1)..(1)
<223> OTHER INFORMATION: Xaa is Lys or Asn
<220> FEATURE:
<221> NAME/KEY: MISC_FEATURE
<222> LOCATION: (6)..(6)
<223> OTHER INFORMATION: Xaa at positoin 6 can be any amino acid
<220> FEATURE:
<221> NAME/KEY: MISC_FEATURE
<222> LOCATION: (8)..(8)
<223> OTHER INFORMATION: Xaa can be any amino acid

<400> SEQUENCE: 93

Xaa Val Ile Arg Ile Xaa Gly Xaa Thr Asp
 1               5                  10

<210> SEQ ID NO 94
<211> LENGTH: 11
<212> TYPE: PRT
```

<213> ORGANISM: Mycobacterium tuberculosis strain H37Rv

<400> SEQUENCE: 94

Met Ala Arg Ala Val Gly Ile Asp Leu Gly Thr
 1               5                  10

<210> SEQ ID NO 95
<211> LENGTH: 16
<212> TYPE: PRT
<213> ORGANISM: Mycobacterium tuberculosis strain H37Rv

<400> SEQUENCE: 95

Phe Ser Arg Pro Gly Leu Pro Val Glu Tyr Leu Gln Val Pro Ser Pro
 1               5                  10                  15

<210> SEQ ID NO 96
<211> LENGTH: 21
<212> TYPE: PRT
<213> ORGANISM: Mycobacterium tuberculosis strain H37Rv

<400> SEQUENCE: 96

Thr Glu Lys Thr Pro Asp Asp Val Phe Lys Leu Ala Lys Asp Glu Lys
 1               5                  10                  15

Val Glu Tyr Val Asp
            20

<210> SEQ ID NO 97
<211> LENGTH: 10
<212> TYPE: PRT
<213> ORGANISM: Mycobacterium tuberculosis strain H37Rv

<400> SEQUENCE: 97

Phe Ser Arg Pro Gly Leu Pro Val Glu Tyr
 1               5                  10

<210> SEQ ID NO 98
<211> LENGTH: 15
<212> TYPE: PRT
<213> ORGANISM: Mycobacterium tuberculosis strain H37Rv
<220> FEATURE:
<221> NAME/KEY: MISC_FEATURE
<222> LOCATION: (15)..(15)
<223> OTHER INFORMATION: Xaa is Glu or Thr

<400> SEQUENCE: 98

Thr Glu Lys Thr Pro Asp Asp Val Phe Lys Leu Asp Glu Val Xaa
 1               5                  10                  15

<210> SEQ ID NO 99
<211> LENGTH: 10
<212> TYPE: PRT
<213> ORGANISM: Mycobacterium tuberculosis strain H37Rv

<400> SEQUENCE: 99

Met Pro Glu Gln His Pro Pro Ile Thr Glu
 1               5                  10

<210> SEQ ID NO 100
<211> LENGTH: 15
<212> TYPE: PRT
<213> ORGANISM: Mycobacterium tuberculosis strain H37Rv
<220> FEATURE:
<221> NAME/KEY: MISC_FEATURE
<222> LOCATION: (1)..(1)
<223> OTHER INFORMATION: Xaa can be any amino acid
<220> FEATURE:

-continued

```
<221> NAME/KEY: MISC_FEATURE
<222> LOCATION: (4)..(4)
<223> OTHER INFORMATION: Xaa is Met or Leu
<220> FEATURE:
<221> NAME/KEY: MISC_FEATURE
<222> LOCATION: (6)..(6)
<223> OTHER INFORMATION: Xaa can be any amino acid
<220> FEATURE:
<221> NAME/KEY: MISC_FEATURE
<222> LOCATION: (9)..(9)
<223> OTHER INFORMATION: Xaa can be any amino acid
<220> FEATURE:
<221> NAME/KEY: MISC_FEATURE
<222> LOCATION: (11)..(11)
<223> OTHER INFORMATION: Xaa can be any amino acid
<220> FEATURE:
<221> NAME/KEY: MISC_FEATURE
<222> LOCATION: (12)..(12)
<223> OTHER INFORMATION: Xaa can be any amino acid

<400> SEQUENCE: 100

Xaa Pro Val Xaa Val Xaa Pro Gly Xaa Glu Xaa Xaa Gln Asp Asn
  1               5                  10                  15

<210> SEQ ID NO 101
<211> LENGTH: 10
<212> TYPE: PRT
<213> ORGANISM: Mycobacterium tuberculosis strain H37Rv

<400> SEQUENCE: 101

Phe Ser Arg Pro Gly Leu Pro Val Glu Tyr
  1               5                  10

<210> SEQ ID NO 102
<211> LENGTH: 11
<212> TYPE: PRT
<213> ORGANISM: Mycobacterium tuberculosis strain H37Rv

<400> SEQUENCE: 102

Ala Pro Tyr Glu Asn Leu Met Val Pro Ser Val
  1               5                  10

<210> SEQ ID NO 103
<211> LENGTH: 12
<212> TYPE: PRT
<213> ORGANISM: Mycobacterium tuberculosis strain H37Rv
<220> FEATURE:
<221> NAME/KEY: MISC_FEATURE
<222> LOCATION: (1)..(1)
<223> OTHER INFORMATION: Xaa can be any amino acid

<400> SEQUENCE: 103

Xaa Val Tyr Asp Val Ile Met Leu Thr Ala Gly Pro
  1               5                  10

<210> SEQ ID NO 104
<211> LENGTH: 10
<212> TYPE: PRT
<213> ORGANISM: Mycobacterium tuberculosis strain H37Rv

<400> SEQUENCE: 104

Met Ala Glu Tyr Thr Leu Pro Asp Leu Asp
  1               5                  10

<210> SEQ ID NO 105
<211> LENGTH: 15
<212> TYPE: PRT
<213> ORGANISM: Mycobacterium tuberculosis strain H37Rv

-continued

```
<400> SEQUENCE: 105

Asp Pro Val Leu Val Phe Pro Gly Met Glu Ile Arg Gln Asp Asn
 1               5                  10                  15

<210> SEQ ID NO 106
<211> LENGTH: 741
<212> TYPE: PRT
<213> ORGANISM: Mycobacterium tuberculosis

<400> SEQUENCE: 106

Met Thr Asp Arg Val Ser Val Gly Asn Leu Arg Ile Ala Arg Val Leu
 1               5                  10                  15

Tyr Asp Phe Val Asn Asn Glu Ala Leu Pro Gly Thr Asp Ile Asp Pro
                20                  25                  30

Asp Ser Phe Trp Ala Gly Val Asp Lys Val Val Ala Asp Leu Thr Pro
            35                  40                  45

Gln Asn Gln Ala Leu Leu Asn Ala Arg Asp Glu Leu Gln Ala Gln Ile
        50                  55                  60

Asp Lys Trp His Arg Arg Val Ile Glu Pro Ile Asp Met Asp Ala
 65                 70                  75                  80

Tyr Arg Gln Phe Leu Thr Glu Ile Gly Tyr Leu Leu Pro Glu Pro Asp
                85                  90                  95

Asp Phe Thr Ile Thr Thr Ser Gly Val Asp Ala Glu Ile Thr Thr Thr
            100                 105                 110

Ala Gly Pro Gln Leu Val Val Pro Val Leu Asn Ala Arg Phe Ala Leu
        115                 120                 125

Asn Ala Ala Asn Ala Arg Trp Gly Ser Leu Tyr Asp Ala Leu Tyr Gly
    130                 135                 140

Thr Asp Val Ile Pro Glu Thr Asp Gly Ala Glu Lys Gly Pro Thr Tyr
145                 150                 155                 160

Asn Lys Val Arg Gly Asp Lys Val Ile Tyr Ala Arg Lys Phe Leu
                165                 170                 175

Asp Asp Ser Val Pro Leu Ser Ser Gly Ser Phe Gly Asp Ala Thr Gly
            180                 185                 190

Phe Thr Val Gln Asp Gly Gln Leu Val Val Ala Leu Pro Asp Lys Ser
        195                 200                 205

Thr Gly Leu Ala Asn Pro Gly Gln Phe Ala Gly Tyr Thr Gly Ala Ala
    210                 215                 220

Glu Ser Pro Thr Ser Val Leu Leu Ile Asn His Gly Leu His Ile Glu
225                 230                 235                 240

Ile Leu Ile Asp Pro Glu Ser Gln Val Gly Thr Thr Asp Arg Ala Gly
                245                 250                 255

Val Lys Asp Val Ile Leu Glu Ser Ala Ile Thr Thr Ile Met Asp Phe
            260                 265                 270

Glu Asp Ser Val Ala Ala Val Asp Ala Asp Lys Val Leu Gly Tyr
        275                 280                 285

Arg Asn Trp Leu Gly Leu Asn Lys Gly Asp Leu Ala Ala Ala Val Asp
    290                 295                 300

Lys Asp Gly Thr Ala Phe Leu Arg Val Leu Asn Arg Asp Arg Asn Tyr
305                 310                 315                 320

Thr Ala Pro Gly Gly Gly Gln Phe Thr Leu Pro Gly Arg Ser Leu Met
                325                 330                 335

Phe Val Arg Asn Val Gly His Leu Met Thr Asn Asp Ala Ile Val Asp
            340                 345                 350
```

-continued

```
Thr Asp Gly Ser Glu Val Phe Glu Gly Ile Met Asp Ala Leu Phe Thr
        355                 360                 365
Gly Leu Ile Ala Ile His Gly Leu Lys Ala Ser Asp Val Asn Gly Pro
        370                 375                 380
Leu Ile Asn Ser Arg Thr Gly Ser Ile Tyr Ile Val Lys Pro Lys Met
385                 390                 395                 400
His Gly Pro Ala Glu Val Ala Phe Thr Cys Glu Leu Phe Ser Arg Val
                405                 410                 415
Glu Asp Val Leu Gly Leu Pro Gln Asn Thr Met Lys Ile Gly Ile Met
            420                 425                 430
Asp Glu Glu Arg Arg Thr Thr Val Asn Leu Lys Ala Cys Ile Lys Ala
            435                 440                 445
Ala Ala Asp Arg Val Val Phe Ile Asn Thr Gly Phe Leu Asp Arg Thr
    450                 455                 460
Gly Asp Glu Ile His Thr Ser Met Glu Ala Gly Pro Met Val Arg Lys
465                 470                 475                 480
Gly Thr Met Lys Ser Gln Pro Trp Ile Leu Ala Tyr Glu Asp His Asn
                485                 490                 495
Val Asp Ala Gly Leu Ala Ala Gly Phe Ser Gly Arg Ala Gln Val Gly
            500                 505                 510
Lys Gly Met Trp Thr Met Thr Glu Leu Met Ala Asp Met Val Glu Thr
            515                 520                 525
Lys Ile Ala Gln Pro Arg Ala Gly Ala Ser Thr Ala Trp Val Pro Ser
    530                 535                 540
Pro Thr Ala Ala Thr Leu His Ala Leu His Tyr His Gln Val Asp Val
545                 550                 555                 560
Ala Ala Val Gln Gln Gly Leu Ala Gly Lys Arg Arg Ala Thr Ile Glu
                565                 570                 575
Gln Leu Leu Thr Ile Pro Leu Ala Lys Glu Leu Ala Trp Ala Pro Asp
            580                 585                 590
Glu Ile Arg Glu Glu Val Asp Asn Asn Cys Gln Ser Ile Leu Gly Tyr
            595                 600                 605
Val Val Arg Trp Val Asp Gln Gly Val Gly Cys Ser Lys Val Pro Asp
    610                 615                 620
Ile His Asp Val Ala Leu Met Glu Asp Arg Ala Thr Leu Arg Ile Ser
625                 630                 635                 640
Ser Gln Leu Leu Ala Asn Trp Leu Arg His Gly Val Ile Thr Ser Ala
                645                 650                 655
Asp Val Arg Ala Ser Leu Glu Arg Met Ala Pro Leu Val Asp Arg Gln
            660                 665                 670
Asn Ala Gly Asp Val Ala Tyr Arg Pro Met Ala Pro Asn Phe Asp Asp
            675                 680                 685
Ser Ile Ala Phe Leu Ala Ala Gln Glu Leu Ile Leu Ser Gly Ala Gln
    690                 695                 700
Gln Pro Asn Gly Tyr Thr Glu Pro Ile Leu His Arg Arg Arg Arg Glu
705                 710                 715                 720
Phe Lys Ala Arg Ala Ala Glu Lys Pro Ala Pro Ser Asp Arg Ala Gly
                725                 730                 735
Asp Asp Ala Ala Arg
            740
```

EARLY DETECTION OF MYCOBACTERIAL DISEASE

This application is a continuation-in-part of U.S. Ser. No. 09/001,984, filed Dec. 31, 1997, now U.S. Pat. No. 6,245,331 which is incorporated by reference in its entirety.

STATEMENT OF RIGHTS TO INVENTIONS MADE UNDER FEDERALLY SPONSORED RESEARCH

This invention was funded in part by grants and contracts from the National Institute of Allergy and Infectious Diseases, National Institutes of Health, and from the Department of Veterans Affairs, which provides to the United States government certain rights in this invention.

BACKGROUND OF THE INVENTION

1. Field of the Invention

The invention in the fields of microbiology and medicine relates to methods for rapid early detection of mycobacterial disease in humans based on the presence of antibodies to particular "early" mycobacterial antigens which have not been previously recognized for this purpose. Assay of such antibodies on select partially purified or purified mycobacterial preparations containing such early antigens permits diagnosis of TB earlier than has been heretofore possible. Also provided is a surrogate marker for screening populations at risk for TB, in particular subjects infected with human immunodeficiency virus (HIV).

2. Description of the Background Art

Recent estimates by the World Health Organization (WHO) suggest that approximately 90 million new cases of tuberculosis ("TB") will occur during this decade leading to about 30 million deaths (Raviglione, M. C. et al., 1995, JAMA. 273:220–226). The spread of HIV in populations already having a high incidence of TB related to socioeconomic factors and malnutrition has resulted in a resurgence of TB all over the world (Raviglione, M. C. et al., 1992, Bull World Health Organ 70:515–526; Harries A. D., 1990, Lancet. 335:387–390). This resurgence has renewed interest in developing improved vaccines, diagnostics, drugs and drug delivery regimens for TB. Furthermore, the immune dysfunction caused by HIV infection leads to a high rate of reactivation of latent TB, increased susceptibility to primary disease, as well as an accelerated course of disease progression (Raviglione et al., 1992, supra; 1995, supra; Shafer R. W. et al., 1996, Clin. Infect. Dis. 22:683–704; Barnes P. F. et al., 1991, N. Engl. J. Med. 324:1644–1650; Selwyn P. A. et al., 1989, N. Engl. J. Med. 320:545–550).

It is well established that cellular immunity is critical for protection against TB. Much of the work in this field is focused on defining the antigens of the causative bacterium, Mycobacterium tuberculosis (M. tuberculosis; also abbreviated herein as "Mt") that can elicit effective immunity and on understanding the role of various cell populations in host-pathogen interactions (Andersen, P. et al., 1992, Scand. J. Immunol. 36:823–831; Havlir, D. V. et al., 1991, Infect. Immun. 59:665–670; Orme, I. M. et al., 1993, J. Infect. Dis. 167:1481–1497).

Delayed hypersensitivity measured as cutaneous immune reactivity to a purified protein derivative of Mt (abbreviated "PPD") is the only marker available for detection of latent infection with Mt. However, the sensitivity of the PPD skin test is substantially reduced during HIV infection (Raviglione et al., 1992, supra, 1995, supra; Graham N. M. H. et al., 1991, JAMA 267:369–373; Huebner R. E. et al., 1994, Clin. Infect. Dis. 19:26–32; Huebner R. E. et al., 1992, JAMA 267:409–410; Caiaffa W. T. et al., 1995, Arch. Intern. Med. 155:2111–2117). Furthermore, vaccination with a closely related mycobacterium designated Bacillus Cahnette-Guerin (BCG) or previous exposure to other mycobacterial species can lead to false positive results in a PPD skin test. Not only does PPD reactivity fail to distinguish active, subclinical disease from latent infection, but the time between a positive skin test and development of clinical disease may range from months to several years (Selwyn P. A. et al., supra).

Because of the susceptibility of immunocompromised individuals to TB, the U.S. Centers for Disease Control and Prevention recommends preventive isoniazid therapy for all HIV seropositive (HIV$^+$), PPD-positive (PPD$^+$) individuals. However, the optimal time for such therapy is not clear and, ideally, should coincide with replication of previously latent bacteria. Unnecessary therapy must be minimized because prolonged isoniazid treatment can have serious toxic side effects (Shafer et al., supra). The impact of such treatment on emergence of drug resistant bacteria is still unclear. The use of preventive therapy in developing countries is seriously limited by the high frequency of PPD$^+$ individuals coupled with the lack of adequate medico-social infrastructure and economic resources. High risk populations are also found in the United States, primarily intravenous drug users, homeless people, prison inmates and residents of slum areas (Fitzgerald, J. M. et al., 1991, Chest 100:191–200; Graham, N. M. H. et al., 1992, JAMA 267:369–373; Friedman, L. N. et al., 1996, New Engl. J. Med. 334:828–833) as well as household contacts of TB patients. Thus, discovery of additional surrogate markers for early detection and prompt treatment of active, subclinical TB in such high risk populations is urgently required.

Antibody responses in TB have been studied for several decades primarily for the purpose of developing serodiagnostic assays. Although some seroreactive antigens/epitopes have been identified, interest in antibody responses to M. tuberculosis has waned because of the lack of progress in simple detection of corresponding antibodies. Studies using crude antigen preparations revealed that healthy individuals possess antibodies that cross-react with several mycobacterial antigens. Such antibodies are believed to have been elicited by exposure to commensal and environmental bacteria and vaccinations (Bardana, E. J. et al., 1973, Clin. Exp. Immunol. 13:65–77; Das, S. et al., 1992, Clin. Exp. Immunol. 89:402–406; Del Giudice, G. et al., 1993, J. Immunol. 150:2025–2032; Grange, J. M., 1984, Adv. Tuberc. Res. 21:1–78; Havlir, D. V. et al., supra; Ivanyi, J. et al., 1989, Brit. Med. Bull. 44:635–649; Verbon, A. et al., 1990, J. Gen. Microbiol. 136:955–964). During the last decade, several mycobacterial antigens have been isolated and characterized (Young, D. B. et al., 1992, Mol. Microbiol. 6:133–145), including the 71 kDa DnaK, 65 kDa GroEL, 47 kDa elongation factor tu, 44 kDa PstA homologue, 40 kDa L-alanine dehydrogenase, 38 kDa PhoS, 23 kDa superoxide dismutase, 23 kDa outer membrane protein, 12 kDa thioredoxin, and the 14 kDa GroES. However, a majority of the antigens identified so far bear significant homology to the analogous proteins in other mycobacteria and non-mycobacterial prokaryotes (Andersen, A. B. et al., 1992, Infect. Immun. 60:2317–2323; Andersen, A. B. et al., 1989, Infect. Immun. 57:2481–2488; Braibant, M. et al., 1994, Infect. Immun. 62:849–854; Carlin, N. I. A. et al., 1992, Infect. Immun. 60:3136–3142; Garsia, R. J. et al., 1989, Infect. Immun. 57:204–212; Hirschfield, G. R. et al., 1990, J. Bacteriol. 172:1005–1013; Shinnick, T. M. et al., 1989, Nucl. Acids Res. 1 7:1254; Shinnick, T. M. et al., 1988, Infect. Immun. 56:446–451; Wieles, B. et al., 1995, Infect. Immun. 63:4946–4948; Young, D. B. et al., supra; Zhang, Y. et al., 1991, Mol. Microbiol. 5:381–391). Thus, almost all individuals (healthy or diseased) have antibodies to epitopes of conserved regions of these antigens. These antibodies are responsible for the uninformative (and possibly misleading) cross-reactivity observed with crude Mt antigen preparations (Davenport, M. P. et al., 1992, Infect. Immun. 60:1170–1177; Grandia, A. A. et al., 1991, Immunobiol. 182:127–134; Meeker, H. C. et al., 1989, Infect. Immun. 57:3689–3694; Thole, J. et al., 1987, Infect. Immun. 55:1466–1475).

Because such cross-reactive antibodies would mask the presence of antibodies specific for Mt antigens, some of the purified antigens such as the 38 kDa PhoS, the 30/31 kDa "antigen 85" (discussed in more detail below), 19 kDa lipoprotein, 14 kDa GroES and lipoarabinomannan have been prepared and tested (Daniel, T. et al., 1985 Chest. 88:388–392; Drowart, L. et al., 1991, Chest. 100:685–687; Jackett, P. S. et al., 1988, J. Clin. Microbiol. 26:2313–2318; Ma, Y. et al., 1986, Am. Rev. Respir. Dis. 134:1273–1275; Sada, E. et al., 1990, J. Clin. Microbiol. 28:2587–2590; Sada, E. D. et al., 1990, J. Infect. Dis. 162:928–931; Van Vooren, J. P. et al., 1991, J. Clin. Microbiol. 29:2348–2350). It is noteworthy that the choice of which antigen to test was dictated primarily by (a) its availability, (b) its immunodominance in animal immunizations, or (c) ease of its biochemical purification. None of these criteria take into account the reactivity of the antigen which occurs naturally in the human immune response to mycobacterial diseases. Use of the 38 kDa antigen has provided the highest serological sensitivity and specificity so far (Daniel, T. M. et al., 1987, Am. Rev. Respir. Dis. 135:1137–1151; Harboe, M. et al., 1992, J. Infect. Dis. 166:874–884; Ivanyi, J. et al., 1989, supra). However, in contrast to the present invention, the presence of anti-38 kDa antibodies is associated primarily with treated, advanced and recurrent TB (Bothamley, G. H. et al., 1992, Thorax. 47:270–275; Daniel, T. M. et al., 1986, Am. Rev. Respir. Dis. 134:662–665; Ma, Y. et al., 1986, Am. Rev. Respir. Dis. 134:1273–1275).

One convention in mycobacterial protein nomenclature is the use of MPB and MPT numbers. MPB denotes a protein purified from M. bovis BCG followed by a number denoting its relative mobility in 7.7% polyacrylamide gels at a pH of 9.5. MPT denotes a protein isolated from M. tuberculosis. In proteins examined prior to this invention, no differences in the N-terminal amino acid sequence were shown between these two mycobacterial species.

Wiker and colleagues have studied a family of secreted Mt proteins which include a complex of 3 proteins termed antigens 85A, 85B and 85C (also known as the "85 complex" or "85cx") (Wiker, H. G. et al., 1992, Scand. J. Immunol. 36:307–319; Wiker, H. G. et al., 1992, Microbiol. Rev. 56:648–661). This complex was originally found in M. bovis BCG preparations which produced a secreted antigen comprising a complex of three closely related components, antigen 85A, 85B, and 85C (Wiker, H. G. et al. 1986, Int. Arch. Allergy Appl. Immunol. 81:289–306). The corresponding components of Mt are also actively secreted. The 85 complex is considered the major secreted protein constituent of mycobacterial culture fluids though it is also found in association with the bacterial surface. In most SDS-polyacrylamide gel electrophoresis (SDS-PAGE) analyses, 85A and 85C are not properly resolved, whereas isoelectric focusing resolves three distinct bands.

Genes encoding six of the secreted proteins: 85A, 85B, 85C, "antigen 78" (usually referred to as the 38 kDa protein), MPB64 and MPB70 have been cloned. Three separate genes located at separate sites in the mycobacterial genome encode 85A, B and C (Content, J. et al., 1991, Infect. Immun. 59:3205–3212). A gene encoding the antigen known as MPT-32 (reported as a 45/47 kDa secreted antigen complex) has been cloned, sequenced and expressed (Laqueyrerie, A. et al., 1995, Infec. Immun. 63:4003–4010) and designated as the apa gene. One of the present co-inventors and his collaborators provided evidence for glycosylation sites on this protein (Dobos, K. M. et al., 1996, J. Bacteriol. 178:2498–2506 and Example III herein). However, the need continues for further elucidation of the biochemistry and immunochemistry of Mt proteins and glycoproteins which are potentially important as serodiagnostic tools. The fall definition of glycosylation sites and the nature and extent of glycosylation of glycosylated proteins has been scant. Initial evidence for the presence of glycoproteins in Mt was based on the observation of discrete concanavalin A (ConA)-binding products upon PAGE and electroblotting of protein preparations. However, since these patterns occurred in the midst of considerable quantities of mannose (Man)-containing lipoglycans and phospholipids (Dobos et al., supra), chemical proof of amino acid glycosylation is still considered necessary and is provided as part of this invention.

The antigen 85 complex is often referred to as the "30/31 kDa doublet," although slightly different molecular mass designations have been reported. The following list shows the molecular masses of the individual components of antigen 85 complex plus two additional antigens (in SDS-PAGE) as described by Wiker and colleagues, along with alternative nomenclatures:

Ag85A = MPT44 = 31 kDa
Ag85B = MPT59 = 30 kDa
Ag85C = MPT45 = 31.5 kDa
          MPT64 = 26 kDa
          MPT51 = 27 kDa
Ag78      ··· = 38 kDa
          MPT32 = 45/47 kDa (found to be 38/42 kDa by the present inventors)

Wiker's group studied cross-reactions between five actively secreted Mt proteins by crossed immunoelectrophoresis, SDS-PAGE with immunoblotting and enzyme immunoassay (EIA) using (1) polyclonal rabbit antisera to the purified proteins and (2) a mouse monoclonal antibody ("mAb"). The mAb HBT4 reacted with the MPT51 protein. The 85A, 85B, and 85C constituents cross-reacted extensively, though each had component-specific in addition to cross-reacting epitopes. These components also cross-reacted with MPT51 and MPT64. Amino acid sequence homology was shown between 85A, 85B, 85C and MPT51. MPT64 showed less homology. Striking homology was also found between two different structures within the 85B sequence. Thus a family of at least four secreted proteins with common structural features has been demonstrated in mycobacteria. Three of these proteins bind readily to fibronectin (Abou-Zeid, C., 1988, Infect. Immun. 56:3046–3051; Abou-Zeid, C., 1988, Infect. Immun. 59:2712–2718; Harboe, M. et al., 1992, Clin. Inf. Dis. 14:313–319).

The aligned amino acid sequences listed below illustrate the homology of a fragment of 85A, 85B, 85C, MPT51 and MPT64. The numbers at the top correspond to the part of the sequence shown. The N-terminal sequences were determined on isolated proteins and aligned by visual inspection. The sequence from position 66 to 91 of MPT64 is the sequence deduced from the cloned gene.

|            | 1 | 5 | 10 | 15 | 20 | 25 | 30 | 35 | SEQ ID NO |
|---|---|---|---|---|---|---|---|---|---|
| 85A(1-39) | FSRPGLPVEYLQVPS | PSMGRDIKVQFQSGGANSP | ALYLL | 1 |
| 85B(1-39) | FSRPGLPVEYLQVPS | PSMGRDIKVQFQSGGNNSP | AVYLL | 2 |
| 85C(1-37) | FSRPGLPVEYLQVPSA | SMGRDIKVQFQGGG | PHAVYLL | 3 |
| MPT51(1-32) | APYENLMYPS | PSMGRDKPVAFLAGG | PHAVYLL | 4 |
| MPT64(66-91) | APYE LNITSATYQS | AIPPRG | TQAVVL | 5 |

The N-terminal sequence of MPT51 showed 72% homology with the sequence of the Ag 85 components (when P at position 2 is aligned with P at position 7 of the three Ag 85 components.

Apart from fibronectin binding, little information concerning the primary functions of antigen 85 complex proteins is available. Although the art has not considered antibodies as playing a significant role in protective immunity against mycobacterial infections, Wiker et al. (supra) speculated that the existence of interactions between Ag 85 and fibronectin implied that an antibody to Ag 85 which could block this interaction might affect early events in disease progression and increase host resistance.

Studies of TB patients showed that assays of antibodies to the Ag 85 complex had a sensitivity of about 50%. With regard to specificity, the Ag 85 components are highly cross-reactive so that positive responses are expected (and found) in healthy controls, particularly in geographic areas of high exposure to atypical mycobacteria. The different degree of specificity is thus highly dependent on the kind of control subjects used. It is noteworthy that traditional BCG vaccination does not appear to induce a significant antibody response, though it is interesting that antibodies to mycobacterial antigens increased when anti-TB chemotherapy was initiated.

C. Espitia et al., 1989, *Clin Exp Immunol* 77:373–377, found antibodies to the 30/31 kDa doublet band (presumably 85A and 85C) in 55.9% of TB patient sera (and in 56.5% of lepromatous leprosy sera). Sera from healthy individuals often showed binding which was weaker than TB patients. Van Vooren, J. P. et al., 1991, *J. Clin. Microbiol.* 29:2348–2350, found that antigen 85A reacted with sera from tuberculous as well as nontuberculous individuals. By contrast, 85B and 85C did not react with the control sera but reacted with 20 of 28 serum samples (71%) from tuberculous patients. Wiker and colleagues concluded that the future of the serology of antibody responses to antigen 85 would require investigation of antibodies to component-specific epitopes and in particular to species-specific epitopes. The extensive cross-reactivity of antigen 85 in different species of mycobacteria suggested to Wiker et al. (supra) that tests could attain sufficient sensitivity, though suitable mAbs were said to be essential for further development of tests for infection with Mt (and atypical mycobacteria). Importantly, the present inventors note the deficiency in the art of analysis of antibodies at different stages of disease. This is one of the primary deficiencies addressed by this invention.

C. Espitia et al., 1995, *Infect. Immun.* 63:580–584, found reciprocal cross-reactivity between a Mt 50/55 kDa protein and a *M. bovis* BCG 45/47 kDa antigen using a rabbit polyclonal antiserum against the *M. bovis* protein and a mAb against the Mt antigen. Both antigens were secreted glycoproteins. The N-terminal sequences and total amino acid content of these proteins were very similar. Analysis by 2D gel electrophoresis showed at least seven different components in the Mt 50/55 kDa antigen. In solid-phase immunoassays, purified Mt 50/55 kDa protein was recognized by sera from 70% of individuals (n=77) with pulmonary TB. The N-terminus of the Mt 41 kDa antigen known as MPT32 was very similar to the N-termini of the 50/55 kDa—and the 45–47 kDa proteins. The molecular mass of this Mt protein was deduced to be 45–47 kDa. Espitia et al., supra, speculated about a diagnostic potential for these antigens based on their observation of antibodies in 70% of their TB patients. However, the potential of this antigen as an early diagnostic agent for TB was neither analyzed nor even suggested.

In sum, none of the antigens studied so far, with the possible exception of MPT32 (as will be described herein) has emerged as a suitable candidate for development of a diagnostic assay for early stages of TB. Since antigens/epitopes recognized during natural infection and disease progression in humans may differ substantially from those recognized by animals upon artificial immunization (Bothamley, G. et al., 1988, *Eur. J. Clin. Microbiol. Infect. Dis.* 7:639–645; Calle, J. et al., 1992, *J. Immunol.* 149:2695–2701; Hartskeerl, R. A. et al., 1990, *Infect. Immun.* 58:2821–2827; Laal, S. et al., 1991, *Proc. Natl. Acad. Sci. USA.* 88:1054–1058; Meeker, H. C. et al., 1989, *Infect. Immun.* 57:3689–3694; Verbon, A., 1994, *Trop. Geog. Med.* 46:275–279), there is a pressing need in the art for selection of antigens based on their ability to stimulate the human immune system. This would permit the identification of such useful antigens and design of diagnostic assays for early detection of TB.

TB in HIV Infected Subjects

Studies aimed at determining the integrity of humoral immune memory during HIV infection have shown that the ability to respond to recall antigens by producing significant amounts of high-affinity specific IgG antibodies was maintained during the time prior to onset of clinical AIDS (Janoff, E. N. et al., 1991, *J. Immunol* 147:2130–2135). Secondary antibody responses are relatively independent of T cell help, and B cells specific for recall antigens are present in normal frequency in HIV-infected individuals (Janoff et al. (supra); Kroon F. P. et al., 1995, *Clin. Infect. Dis.* 21:1197–1203). Comparison of secondary responses to different antigens in HIV-infected individuals also suggested that the level of immunologic memory established prior to HIV infection may influence the ability of the subject to respond post-infection (Janoff et al. (supra)). Since TB in HIV-infected individuals often results from reactivation of latent infection, and reactivated TB is known to occur relatively early during the course of HIV disease progression, the immune system may be sufficiently intact to generate antibody responses towards bacteria emerging from latency. If this occurs, HIV-infected subjects with active TB infection should have detectable antibodies directed towards Mt antigens.

Although the literature on TB infection in subjects not infected with HIV is extensive, reports on antibody responses of HIV/TB patients to *M. tuberculosis,* have been scant and controversial. Farber, C. et al., 1990, *J. Infect. Dis,* 162:279–280, reported the presence of antibodies to the p32 antigen (same as 85A) in 7 of 8 HIV/TB patients. Da Costa, C. et al., 1993, *Clin. Exp. Immunol.* 91:25–29, reported the presence of anti-lipoarabinomannan (LAM) antibodies in 35% of such patients. Barer, L. et al., 1992, *Tuber. Lung. Dis.* 73:187–191, reported anti-PPD antibodies in 36% of HIV/TB patients. Martin-Casabona, N. et al., 1992, *J. Clin. Microbiol.* 30:1089–1093, reported anti-sulfolipid (SLIV) antibodies in 73% of their patients. In addition, van Vooren, P. et al., 1988, *Tubercle.* 69:303–305, reported that anti-p32 antibodies were detectable in an HIV/TB patient for several months prior to clinical manifestation of TB. In contrast, analysis of responses to Ag60 (Saltini C. et al., 1993, *Am. Rev. Respir. Dis.* 145:1409–1414; van der Werf, T. S. et al., 1992. *Med Microbiol Immunol* 181:71–76) and Ag85B (McDonough, J. A. et al., 1992, *J. Lab. Clin. Med.* 120:318–322) failed to detect antibodies in these patients.

Hence, there is a particular need in the art for methods to detect TB infections at early stages in HIV patients since they comprise one of the largest populations at risk for TB throughout the world.

A number of laboratories have reported on antibodies, mainly to infectious agents, in urine. For example, Takahashi S; et al. (*Clin Diagn Lab Immunol,* 1998, 5:24–27) found antibodies to rubella virus in urine and serum samples from healthy individuals who underwent rubella vaccination. Shutov AM et al. *Arkh* (*RUSSIA*) 1996, 68:35–37 detected antibodies in urine to the virus causing hemorrhagic fever with renal syndrome (HFRS) and concluded that detection of antibodies to the virus both in the blood and urine can be used for earlier diagnosis Vereta LA; et al. (*Vopr Virusol* (*RUSSIA*) 1993, 38:18–21) used a a commercial diagnostic indirect imunofluorescence assay to detection antibodies to the hanta virus in the urine of patients with HFRS.

Koopmans M et al. (*J Med Virol,* 1995, 46:321–328) demonstrated presence of antibodies to human cytomegalovirus (HCMV) in urine samples by ELISA and immunoblot using a recombinant form of the major antigenic protein of HCMV designated pp150). The presence of HCMV antibodies correlated significantly with congenital infection (as detected by tissue culture isolation of virus from urine samples of newborns), especially with asymptomatic cases (sensitivity 70%; specificity 94%). The authors interpreted this reflect a local (renal) immune response to HCMV in congenitally infected children, which may have diagnostic applications.

Zhang X et al. (*J Med Virol,* 1994,44:187–191) used commercial immunoassays to detect antibodies to hepatitis C virus (HCV) in urine (229 serum/urine matched samples from forensic autopsy cases). The urine samples produced positive results on 44–45 of the 46 samples that were positive by conventional screening tests and by supplemental tests. Generally, five times the serum volume was required for the screening tests to be optimal for urine samples. The same group (Constantine N T et al., *Am J Clin Pathol,* 1994, 101:157–161) detected antibodies to HIV in urine.

A group of Japanese investigatos (Hashida S et al., *J Clin Lab Anal,* 1994, 8:237–246; Hashinaka K et al., *J. Clin Microbiol* 1994, 32:819–22; Hashida S et al., *J Clin Lab Anal* 1994, 8:149–156 Hashida S et al., *J Clin Lab Anal* 1994, 8:86–95) diagnosed HIV-1 infection in asymptomatic carriers by detecting IgG antibody to HIV-1 in urine using an ultrasensitive enzyme immunoassay (immune complex transfer enzyme immunoassay) with recombinant proteins as antigen. They reported that sensitivity could be improved by a longer assay of bound enzyme activity by using concentrated urine samples and by the combined use of thee different recombinant HIV antigens.

Urnovitz HB et al., (*Lancet* Dec. 11, 1993, 342:1458–9), discovered that 7 individuals who were negative for HIV-1 antibody in a licensed serum EIA were positive in a urine EIA and western blot (WB).

Connell J A et al., *J Med Virol* 1993, 41:159–64, described a rapid, simple, and robust IgG-capture enzyme-linked immunosorbent assay (GACELISA) suitable for the detection of anti-HIV 1 and 2 antibodies in saliva and urine The assay was 100% sensitive on 126 urine specimens collected from anti-HIV-positive patients and 100% patient on 422 uriney specimens collected from anti-HIV-negative individuals. An earlier study from this laboratory (Connell J A et al., *Lancet,* 1990, 335:1366–1369) described anti-HIV antibodies in urine by GACELISA). Gershy-Damet G M et al. *Trans R Soc Trop Med Hyg* 1992, 86:670–671, used these assays successfully for urinary diagnosis of HIV-1 and HIV-2 in Africa, using to unprocessed saliva and urine specimens. They found the assay to be as accurate as conventional EIAs on serum tested under similar conditions.

Perry K R et al., *J Med Virol* 1992, 38:265–270, detected IgG and IgM antibodies to hepatitis A and hepatitis B core antigens in urine specimens.

As an example of urinary autoantibodies, Ben-Yehuda A et al. (*J Autoimmun,* 1995, 8:279–291) found that urine of patients with active SLE and of MRL-1/1 mice contained antibodies that bind extracellular matrix, primarily the 200 kDa light chain of laminin. The level of the anti-laminin antibodies correlated with disease activity.

Dr. A. Friedman-Kien and his colleagues have examined paired urine and serum samples in a search for antibodies to hepatitis B surface anitgen (HBs), hepatitis B core antigen (HBc), CMV and HIV in paired urine and serum samples from the same HIV-infected individuals (Cao Y et al., 1989, *AIDS. Res. Hum. Retrovir.* 5:311). In all individuals with anti-HIV antibodies in serum, anti-HIV antibodies were found in their urine; no such correlation was observed for HBs and CMV antibodies. The anti-HIV urine antibodies were of the IgG class, and gp160 and gp120 were the most consistently recognized proteins. Based on these observations, a urine based diagnostic assay for HIV-1 was been developed at by these investigators.

In view of the prevalence of TB in the HIV-infected individuals, especially in the developing countries, and the risks and costs involved in collection of blood/serum for serodiagnosis, the present inventors evaluated the urine of TB patients for presence of anti-mycobacterial antibodies. They reasoned that since *M. tuberculosis* infects the mucosal surfaces in the lung, it may induce antibodies in mucosal tissues resulting in the presence of antibodies in the urine. The positive results of these studies are presented below. The ability to use urine as the sample material will make the test extremely attractive to public health officials and to industry.

Citation of the above documents is not intended as an admission that any of the foregoing is pertinent prior art. All statements as to the date or representation as to the contents of these documents is based on the information available to the applicant and does not constitute any admission as to the correctness of the dates or contents of these documents.

SUMMARY OF THE INVENTION

The present inventors have systematically analyzed the reactivity of sera and urine from TB patients with antigens from Mt to delineate the major targets of human antibody responses which occur relatively early in the progression of the infection to disease. They observed that initial immunoadsorption of patient sera with E. coli antigens successfully reduced interference by cross-reactive antibodies, thus allowing a new approach to serological studies. The immunoadsorbed sera allowed identification of a number of antigens of Mt that are recognized by antibodies in a large proportion of patients, and during earlier stages of disease progression. These antigens are therefore useful tools in methods of diagnosing TB. Prominent among these antigens is a high molecular weight secreted protein of 88 kDa or 85 kDa (depending on conditions as will be described below). This protein is termed "the 88 kDa protein".

In addition to its utility for early diagnosis of mycobacterial disease in a subject prior to the development of radiographic or bacteriological evidence of the disease, the present invention also provides for the first time a surrogate marker that can be used in an inexpensive screening method in individuals at heightened risk for developing TB. This utility was discovered by applying the approach described herein to analyze antibody responses of HIV-infected TB patients (HIV/TB) to the secreted antigens of Mt during different stages of disease progression. A majority of the HIV/TB patients had detectable antibodies to the secreted antigens of Mt for months, even years, prior to the clinical manifestation of active tuberculous disease. These patients are termed "HIV/pre-TB". However, compared to the TB patients not infected with HIV (designated "non-HIV/TB"), HIV/TB patients had significantly lower levels of antibodies which showed specificity for a restricted repertoire of Mt antigens. Antibodies to the 88 kDa antigen mentioned above were present in about 75% of the HIV/pre-TB sera patients who eventually developed clinical TB. HIV/TB patients who failed to develop anti-Mt antibodies did not differ in their lymphocyte profiles from those that were antibody-positive. These discoveries led to the invention of a serological surrogate marker for active pre-clinical TB in HIV-infected subjects as well as in any other high risk population. Thus, this invention provides for the first time a method for early detection of Mt infection in immunocompromised subjects. Exploitation of this discovery should make a significant contribution to the early detection of the tubercular disease and will permit a more rapid institution of therapy.

The present invention is directed to a method for the early detection of a mycobacterial disease or infection in a subject, comprising:
(a) before the onset of symptoms identifiable as clinical disease, obtaining a biological fluid sample from the subject; and
(b) assaying the sample for the presence of antibodies specific for one or more early Mt antigens, wherein detection of the antibodies is indicative of the presence of the disease or infection.

The early antigen used above may be in the form of a fraction of the lipoarabinomannan-free culture supernatant of Mt having one of the following groups of characteristics:
(a) a fraction, having a molecular weight range of about 18–45 kDa and including an approximately 42 kDa glycoprotein reactive with anti-MPT32 antibody; or
(b) a fraction having a molecular weight range of about 18–94 kDa and including an 88 kDa protein that is not reactive with mAb IT-42 or IT-57 and is characterized as having the amino acid sequence SEQ ID NO:106.

A preferred embodiment of the above method includes, prior to step (b), the step of removing from the sample antibodies specific for cross-reactive epitopes or antigens between the proteins of Mt and the proteins other bacterial genera, such as by immunoadsorption of the sample with E. coli antigens.

In the above, methods, one or more of the early antigens is preferably a secreted Mt protein or glycoprotein selected from the group consisting of
(a) an 88 kDa protein having a pI of about 5.2 characterized as having the amino acid sequence SEQ ID NO:106, which may be, but is not necessarily, obtained as a secreted protein present in Mt lipoarabinomannan-free culture filtrate;
(b) a protein characterized as Mt antigen 85C;
(c) a protein characterized as Mt antigen MPT51;
(d) a glycoprotein characterized as Mt antigen MPT32;
(e) a 49 kDa protein having a pI of about 5.1 corresponding to a spot identified as Ref. No. 82 in FIGS. 15A–F, FIG. 18, Table 9 or Table 11; and
(f) a mixture of any one or more of (a)–(e).

In one embodiment, the method for the early detection of the presence of a mycobacterial disease or infection in a subject, comprises:
(a) before the onset of symptoms identifiable as clinical disease, obtaining a biological fluid sample, preferably serum, urine or saliva, from the subject
(b) assaying the sample to detect the presence of antibodies specific for one or more early Mt antigens selected from the group consisting of
(i) a Mt 88 kDa secreted protein having a pI of about 5.2, characterized as having the amino acid sequence SEQ ID NO:106;
(ii) a protein characterized as Mt antigen 85C;
(iii) a protein characterized as Mt antigen MPT51; and
(iv) a 49 kDa protein having a pI of about 5.1 corresponding to the spot identified as No. 82 in one or more of FIGS. 15A–F, FIG. 18, Table 9 or Table 11.

In the foregoing methods, the subject is preferably a human. In one embodiment, the subject is preferably a human infected with HIV-1 or at high risk for tuberculosis. A high risk subject includes an HIV infected individuals, an intravenous drug user, a prison inmate, a homeless person, a resident of a slum area or a household contact of a TB patient.

The present invention also includes a method for the early detection of mycobacterial disease or infection in a subject, comprising:
(a) before the onset of symptoms identifiable as clinical disease, obtaining a biological fluid sample from the subject;
(b) optionally, culturing the biological fluid under conditions permitting the growth of mycobacteria and obtaining a culture supernatant or fraction thereof;
(c) assaying the sample of step (a) or the culture supernatant or fraction of step (b) for the presence of an early Mt antigen using an antiserum or mAb specific for the early antigen;
wherein detection of the antigen is indicative of the presence of the disease or infection.

Also provided is a method for the early detection of the presence of a mycobacterial disease or infection in a subject, comprising:
(a) before the onset of symptoms identifiable as clinical disease, obtaining a biological fluid sample from the subject;
(b) assaying the sample for the presence of immune complexes consisting of one or more early Mt antigens complexed with an antibody specific for the antigen, wherein detection of the immune complexes is indicative of the presence of the disease.

The present invention is further directed to an antigenic composition useful for early detection of Mt infection or disease comprising a mixture of two or more early Mt antigens substantially free of other proteins with which the early Mt antigens are natively admixed in a culture of Mt and which other proteins are not early Mt antigens. In a preferred embodiment, of the composition the two or more early antigens are selected from the group consisting of (a) an 88 kDa protein having a pI of about 5.2, characterized as having the amino acid sequence SEQ ID NO:106;

(b) a protein characterized as Mt antigen 85C;

(c) a protein characterized as Mt antigen MPT51;

(d) a glycoprotein characterized as Mt antigen MPT32; and (e) a 49 kDa protein having a pI of about 5.1 corresponding to a spot identified as Ref. No. 82 in FIGS. 15A–F, FIG. 18, Table 9 or Table 11.

The foregoing composition may be further supplemented with one or more of the following Mt antigenic proteins:

(i) a 28 kDa antigen corresponding to the spot identified as Ref. No. 77 in FIGS. 15A–F, FIG. 18, Table 9 or Table 11;

(ii) a 29/30 kDa antigen corresponding to the spot identified as Ref. No. 69 or 59 in FIG. 15A–F, FIG. 18, Table 9 or Table 11;

(iii) a 31 kDa antigen corresponding to the spot identified as Ref. No. 103 in FIGS. 15A–F, FIG. 18, Table 9 or Table 11;

(iv) a 35 kDa antigen corresponding to the spot identified as Ref. No. 66 in FIGS. 15A–F, FIG. 18, Table 9 or Table 11 and reactive with mAb IT-23;

(v) a 42 kDa antigen corresponding to the spot identified as Ref. No. 68 or 80 in FIG. 15A–F, FIG. 18, Table 9 or Table 11;

(vi) a 48 kDa antigen corresponding to the spot identified as Ref. No. 24 in FIGS. 15A–F, FIG. 18, Table 9 or Table 11; and (vii) a 104 kDa antigen corresponding to the spot identified as Ref. No. 111 in FIGS. 15A–F, FIG. 18, Table 9 or Table 11.

In the present composition, any one of the early Mt antigens may be a recombinant protein or glycoprotein, preferably produced in a mycobacterial or eukaryotic expression system.

The antigenic protein may comprise either (a) an 88 kDa protein having a pI of about 5.2 characterized as having the amino acid sequence SEQ ID NO:106;

(b) a 49 kDa protein having a pI of about 5.1 corresponding to the spot identified as Ref. No. 82 in FIGS. 15A–F, FIG. 18, Table 9 or Table 11; or (c) a mixture of (a) and (b), wherein the protein, glycoprotein or mixture is substantially free of (i) other early Mt antigens and (ii) other proteins or glycoproteins with which it is natively admixed in a culture of Mt.

The present invention also provides a kit useful for early detection of Mt disease or infection comprising an antigenic composition as described above in combination with reagents necessary for detection of antibodies which bind to the early Mt antigen or antigens. Preferably, in the above kit, the early Mt antigen is a recombinant protein or glycoprotein. The kit may further comprise one or more of the following Mt antigenic proteins listed above as (i)–(vii).

Also provided is a kit useful for early detection of an antibody specific for an early Mt antigen in a subject, comprising (a) an early Mt antigen as described herein; and (b) one or more reagents necessary for detection of antibodies which bind to the early Mt antigen or antigens. The kit may also include at least one mAb specific for an epitope the early antigen.

In another embodiment, this invention is directed to a method for obtaining a desired mAb useful (i) for detecting an early Mt antigen or anti-Mt antibody in a sample or (ii) for isolating an early Mt antigen or epitope, which method comprises:

(a) isolating a Mt early antigen by biochemical purification or by recombinant expression;

(b) using the early antigen of step (a) to generate a collection of monoclonal antibodies each of which is specific for an epitope of the early antigen;

(c) screening the collection of monoclonal antibodies for the desired mAb which competes with
   (i) a patient antiserum or antibody preparation containing an early antibody
   (ii) a preexisting mAb specific for the early antigen for binding to the mycobacterial early antigen and selecting hybridoma cells which produce the competing mAb;

(d) growing the selected hybridoma cells and collecting the desired mAb produced by the cells; thereby obtaining the desired mAb.

The foregoing method is used for obtaining a mAb that is employed in an immunoassay that detects an early mycobacterial antigen or an epitope thereof, which assay comprises incubating the above mAb with a biological fluid sample suspected of containing the protein or epitope and measuring the binding of the mAb to the protein or epitope in the sample. In another embodiment, the immunoassay comprises incubating the mAb obtained as above with a biological fluid sample suspected of containing the early antibody and with a mycobacterial preparation containing an early antigen for which the early antibody is specific, and measuring the ability of the sample to compete with the mAb for binding to the early antigen.

BRIEF DESCRIPTION OF THE DRAWINGS

FIGS. 15B, C and F are digitized images of the 2-D gels of M. tuberculosis H37Rv, Erdman and H37Ra, respectively. Reference numbers of individual protein spots correspond to those listed and described in Table 9. Matched proteins between strains have identical reference numbers.

FIG. 22A shows agarose gel electrophoresis of the DNA from λgt11 (IT-57) before (lane 2) and after digestion with EcoR1 enzyme (lane 3); and plasmid pMD31 DNA containing the katG gene (lane 4) and after digestion with KpnI and XbaI (lane 5). FIG. 22B is a nitrocellulose blot of the gel of FIG. 22A probed with $^{32}$P-labeled insert DNA from the λgt11 (IT-57). The 1 kb DNA ladder is shown in lane 1 and the sizes of the fragments are shown on the right.

In FIG. 24A, lane 1 contains molecular weight markers, lanes 2, 4, and 6 contain the LFCFP and lanes 3, 5 and 7 contain the culture filtrates of the katG-negative strain of M. tuberculosis. Lanes 2 and 3 were probed with mmAb IT-57, lanes 4 and 5 with mAb IT-42 and lanes 6 and 7 with anti-catalase/peroxidase polyclonal sera. FIG. 24B shows a Western blot analysis of 1-D fractionated KatG-deleted M. tuberculosis LFCFP with E. coli absorbed sera. Lanes 1, 6, 12 and 18: molecular weight markers. Lanes 2–5: sera of PPD positive healthy individuals (group I); lanes 7–11: group II; lanes 13–17: group III; lanes 19–23: group IV.

FIG. 26A shows reactivity with untreated F13. FIG. 26B shows reactivity of sera with periodate-treated F13, in which glycosylation is destroyed by oxidation.

FIG. 33 shows the amino acid sequence (SEQ ID NO:106) of the 88 kDa Mt protein along with additional characterizing and background information from the Genbank database.

DESCRIPTION OF THE PREFERRED EMBODIMENTS

Figure 1:
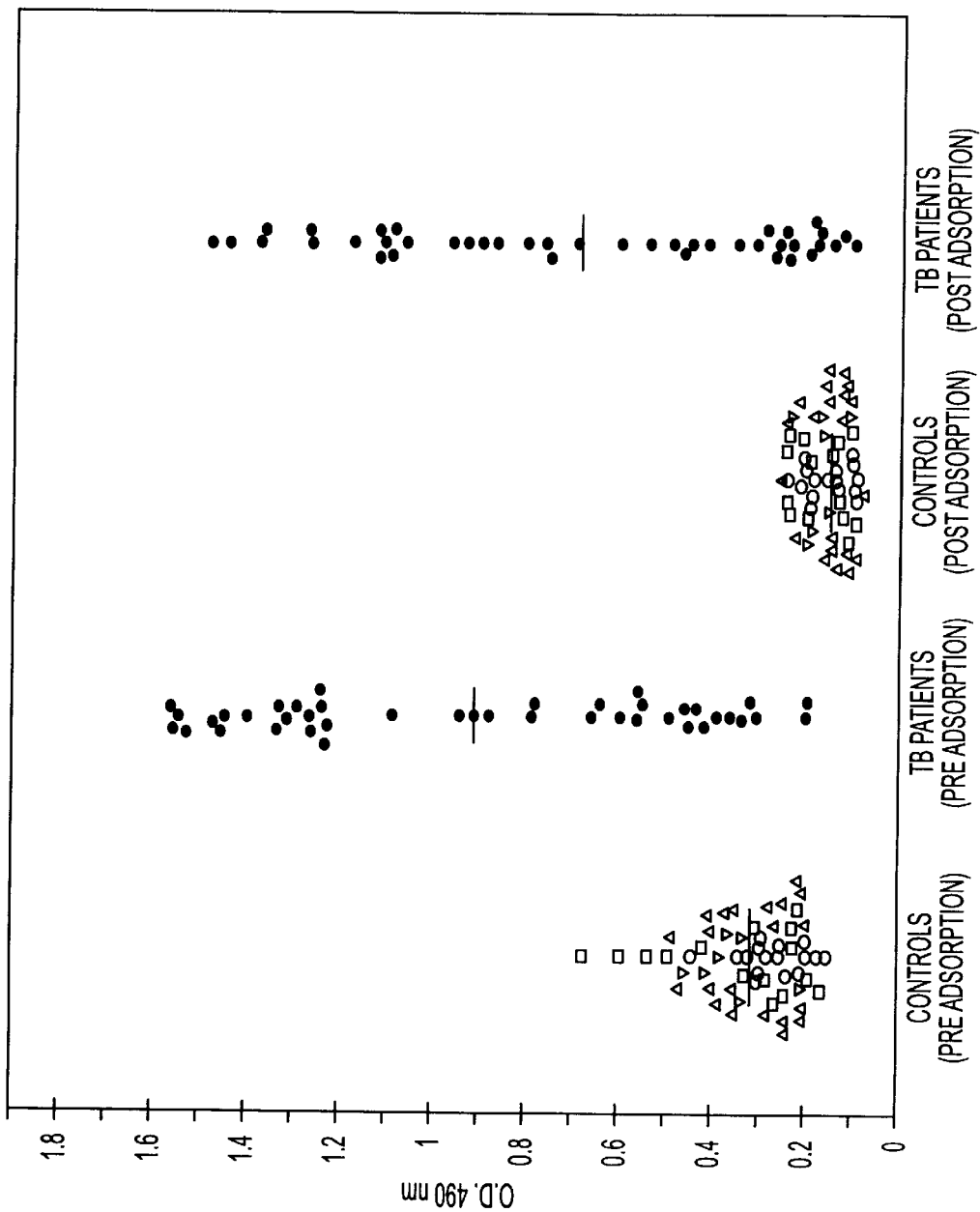
FIG. 1 shows the reactivity of sera from TB$^{neg}$HIV$^{neg}$PPD$^+$ controls(○); TB$^{neg}$HIV$^{neg}$PPD$^{neg}$ controls (▽), TB$^{neg}$, HIV$^+$, asymptomatic controls (Δ); and TB patients (●) with LAM-free culture filtrate proteins (LFCFP) of *M. tuberculosis* H$_{37}$Rv, before and after adsorption with *E. coli* lysate. Values are individuals OD's with the mean shown as a horizontal bar.

In the following description, reference will be made to various methodologies known to those of skill in the art of immunology. Publications and other materials setting forth such known methodologies to which reference is made are incorporated herein by reference in their entireties as though set forth in fall. Standard reference works setting forth the general principles of immunology include Roitt, I., *Essential Immunology*, 6th Ed., Blackwell Scientific Publications, Oxford (1988); Roitt, I. et al., *Immunology*, C. V. Mosby Co., St. Louis, Mo. (1985); Klein, J., Immunology, Blackwell Scientific Publications, Inc., Cambridge, Mass., (1990); Klein, J., *Immunology: The Science of Self-Nonself Discrimination*, John Wiley & Sons, New York, N.Y. (1982)); and Eisen, H. N., (In: *Microbiology*, 3rd Ed. (Davis, B. D., et al., Harper & Row, Philadelphia (1980)); A standard work setting forth details of mAb production and characterization, and immunoassay procedures, is Hartlow, E. et al., *Antibodies: A Laboratory Manual*, Cold Spring Harbor Laboratory Press, Cold Spring Harbor, N.Y., 1988.

The present invention provides a diagnostic immunoassay method to detect and/or quantitate antibodies specific for mycobacterial antigens, in particular, antibodies developing early in the progression of *M. tuberculosis* infection to disease and before clinical manifestations of that disease. On the basis of such an assay, it is possible to detect TB earlier than ever before and to institute appropriate therapy. The best antigen available prior to this invention for serodiagnosis of TB was the 38 kDa secreted protein also known as Ag 78 (see above). However, the present invention permits detection of serological reactivity in subject who lack detectable antibodies to this 38 kDa antigen.

The immunoassay method is based upon the present inventors' discovery that certain Mt antigens induce in humans an earlier response than do other antigens which elicit antibodies only after the disease is already clinically advanced. In HIV-infected subjects with dysfunctional immune systems, antibodies to some of these antigens are detectable long before TB is clinically manifest. Five secreted proteins have been identified as early antigens with diagnostic value. In particular a preferred early antigen is a 88 kDa secreted protein of Mt, preferably enriched or semipurified (at least 50% pure) or highly purified (at least 95% pure, preferably at least 99% pure).

The present method is further based on the inventors' conception of the importance of first removing antibodies specific for cross-reactive antigens (which are not Mt-specific) prior to analyzing the antigenic reactivity and specificity of serum from patients infected with Mt on crude or semipurified antigenic preparations. However, once purified antigens are provided or epitope-specific competitive EIAs are established based on this invention (see, for example, Wilkins, E. et al., 1991, *Eur. J. Clin. Microbiol. Infect. Dis.* 10:559–563), the need for such prior absorption steps should be obviated.

As used herein, the term "early" and "late" in reference to (1) Mt infection or disease, or the subject having the infection or disease, (2) the antibody response to an Mt antigen, (3) an Mt antigen itself or (4) a diagnostic assay, are defined in terms of the stage of development of TB. Early and late (or advanced) TB are defined in the table below.

Thus, a subject with early TB is asymptomatic or, more typically, has one or more "constitutional symptoms" (e.g., fever, cough, weight loss). In early TB, Mt bacilli are too few to be detectable as acid-fast bacilli in smears of sputum or other body fluid, primarily those fluids associated with the lungs (such as bronchial washings, bronchoalveolar lavage, pleural effusion). However, in these subjects, Mt bacilli are present and culturable, i.e., can be grown in culture from the above body fluids. Finally, early TB subjects may have radiographically evident pulmonary lesions which may include infiltration but without cavitation. Any antibody present in such early stages is termed an "early antibody" and any Mt antigen recognized by such antibodies is termed an "early antigen." The fact that an antibody is characterized as "early" does not mean that this antibody is absent in advanced TB. Rather, such antibodies are expected to persist across the progression of early TB to the advanced stage.

| Early TB | 1. Smear of sputum, bronchial washing, bronchoalveoiar lavage or pleural effusion is negative for acid fast bacilli |
| --- | --- |
| | 2. Direct culture of sputum, bronchial washing, bronchoalveolar lavage or pleural effusion is positive for acid fast bacilli |
| | 3. Chest x-ray is normal or shows infiltration in the lungs |

-continued

| | 4. Constitutional symptoms are present (fever, cough, appetite and weight loss) |
| --- | --- |
| Late/Advanced TB | 1. Smear of sputum, bronchial washing, bronchoalveolar lavage or pleural effusion is positive (with possible hemoptysis) |
| | 2. Direct culture of sputum, bronchial washing, bronchoalveolar lavage or pleural effusion is positive |
| | 3. Chest x-ray shows cavitary lesions in the lungs |
| | 4. Constitutional symptoms are present (see above) |

Accordingly, the term "late" or "advanced" is characterized in that the subject has frank clinical disease and more advanced cavitary lesions in the lungs. In late TB, Mt bacilli are not only culturable from smears of sputum and/or the other body fluids noted above, but also present in sufficient numbers to be detectable as acid-fast bacilli in smears of these fluids. Again, "late TB" or "late mycobacterial disease" is used interchangeably with "advanced TB" or "advanced mycobacterial disease." An antibody that first appears after the onset of diagnostic clinical and other characterizing symptoms (including cavity pulmonary lesions) is a late antibody, and an antigen recognized by a late antibody (but not by an early antibody) is a late antigen.

To be useful in accordance with this invention, an early diagnostic assay must permit rapid diagnosis of Mt disease at a stage earlier than that which could have been diagnosed by conventional clinical diagnostic methods, namely, by radiologic examination and bacterial smear and culture or by other laboratory methods available prior to this invention. (Culture positivity is the final confirmatory test but takes two weeks and more)

The present immunoassay typically comprises incubating a biological fluid, preferably serum or urine, from a subject suspected of having TB, in the presence of an Mt antigen-containing reagent which includes one or more Mt early antigens, and detecting the binding of antibodies in the sample to the mycobacterial antigen(s). By the term "biological fluid" is intended any fluid derived from the body of a normal or diseased subject which may contain antibodies, such as blood, serum, plasma, lymph, urine, saliva, sputum, tears, cerebrospinal fluid, bronchioalveolar lavage fluid, pleural fluid, bile, ascites fluid, pus and the like. Also included within the meaning of this term as used herein is a tissue extract, or the culture fluid in which cells or tissue from the subject have been incubated.

Mycobacterial Antigen Compositions

The mycobacterial antigen composition or preparation of the present invention may be a "fraction" of total *M. tuberculosis* secreted proteins based on a selected molecular weight range and reactivity with patient sera. Such a fraction will containing at least one, and possibly two or more, early antigen proteins (such as in the fractions exemplified in Examples I and II). A preferred molecular weight range of proteins/glycoproteins in such a fraction is between about 30 kDa and about 90 kDa. The selection of antigen or antigens to be included in the composition is based on reactivity of TB patient sera with the antigen (or with the fraction containing the antigen).

The antigen composition may be a substantially purified or recombinantly produced preparation of one or more *M. tuberculosis* proteins. Alternatively, the antigen composition may be a partially purified or substantially pure preparation containing one or more *M. tuberculosis* epitopes which are capable of being bound by antibodies of a subject with TB.

Such epitopes may be in the form of peptide fragments of the early antigen proteins or other "functional derivatives" of *M. tuberculosis* proteins as described below.

By "functional derivative" is meant a "fragment," "variant," "analogue," or "chemical derivative" of an early antigen protein, which terms are defined below. A functional derivative retains at least a portion of the function of the protein which permits its utility in accordance with the present invention—primarily the capacity to bind to an early antibody. A "fragment" refers to any subset of the molecule, that is, a shorter peptide. A "variant" refers to a molecule substantially similar to either the entire protein or fragment thereof. A variant peptide may be conveniently prepared by direct chemical synthesis or by recombinant means. An "analogue" of the protein or peptide refers to a non-natural molecule substantially similar to either the entire molecule or a fragment thereof. A "chemical derivative" of the antigenic protein or peptide contains additional chemical moieties not normally part of the peptide. Covalent modifications of the peptide are included within the scope of this invention. Such modifications may be introduced into the molecule by reacting targeted amino acid residues of the peptide with an organic derivatizing agent that is capable of reacting with selected side chains or terminal residues.

Four proteins or glycoproteins, identified in culture filtrates of Mt, are the preferred early Mt antigens of the present invention. Thus, athough these proteins are probably secreted proteins, they may also be present in cellular prepartions of the bacilli. Thus, these early antigens are not intended to be limited to the secreted protein form. The proteins are characterized as follows:

(1) 88 kDa Protein

This protein is an Mt secreted protein having an apparent molecular mass of about 85 kDa or about 88 kDa (depending in which of two different laboratories of the present inventors the determination is made). This protein is further characterized by an isoelectric point of about pH 5.2. This protein was originally thought to react with mAbs IT-42 and IT-57, but has been distinguished from the katG protein of similar size which is reactive with those mAbs. The 88 kDa protein is a major antigenic component of Fraction 15 (Example I) and Fraction 14 (Example II). This protein corresponds to the protein spot designated Ref. No. 124 in FIGS. 15A–F, FIG. 18, Table 9 or Table 11. Hence, despite a small apparent difference in molecular mass, a single protein is intended (although different isoforms may be found to exist). This protein is referred to herein as the 88 kDa protein, to help distinguish it from the three Ag85 proteins (85AB and C), the naming of which bears no relation to molecular mass.

(2) Antigen 85C

This is an Mt secreted protein having an apparent molecular weight of about 31 kDa and an isoelectric point of about pH 5.17. This protein is reactive with mAb IT-49 and has also been designated MPT45. Ag85C corresponds to the protein spot designated Ref. No. 119 in FIGS. 15A–F, FIG. 18, Table 9 or Table 11.

(3) MPT51

This Mt secreted protein has an apparent molecular mass of about 27 kDa and an isoelectric point of about 5.91. It is reactive with mAb IT-52. This protein corresponds to the protein spot designated Ref. No. 170 in FIGS. 15A–F, FIG. 18, Table 9 or Table 11.

(4) MPT32

This glycoprotein has an apparent molecular mass (as a doublet peak) of 38 and 42 kDa (42/45 kDa according to Espitia et al (supra)) and an isoelectric point of about pH 4.51. It is reactive with a polyclonal anti-MPT 32 antiserum. This protein is a major antigenic component of Fraction 13 (see Examples). MPT32 corresponds to the protein spot designated Ref. No. 14 in FIGS. 15A–F, FIG. 18, Table 9 or Table 11.

One additional protein, termed the "49 kDa protein," has an apparent molecular mass of about 49 kDa and an isoelectric point of about pH 5.1. This protein reacts with mAb IT-58 and corresponds to a spot identified as Ref. No. 82 in FIGS. 15A–F, FIG. 18, Table 9 or Table 11.

In a preferred embodiment, the mycobacterial antigen composition is brought in contact with, and allowed to bind to, a solid support or carrier, such as nitrocellulose or polystyrene, allowing the antigen composition to adsorb and become immobilized to the solid support. This immobilized antigen is then allowed to interact with the biological fluid sample which is being tested for the presence of anti-Mt antibodies, such that any antibodies in the sample will bind to the immobilized antigen. The support to which the antibody is now bound may then be washed with suitable buffers after which a detectably labeled binding partner for the antibody is introduced. The binding partner binds to the immobilized antibody. Detection of the label is a measure of the immobilized antibody.

A preferred binding partner for this assay is an anti-immunoglobulin antibody ("second antibody") produced in a different species. Thus to detect a human antibody, a detectably labeled goat anti-human immunoglobulin "second" antibody may be used. The solid phase support may then be washed with the buffer a second time to remove unbound antibody. The amount of bound label on the solid support may then be detected by conventional means appropriate to the type of label used (see below).

Such a "second antibody" may be specific for epitopes characteristic of a particular human immunoglobulin isotype, for example IgM, $IgG_1$, $IgG_{2a}$, IgA and the like, thus permitting identification of the isotype or isotypes of antibodies in the sample which are specific for the mycobacterial antigen. Alternatively, the second antibody may be specific for an idiotype of the ant-Mt antibody of the sample.

As alternative binding partners for detection of the sample antibody, other known binding partners for human immunoglobulins may be used. Examples are the staphylococcal immunoglobulin binding proteins, the best know of which is protein A. Also intended is staphylococcal protein G, or a recombinant fusion protein between protein A and protein G. Protein G of group G and group C streptococci binds to the Fc portion of Ig molecules as well as to IgG Fab fragment at the $V^H$3 domain. Protein C of *Peptococcus magnus* binds to the Fab region of the immunoglobulin molecule. Any other microbial immunoglobulin binding proteins, for example from Streptococci, are also intended (for example, Langone, J. J., *Adv. Immunol.* 32:157 (1982)).

In another embodiment of this invention, a biological fluid suspected of containing antibodies specific for a Mt antigen may be brought into contact with a solid support or carrier which is capable of immobilizing soluble proteins. The support may then be washed with suitable buffers followed by treatment with a mycobacterial antigen reagent, which may be detectably labeled. Bound antigen is then measured by measuring the immobilized detectable label. If the mycobacterial antigen reagent is not directly detectably labeled, a second reagent comprising a detectably labeled binding partner for the Mt antigen, generally a second anti-Mt antibody such as a murine mAb, is allowed to bind to any immobilized antigen. The solid phase support may then be washed with buffer a second time to remove unbound antibody. The amount of bound label on said solid support may then be detected by conventional means.

By "solid phase support" is intended any support capable of binding a proteinaceous antigen or antibody molecules or other binding partners according to the present invention. Well-known supports, or carriers, include glass, polystyrene, polypropylene, polyethylene, polyvinylidene difluoride, dextran, nylon, magnetic beads, amylases, natural and modified celluloses, polyacrylamides, agaroses, and magnetite. The nature of the carrier can be either soluble to some extent or insoluble for the purposes of the present invention. The support material may have virtually any possible structural configuration so long as it is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads, 96-well polystyrene microplates and test strips, all well-known in the art. Those skilled in the art will know many other suitable carriers for binding antibody or antigen, or will be able to ascertain the same by use of routine experimentation.

Using any of the assays described herein, those skilled in the art will be able to determine operative and optimal assay conditions for each determination by employing routine experimentation. Furthermore, other steps as washing, stirring, shaking, filtering and the like may be added to the assays as is customary or necessary for the particular situation.

A preferred type of immunoassay to detect an antibody specific for a mycobacterial antigen according to the present invention is an enzyme-linked immunosorbent assay (ELISA) or more generically termed an enzyme immunoassay (EIA). In such assays, a detectable label bound to either an antibody-binding or antigen-binding reagent is an enzyme. When exposed to its substrate, this enzyme will react in such a manner as to produce a chemical moiety which can be detected, for example, by spectrophotometric, fluorometric or visual means. Enzymes which can be used to detectably label the reagents useful in the present invention include, but are not limited to, horseradish peroxidase, alkaline phosphatase, glucose oxidase, β-galactosidase, ribonuclease, urease, catalase, malate dehydrogenase, staphylococcal nuclease, asparaginase, Δ-5-steroid isomerase, yeast alcohol dehydrogenase, α-glycerophosphate dehydrogenase, triose phosphate isomerase, glucose-6-phosphate dehydrogenase, glucoamylase and acetylcholinesterase. For descriptions of EIA procedures, see Voller, A. et al., J. Clin. Pathol. 31:507–520 (1978); Butler, J. E., Meth. Enzymol 73:482–523 (1981); Maggio, E. (ed.), Enzyme Immunoassay, CRC Press, Boca Raton, 1980; Butler, J. E., In: Structure of Antigens, Vol. 1 (Van Regenmortel, M., CRC Press, Boca Raton, 1992, pp. 209–259; Butler, J. E., In: van Oss, C. J. et al., (eds), Immunochemistry, Marcel Dekker, Inc., New York, 1994, pp. 759–803; Butler, J. E. (ed.), Immunochemistry of Solid-Phase Immunoassay, CRC Press, Boca Raton, 1991)

In another embodiment, the detectable label may be a radiolabel, and the assay termed a radioimmunoassay (RIA), as is well known in the art. See, for example, Yalow, R. et al., Nature 184:1648 (1959); Work, T. S., et al., Laboratory Techniques and Biochemistry in Molecular Biology, North Holland Publishing Company, NY, 1978, incorporated by reference herein. The radioisotope can be detected by a gamma counter, a scintillation counter or by autoradiography. Isotopes which are particularly useful for the purpose of the present invention are $^{125}$I, $^{131}$I, $^{35}$S, $^3$H and $^{14}$C.

It is also possible to label the antigen or antibody reagents with a fluorophore. When the fluorescently labeled antibody is exposed to light of the proper wave length, its presence can then be detected due to fluorescence of the fluorophore. Among the most commonly used fluorophores are fluorescein isothiocyanate, rhodamine, phycoerythrin, phycocyanin, allophycocyanin, o-phthaldehyde, fluorescamine or fluorescence-emitting metals such as $^{152}$Eu or other lanthanides. These metals are attached to antibodies using metal chelators.

The antigen or antibody reagents useful in the present invention also can be detectably labeled by coupling to a chemiluminescent compound. The presence of a chemiluminescent-tagged antibody or antigen is then determined by detecting the luminescence that arises during the course of a chemical reaction. Examples of usefuil chemiluminescent labeling compounds are luminol, isoluminol, theromatic acridinium ester, imidazole, acridinium salt and oxalate ester. Likewise, a bioluminescent compound such as a bioluminescent protein may be used to label the antigen or antibody reagent usefuil in the present invention. Binding is measured by detecting the luminescence. Usefuil bioluminescent compounds include luciferin, luciferase and aequorin.

Detection of the detectably labeled reagent according to the present invention may be accomplished by a scintillation counter, for example, if the detectable label is a radioactive gamma emitter, or by a fluorometer, for example, if the label is a fluorophore. In the case of an enzyme label, the detection is accomplished by colorimetry to measure the colored product produced by conversion of a chromogenic substrate by the enzyme. Detection may also be accomplished by visual comparison of the colored product of the enzymatic reaction in comparison with appropriate standards or controls.

The immunoassay of this invention may be a "two-site" or "sandwich" assay. The fluid containing the antibody being assayed is allowed to contact a solid support. After addition of the mycobacterial antigen(s), a quantity of detectably labeled soluble antibody is added to permit detection and/or quantitation of the ternary complex formed between solid-phase antibody, antigen, and labeled antibody. Sandwich assays are described by Wide, Radioimmune Assay Method, Kirkham et al., Eds., E. & S. Livingstone, Edinburgh, 1970, pp 199–206.

Alternatives to the RIA and EIA are various types of agglutination assays, both direct and indirect, which are well known in the art. In these assays, the agglutination of particles containing the antigen (either naturally or by chemical coupling) indicates the presence or absence of the corresponding antibody. Any of a variety of particles, including latex, charcoal, kaolinite, or bentonite, as well as microbial cells or red blood cells, may be used as agglutinable carriers (Mochida, U.S. Pat. No. 4,308,026; Gupta et al., J. Immunol. Meth. 80:177–187 (1985); Castelan et al., J. Clin. Pathol. 21:638 (1968); Singer et al., Amer. J. Med. (December 1956, 888; Molinaro, U.S. Pat. No. 4,130,634). Traditional particle agglutination or hemagglutination assays are generally faster, but much less sensitive than RIA or EIA. However, agglutination assays have advantages under field conditions and in less developed countries.

In addition to detection of antibodies, the present invention provides methods to detect and enumerate cells secreting an antibody specific for a mycobacterial antigen. Thus, for example, any of a number of plaque or spot assays may be used wherein a sample containing lymphocytes, such as peripheral blood lymphocytes, is mixed with a reagent containing the antigen of interest. As the antibody secreting cells of the sample secrete their antibodies, the antibodies react with the antigen, and the reaction is visualized in such a way that the number of antibody secreting cells (or plaque forming cells) may be determined. The antigen may be coupled to indicator particles, such as erythrocytes, preferably sheep erythrocytes, arranged in a layer. As antibodies are secreted from a single cell, they attach to the surrounding antigen-bearing erythrocytes. By adding complement components, lysis of the erythrocytes to which the antibodies have attached is achieved, resulting in a "hole" or "plaque" in the erythrocyte layer. Each plaque corresponds to a single antibody-secreting cell. In a different embodiment, the sample containing antibody-secreting cells is added to a surface coated with an antigen-bearing reagent, for example, a mycobacterial antigen alone or conjugated to bovine serum albumin, attached to polystyrene. After the cells are allowed to secrete the antibody which binds to the immobilized antigen, the cells are gently washed away. The presence of a colored "spot" of bound antibody, surrounding the site where the cell had been, can be revealed using modified EIA or other staining methods well-known in the art. (See, for example, Sedgwick, J. D. et al., J. Immunol. Meth. 57:301–309 (1983); Czerkinsky, C. C. et al., J. Immunol. Meth. 65:109–121 (1983); Logtenberg, T. et al., Immunol. Lett. 9:343–347 (1985); Walker, A. G. et al., J. Immunol. Meth. 104:281–283 (1987).

The present invention is also directed to a kit or reagent system useful for practicing the methods described herein. Such a kit will contain a reagent combination comprising the essential elements required to conduct an assay according to the disclosed methods. The reagent system is presented in a commercially packaged form, as a composition or admixture (where the compatibility of the reagents allow), in a test device configuration, or more typically as a test kit. A test kit is a packaged combination of one or more containers, devices, or the like holding the necessary reagents, and usually including written instructions for the performance of assays. The kit may include containers to hold the materials during storage, use or both. The kit of the present invention may include any configurations and compositions for performing the various assay formats described herein.

For example, a kit for determining the presence of anti-Mt early antibodies may contain one or more early Mt antigens, either in immobilizable form or already immobilized to a solid support, and a detectably labeled binding partner capable of recognizing the sample anti-Mt early antibody to be detected, for example. a labeled anti-human Ig or anti-human Fab antibody. A kit for determining the presence of an early Mt antigen may contain an immobilizable or immobilized "capture" antibody which reacts with one epitope of an early Mt antigen, and a detectably labeled second ("detection") antibody which reacts with a different epitope of the Mt antigen than that recognized by the (capture) antibody. Any conventional tag or detectable label may be part of the kit, such as a radioisotope, an enzyme, a chromophore or a fluorophore. The kit may also contain a reagent capable of precipitating immune complexes.

A kit according to the present invention can additionally include ancillary chemicals such as the buffers and components of the solution in which binding of antigen and antibody takes place.

The present invention also provides an approach to the identification, isolation and characterization of early Mt antigens. For example, an adsorbed patient serum or pool of sera containing antibody for one or more antigens can be used in initial stages of antigen preparation and purification, as well as in the process of cloning of a protein antigen. This antiserum can be further adsorbed with an Mt or other mycobacterial preparation to render it functionally monospecific or oligospecific. This "enriched" antiserum can be used along with standard biochemical purification techniques to assay for the presence of the antigen it recognizes in fractions obtained during the purification process. The antiserum can also be used in immobilized form as an immunoadsorbent in affinity purification of the antigen in accordance with standard methods in the art. In addition, the antiserum can be used in an expression cloning method to detect the presence of the antigen in bacterial colonies or phage plaques where the antigen is expressed.

Once an antigen has been purified, for example by using patient early antibodies that have been determined to be specific fore the subject antigen, the antigen can be used to immunize animals to prepare high titer antisera or, preferably, to obtain a mAb specific for that antigen. Such an animal antiserum or mAb can be employed advantageously in place of the patient antiserum or in combination with a test body fluid sample in a competition immunoassay. Thus, the antiserum or mAb can be used for antigen production or purification, or in an immunoassay for detecting the antigen, for example as a binding partner (either the capture antibody or the detection antibody) in a sandwich immunoassay.

The present invention provides an immunoassay for detecting the presence of an Mt early antigen in a body fluid or in a bacterial culture grown from a body fluid of a subject suspected of being infected with Mt. A sensitive immunoassay, such as a direct sandwich EIA or a competitive EIA can detect an Mt protein (early antigen) in picogram amounts. A competitive assay allows detection of specific epitopes of the Mt antigen without the necessity of starting with a purified antigen preparation. Such assays permits detection of Mt in the patient sample at an earlier time than standard bacteriological analysis (i.e., appearance of colonies on agar). This method therefore provides a basis for clinical decisions to initiate therapy after several hours or days if the antigen can be detected in a body fluid. In any case, this is a major advantage over the conventional two to four (or more) weeks commonly needed to grow out Mt organisms from a patient sample. The earlier the stage of the infection, the lower would be the titer of Mt in a given body fluid, and the greater would be the advantage of the present assay over conventional diagnosis. A number of immunoassays for various Mt antigens are known in the art and can serve as the basis for development of assays for the early antigens of the present invention (Wilkins et al., supra; Verbon, 1994, supra; Benjamin, R. G. et al., 1984, *J. Med. Micro.* 18:309–318; Yanez, M. A. et al., 1986, *J. Clin. Microbiol.* 23:822–825; Ma et al., supra; Daniel et al., 1986, 1987, supra; Watt, G. et al., 1988, *J. Infec. Dis.* 158:681–686; Wadee, A. A. et al., 1990, *J. Clin. Microbiol.* 23:2786–2791). For an example of a competition EIA for a Mt antigen, see Jackett et al., supra).

In a preferred sandwich immunoassay, a human antisera (or pool) or a mAb, preferably murine, serving as the capture antibody, is immobilized to a solid phase, preferably a microplate. The test antigen preparation, for example an Mt culture supernatant or extract is added to the immobilized antibody. After appropriate washing, a second "detection" antibody, such as a murine mAb specific for the same antigen or preferably for a different epitope of the same protein, allowed to bind in the presence of a fixed amount of a mAb, preferably of murine origin, specific for the epitope of interest. The detection mAb may be enzyme-conjugated. Alternatively, a second step reagent such as an enzyme-labeled antibody specific for murine immunoglobulin may be used for detection of antigen which has become immobilized.

The present invention permits isolation of an Mt early antigen which is then used to produce one or more epitope-specific mAbs, preferably in mice. Screening of these putative early Mt-specific mAbs is done using known patient sera which have been characterized for their reactivity with the early antigen of interest. The murine mAbs produced in this way are then employed in a highly sensitive epitope-specific competition immunoassay for early detection of TB. Thus, a patient sample is tested for the presence of antibody specific for an early epitope of Mt by its ability to compete with a known mAb for binding to a purified early antigen. For such an assay, the mycobacterial preparation may be less than pure because, under the competitive assay conditions, the mAb provides the requisite specificity for detection of patient antibodies to the epitope of choice (for which the mAb is specific).

In addition to the detection of early Mt antigens or early antibodies, the present invention provides a method to detect immune complexes containing early Mt antigens in a subject using an EIA as described above. Circulating immune complexes have been suggested to be of diagnostic value in TB. (See, for example, Mehta, P. K. et al., 1989, *Med. Microbiol. Immunol.* 178:229–233; Radhakrishnan, V. V. et al., 1992, *J. Med. Microbiol.* 36:128–131). Methods for detection of immune complexes are well-known in the art. Complexes may be dissociated under acid conditions and the resultant antigens and antibodies detected by immunoassay. See, for example, Bollinger, R. C. et al., 1992, *J. Infec. Dis.* 165:913–916. Immune complexes may be precipitated for direct analysis or for dissociation using known methods such as polyethylene glycol precipitation.

Purified Mt early antigens as described herein are preferably produced using recombinant methods. See Example VI. Conventional bacterial expression systems utilize Gram negative bacteria such as *E. coli* or Salmonella species. However, it is believed that such systems are not ideally suited for production of Mt antigens (Burlein, J. E., In: *Tuberculosis: Pathogenesis, Protection and Control*, B. Bloom, ed., Amer. Soc. Microbiol., Washington, D.C., 1994, pp. 239–252). Rather, it is preferred to utilize homologous mycobacterial hosts for recombinant production of early Mt antigenic proteins or glycoproteins. Methods for such manipulation and gene expression are provided in Burlein, supra. Expression in mycobacterial hosts, in particular *M. bovis* (strain BCG) or *M. smegmatis* are well-known in the art. Two examples, one of mycobacterial genes (Rouse, D. A. et al., 1996, *Mol. Microbiol.* 22:583–592) and the other of non mycobacterial genes, such as HIV-1 genes (Winter, N. et al., 1992, *Vaccines* 92, Cold Spring Harbor Press, pp. 373–378) expressed in mycobacterial hosts are cited herein as an example of the state of the art. The foregoing three references are hereby incorporated by reference in their entirety.

Urine-Based Antibody Assay

The present invention also provides a urine based diagnostic method for TB that can be used either as a stand-alone test, or as an adjunct to the serodiagnostic methods described herein. Such a method enables the practitioner to (1) determine the presence of anti-mycobacterial antibodies in urine from TB patients with early disease (non-cavitary, smear negative TB patients) and from HIV-infected TB patients; (2) determine the profile of specific mycobacterial antigens, such as those in the culture filtrate, that are consistently and strongly reactive with the urine antibodies; and (3) obtain the antigens that are recognized by the urine antibodies.

Smear positive (=late) cases constitute only about 50% of the TB cases, and patients with relatively early disease are generally defined as being smear negative. Moreover, as the HIV-epidemic spreads in developing countries, the numbers and proportions of HIV-infected TB patients increases.

Serum and urine samples from non-cavitary and/or smear negative, culture positive TB patients and from HIV-infected TB patients are obtained Cohorts comprising PPD-positive and PPD-negative healthy individuals, non-tuberculous HIV-infected individuals, or close contacts of TB patients can serve as negative controls.

The reactivity of the serum samples with culture filtrate proteins of *M. tuberculosis*, and the purified antigens (MPT 32, Ag 85C and the 88 kDa, as described herein) is preferably determined by ELISA as described herein. All sera are preferably depleted of cross-reactive antibodies prior to use in ELISA.

The following description is of a preferred assay method and approach, and is not intended to be limiting to the particular steps (or their sequence), conditions, reagents and amounts of materials.

Briefly, 200 $\mu$l of *E. coli* lysates (suspended at 500 $\mu$g/ml) are coated onto wells of ELISA plates (Immulon 2, Dynex, Chantilly, Va.) and the wells are blocked with 5% bovine serum albumin (BSA). The serum samples (diluted 1:10 in PBS-Tween-20) are exposed to 8 cycles of absorption against the *E. coli* lysates. The adsorbed sera are then used in the ELISA assays.

Fifty $\mu$l of the individual antigens, suspended at 2 $\mu$g/ml in coating buffer (except for the total culture filtrate proteins which is used at 5 $\mu$g/ml), are allowed to bind overnight to wells of ELISA plates. After 3 washes with PBS (phosphate buffered saline), the wells are blocked with 7.5% FBS (fetal bovine serum, Hyclone, Logan, Utah) and 2.5% BSA in PBS for 2.5 hr at 37° C. Fifty ul of each serum sample are added per well at predetermined optimal dilutions (1:1000 for the culture filtrate proteins, 1:50 for Ag 85C, 1:150 for the MPT32, and 1:200 for the 88 kDa antigen). The antigen-antibody binding is allowed to proceed for 90 min at 37° C. The plates are washed 6 times with PBS-Tween 20 (0.05%) and 50 $\mu$l/well of alkaline phosphatase-conjugated goat anti-human IgG (Zymed, Calif.), diluted 1:2000 in PBS/Tween 20 is added. After 60 min the plates are washed 6 times with Tris buffered saline (50 mM Tris, 150 mM NaCl) and the Gibco BRL Amplification System (Life Technologies, Gaithersburg, Md.) used for development of color. The absorbance is read at 490 nm after stopping the reaction with 50 $\mu$l of 0.3M $H_2SO_4$. The cutoff in all ELISA assays is determined by using mean absorbance (=Optical Density O.D.)+3 standard deviations (SD) of the negative control group comprising PPD positive and PPD negative healthy individuals.

The reactivity of the urine samples with the various antigens is determined initially with undiluted urine samples as described above. For the urine ELISA, results obtained by the present inventors (see Example IX) showed that the optimal concentration of the culture filtrate protein preparation is 125 $\mu$l/well of 4 $\mu$g/ml suspension, and for MPT 32 is 125 $\mu$l/well of 2 $\mu$g/ml. Also, the urine is left overnight in the antigen coated wells. However, if urine antibody titers of smear-negative and HIV-infected patients are lower than those observed in smear positive patients, it may be necessary to first concentrate the urine samples. For concentration, Amicon concentrators with a molecular weight cut off of 30 kDa is preferred. Concentrated urine samples are evaluated for the presence of antibodies to the above mentioned antigens. Optimal conditions for these assays are determined readily. The sensitivity and specificity of antibody detection by use of one or more of the antigens, with both urine and serum samples is also readily determined.

Investigations described in Example IX, with the ELISA and 1D SDS-PAGE fractionated culture filtrate proteins suggested that the urine antibodies are directed against the same antigens that are recognized by the serum antibodies (FIGS. 30 and 31) although, the urine antibody titers are lower. A 2-D map of the culture filtrate proteins has been prepared on which several proteins have been identified on the basis of their reactivity with different anti-mycobacterial monoclonal antibodies, or peptide sequencing (as described herein; see also Sonnenberg, M. G. et al., 1997, *Infect. Immun.* 65:4515)

Based on this map, the present inventors generated a 2-D map of the antigens that are recognized by the early serum antibodies (from smear-negative patients), antibodies from advanced, smear-positive HIV-uninfected TB patients, and from HIV-infected TB patients (described in the Examples). Screening permits the determination of whether additional antigens besides the MPT 32, Ag 85C and the 88 kDa protein are to be included in the assay for its optimization. It is preferred to determine if the anti-MPT 51 antibodies are well represented in the urine since this protein is highly recognized by serum antibodies during both early and late stages of TB, and its identity and sequence are known.

Culture filtrate antigens of *M. tuberculosis* are fractionated on 2-D gels and transferred to obtain 2-D blots as described below. Briefly, 70 μg of culture filtrate proteins are resuspended in 30 μl of isoelectric focusing sample buffer (e.g., 9M urea, 2% Nonidet P-40, 5% β-mercaptoethanol, and 5% Pharmalytes™, pH 3–10; Pharmalytes™ are co-polymers glycine, glycylglycine, amines and epichlorohydrin. For the present invention, two different Pharmalytes™ with different pH ranges in are preferably used in the isoelectric focusing step of the 2-D gel analysis (pH 3–10 and pH 4–6.5). The Phamacia catalog numbers for these two Pharmalytes™ are 17-0456-01 and 17-0452-01, respectively. The above samples are incubated for 3 hrs at 20° C. A 25 μl aliquot of this preparation is applied to a 6% polyacrylamide IEF tube gel containing 5% Pharmalytes™ pH 3–10 and 4–6.5 at a 1:4 ratio and focused for 3 hrs at 1 kV. After focusing, the tube gels are soaked in sample transfer buffer for 30 min and then electrophoresed in the second dimension by using a 15% SDS-polyacrylamide gel. This is carried out at 20 mA per gel for 0.3 hrs followed by 30 mA per gel for 1.8 hrs. The separated proteins are then transferred for subsequent immunoblotting. The 2-D western blots are washed with PBS, and blocked for 2–2.5 hr. with 5% BSA. After washing the blots again, they are exposed to the individual urine samples (undiluted, or concentrated) overnight with shaking. After subsequent washing with PBS-Tween, the blots are exposed to alkaline-phosphtase conjugatedanti-human IgG, and then to the appropriate substrate. The antigens that are reactive with the urine samples are identified on the basis of the 2-D maps already generated. The antigens that are recognized by urine antibodies from smear negative, non-cavitary (=early) TB patients, smear positive (=late) TB patients, as well as HIV-infected TB patients are thus delineated.

Antigens that are strongly recognized by the urine antibodies, as well as by the serum antibodies, are candidates for inclusion in the preferred diagnostic assay. One preferred antigen is MPT 51. The gene encoding this protein is cloned to obtain expression.

As described herein, the culture filtrate preparation contains>100 different proteins (205 protein spots), and most of the proteins in the 49–76 kDa range are expressed in low abundance in the culture medium (Sonnenberg et al., supra). This may be a result of growing *M. tuberculosis* is in minimal medium to obtain these proteins, to avoid difficulties associated with the proteins of enriched media (BSA, casein digests, etc.). If the immunoreactive protein is well-expressed in the culture filtrate, and reasonably isolated on the gel, it can be excised from the PVDF blot and sequenced. Since the entire genomic sequence of *M. tuberculosis* is known, the peptide sequence is used to identify the protein with complete precision.

The nucleotide sequence of the gene encoding that protein then becomes the basis for PCR amplification of the relevant DNA from genomic DNA, followed by cloning into an expression vector. Since many of the culture filtrate proteins are present in small quantities, an alternative, possibly more reliable, approach would utilize the urine antibodies to immunoscreen an expression library of *M. tuberculosis* to obtain the gene(s) encoding the relevant protein(s).

These approaches may be used, for example, to clone the MPT 51 gene or to identify the immunoreactive proteins in the 49–76 kDa region. For expression of MPT 51, the shuttle vector pVV16 is preferred; this vector has an *E. coli* origin of replication, the mycobacterial pAL5000 origin of replication, a gene for hygromycin resistance and the hsp60 promoter. It has been modified to encode six His residues at the C terminus. This vector can be used for expression in *E. coli* or in *M. smegmatis*. Since mycobacterial proteins expressed in *E. coli* host often show poorer immunological reactivity than the same proteins expressed in the mycobacterial host, it would be preferred to express the antigen in *M. smegmatis*. The methods for expression of genes in mycobacterial hosts are well described (Gaora, P O et al., 1997, *Med. Principles Pract.* 6:91).

Briefly, for cloning of the specific gene into the expression vector, PCR amplification of the target gene using primers that contain restriction sites to generate in-frame fusions is performed. The PCR product is purified, and digested with the appropriate restriction enzymes and purified again. The vector DNA is cut with the appropriate restriction enzymes and purified. The PCR product and the vector are ligated, electroporated into DH5α, and grown in the presence of hygromycin overnight. Several antibiotic-resistant colonies are grown in a small volume of medium, and the plasmid DNA isolated by miniprep. The size of the insert is checked in these colonies. Inserts from one or more colonies are sequenced.

For electroporation into *M. smegmatis*, the bacteria are grown shaking in 7H9 medium till they reach an absorbance of 0.8–1.0. The bacteria are harvested, washed twice with ice cold water, once with ice-cold 10% glycerol and suspended in the same. An aliquot of the cells are electroporated with the plasmid DNA from the colony whose insert was sequenced. The electroporated cells are grown for 3–4 hrs in 7H9, and plated on antibiotic containing plates. Several resistant colonies are grown in minimal media for 48–72 hrs. The *M. smegmatis* cell pellets are sonicated, the lysates fractionated by SDS-PAGE and the presence of the immunoreactive protein confirmed by reactivity with the antibody-containing urine samples. Colonies which express the desired protein are expanded, and the His-tagged recombinant protein ispurified using of commercially available Nickel-agarose columns (Qiagen).

The reactivity of the recombinant protein with the entire cohort of urine samples is evaluated by ELISA as described herein. Combinations of antigens that provide the best sensitivity and specificity are delineated.

To produce one or more of the proteins in the 49–67 kDa range, an expression library of *M. tuberculosis* genomic DNA is screened with the antibody-positive urine samples. A pool of TB patient urine samples (which show strong reactivity on western blots with culture filtrate proteins of *M. tuberculosis*) from 10–15 TB patients is adsorbed against *E. coli* lysate, and used at an appropriate dilution to screen the library.

Briefly, *E. coli* Y1090, infected with appropriate plaque forming units of the phage from the library are plated in top agar on LB plates. After 2.5 hrs at 42° C., Isopropyl β-D thiogalactoside (IPTG) saturated nitrocellulose filters are overlaid on the top of the plates for 2.5 hrs at 37° C. The filters are removed, washed extensively, and exposed to the pooled urine overnight. After washing again, the filters are exposed to 1:1000 dilution of Alkaline Phosphatase conjugated anti-human IgG, followed by BCIP-NBT substrate. The positive plaques (recombinant phages) are located on the original plates, excised and re-screened till purified.

The screening of the library by the urine antibodies can be expected to identify several proteins. To identify the clone(s) that expresses the antigen(s) which is recognized by antibodies from a large proportion of patients, the cloned phages are used to establish lysogens in *E. coli* Y1089. Single colonies from lysogens are grown in LB medium at 32° C. till an absorbance (at 600 nm) of 0.5 is obtained. The lysogens are induced to express the recombinant proteins by raising the temperature to 45° C. and addition of IPTG (10 mM). The cultures are grown for additional 1.5 hrs at 37° C. to allow accumulation of the recombinant proteins, and the bacterial pellets are obtained. The pellets are sonicated in small volume of PBS and the lysates fractionated on 10% SDS-PA gels and electroblotted onto nitrocellulose membranes. The blots are probed with individual urine samples from 20–25 TB patients, and clones coding for strongly immuno-reactive proteins recognized by all or a vast majority of the urine samples are identified. Lysates from *E. coli* Y1089 alone or Y1089 lysogenized with lambda gt11 vector are used as controls.

DNA from the recombinant clones encoding strongly immunoreactive proteins is isolated by the commercial Wizard Lambda Preps DNA Purification system (Promega), digested with EcoR1 and the insert obtained. The insert DNA from the clone(s) is subcloned into pGEMEX-1 vector (Promega) whose reading frame at the EcoR1 cloning site is identical to lambda gt11. Competent *E. coli* JM 109 cells are transformed with the recombinant plasmid (pGEMEX plus insert from the clone(s)). Plasmid DNA is isolated using Wizard Plus Minipreps (Promega), and used for automated sequencing with primers from SP6 and T3 promoter specific primers flanking the multiple cloning site in the pGEMEX-1 followed by 'primer-walking'. The nucleotide sequence is used in similarity searches against the *M. tuberculosis* genomic sequence to identify the protein and to obtain the sequence of the whole gene.

Once the protein has been identified and the sequence of the gene is known, cloning it for expression is done as was described above for the exemplary cloning of the MPT 51 gene.

To summarize, a combination of the antigens already defined by serological studies, and the new antigens identified and produced as above, will form the basis of a sensitive diagnostic test for TB. If the sensitivity of antibody detection in urine samples is adequate, blood is no longer needed. If not, the combined serum+urine test provides a very sensitive diagnostic test. Use of the correct, well defined antigens on inexpensive formats (dip stick or flow through cassettes) can be the basis of an inexpensive, rapid diagnostic test for TB.

Vaccines

The foregoing disclosure and the Examples below prove that human subjects infected with Mt indeed do make antibodies to the early antigens of this invention. Thus the antigens are available to the immune system and are immunogenic. Hence, the vaccine compositions and methods are designed to augment this immunity, and preferably, to induce it a stage wherein the bacterial infection can be prevented or curtailed. The vaccine compositions are particularly useful in preventing Mt infection in subjects at high risk for such an infection, as discussed above. The vaccine compositions and methods are also applicable to veterinary uses.

Thus, this invention includes a vaccine composition for immunizing a subject against Mt infection. An Mt early antigen preferably one of the four described herein in more detail, is prepared as the active ingredient in a vaccine composition. These four proteins are (a) the 88 kDa protein having a pI of about 5.2 and SEQ ID NO:106; (b) the protein characterized as *M. tuberculosis* antigen 85C; (c) the protein characterized as *M. tuberculosis* antigen MPT51; and (d) the glycoprotein characterized as *M. tuberculosis* antigen MPT32. The vaccine may also comprises one or more of the proteins described herein, peptides thereof or functional derivatives as described, or DNA encoding the protein, and a pharmaceutically acceptable vehicle or carrier. In one embodiment, the vaccine comprises a fusion protein which includes an Mt early antigen. The vaccine composition may further comprise an adjuvant or other immune stimulating agent. For use in vaccines, the Mt early antigen protein or epitope-bearing peptide thereof is preferably produced recombinantly, preferably in prokaryotic cells.

Full length proteins or longer epitope-bearing fragments of the Mt early antigen proteins are preferred immunogens, in particular, those reactive with early antibodies. If a shorter epitope-bearing fragment, for example containing 20 amino acids or less, is the active ingredient of the vaccine, it is advantageous to couple the peptide to an immunogenic carrier to enhance its immunogenicity. Such coupling techniques are well known in the art, and include standard chemical coupling techniques using linker moieties such as those available from Pierce Chemical Company, Rockford, Ill. Suitable carriers are proteins such as keyhole limpet hemocyanin (KLH), *E. coli* pilin protein k99, BSA, or rotavirus VP6 protein.

Another embodiment is a fusion protein which comprise the Mt early antigen protein or epitope-bearing peptide region fused linearly to an additional amino acid sequence. Because of the ease with which recombinant materials can be manipulated, multiple copies a selected epitope-bearing region may be included in a single fusion protein molecule. Alternatively, several different epitope-bearing regions can be "mixed and matched" in a single fusion protein.

The active ingredient such, preferably a recombinant product, is preferably administered as a protein or peptide vaccine. In another embodiment, the vaccine is in the form of a strain of bacteria (preferably a known "vaccine strain") which has been genetically transformed to express the protein or epitope-bearing peptide. Some known vaccine strains of Salmonella are described below. *Salmonella dublin* live vaccine strain SL5928 aro A148 fliC(i)::Tn10 and *S. typhimurium* LB5000 hsdSB121 leu-3121 (Newton S. M. et al., *Science* 1989, 244:70.

A Salmonella strain expressing the Mt protein or fragment of this invention may be constructed using known methods.

Thus, a plasmid encoding the protein or peptide. The plasmid may first be selected in an appropriate host, e.g., *E. coli* strain MC1061. The purified plasmid is then introduced into *S. typhimurium* strain LB5000 so that the plasmid DNA is be properly modified for introduction into Salmonella vaccine strains. Plasmid DNA isolated from LB5000 is introduced into, e.g., *S. dublin* strain SL5928 by electroporation. Expression of the Mt protein or fragment encoded by the plasmid in SL5928 can be verified by Western blots of bacterial lysates and antibodies specific for the relevant antigen or epitope.

The active ingredient, or mixture of active ingredients, in protein or peptide vaccine composition is formulated conventionally using methods well-known for formulation of such vaccines. The active ingredient is generally dissolved or suspended in an acceptable carrier such as ph Antizens The antigen preparations were total cellular sonicate (CS), total culture filtrate (CF), lipoarabinomannan (LAM), LAM-free culture filtrate proteins (LFCFP), whole cell walls (CW), SDS-soluble cell wall proteins (SCWP), and cell wall core (CWC), all isolated from *M. tuberculosis* $H_{37}Rv$.

CS was obtained from *M. tuberculosis* grown in Middlebrook 7H9 broth (Difco Laboratories, Detroit, Mich.) for 2–3 weeks. The bacilli were harvested by centrifugation at 1000 rpm for 30 min and the pellet resuspended in phosphate buffered saline (PBS) containing PMSF, EDTA and DTT at a final concentration of 1 mM each. The suspension was frozen in liquid nitrogen and thawed (several times) to weaken the cell walls, following which the suspension was sonicated for 20 min at 4° C. The sonicate was centrifuged for 10 min at 10,000 rpm and the supernatant collected.

To obtain the remaining antigens, *M. tuberculosis* was grown to mid-logarithmic phase (14 days) in glycerol-alanine-salts medium. The cells were removed by filtration through a 0.22 $\mu$m membrane, and the culture supernatant was concentrated by ultrafiltration using an Amicon apparatus (Beverly, Mass.) with a 10,000 MW cut-off membrane. The concentrated material (CF) was dialyzed against 100 mM ammonium bicarbonate and dried by lyophilization.

To obtain the LFCFP, CF was suspended (7 mg/ml) in a buffer containing 50 mM Tris HCl (pH 7.4), and 150 mM NaCl, following which 20% Triton X-114 was added to obtain a final concentration of 4%. The suspension was allowed to rock overnight at 4° C. A biphasic partition was set up by warning the 4% Triton X-114 suspension to 37° C. for 40 minutes, followed by centrifugation at 12,000×g. The aqueous phase was re-extracted twice with 4% Triton X-114 to ensure complete removal of the lipoarabinomannan, lipomannan (LM) and phosphatidyl-inositol-mannoside (PIM). The final aqueous phase was precipitated with 10 volumes of cold acetone, and the pellet washed several times with cold acetone to remove residual Triton X-114. The LAM-free aqueous phase CFPs were suspended in 100 mM ammonium bicarbonate, aliquoted and dried by lyophilization.

LAM, LM and PIM were extracted from whole cells by mechanical lysis of the bacilli in PBS (pH 7.4) containing 4% Triton-X 114 in a Bead Beater (Biospec Products, Bartelsville, Okla.). Unbroken cells and cell wall material were removed by centrifugation at 12000 g, 4° C. for 15 min. The supernatant was collected and a biphasic partition set up. The detergent phase was obtained, back-extracted several times with cold PBS and the macromolecules in the final detergent phase were precipitated with 10 volumes of cold acetone. The precipitate was collected by centrifugation and allowed to air dry. This material (which contained the lipoglycans) was suspended in PBS and residual proteins were removed by extraction with PBS-saturated phenol. The aqueous phase was collected and, after dialyses against distilled water, the lipoglycans were lyophilized. LAM was further purified away from LM and PIM by size exclusion chromatography as previously described (Chatteijee, D. et al., 1992, *J. Biol. Chem.* 269:66228–66233).

To isolate total CW, *M. tuberculosis* cells were inactivated by isothermal killing at 80° C. for 1 h and suspended at a concentration of 0.5 g cells/ml, in a buffer containing PBS, pH 7.4, 4% Triton X-114, PMSF, pepstatin, EDTA, and DNase. The cells were disrupted in a Bead Beater using 0.1 mm Zirconia beads. The lysed cells were first centrifuged at 3000×g for 5 min to remove unbroken cells followed by centrifugation at 27,000×g, 4° C. for 20 min. The resulting pellet was washed three times with cold PBS at room temperature. This final pellet was termed the CW.

The SCWP were obtained by washing the CW twice with 2% SDS in PBS, pH 7.4 at room temperature. The tightly associated proteins were isolated by extracting the CW pellet three times with 2% SDS in PBS, pH 7.4, at 55° C. The 55° C., 2% SDS extract was recovered, and the SDS was removed by using an Extracti Gel column (Pierce, Rockford, Ill.). The eluate from the column was dialyzed against twice-distilled $H_2O$, aliquoted and dried by lyophilization.

The CWC (mycolyl-arabinogalactan-peptidoglycan complex) was generated as described (Daffe, M. et al., 1990, *J. Biol. Chem.* 265:6734–6743) with minor modifications. The SDS-insoluble material obtained after extraction of the SCWP was suspended in PBS, 1% SDS, 0.1 mg/ml proteinase K and incubated for 20 h at 50° C. The insoluble material was pelleted by centrifugation, washed twice with 2% SDS at 95° C. for 1 h and collected by centrifugation. This was washed several times with water and 80% acetone to remove SDS.

Fractionation of LFCFP by size was performed by using a preparative SDS-PAGE system (model 491 Prep cell, Bio-Rad, Hercules, Calif.). CFP (20–25 mg) was loaded directly onto a 30 ml 10% preparative polyacrylamide tube gel containing a 6% stacking gel, that was poured in a casting tube with a 37 mm internal diameter. The running buffer used consisted of 25 mM Tris, pH 8.3, 192 mM glycine, 0.1% SDS. The proteins were separated by electrophoresis using an increasing wattage gradient of 8 W for 3.13 h, 12 W for 2.5 h, and finally 20 W for 11.1 h. Proteins were eluted from the bottom of the tube gel with a constant flow of 5 mM sodium phosphate, pH 6.8. The initial 65 ml of eluant were collected as the void volume, after which 80 fractions of 4.2 ml were collected at a rate of 0.4 ml/min. Individual fractions were assayed by one dimensional SDS-PAGE and were pooled accordingly. SDS was removed from the pooled concentrated fractions by elution through an Extracti-Gel (Pierce) column. The pooled fractions were dried and stored frozen until testing.

Adsorption of Sera with *E. coli* Sonicate

Overnight cultures of *E. coli* (Y1090) grown in Luria-Bertani medium were centrifuged to obtain bacterial pellets that were treated as described for the *M. tuberculosis* sonicate, except that sonication was performed for 30 sec. Two hundred $\mu$l of *E. coli* lysate suspended at 500 $\mu$g/ml in 20 mM carbonate buffer, pH 9.6, was coated into each well of an Immulon 2® ELISA plate (Dynatech, Alexandria, Va.) overnight. The plates were washed and blocked with 5% BSA (bovine serum albumin, Sigma Immunochemicals, St. Louis) in PBS for 90 min. HIV was inactivated by addition of Triton X-100 (1% final concentration) to each serum sample, followed by heating at 55° C. for 60 min. Samples from non-HIV infected individuals were treated in the same manner to maintain consistency in sample preparation. Serum from each individual (20 $\mu$l) was diluted to 200 $\mu$l in PBS/Tween 20 (0.05%) in a 96-well tissue culture plate. The diluted serum samples were transferred to the *E. coli*-coated, blocked ELISA plate by using a multichannel pipetter. The sera samples were exposed to the bound *E. coli* antigens for 90 min after which they were transferred to another ELISA plate that had been coated with *E. coli* and blocked as above. The serum samples were exposed to 8 cycles of adsorption with *E. coli* antigens, following which they were transferred to a 96-well tissue culture plate where sodium azide (1 mM final concentration) was added to each well. This protocol allows rapid and efficient processing of small volumes of multiple samples. Adsorbed serum samples were used within one week.

ELISA with *M. tuberculosis* Antigens

Fifty μl of antigen, suspended at 5 μg/ml (except CS and SCWP, which were used at 15 μg/ml and 1 μg/ml respectively) in coating buffer were allowed to bind overnight to wells of ELISA plates. After 3 washes with PBS, the wells were blocked with 7.5% FBS (fetal bovine serum, Hyclone, Logan, Utah) and 2.5% BSA in PBS for 2.5 h at 37° C. Following this, sera were diluted to 1:1000 final dilution in PBS/Tween 20 (0.05%, PBST) containing 1% FCS and 0.25% BSA, and 50 μl of each serum sample was added per well. The antigen-antibody binding was allowed to proceed for 90 min at 37° C., following which the plates were washed 6 times with PBST. Fifty μl of alkaline phosphatase-conjugated goat anti-human IgG (Zymed, Calif.), diluted 1:2000 (in the same diluent as the serum samples) were added to each well. After 60 min the plates were washed 6 times with Tris-buffered saline (50 mM Tris, 150 mM NaCl) and the Gibco BRL Amplification System (Life Technologies, Gaithersburg, Md.) used for development of color. The plates were read at 490 nm after stopping the reaction with 50 μl of 0.3M $H_2SO_4$.

The optimal antigen and antibody concentrations for each antigen were determined by checkerboard titration with limited numbers of control and non-TB sera prior to performing the ELISA with the total serum panel.

The ELISA with each of the sized fractions generated by preparative polyacrylamide gel electrophoresis was performed as described as above, except that antigen was coated at 2 μg/ml and the sera were tested at a final dilution of 1:200. Forty-two TB sera and 44 non-TB TB controls (16 $PPD^+$; 7 $HIV^{neg}$, $PPD^{neg.}$; and 21 $HIV^+$, asymptomatic individuals) were included in these assays.

Characterization of Known Antigens of *M. tuberculosis* in the Sized Fractions of LAM-free CFP The following mAbs were obtained from the World Health Organization (courtesy of Dr. Thomas M. Shinnick, Centers for Disease Control, Atlanta):

| | | | | | | |
|---|---|---|---|---|---|---|
| IT-53 | IT-13 | IT-46 | IT-63 | IT-61 | IT-51 | MLO4-A2 |
| IT-45 | IT-64 | IT-15 | IT-49 | IT-52 | IT-69 | SAID2D |
| IT-42 | IT-70 | IT-23 | IT-48 | IT-67 | IT-4 | CS-01 |
| IT-41 | IT-43 | IT-62 | IT-59 | IT-68 | IT-1 | |
| IT-56 | IT-58 | IT-47 | IT-60 | IT-19 | IT-20 | |

The "IT" designations are World Health Organization standards for its collection of anti-Mt antibodies. The alternative names of the mAbs, the antigens they recognize and the laboratory of origin are provided in Engers, H. et al., 1986, *Infect. Immun.* 51:718–720; Khanolkar-Young, S. et al., 1992, *Infect. Immun.* 60:3925–3925; Young et al., supra, which are incorporated by reference in their entirety. Antiserum to the 50/55 kDa antigen, MPT32, was obtained from the NIH, Contract 1-AI-25147. The table below summarizes these antibodies and their reactivities.

The composition of the sized fractions was probed with the antibodies in an ELISA, similar to what was used for assessment of reactivity with human sera, except that 50 μl/well of each antibody defined above was used at a concentration recommended by the contributing laboratory. For these ELISAs, the second antibody was an alkaline phosphatase-conjugated rabbit anti-mouse IgG or goat anti-rabbit IgG (1:2000, Sigma Immunochemicals) added in a volume of 50 μl/well.

SDS-PAGE and Immunoblotting

All fractionations (LFCFP and fractions thereof) were done on 10% SDS-PA mini-gels, and the proteins transferred to nitrocellulose membranes before probing with the antibodies. To better identify the antigens in fraction 15 recognized in ELISA by the test sera, blots of total LFCFP and fractions 10 and 15, were probed with (a) a pool of 6 TB sera that were positive for reactivity with LFCFP by ELISA;

(b) a pool of 6 TB sera that were negative by ELISA; and (c) a pool of 6 sera from $PPD^+$ healthy controls.

All blots were screened for antibody binding by use of alkaline phosphatase-conjugated rabbit anti-human IgG and subsequently developing the color reaction with BCIP/NBT substrate (Kirkegaard & Perry Laboratories, Gaithersburg, Md.).

Statistical Analyses

The cutoff for positivity in all ELISA assays was set to be the mean absorption or optical density (OD)±3 standard deviations (SD) of the control group. The Wilcoxon signed rank test for paired samples was used to compare reactivity of sera pre- and post-adsorption. The SD of the above two groups were compared by using the F test. The reactivity of TB sera with LFCFP was compared to the reactivity with the other antigen preparations by using McNemar's paired test. The Graphpad Instat program was used for all statistical analyses.

Characterization of the LAM-free CFP (LFCFP) with antibodies

| Antibodies | | Antigens (Mol. Wt.) | LFCFP (ELISA) | LFCFP (Western) | Reference |
|---|---|---|---|---|---|
| IT-53 | (HBT5) | | NEG | POS | 16 |
| IT-45 | (HDT8) | | NEG | POS | 16 |
| IT-57 | (CBA4) | 82 | SP | POS | 12 |
| IT-42 | (HBT1) | | NEG | POS | 16 |
| IT-41 | (HAT3) | 71 (DnaK) | SP | POS | 2 |
| IT-56 | (CBA1) | 65 (GroEL) | SP | N.D. | 12 |
| mc2009 | (ML30) | | NEG | POS | 9 |
| IT-13 | (TB78) | | NEG | POS | 7 |
| IT-64 | (HAT5) | 96 | NEG | N.D. | 4 |
| IT-70 | (DCA416) | | POS | N.D. | 5 |
| IT-43 | (HBT3) | 56 | NEG | POS | 12 |
| Anti-MPT32 | (polyclonal) | 50/55 | SP | N.D. | 6 |
| IT-58 | (CBA5) | 47 | NET | POS | 12 |
| IT-46 | (HBT10) | 40 (L-alanine dehydrogenase) | POS | POS | 12 |
| IT-7 | (F29-29) | 40 | SP | POS | 11 |
| IT-15 | (TB72) | 38 (Pho S) | NEG | POS | 7 |
| IT-23 | (T871) | | SP | POS | 7 |
| IT-62 | (F67-19) | | POS | N.D. | 11 |
| IT-65 | (HAT2) | | NEG | N.D. | 3 |
| IT-47 | (HBT12) | | wP | N.D. | 12 |
| Mc36O7 | (ML04-A2) | 35 | NEG | POS | 9 |
| IT-63 | (F86-2) | | NEG | N.D. | 14 |
| IT-49 | (HYT27) | 33–32 (Age 85 complex) | SP | POS | 13 |
| IT-48 | (HYT2) | 33 | NEG | NEG | 5 |
| IT-59 | (F67-1) | 33 | NEG | N.D. | 11 |
| IT-60 | (F126-5) | | WP | N.D. | 15 |
| IT-44 | (HBT7) | 33 | NEG | POS | 12 |
| IT-52 | (HBT4) | 25 | NEG | POS | 16 |
| IT-67 | (L24.b4) | 24 | SP | POS | 4 |
| IT-68 | (C24.b1) | | NEG | POS | 10 |
| Mc5041 | (SA1D2D) | 23 (SOD) | SP | POS | 5 |
| IT-61 | (F116-5) | | NEG | N.D. | 15 |
| IT-19 | (TB23) | 19 | NEG | NEG | 7 |
| IT-51 | (HBT2) | 17 | NEG | POS | 16 |
| IT-69 | (HBT11) | | NEG | N.D. | 16 |
| IT-4 | (F24-2) | 14 | SP | POS | 11 |

-continued

Characterization of the LAM-free CFP (LFCFP) with antibodies

| Antibodies | Antigens (Mol. Wt.) | LFCFP (ELISA) | LFCFP (Western) | Reference |
|---|---|---|---|---|
| IT-1 | (F23-49) | | NEG | N.D. | 11 |
| IT-20 | (TB68) | | SP | POS | 7 |
| Mc9245 | (CS-01) | 12 (GroES) | SP | POS | 1 |
| Mc0313 | (L4) | 4.5–6 | SP | N.D. | 8 |

NEG: Negative;
SP: Strong positive = Optical Density (OD) >1.0
POS: Positive-OD 0.5–0.999;
WP: Weak Positive = OD 0.2 = 0.499
Alternative names of some antigens are given in parentheses. SOD: superoxide dismutase
References: [1]Andersen et al., 1984; [2]Andersen et al., 1986; [3]Andersen et al, 1989; [4]Andersen et al., 1991; [5]Andersen et al, 1994; [6]Brennan et al.; [7]Coates et al., 1981; [8]Foumle et al., 1991; [9]Ivanyi et al., 1983; [10]Khanolkar-Young et al., 1992; [11]Kolk et al., 1984; [12]Ljungquist et al., 1988; [13]Schou et al, 1985; [14]Verbon et al., 1980; [15]Verbon et al., 1990; [16]Worsaae et al., 1988

Results

A. Effect of Adsorption of Test Sera with E. coli Lysate

The reactivity of sera from 38 HIV$^{neg}$ (16 PPD$^+$, 7 PPD$^{neg}$, 15 PPD unknown) non-tuberculous individuals, 21 HIV-infected asymptomatic individuals, and 42 TB patients with the LFCFP was evaluated before and after depletion of cross-reactive antibodies by adsorption with E. coli lysate (FIG. 1). There was no difference in the reactivity of the different subgroups of the control sera. The mean absorption (O.D.±SD) of the unadsorbed control sera was 0.316±0.111, and of the same sera after adsorption was 0.165±0.05 (Table 1). This reduction in reactivity was statistically significant (p<0.0001). In addition, the variance (expressed as SD) of the control sera samples post-adsorption was significantly lower (p<0.0001) when compared to the SD of the same sera preadsorption (FIG. 1, Table 1). The mean O.D. for the preadsorbed TB sera was 0.911±0.454, and the same sera post-adsorption had a mean O.D. of 0.694±0.440 (FIG. 1). Although the reactivity of the adsorbed TB sera was also reduced significantly as compared to preadsorbed sera (p<0.0001), the SD of the pre-adsorbed and post-adsorbed TB samples were similar (Table 1). Thus, significant levels of cross-reactive antibodies that were adsorbable to the E. coli lysate were present both in the control and test sera. For the control group, removal of these antibodies reduced the baseline sera reactivity. However, as expected, despite the decreased antibody levels, the variability between individual TB sera was unaffected. Three S.D. above the mean of the respective control sera was set as the threshold values for positive reactivity.

Antibodies reactive with LFCFP were detectable in 25/42 (60%) of the unadsorbed TB sera (FIG. 1). When tested postadsorption, anti-mycobacterial antibodies were detectable in 4/17 (24%) additional, previously negative sera, raising the sensitivity to 69% (FIG. 1).

TABLE 1

Comparison of preadsorbed sera with E. coli-adsorbed sera

| | Mean O.D. ± S.D. | | | |
|---|---|---|---|---|
| Sera | Pre Adsorption | Post Adsorption | p value[a] | p value[b] |
| Controls | 0.316 ± 0.111 | 0.165 ± 0.050 | <0.0001 | <0.001 |
| TB Patients | 0.911 ± 0.454 | 0.694 ± 0.440 | <0.0001 | NS |

[a]Wilcoxon signed rank test comparing the preadsorbed and post adsorbed sera.
[b]F test comparing the standard deviations of the preadsorbed and post adsorbed sera.
NS: not significant.

These experiments were also analyzed by using the highest O.D. in the control sera group as the cutoff, as has been done by others(Ivanyi et al., 1989, supra). Prior to adsorption, O.D.s obtained with 59 control sera ranged from 0.16 to 0.68 (FIG. 1). Twenty-four of the 42 (57%) TB sera had O.D.s greater than the highest control value. After adsorption, the range of O.D.s with the same control sera was 0.08 to 0.25, and 31/42 (74%) TB sera were found to be antibody positive. Thus, antibodies to M. tuberculosis antigens were now detectable in 7/18 (39%) additional, previously negative sera. In view of the increased sensitivity obtained with adsorbed sera, all sera were hereafter preadsorbed prior to use in any assay.

B. Reactivity of the Adsorbed Sera with Different Antigenic Preparations of M. tuberculosis The reactivity of sera from 87 non-TB controls and 58 TB patients with different antigen preparations of M. tuberculosis were analyzed (Table 2).

With the total CF preparation, which contains all the secreted antigens (protein and non-protein), 39/58 (67%) of the sera from TB patients had detectable antibodies, while 2/87 control sera were positive.

With the LFCFP, 41/58 (71%) of the TB sera were antibody positive and none of the 87 control sera were reactive.

Thirty-six TB patients (62%) had antibodies to the CS, as had 2/87 of the control subjects.

CW of M. tuberculosis were tested with sera from 48 TB patients and 54 non-TB controls. Among the TB patients, 28/48 (58%) were antibody positive, whereas only 1/54 controls had antibodies to this antigen preparation.

The difference in reactivity of the TB sera with the CF, CS and CW preparations was not significantly different from the reactivity with LFCFP (Table 2). With SCWP, only 52% (30/58) TB patients were antibody positive, although 99% of the control subjects lacked antibodies. Fifty-five percent (32/58) TB patients had antibodies to LAM, when only 2 of the controls were positive. Antibodies to the cell wall core were detectable in only 8.6% of the patients. Reactivity of TB sera with the SCWP, LAM and CWC antigen preparations was significantly lower than the reactivity with the LFCFP preparation (Table 2). Since the highest sensitivity and specificity were obtained with the LFCFP, it was used for all further analysis.

TABLE 2

Reactivity of sera with antigens of M. Tuberculosis

| Antigen | Sensitivity in % | Specificity in % | p value[a] |
|---|---|---|---|
| Culture Filtrate | 67 | 98 | N.S. |
| LFCFP | 71 | 100 | — |

TABLE 2-continued

Reactivity of sera with antigens of M. Tuberculosis

| Antigen | Sensitivity in % | Specificity in % | p value[a] |
|---|---|---|---|
| Cellular sonicate | 62 | 98 | N.S. |
| Cell walls | 58 | 99 | N.S. |
|  | (n = 48) | (n = 54) |  |
| LAM | 55 | 98 | 0.039 |
| SDS-cell wall proteins | 52 | 99 | 0.015 |
| Cell wall core | 8.6 | 100 | <0.0001 |

[a]p value obtained by using McNemar's paired test to compare the reactivity of TB sera with LFCFP, to reactivity with other antigens.
N.S.: not significant.
58 sera were tested for sensitivity and 87 sera were tested for specificity except where shown in the "cell walls" group.

C. Seroreactivity to Fractions of LFCFP

Figure 2:
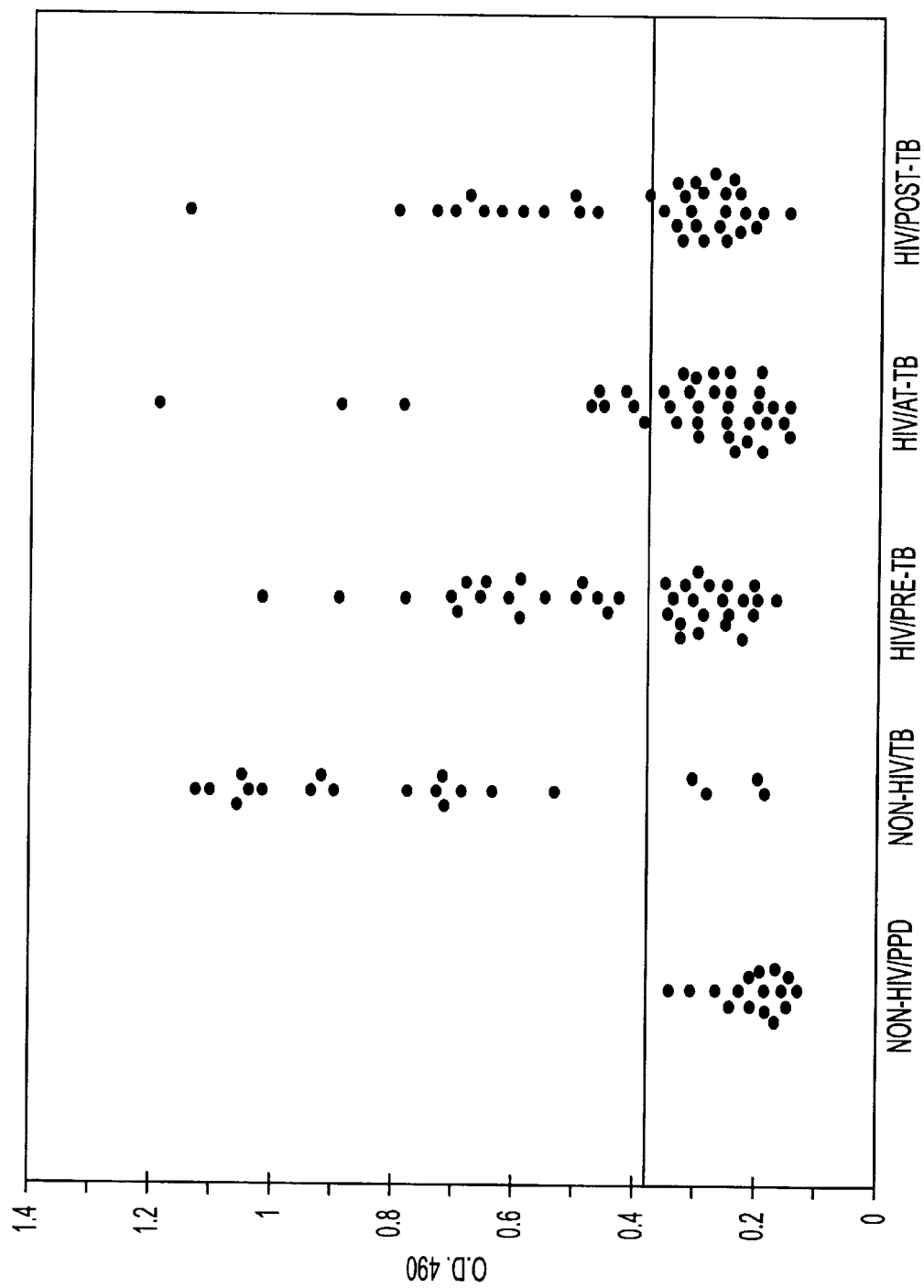
FIG. 2 shows the reactivity with fractions of LFCFP of sera from TB patients which were reactive with total LFCFP

In order to narrow the search for the serologically dominant antigens in LFCFP, reactivity of sera from 42 TB patients and 44 healthy control subjects was tested with the sized fractions. Seventy-two percent (30/42) of the TB sera had antibodies to the unfractionated LFCFP when none of the controls was positive. The sera that showed positive reactivity with the total LFCFP were compared with those showing reactivity with the 15 fractions (FIG. 2). Less than 25% of the patients who were reactive with the total LFCFP showed reactivity with antigens in fractions 1–9. In contrast, 50–60% of the sera were reactive with antigens in fractions 10–13, 80% in fraction 14 and 96% in fraction 15 (FIG. 2A). Any combinations of fractions (14+15; 12+13; 10+14; and 10+14+15) failed to show any improvement over the use of fraction 15 alone. None of the sera that failed to react with the total LFCFP, were reactive with any of the fractions.

D. Characterization of Antigens in Sized Fractions of LFCFP

To determine which of the previously defined proteins were present in the seroreactive antigenic fractions, the reactivity of sized fractions with 36 different murine mAbs, and with an antiserum specific for MPT32, was assessed in ELISA The results with fractions 10–15 are shown in Table 3. Murine mAbs IT-62 and IT-23, both of which recognize epitopes on the 38 kDa protein, reacted exclusively with fractions 10 and 11. Fractions 12 and 13 were reactive only with the rabbit antiserum to MPT32. Fraction 14 reacted with mAb IT-41 which recognizes an epitope on the 71 kDa DnaK protein. Fraction 15 showed reactivity with mAbs IT-41 and IT-57; the latter mAb reacts with an 82 kDa antigen (Table 3).

TABLE 3

Reactivity of fractions of LAM-free CFP

| Fraction number | Reactive Ab | % Reactive patients |
|---|---|---|
| F10 | IT-62,IT-23 | 33 |
| F11 | IT-62,IT-23 | 37 |
| F12 | Anti-MPT32 | 36 |
| F13 | Anti-MPT32 | 43 |
| F14 | IT-41 | 55 |
| F15 | IT-41,IT-57 | 73 |

Specificity of murine mAbs: IT-62 and IT-23 are anti-38 kDa;
IT-41 is anti-71 kDa;
IT-57 is anti-82 kDa.
Anti-MPT32 antiserum was raised in rabbits.

E. Comparison Between Reactivity of Advanced and Early TB Patients

Figure 3:
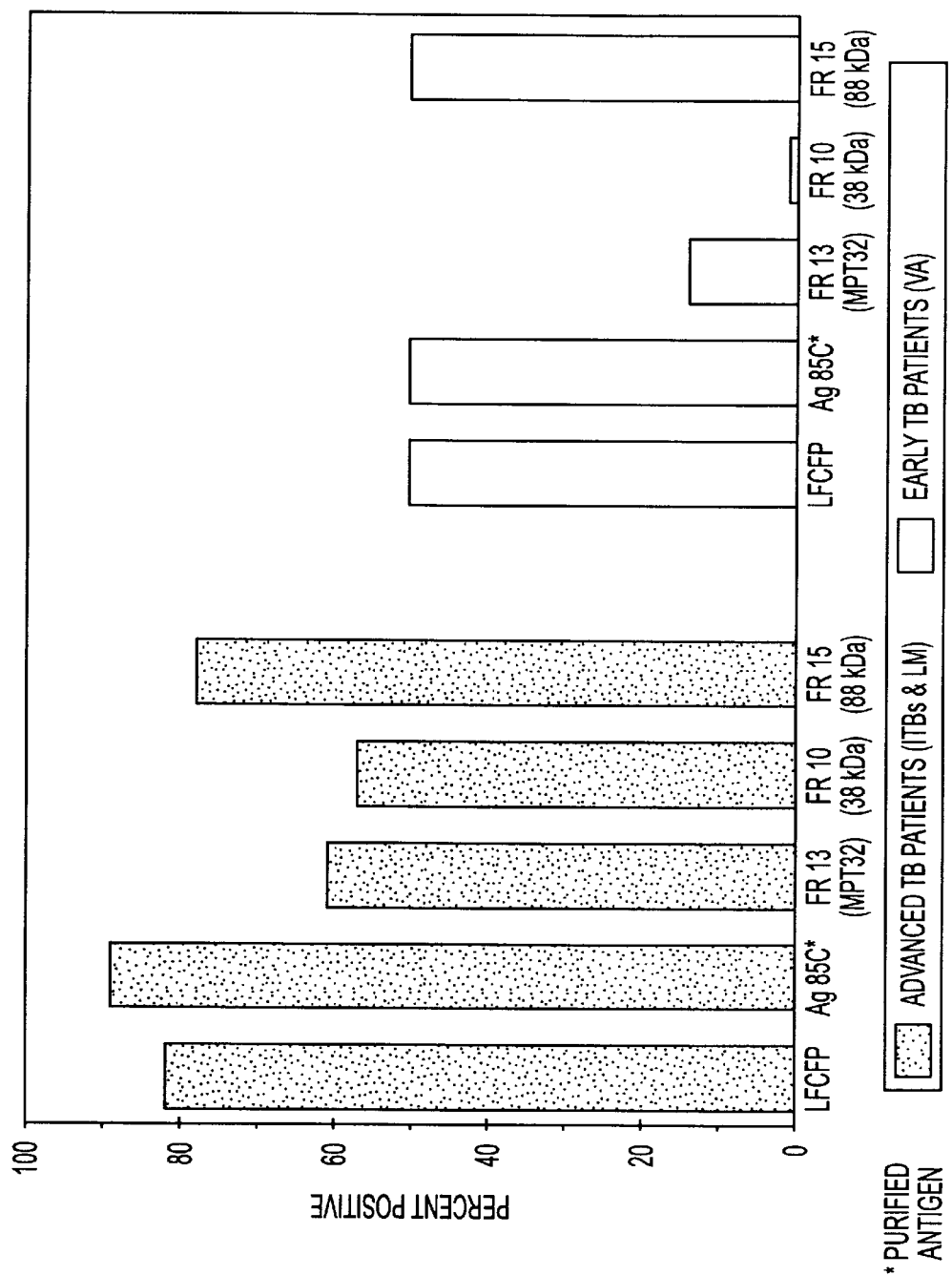
FIG. 3 shows a comparison of reactivity of advanced, partially treated (black bars) and early, minimally treated (stippled bars) TB patients with LFCFP (LFCF), fraction 10 (F10) and fraction 15 (F15).

In view of the reported association of the anti-38 kDa antibodies with advanced/treated TB, and because no two cohorts of patients can be identical, the reactivity of sera from treated, relatively advanced TB patients (sera from Bombay, India, and Denver, Colo.; see above), and sera from untreated (or minimally treated) early TB patients (from VA Medical Center, New York; see above) in the inventors' cohort was compared. Reactivity of the two groups of patients with LFCFP, fraction 10 (which contains the 38 kDa antigen,) and fraction 15, is shown in FIG. 3. Eighty-two percent (23/28) of the advanced, and 50% (7/14) of the early TB patients had antibodies to the total LFCFP. Sera from all but one of the advanced TB patients (22/28), and all 50% of the early TB patients that were reactive with the LFCFP, were also reactive with antigens in fraction 15. In contrast, although 57% (16/28) of the advanced TB patients were reactive with fraction 10, none of the sera from untreated patients with relatively early disease were reactive.

F. Immunoblot Analyses of Fractions

Figure 4:
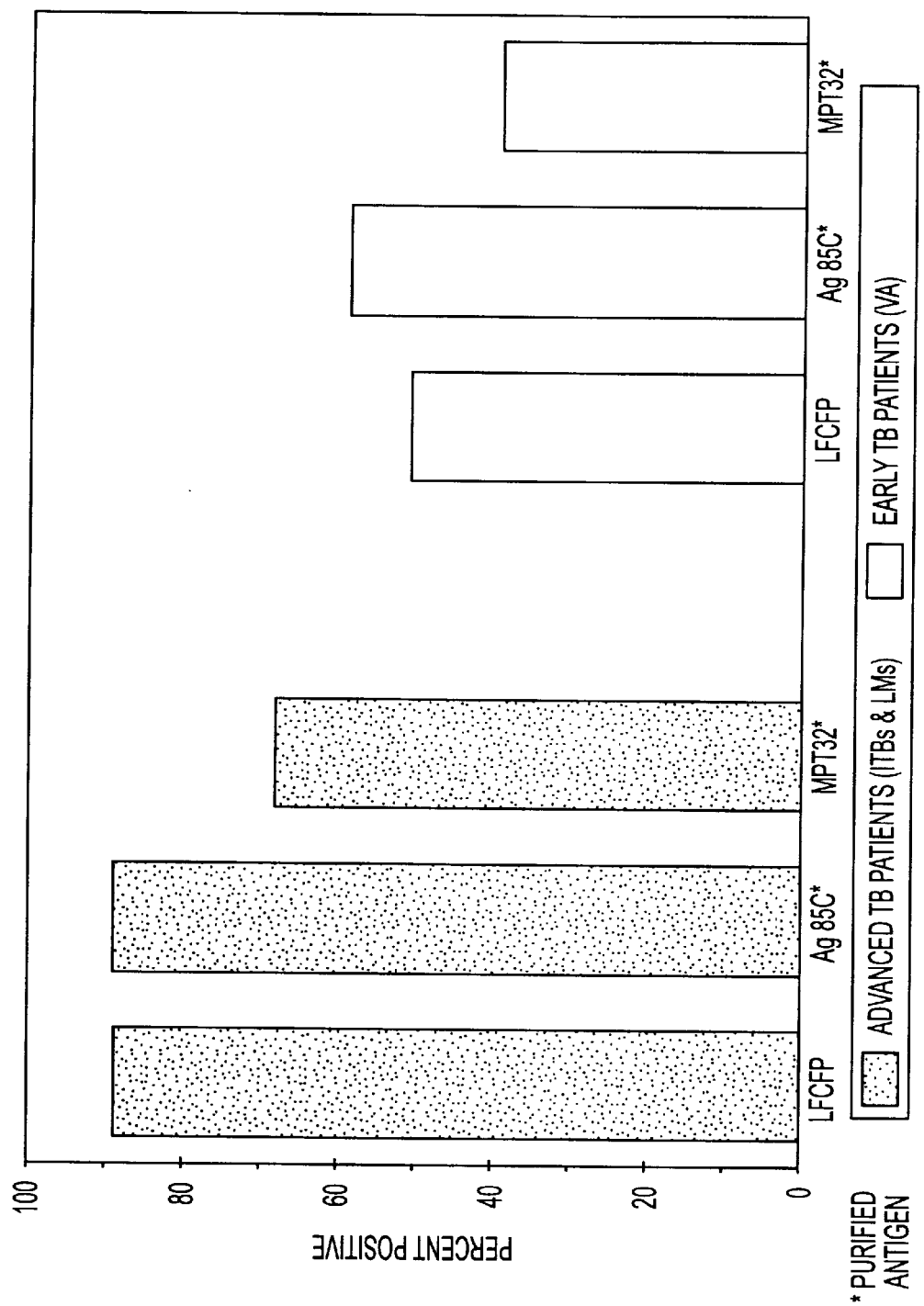
FIG. 4 shows an immunoblot analysis of total LFCFP, and fractions 10 and 15. Lanes 1, 5, and 9 contain molecular weight markers. Lanes 2, 6 and 10 contain LAM-free CFP, lanes 3, 7 and 11 contain Mt fraction 10 and lanes 4, 8 and 12 contain Mt fraction 15. The following antibody probes were used: lanes 1 to 4 were probed with pooled sera (1:200) from ELISA$^+$ TB patients,; lanes 5–8 were probed with pooled sera from ELISA$^{neg}$ TB patients; lanes 9–12 were probed with pooled sera from PPD$^+$, healthy controls.

Since each of the fractions contain proteins in addition to those which reacted with the murine mAbs, LFCFP, fraction 10 and fraction 15, were further fractionated by SDS-PAGE, transferred to nitrocellulose and the blots probed with a serum pool from 6 TB patients who were ELISA+ with the LFCFP (FIG. 4, lanes 2–4). Serum pools from 6 ELISG$^{neg}$ TB patients (lanes 5–8) and 6 healthy controls (lanes 10–12) were tested (as negative controls). Proteins of 65 kDa and 31–31 kDa in the LFCFP and in the two fractions were reactive with all three serum pools.

The ELISA+ TB serum pool recognized at least 10 additional distinct bands in the fractionated total LFCFP (FIG. 4, lane 2). The molecular weights of the antigens ranged from 33 kDa to 112 kDa. The 38 kDa antigen was the most dense band observed, indicating that it is the most abundant antigen recognized by this serum pool in the LFCFP. Since it is a strongly seroreactive antigen in several patients (FIG. 3), the 38 kDa antigen appeared as a prominent band. Another dark band was observed at 88 kDa, but this antigen is present in smaller amounts in the LFCFP, (the band being much less dense than the 38 kDa antigen. Weaker reactivity with antigens having apparent molecular weights of 33, 36, 58, 60, 62, 70, 84 kDa was also observed.

Fraction 10 contained large amounts of the 38 kDa antigen, which was the strongest band, and smaller amounts of other seroreactive proteins ranging from 30–43 kDa. In contrast fraction 15 contained several high molecular weight antigens ranging from 72–88 kDa, and a small amount of the 38 kDa antigen (which was not detected by anti-38 kDa mAbs, Table 3). Strong seroreactivity with a doublet at 88–84 kDa, and weaker reactivity with 78 kDa and 72 kDa antigens was seen.

The pattern of reactivity of sera from TB patients who were negative in ELISA with fraction 15 antigens is shown in FIG. 4, lanes 6–8. The pattern of reactivity of sera from healthy controls is shown in FIG. 4, lanes 10–12. These patterns indicated absence of reactivity with the 88/84 kDa antigens. Since the 72–88 kDa antigens are absent from fraction 10, it was concluded that the reactivity of ELISA+ TB sera with antigens in fraction 15 is directed to these antigens. The strong reactivity of the 88 kDa antigen in fraction 15 and in the total LFCFP suggests that the 88 kDa antigen is responsible for the reactivity of individual patient sera in the ELISA.

Discussion

As stated above, the reactivity of sera from normal healthy individuals (Daniel et al., 1987, supra; Grange, supra) to antigens of M. tuberculosis has been a major hindrance in the direct analysis of antibody responses in TB patients. Several studies (Das, S. et al., supra; Espitia et al., 1989, supra; Verbon, A. et al., 1990, supra) have reported that sera from control individuals recognize several antigens of *M. tuberculosis* . Since most proteins of *M. tuberculosis* isolated so far possess significant homology with analogous proteins in other prokaryotes (Andersen et al., 1989 (supra), 1992 (supra); Braibant et al., (supra); Carlin et al. (supra), ; Garsia et al., (supra); Hirschfield. et al., (supra); Shinnick et al., 1988 (supra); 1989 (supra); Young et al. (supra); Zhang et al. (supra)), the present inventors reasoned that the reduction of cross-reactive antibodies to homologous proteins from other bacterial species, may enrich for, and allow detection of, specific antibodies to mycobacterial antigens as well as mycobacteria-specific epitopes on conserved proteins (Davenport, M.P. et al., 1992, *Infect. Immun.* 60:1170–1177; Meeker, H. C. et al., 1989, *Infect. Immun.* 57:3689–3694; Thole, J. et al., 1987, *Infect. Immun.* 55:1466–1475). This would permit identification of antigens with strongly seroreactive determinants. The choice of *E. coli* lysates for this purpose was based on *E. coli* being a commensal organism possessing many conserved bacterial proteins. The results above demonstrate that when specificity levels of 98–100% were maintained with all the different antigen preparations of *M. tuberculosis* tested, the LAM depleted CFP provided the highest sensitivity, (although the difference in reactivity with CS, CF, and CW was not statistically significant). Since the LAM migrates as a broad band in the 30–40 kDa region on gels, antibodies reactive to LAM would obscure other useful antigens in this region on immunoblots. The major components of cell walls, i.e., the core, SCWP and LAM, showed reduced reactivity when tested as individual preparations. They did not react with any TB serum that was not also reactive with the LFCFP. For these reasons, this preparation served as the basis for the reported studies.

The LFCFP contains over two hundred different secreted proteins (Example V, below; Sonnenberg, M. G. et al., 1994, *Abstracts: 94th General Meeting of Amer. Soc. Microbiol. Las Vegas, Nev.*; Wallis, R. S. et al., 1993, *Infect. Immun.* 61:627–632), most of which are still undefined. Since our goal was to determine which of these proteins was or were the most frequent targets of the antibody response in TB patients, reactivity of sera with size-fractionated antigens was assessed. The reactivity of TB sera with antigens in fraction 15 suggested that high molecular weight secreted antigen(s) of *M. tuberculosis* elicit antibodies in a majority of TB patients. Since fraction 15 contained antigens reactive with murine mAbs IT-41 and IT-57, the TB patients' antibodies could be directed against these antigens or against other undefined high molecular weight antigens.

Screening of a λgt11expression library with these two mAbs yielded clones that produced recombinant 71 and 82 kDa proteins. However, neither of these recombinant proteins showed significant reactivity with TB patient sera. Immunoblot analyses revealed that the main seroreactive antigens in fraction 15, that were absent in fraction 10, had molecular weights of 88 kDa and 84 kDa. The present inventors concluded that because of the dominant reactivity of the 88 kDa protein (both in the LFCFP preparation and in fraction 15) with the antibody-positive TB serum pool, this antigen is primarily responsible for the strong antigenicity of fraction 15. IT-62 and IT-23 mAbs did not react with fraction 15, and the faint 38 kDa band observed in the blot is inferred to be a degradation product of higher molecular weight antigens.

The prior art teaches that the 38 kDa PhoS protein provides the best sensitivities and specificities for serodiagnosis of TB. However, the presence of antibodies to a 38 kDa antigen was correlated with the extent of pulmonary disease and antituberculous therapy (Ivanyi et al., 1983, (supra); Ma et al. (supra)). Several studies (Bothamley et al., 1992 (supra),; Chan et al., (supra); Daniel et al., 1985 (supra), 1986 (supra); Espitia et al. (supra); Verbon, 1994 (supra)) in different populations (from China, Bolivia, Argentina, South and North America) showed that the sensitivity with the 38 kDa antigen ranged from 45 to 90%, being higher in populations where more patients present with advanced disease. The present results with the 38 kDa antigen are in keeping with those of others (Espitia et al. (supra); Verbon, 1994, (supra)): about 60% of the patients with advanced TB had anti-38 kDa protein antibodies. None of the patients with minimal disease were reactive with the 38 kDa antigen.

However, the present inventors discovered, unexpectedly, that sera of 82% of the advanced, and 50% of the early TB patients, were reactive with antigens in fraction 15 even though the 88 kDa antigen is present in much smaller amounts in the LFCFP. Thus, antibodies to antigens in this fraction are detectable earlier and are more frequent during the course of active TB than are antibodies to the 38 kDa antigen (FIG. 3). The present inventors concluded that this higher MW antigen is more commonly immunogenic in TB patients.

Using a similar approach, but with unadsorbed sera, Verbon and colleagues (1990 (supra), 1994 (supra)) reported that 29, 50 and 50% of TB sera react with antigens of 12, 16 and 24 kDa respectively. Based on reactivity with mAbs, these antigens should be present in fractions 2 through 6 in the present study. However, less than 20% of TB sera showed reactivity with these fractions. Since the 12 and 16 kDa proteins are heat shock proteins, antibodies to conserved regions of these antigens would have been removed by adsorption from the sera tested herein. Besides, antibodies in human sera are known to recognize conformational epitopes on these proteins (Verbon, 1994 (supra)), epitopes which may have been destroyed during the fractionation procedure. Either or both of the above reasons could explain the decreased reactivity observed with the lower molecular weight antigens in this study.

Comparative studies with recombinant 38 kDa and 12 kDa antigens, and the corresponding native proteins from cultures of *M. tuberculosis* show that human sera are poorly reactive with the former (Verbon, 1994, supra). In addition, reactivity of human sera with overlapping peptides of 12 and 16 kDa was 20–50% lower than the reactivity with the native antigens (Verbon, 1994, supra). These, and other studies on reactivity of human and murine sera with *M. tuberculosis* antigens suggest that, in contrast to murine antibodies, human antibodies elicited during natural disease progression recognize glycosylated, conformational epitopes (Saxena, U. et al., 1991, *FEMS Microbiol. Immunol.* 76:7–12) on the native proteins.

Use of purified antigen/epitopes will obviate the requirement of adsorbing the sera for obtaining high sensitivities in assays. Whether immune-complexes containing the 88 kDa protein are present and can be detected in the sera of patients who lack evidence of these antibodies in standard immunoassay such as those performed here remains to be tested. Interestingly, recent studies by Raja et al. (Raja, A. et al., 1995, *Lab. Clin. Med.* 5:581–587) showed that immune complexes in the sera of smear-negative TB patients, but not of healthy controls, contained antigens having molecular masses>70 kDa.

The present results show that direct analysis of human antibody responses permits identification of new antigens that were not discerned thus far to be important for antibody responses (Engers et al., supra; Khanolkar-Young, S. et al., 1992, *Infect. Immun.* 60:392–3925). The present results highlight the importance of the present inventors' discovery that depletion of antibodies to cross-reactive regions on common bacterial proteins enables recognition of antigens with strong seroreactive determinants. Use of these antigens, selected on the basis of their reactivity with the human immune system during active disease progression, provides the basis for useful serodiagnostic assays for TB disclosed herein.

EXAMPLE II

Antibodies to an 88 kDa Secreted Antigen of *M. tuberculosis* Serve as a Surrogate Marker of Preclinical TB in HIV-infected Subjects A. Materials and Methods 1. Sera The study population included 49 HIV-infected individuals attending the Infectious Disease Clinic at the V. A. Medical Center, New York, who developed or presented with TB (HIV/TB) during the last several years. A total of 259 serum samples were available from these individuals. Of these samples:

(a) 136 were obtained from 38 patients on several occasions prior to manifestation of clinical TB ("HIV/pre-TB");

(b) 37 samples were obtained from 37 patients at the time of clinical and bacteriological diagnosis of TB ("HIV/at-TB") and included several patients from group (a); and (c) 86 sera were obtained from 35 patients within a few months of initiation of therapy for TB ("HIV/post-TB"). A majority of patients in group (c) were also members of groups (a) and/or (b).

The diagnosis of TB was based on positive cultures for *M. tuberculosis*.

Sera from 20 non-HIV TB patients (non-HIV/TB), 19 of whom were smear-positive, and all of whom showed radiological evidence of moderate to advanced cavitary disease, were included as positive controls. Sera from 19 non-HIV/PPD skin test-positive individuals were included as negative controls. To rule out nonspecific reactivity, the study included (i) sera from 35 HIV-infected, asymptomatic individuals, with CD4 cell counts >800 and (ii) 48 serum samples from 16 HIV-infected subjects whose blood cultures were positive for *Mycobacterium avium-intracellulare* ("HIV/MAI". Of these, 28 HIV/MAI serum samples were obtained during the months preceding advent of MAI bacteremia.

The secreted antigens of *M. tuberculosis* H37Rv (referred to as LAM-free culture filtrate proteins (LFCFP) were prepared as described in Example I. This antigen mixture was subsequently fractionated based on the molecular weight of the proteins using a BioRad 491 Prep Cell (Hercules, Calif.) with a 30 ml 10% preparative polyacrylamide tube gel containing a 6% stacking gel as above. Fractions were pooled according to molecular weights (as determined by SDS-PAGE) and dried.

The LFCFP and the sized fractions thereof, were resolved on 10% SDS-PA mini gel and transferred onto a nitrocellulose membrane prior to probing with sera. The second antibody used was alkaline-phosphatase conjugated rabbit anti- human IgG and the substrate was BCIP/NBT (Kirkegaard and Perry Laboratories, Gaithersburg, Md.).

All sera were adsorbed with *E. coli* lysates prior to use in ELISA assays. Adsorptions and ELISAs were performed as described in Example I.

2. Staining of Lymphocytes and Flow Cytometric Analyses

Staining of cells was done by standard procedures (Gordin F. M. et al., 1994, *J. Infect. Dis.* 169:893–897) using the Simultest CD3/CD4 and CD3/CD8 (Becton Dickinson Immunocytochemistry systems, San Jose, Calif.) reagents. Flow cytometry was carried out with a Becton Dickinson FACScan.

3. Statistical Analysis: Performed as Above

B. Results

1. Reactivity of Sera From HIV/TB Patients with *M. tuberculosis* Antigens

Figure 5:
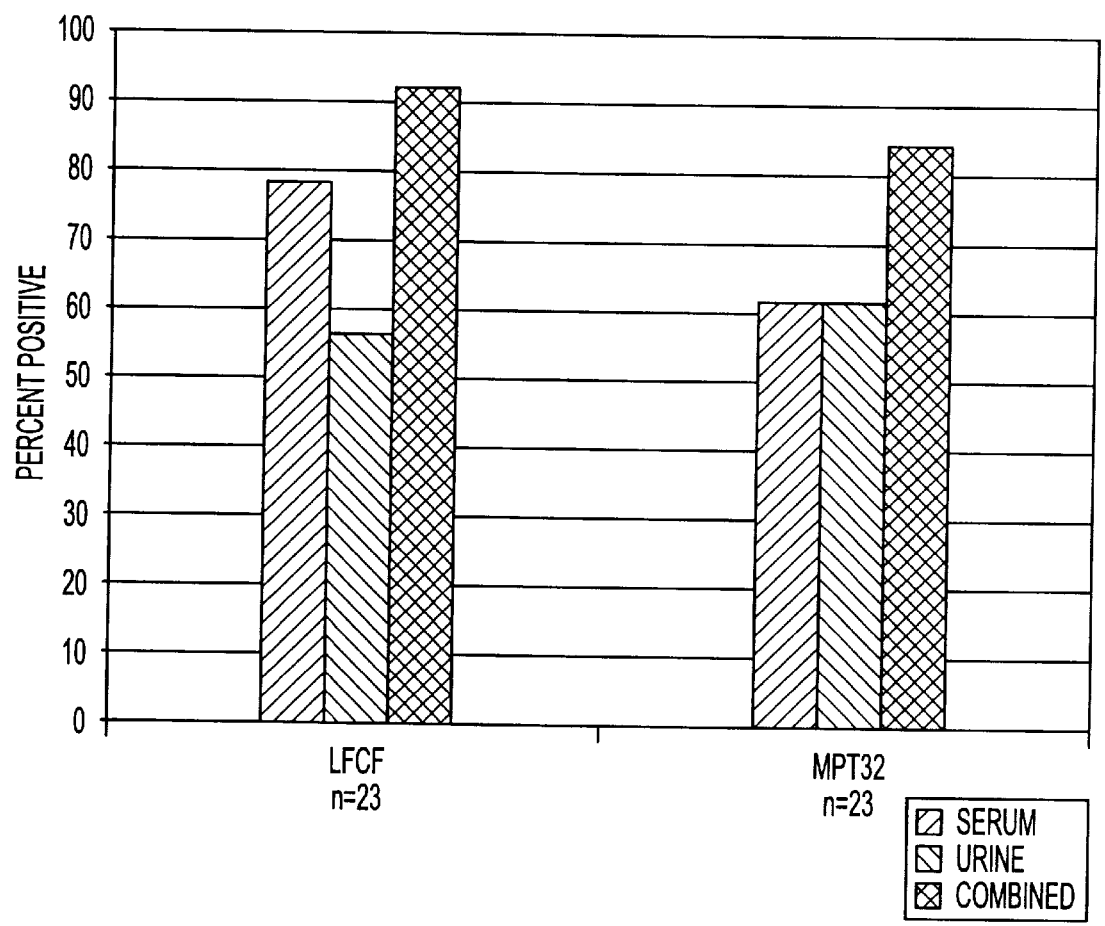
FIG. 5 shows reactivity of sera from non-HIV, PPD skin test positive (PPD+) healthy controls (non-HIV/PPD), non-HIV TB patients (non-HIV/TB) and HIV-infected TB patients (HIV/pre-TB, HIV/at-TB and HIV/post-TB) with total LFCFP of M. tuberculosis. The cut-off was determined by the mean optical density (OD)±3 standard deviations, obtained with the healthy control sera.

The reactivity of 259 sera from 49 HIV/TB patients with the total LFCFP of *M. tuberculosis* was compared to reactivity of sera from 16 non-HIV/PPD$^+$ individuals (negative controls) and 20 non-HIV/TB patients (positive controls). Each serum sample from each subject was evaluated at least three times for presence of anti-*M. tuberculosis* antibodies. A representative ELISA assay showing the antibody levels for each of these groups is presented in FIG. 5. With the cutoff set as the mean OD±3SD of the 16 sera from non-HIV/PPD$^+$ individuals, antibodies to the LFCFP were found in 16/20 (80%) of non-HIV/TB sera. In contrast, only 9/37 (24%) of the HIV/at-TB sera had such antibody reactivity. However, HIV/pre-TB sera from 17/38 (45%) of HIV/TB patients were positive, as were 13/35 (34%) HIV/post-TB sera.

In general, sera of HIV$^+$ subjects had lower levels of antibody than did non-HIV subjects (in all three groups). The difference between mean O.D. of the non-HIV/TB and the mean O.D. of the HIV/at-TB group was statistically significant (in comparisons of either all sera (p=0.0001 ), or of only antibody-positive sera (p=0.0165)). Antibody levels measured as OD in HIV/pre-TB sera were significantly lower than in non-HIV/TB sera (p=0.0001 for all sera; p=0.0007 for antibody-positive sera).

Figure 6:
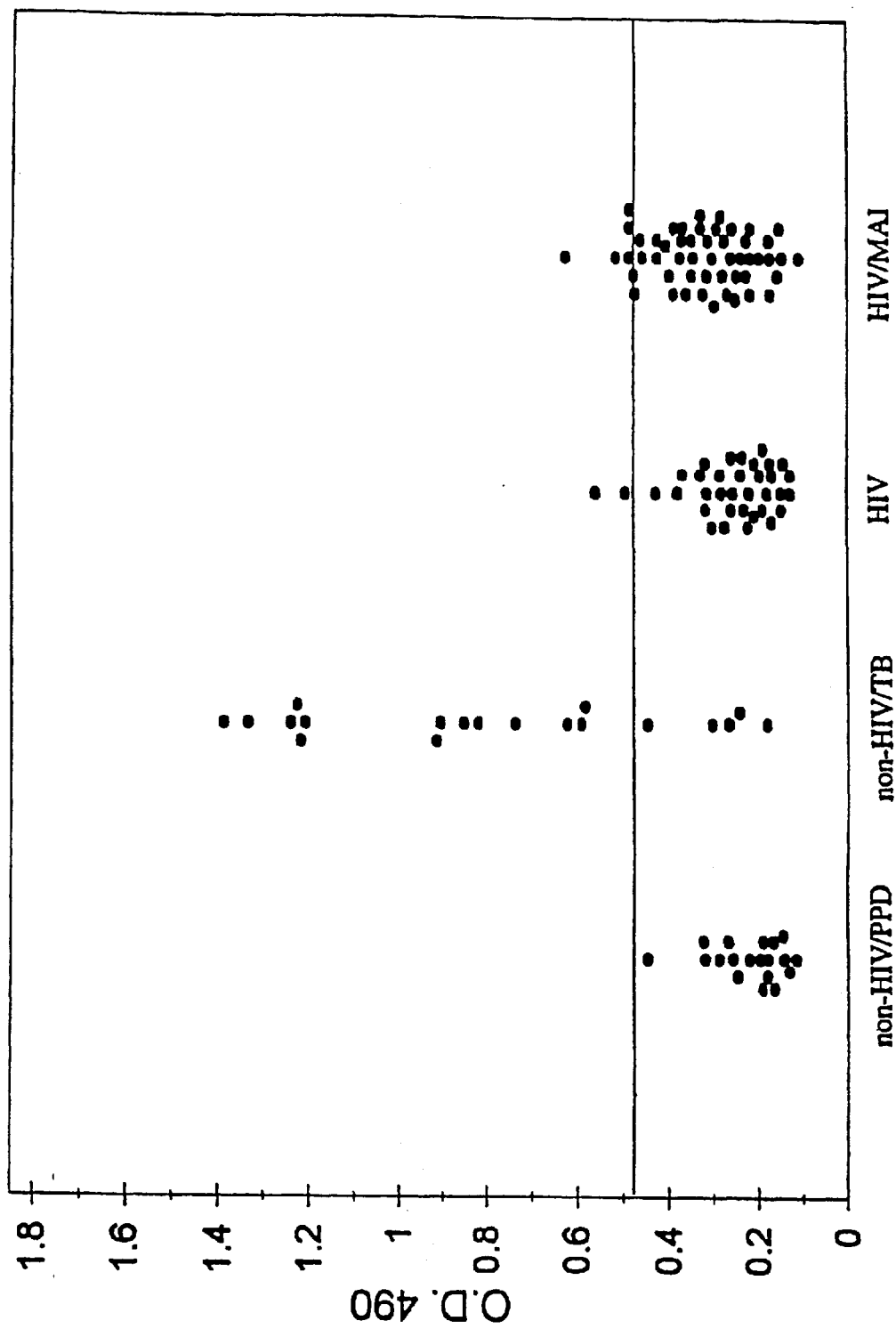
FIG. 6 shows reactivity of sera from non-HIV, PPD+ healthy controls (non-HIV/PPD), non-HIV TB patients (non-HIV/TB), asymptomatic HIV-infected individuals (HIV) and HIV-infected individuals with M. avium-intracellulare bacteremia (HIV/MAI), with total LFCFP. Cut-off was determined as for FIG. 5.
Figure 7A:
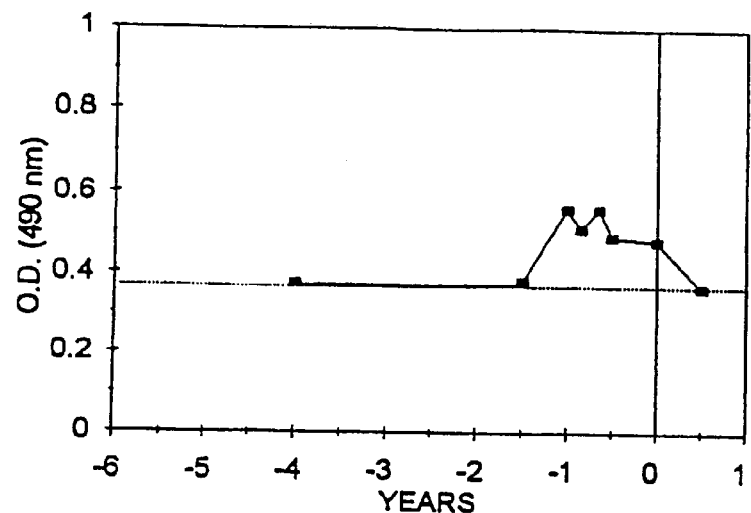
FIG. 7 shows the time course of appearance of antibodies to total LAM-free culture filtrate in the sera of 6 ELISA+ (A–F) and 3 ELISA$^{neg}$ (G) HIV-infected TB patients, and 3 ELISA$^{neg}$ HIV-infected individuals with Mycobacterium avium bacteremia (H). Time point '0' yr. refers to time of clinical diagnosis of TB, negative values refer to the years preceding time '0'. The data in panels A–D and G was derived from an ELISA where the cut-off was determined by mean O.D.±3 S.D. obtained with 16 sera from non-HIV, PPD+ healthy controls. The data in panels E, F, and H was derived from a second ELISA where the cut-off was determined with O.D. values obtained from the same 16 sera, and 3 additional healthy control sera.
Figure 7B:
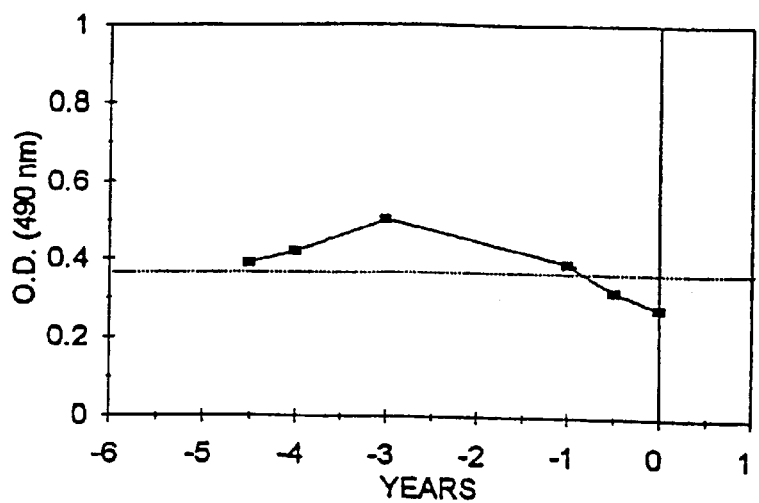
Figure 7C:
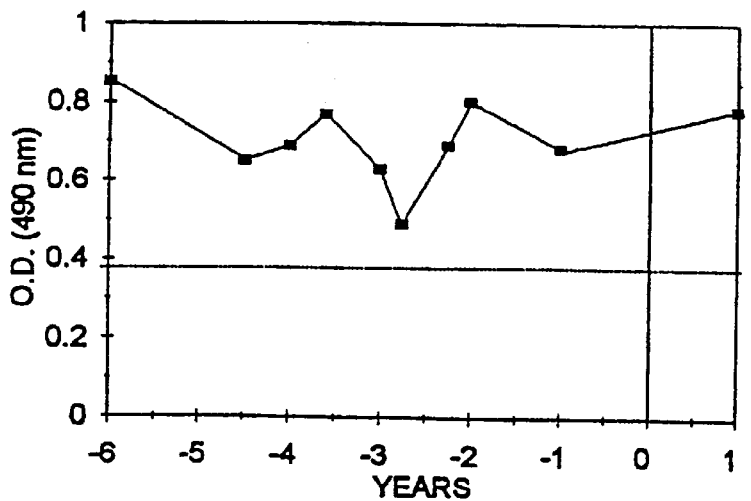
Figure 7D:
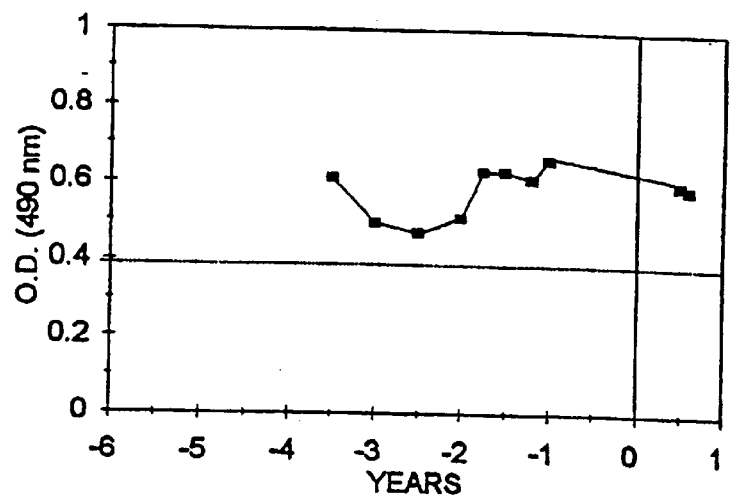
Figure 7E:
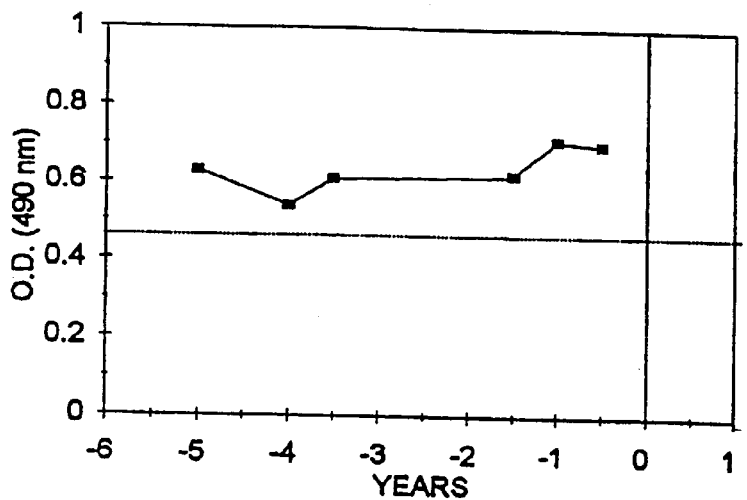
Figure 7F:
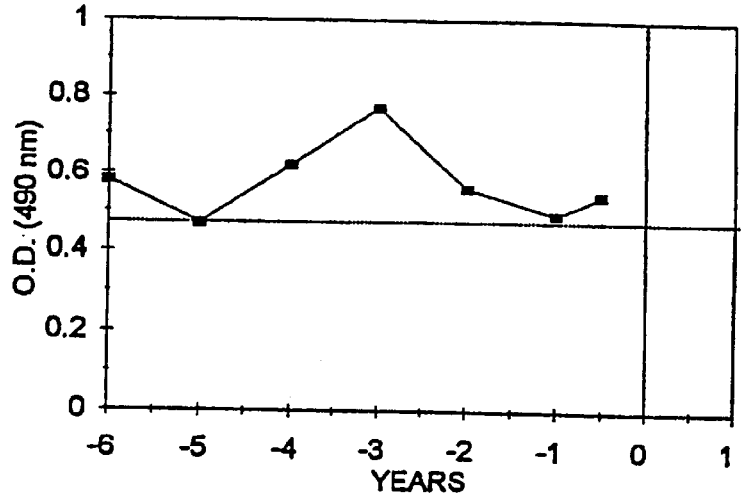
Figure 7G:
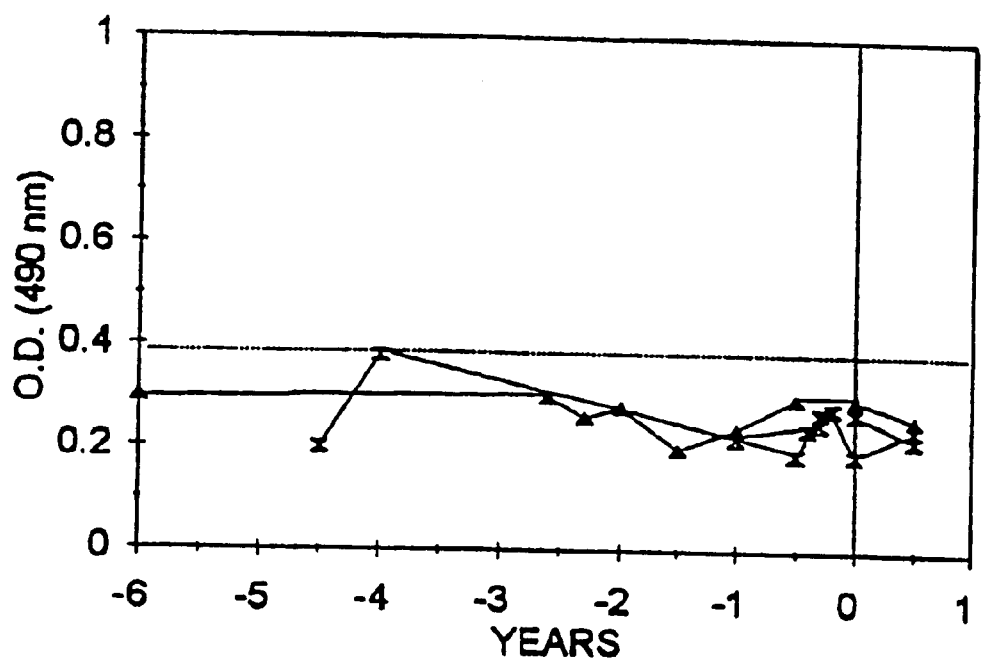
Figure 7H:
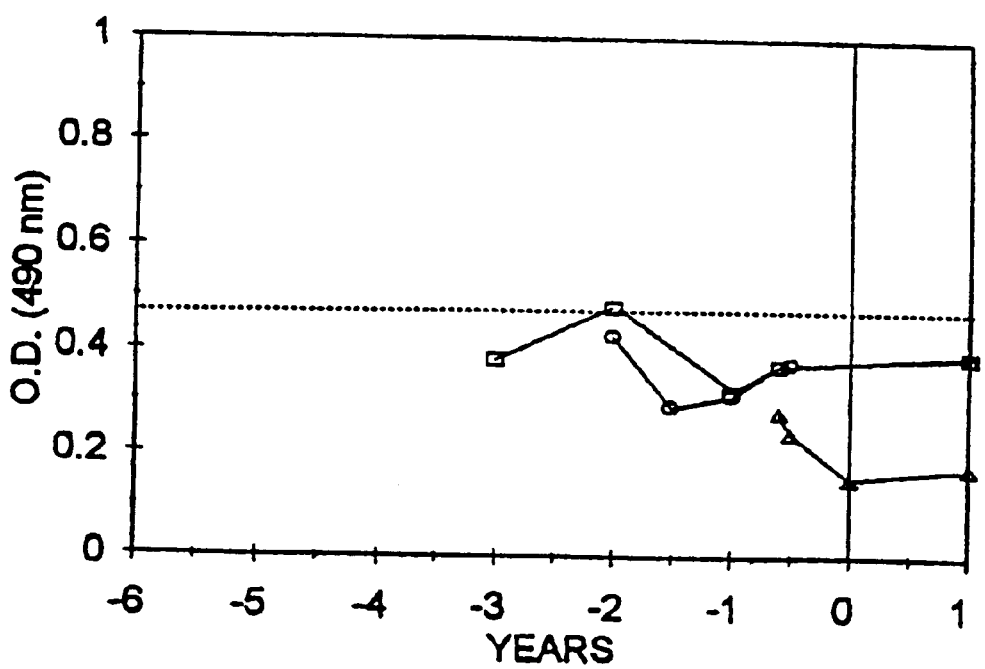

The specificity of the anti-*M. tuberculosis* antibody responses in the HIV/TB patients was evaluated. Sera from 35 HIV-infected asymptomatic individuals (CD4+cell counts >800) and 48 sera from 16 HIV/MAI patients were tested along with 19 non-HIV/PPD$^+$ healthy controls and 20 non-HIV/TB patients. The results are shown in FIG. 6. Using the mean OD±3SD of the 19 non-HIV/PPD$^+$ control sera as the cutoff, 2/35 sera from the HIV-$^+$ group and 7/48 sera from the HIV/MAI group showed minimal reactivity with the *M. tuberculosis* secreted antigens. These results confirmed the specificity of the reactivity of HIV/TB sera with *M. tuberculosis* antigens.

2. Time Course of Appearance of Anti-*M. tuberculosis* Antibodies in HIV/TB Patients Since antibodies to the secreted antigens of *M. tuberculosis* were present in about half of the HIV/pre-TB sera, the presence of these antibodies in the years preceding the clinical presentation of TB was determined. FIG. 7 depicts the presence of anti-*M. tuberculosis* antibodies in multiple sera from 6 antibody- positive (panels A-F), 3 antibody-negative HIV/TB patients (panel G), and 3 HIV/MAI (panel H) patients. All 6 antibody-positive individuals had circulating antibodies for different intervals during the years preceding the clinical manifestation of TB. One of the six patients developed anti-*M. tuberculosis* antibodies about 1.5 yr before clinical diagnosis of TB ((panel A), and another about 4.5 yr prior to that time (panel B). The remaining 4 patients had circulating antibodies for the preceding 5–6 yr. In contrast, similar samples from 3 antibody-negative HIV/TB patients (panel G) and 3 HIV/MAI bacteremia patients (panel H) were consistently negative.

3. Reactivity of HIV/TB Sera with Fractionated Secreted Antigens

Figure 8:
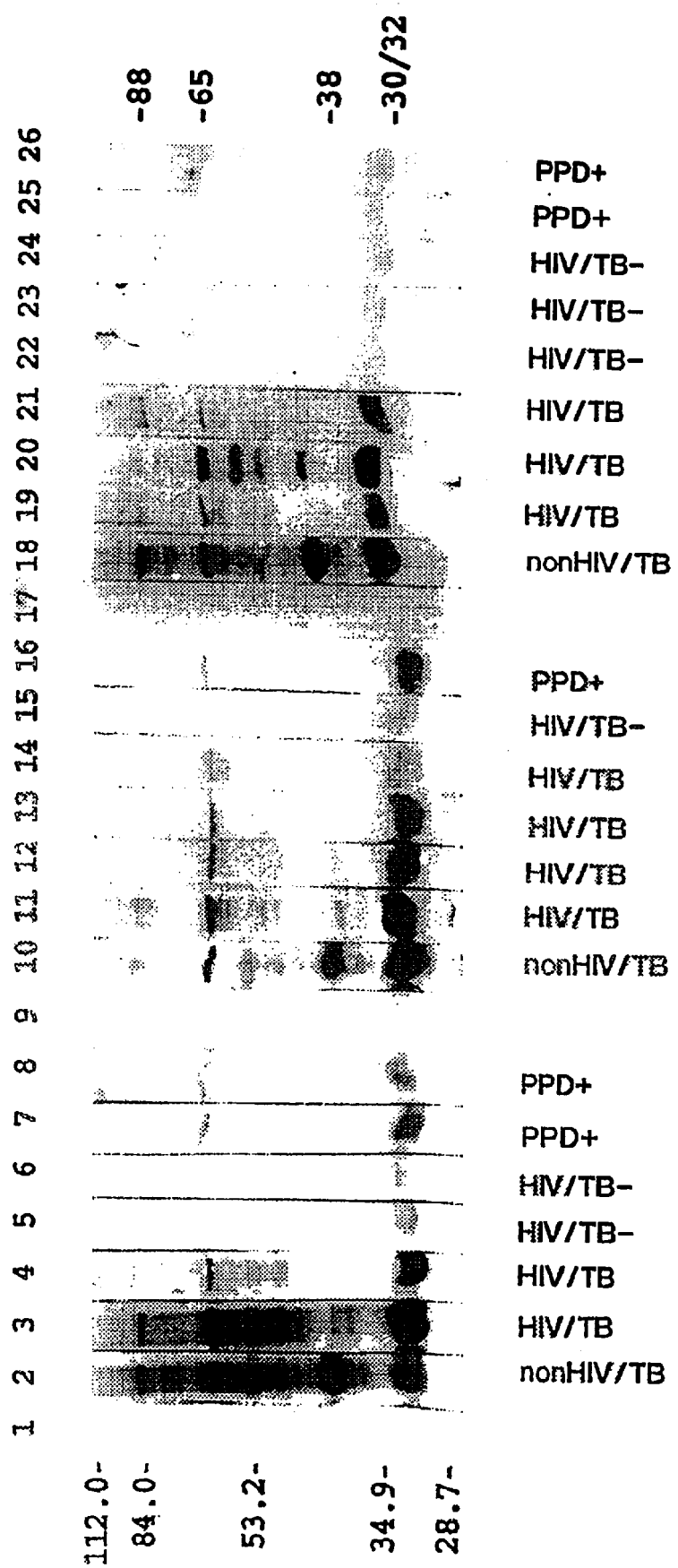
FIG. 8 shows reactivity of sera from 3 non-HIV TB patients (lanes 2, 10, 18); nine HIV-infected TB patients (lanes 3, 4, 11–14, 19–21); HIV-infected asymptomatic individuals (lanes 5, 6, 15, 22–24) and non-HIV, PPD+ healthy controls (7, 8, 16, 25, 26) with fractionated LFCFPs. Lanes 1, 9 and 17 contain molecular weight markers (kDa).

To determine if the profile of antigens (in the LFCFP preparation) reactive with antibodies of HIV/TB patients was different from the profile of antigens recognized by antibodies of non-HIV/TB patients, Western blots prepared from SDS-PAGE-fractionated LFCFP were probed with sera from nine ELISA$^+$ HIV/TB (two HIV/at-TB, seven HIV/pre-TB) and three non-HIV/TB patients. These results were compared to the antibody reactivity of six HIV-$^+$ asymptomatic controls and five non-HIV/PPD$^+$ healthy controls (ELISA$^{neg}$). Results are shown in FIG. 8. As described in Example I, all sera (healthy and disease) reacted with antigens of 65 kDa and 30–32 kDa. The sera from non-HIV/TB patients (lanes 2, 10, 18) reacted with multiple antigens (approximately 20) ranging in size from about 26 kDa to about 115 kDa. Of these, the strongest reactivity was seen with the 38 kDa antigen, which is present in large amounts, and with an 88 kDa antigen, present in lower amounts. Reactivity was also observed with several antigens of molecular weights of 32–38, 45–65, 72–78 and 80–115 kDa.

In contrast, 8/9 of the HIV/TB sera (lanes 3, 4, 11–14, 19–21) showed no reactivity with the 38 kDa antigen, although the reactivity with the antigens in the 45–65 kDa range was detectable, albeit very low in some patients (lanes 4, 19, 21). The reactivity with the 72–78 kDa antigens was also reduced or completely lost. Reactivity to the 80–115 kDa antigens was maintained in two patients (lanes 11, 12), but was significantly reduced in the remaining patients. Reactivity with the 88 kDa antigen appeared to be maintained at higher levels in most HIV/TB sera than was reactivity with the other antigens in this molecular weight range. None of the sera from the asymptomatic HIV-infected individuals (lanes 5, 6, 15 and 22–24) or from PPD$^+$ healthy controls (lanes 7, 8, 16, 25, 26) showed any significant parallel reactivity at similar dilutions. Thus, it was concluded that the repertoire of antigens recognized by the HIV/TB sera was more limited than that recognized by non-HIV/TB sera.

4. Reactivity of HIV/TB Sera with Sized Fractions of LFCFP

Figure 9A:
FIGS. 9A and 9B show reactivity of pooled sera from 6 non-HIV TB patients (FIG. 9A) and 6 HIV-infected TB patients (FIG. 9B) with sized fractions of LFCFPs.
Figure 9B:
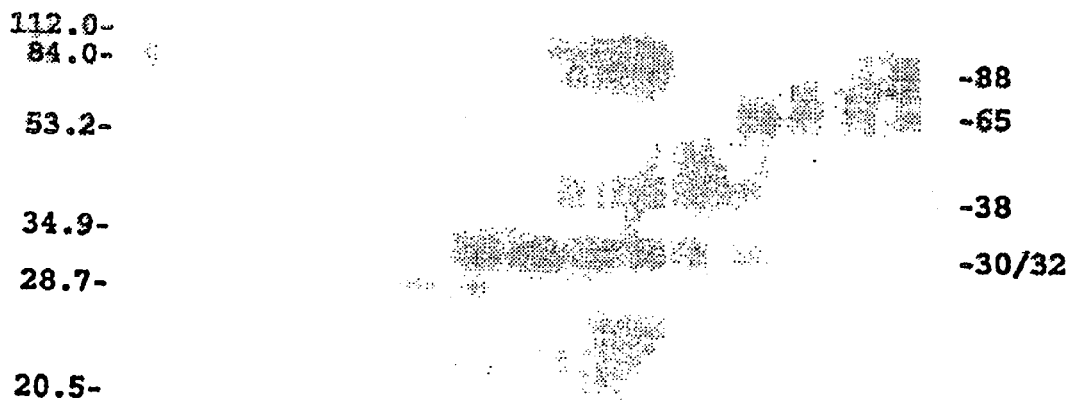

In order to narrow the search for the antigens in the LFCFP that were recognized by HIV/TB patients, the LFCFP material was fractionated into 14 overlapping fractions based on molecular weight. Identification of fractions containing strongly seroreactive proteins was achieved by probing Western blots with pooled sera from six ELISA$^+$ non-HIV/TB or six HIV/TB patients (FIG. 9A and 9B respectively). Besides the 65 kDa and 30–32 kDa antigens which were previously shown (see FIG. 8 and Example I) to be reactive with all sera (healthy and disease), the non-HIV/TB serum pool reacted primarily with antigens with molecular weights above 30–32 kDa in fractions 6–14 (FIG. 8).

More specifically, reactivity was observed with antigens of approximately 32–38 kDa in fractions 6, 7 and 8. A very strong band at 38 kDa was reactive in fractions 9 and 10. In addition, antigens of 45, 50 and 58–60 kDa were also reactive in fraction 10. Although small amounts of the 38 kDa antigen and the 30–32 kDa were found to contaminate fractions 11–14, the dominant seroreactive proteins in fraction 11 ranged from 56–68 kDa, in fraction 12 from 58–76 kDa, in fraction 13 from 65–76 kDa and in fraction 14 from 65–88 kDa. A strong band at 88 kDa was seen exclusively in fraction 14.

When pooled sera from 6 ELISA$^+$ HIV/TB patients (5 HIV/pre-TB and 1 HIV/at-TB) was used to probe a similar blot, antigens in fractions 6–9 reacted poorly (FIG. 9B). In accordance with the results from tests of individual HIV/TB sera (FIG. 8), little or no reactivity was found with the 38 kDa antigen in fractions 9–14. However, reactivity with antigens of 45, 50 and the 58–60 kDa doublet in fraction 10 was discernible, though it was relatively weak. Except for the 68 kDa antigen in fractions 11 and 12 (which reacted strongly with the non-HIV/TB sera pool), reactivity with the other antigens in fractions 11–14 was also maintained. The reactivity with the 88 kDa antigen in fraction 14 was strong and clear (FIG. 9B).

These results suggest that reactivity with antigens in fractions 10–14 is better maintained in HIV/TB sera than with the antigens in the remaining fractions. Thus, of the antigens recognized by non-HIV/TB patients, HIV/TB patients recognize only a subset. For example, antibodies to the 38 kDa antigen are not found in HIV/TB, whereas antibodies to antigens in fraction 10-fraction 14, and in particular to the 88 kDa antigen are maintained despite HIV infection.

5. Reactivity of *M. tuberculosis* Antigen Fractions with Individual Sera

To determine precisely which antigens of *M. tuberculosis* are recognized with high frequency by HIV/TB patients, reactivity with antigens in fractions 7 through 14, and with total LFCFP (as positive control) was tested with 145 sera from 42 HIV/TB patients.

Because the goal of these studies was to identify antigens of *M. tuberculosis* that may be used for developing a surrogate marker for subclinical TB, or as an aid to diagnosis of patients presenting with suspected TB, mostly HIV/pre-TB and HIV/at-TB sera were used for these experiments. Sera from 18 non-HIV/ PPD$^+$ (negative controls) and 20 non-HIV/TB patients (positive controls were included).

Figure 10:
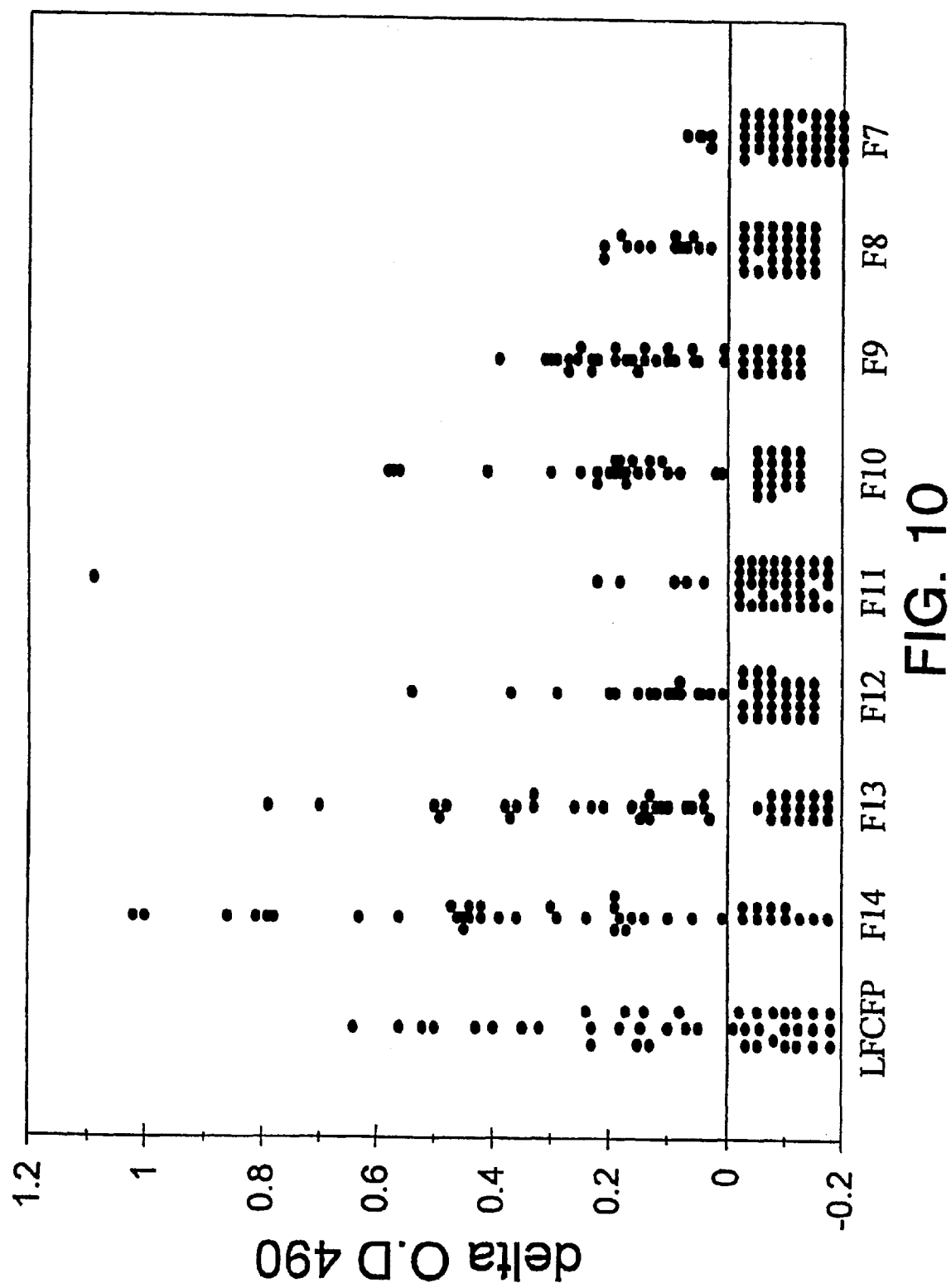
FIG. 10 shows reactivity of sera from HIV/TB patients with total LFCFP and sized fraction numbers 7–14 (F7–14) by ELISA. The Δ O.D. values were calculated by subtracting the mean optical density of the PPD+ healthy control group +3 standard deviations obtained with the antigen (LFCFP or sized fraction) from the optical density of the serum sample with the same antigen.
Figure 11A:
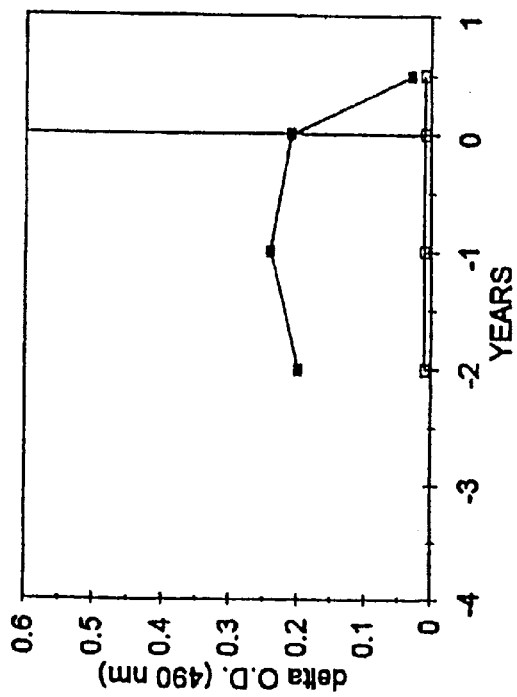
FIG. 11 shows reactivity of sera from HIV-infected TB patients with total LFCFP (□) and antigens in Fraction 14 (■). Time: '0' years refers to time of clinical diagnosis of TB, and negative values refer to the years preceding clinical TB. The Δ O.D. values were calculated by subtracting the mean OD of the PPD+ healthy control group +3 S.D. obtained with the antigen (LFCFP or F14 antigens) from the OD of the serum sample with the same antigen.
Figure 11B:
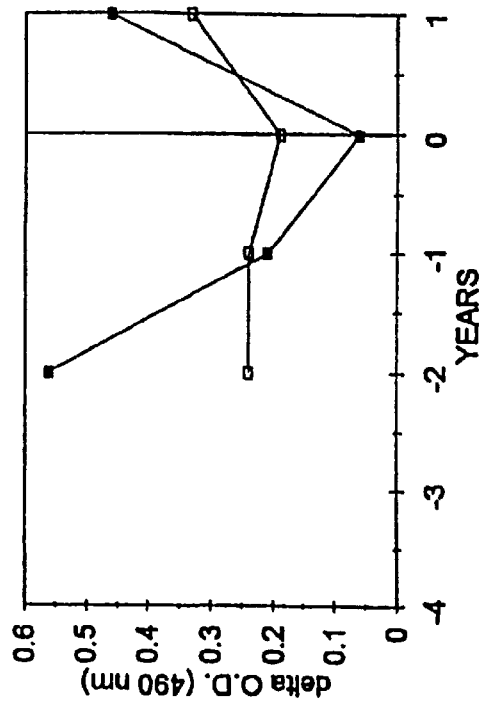
Figure 11C:
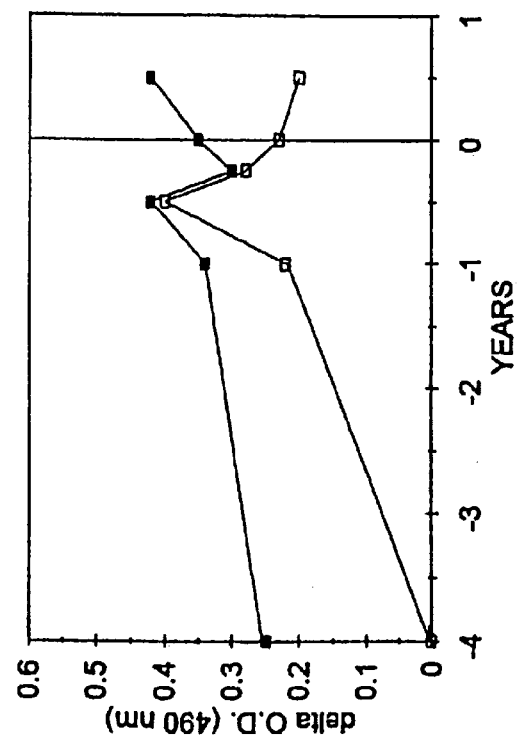
Figure 11D:
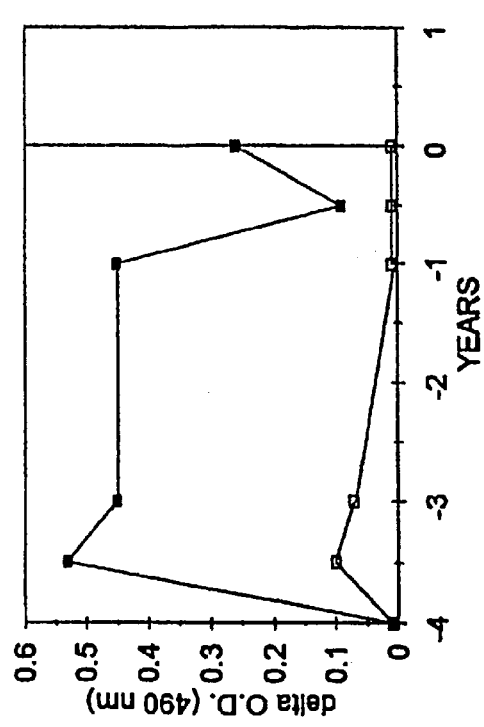

As shown above (FIGS. 5 and 6), using the mean OD±3SD obtained with the non-HIV/PPD$^+$ control sera as cutoff, 16/20 (80%) non-HIV/TB sera had antibodies to the total LFCFP. FIG. 10 shows the reactivity of the 42 HIV/TB patients with the antigens in fractions 7–14. Values obtained with HIV/pre-TB sera have been shown for most patients; and for patients for whom no pre-TB sera were available, HIV/at-TB sera are shown. Fifty percent (21/42) of the HIV/TB patients had antibodies to the unfractionated LFCFP. However, 74% (31/42) of the same patients showed positive reactivity with antigens in fraction 14. Sixty two percent (26/42) patients were reactive with antigens in fraction 13, and 38% (16/42) with fraction 12 (though the O.D. values for fraction 12 and 13 antigens were lower). About 50–60% of sera reacted with antigens in fractions 9 and 10, albeit at lower levels than with fraction 14. As was shown in Example I, the non-HIV/TB patients who were reactive with the unfractionated LFCFP were also reactive with the antigens in fraction 14 in this study The reactivity of HIV/TB sera with the unfractionated LFCFP and antigens in fraction 14 was also analyzed by comparing HIV/pre-TB and HIV/at-TB groups. Thirty-one percent of the HIV/at-TB were reactive with the total LFCFP, as were 55% of the HIV/pre-TB sera. In contrast, 66% of the HIV/at-TB, and 74% of the HIV/pre-TB sera had antibodies which bound fraction 14 antigens.

To follow the time course of appearance of antibodies to fraction 14 antigens, the reactivity of multiple serum samples from individual patients was tested with fraction 14 and with LFCFP (FIG. 11). Antibodies to these antigens were present in the sera of individual (antibody-positive) patients for several years before, and at the time of, clinical manifestation of TB. In contrast, multiple serum samples from antibody-negative patients were consistently negative.

6. Cellular Profiles of Antibody-positive and Negative HIV/TB Patients

The T cell profiles of HIV/TB patients who were antibody-positive with fraction 14 antigens were compared with those who were antibody-negative, both during the HIV/pre-TB and HIV/at-TB stages. As shown in Table 1, there was no significant differences between the two groups of HIV/TB patients.

C. Discussion

This foregoing results prove that antibodies to secreted antigens of *M. tuberculosis* are present in about 74% of the HIV/TB patients for several months to years preceding the clinical manifestation of TB. Prior depletion of cross-reactive antibodies allows the detection in a serum sample of such "early" anti-mycobacterial antibodies, because of their lower levels compared to non-HIV/TB patients and the "unmasking" of their reactivity as a result of the depletion.

The repertoire of *M. tuberculosis* antigens which elicit antibodies in the HIV/TB patients is limited in comparison to non-HIV/TB patients: antibodies to several antigens with molecular weights of 32–45 kDa are absent in these HIV/TB patients. Antibodies to a strongly seroreactive 38 kDa antigen, which are present in 50–60% of non-HIV/TB TB patients, were absent from most HIV/TB patients. (Example I; Daniel et al., 1987, supra; Bothamley, 1992, supra; Espitia C. et al., 1989, supra; Verbon A. et al., 1993, *Am. Rev. Respir. Dis.* 148:378–384) Most noteworthy, among the antigens recognized by antibodies in HIV/TB sera were antigens present in fraction 14, which comprises primarily an 88 kDa reactive antigen. Such antibodies specific for the 88 kDa antigen were detected in pre-TB sera from 74% of the HIV$^+$ individuals who went on to develop clinical TB.

Example I shows that the 88 kDa antigen (present in Fraction 15 in that study, but present in Fraction 14 in the study of Example II) is one of the secreted antigens of *M. tuberculosis* that elicits antibodies during early stages of disease progression (in non-HIV TB patients). Thus, the detection of anti-88 kDa antibodies in the high risk HIV-infected population can serve as a diagnostic test, and the antibody as a surrogate marker, for identifying individuals with active pre-clinical TB. At the time TB appears clinically, only about one-third of the HIV/TB patients are PPD$^+$ (Fitzgerald J. M. et al., *Chest* 100:191–200), a measure of T cell-mediated immunity. In contrast, 66% of these HIV/TB patients have antibodies to the 88 kDa antigen. The discovery of this new surrogate marker, as well as others based on other "early" antibodies, for identifying individuals who are at increased risk of developing TB or have active TB, is a significant contribution to the effort to slow the impending global TB epidemic.

In the U.S., only about 3% of the TB patients are HIV-infected. However, in the developing countries, seroprevalence for HIV ranges from 17% to 66% (Raviglione et al., 1992, supra; Shafer et al., supra). The proportion of HIV patients who are anergic to PPD is large, ranging from 33% in Zaire to over 90% in Brazil, and ranges from 43% in early HIV infection to 100% in advanced HIV disease (Raviglione et al., 1992, supra).

Delayed hypersensitivity skin test reactivity is known to be unstable in HIV$^+$ individuals. Since development of PPD reactivity and production of anti-mycobacterial antibodies do not necessarily occur simultaneously (Das, S. et al., *Clin. Exp. Immunol.* 1992;89:402–06; Kardjito, T. et al., *Tubercle.* 1988, 63:269–274; Balestrino, E. A. et al., *Bull. World Health Org.* 1984, 62:755–761), the simultaneous use of both markers will enhance early detection and our ability to institute timely therapy in such patients.

A number of investigators presented controversial results in their attempts at serological diagnosis of TB in HIV-infected patients. For example, van Vooren et al. (*Tubercle* 1988, 69:303–05) reported that antibodies to total secreted antigens of *M. tuberculosis* were present for several months in a patient who subsequently developed TB. They also reported that 7 of 8 HIV/TB patients had circulating antibodies to antigen p32 (Ag85A). This antigen would be in fractions 6 to 9 in the studies described herein. Indeed, the reactivity of the HIV/TB sera with these fractions (FIGS. 9 and 10) might be attributable to the presence of this antigen, given that antibodies specific for the 38 kDa antigen and the Ag85B antigen (McDonough JA et al., *J Lab Clin Med* 1992;120:318–22) are lacking in these patients. Da Costa et al., *Clin. Exp. Immunol.* 1993, 91:25–29) found anti-LAM antibodies in about 35% of their HIV/TB patients, as did Barer et al. using PPD as the antigen (*Tuber Lung Dis* 1992, 73:187–91). The results reported herein are similar in that, at the time clinical TB is manifest, antibodies to unfractionated LFCFP were detectable in about 25% of the HIV/at-TB sera. However, sera from 66% of these patients were reactive with the fraction 14 antigens. The inability of McDonough et al. (supra) to detect antibodies to Ag85B in sera of HIV/TB patients may be due to the limited numbers of antigens recognized by the HIV/TB patients. The A-60 antigen used by some investigators (Saltini, C. et al., *Am. Rev. Respir. Dis.* 1993, 145:1409–1414; van der Werf, T. S. et al., *Med. Microbiol. Immunol.* 1992, 181:71–76) provides poor sensitivity and poor specificity even in the non-HIV/TB patients, a group known to have higher antibody levels (Charpin D et al., *Am. Rev. Respir. Dis.* 1990, 142:380–384; Qadri, S. et al., *Can J Microbiol* 1991, 38:804–806).

It is not clear why about 25–30% of the HIV/TB patients appear to lack antibodies to the 88 kDa antigen. No correlation was found between the CD4$^+$ cell counts and antibody levels in the HIV/TB patients. Similarly, a lack of correlation between CD4$^+$ cell counts and delayed hypersensitivity responses has also been reported (Huebner, R. E. et al., *Clin Infect Dis* 1994, 19:26–32; Gordin F. M. et al., *J Infect Dis* 1994, 169:893–897), suggesting not only quantitative alterations but also functional differences between T cell subpopulations contributing to the immune status of HIV-infected individuals.

The presence of circulating antibodies to secreted antigens of *M. tuberculosis* long before the development of clinical disease in the HIV/TB patients suggests some replication of *M. tuberculosis* in vivo before the immune system becomes sufficiently dysfunctional to allow the progression to clinical disease. Epidemiological studies show rapid progression of primary infection to clinical disease in HIV-infected individuals (Small, P. M. et al., *N Engl J Med* 1993, 328:1137–1141; Daley, C. L. et al., *N Eng. J Med* 1992, 326:231–235; Edlin B. R. et al., *N Engl J Med* 1992, 326:1514–1521; Coronado V. G. et al., *J Infect Dis* 1993, 328:1137–1155). It is therefore possible that only patients who are reactivating latent TB and are therefore mounting a secondary immune response, have anti-*M. tuberculosis* antibodies. Interesting recent studies analyzing Restriction Fragment Length Polymorphisms (RFLP) of the *M. tuberculosis* strains (Alland D et al., *N Engl J Med* 1994, 330:1710–1716; Small et al., supra) suggest that about 60–70% of the TB cases in New York (and San Francisco) are due to reactivation of latent infection.

Studies are underway in the inventors' laboratory analyzing RFLP in TB isolates obtained from the patients in this cohort to determine if the antibody status reflects primary vs. reactivation TB (per the RFLP criteria), or whether other factors are involved. Anti-mycobacterial antibodies in seemingly antibody-negative patients may be circulating in the form of immune complexes with the antigens, thereby obscuring the presence of antibody in the assay used. That this may occur in at least a proportion of the patients is suggested by the increased frequency of antibodies detected in HIV/post-TB sera.

The present results suggest that patients with persistently circulating antibodies to the 88 kDa antigen of *M. tuberculosis* may benefit from preventive anti-TB therapy, as has been found to be the case with PPD+ HIV-infected individuals (Shafer, et al., supra; Pape, J. W. et al., *Lancet* 1993, 342:268–272). The patients in the present inventors' cohort were chosen on the basis of clinical confirmation of TB. Their PPD reactivity is not known. The length of time from a positive PPD skin test to the development of clinical disease ranges from 1–7 years in HIV-infected individuals (Selwyn PA et al., *N Engl J Med* 1989, 320:545–550; Huebner R. E. et al., *Clin Infect Dis* 1994, 19:26–32). There is no parameter which assists in determining the most appropriate time and duration of prophylactic anti-TB therapy. Further analyses of antibody responses in HIV/PPD+individuals who progress to clinical TB may provide further insight into the most appropriate timing for prophylactic therapy in these individuals.

EXAMPLE III

Definition of the Full Extent of Glycosylation of the 45 kDa Glycoprotein of *M tuberculosis*

The results in this Example appeared in Dobos et al., *J Bacteriology* 178:2498–2506 (1996 May) which is incorporated by reference in its entirety. The figures from that publication are omitted here, although the results are fully described below.

The 45 kDa culture filtrate protein of *M. tuberculosis* is an example of a glycoprotein for which chemical proof of amino acid glycosylation is still lacking. Antibody reactivity studies and N-terminal amino acid sequencing conducted by Espitia et al. (1989, 1995, supra) and Dobos et al. (supra) demonstrated that this 45 kDa protein is the same as MPT 32, a culture filtrate protein originally isolated by Nagai and colleagues (Nagai, S. et al., 1991, *Infect. Immun.* 59:372–382.). As described in the Background, the DNA sequence of a gene designated apa encoding a 45/47 kDa *M. tuberculosis* protein was elucidated by Laqueyrerie et al. (supra), and the deduced amino acid sequence of this gene yielded 100% homology with the N-terminal sequence of the 45 kDa/MPT 32 protein (Dobos et al., supra). The apa sequence further indicated an abundance of Pro and Ala, confirming earlier amino acid compositional analysis. Dobos et al. (supra) found that among the products of proteolysis of this protein was a glycopeptide with an average molecular mass of 1516 AMU which was O-glycosylated at a Thr site with two mannose residues, and, in addition, the glycosylated Thr was the first of a pair of Thr situated at the 10th and 11 th position from the amino terminus of the mature glycoprotein, i.e., DPEPAPPVPTTA-Man-Man [peptide is SEQ ID NO:6]. Other glycopeptides were found to exist but were not further characterized. This Example describes the purification and chemical characterization of five glycopeptides from proteolytic digests of the 45 kDa MPT 32 glycoprotein. N-terminal amino acid sequencing coupled with fast atom bombardment-mass spectrometry (FAB-MS) demonstrates that each contains O-glycosylated Thr residues within a newly recognized, conserved O-glycosylation motif. Carbohydrate and MS analysis established that the glycosylation units in each case consist of single mannose, mannobiose or mannotriose units possessing ($\alpha$1–2) linkages. Also, the recent elucidation of the complete gene sequence for this protein (Laqueyrerie et al., supra) now allows the location of all glycosylation sites within the N-and C-terminal regions of the polypeptide backbone. Moreover, the elucidation of the complete primary structure of this unique glycoprotein enables further work on understanding its biosynthesis and physiological role, and approaches to its use as an antigen in for early diagnosis of TB.

A. Materials and Methods

1. Growth and Metabolic Labeling of *M. tuberculosis* with [U-$^{14}$C]Glucose

*M. tuberculosis* strain Erdman was cultured in glycerol alanine salts medium for 14 days at 37° C. with gentle agitation, conditions considered optimal for the production of culture filtrate proteins including the MPT32. To obtain the radiolabeled glycoprotein, organisms were grown in 51 of the medium at 37° C. with gentle agitation for 5 days, at which time [U-$^{14}$C]D-glucose (3 mCi per mmol; American Radiolabeled Chemicals, Inc., St. Louis, Mo.) was added to a final concentration of 1 mCi per liter, and the culture was incubated for an additional 8 days. The [$^{14}$C] labeled culture filtrate proteins were harvested as described by Dobos et al. (supra).

2. Purification of the 45 kDa Glycoprotein

The protocol described previously was applied with modifications (Dobos et al., supra). The culture filtrate was extracted with Triton X-114 and the aqueous phase applied to a high pressure liquid chromatography (HPLC) column (1 by 10 cm) of Protein-Pak 8HR DEAE (Waters, Milford, Mass.) connected to a Waters 600E HPLC system. The proteins were eluted with a gradient of LiCl $O_4$. Fractions containing the 45 kDa glycoprotein were identified by SDS-PAGE, and immunoblot analysis (Towbin, H. et al., 1979, *Proc. Natl. Acad. Sci. USA* 76:4350–4354) using anti-MPT32 polyclonal serum (provided by S. Nagai) as the probe. Fractions were pooled, dialyzed against 0.1 M $NH_4HCO_3$, dried by lyophilization, dissolved in solvent A (trifluoro acetic acid:water 0.1:99.9) and applied to a reversed phase HPLC (RP-HPLC) column (25 by 1.0 cm) of diphenyl modified silica (Vydac, Hesperia, Calif.) connected to a Waters 600E HPLC system. The 45 kDa protein was eluted at a flow rate of 2 ml per min with a linear gradient of 80% solvent A-20% solvent B (TFA:n-propanol:water 0.1:90:9.9), to 15% solvent A-85% solvent B. Fractions (1 ml) containing the purified 45 kDa glycoprotein were again identified by SDS-PAGE and immunoblot procedures. To ensure that all non-covalently associated carbohydrates were removed from the purified, radiolabeled 45 kDa glycoprotein, the material was rechromatographed using the RP-HPLC approach.

3. Enzymatic Digestions and Peptide Mapping

The purified 45-kDa glycoprotein (500 $\mu$g) was digested with either subtilisin (alkaline protease VIII; Sigma Chemical Co., St. Louis, Mo.) or a mixture of chymotrypsin/trypsin (1:1) (Sigma). The proteolytic digestions were carried out in 0.1 M $NH_4HCO_3$ (pH 7.8), 1 M guanidine-HCl at 37° C. for 2 h (10, 49). Products from both digestions were separated by reversed-phase HPLC on a column (4.6 '250 mm) of $C_{18}$ (Vydac). The peptides resulting from digestion with subtilisin were eluted at a flow rate of 0.5 ml per min with a multi-step, linear gradient of 90% solvent A and 10% solvent C (TFA:acetonitrile:water, 0.1:90:9.9) to 45% solvent A-55% solvent C over 60 min, followed by a linear gradient of 45% solvent A-55% solvent C to 8% solvent A-92% solvent C over 20 min. The peptides generated from the chymotrypsin/trypsin digest were eluted using a linear gradient of 98% solvent A-2% solvent C to 8% solvent A-92% solvent C over a 60 min period. The elution of peptides was monitored by $A_{214}$ using a Waters 486 UV detector.

Digestion of the protein with α-mannosidase was conducted as follows. The radiolabeled 45-kDa glycoprotein (135 μg) or purified glycopeptides (320 ng to 3 μg) were solubilized in 100 μl of 0.05 M $CH_3COONa$, pH 4.5, and incubated with 10 μl of α-mannosidase from *Canavalia ensiformis*, supplied as a 5 mg/ml suspension (Boehringer Mannheim, Indianapolis, Ind.), at 37° C. for 8 h. An additional 10 μl of α-mannosidase was added to the reaction mixture and further incubated for 16 h at 37° C. The digestions were terminated by incubating at 100° C. for 2 min, dried, and suspended in 5% $CH_3COOH$. The released Man residues were separated from the 45 kDa protein by applying the products to a $C_{18}$ reversed-phase Sep Pak cartridge (Waters) and washing with 5% $CH_3COOH$, followed by elution of the α-mannosidase-digested protein with n-propanol:acetic acid:water (50:5:45). The α-mannosidase-digested glycopeptides were separated from the released sugars in a similar manner. After washing the Sep-Pak cartridges with 5% $CH_3COOH$, the peptides were eluted with n-propanol:acetic acid:water (25:5:70) followed by n-propanol:acetic acid:water (50:5:45).

4. Carbohydrate Analysis

To analyze the sugar components of the protein, the radiolabeled 45-kDa protein (100 μg) was hydrolyzed with 2 M TFA at 120° C. for 2 h. The hydrolyzed material was dried under nitrogen, solubilized in water, and applied to an HPLC column (4×250 mm) of CarboPac PA1 (Dionex Corp., Sunnyvale, Calif.) connected to a Dionex HPLC system equipped with an advanced gradient pump and a pulsed amperometric detector. Monosaccharides were eluted from the column with 10 mM NaOH at a flow rate of 1 ml per min (9), collected in 1 ml fractions, counted by liquid scintillation, and the elution profile compared to that of a mixture of known monosaccharides.

5. Mass Spectral Analysis of Peptides and Glycopeptides

The products from subtilisin and chymotrypsin/trypsin digestions of the 45 kDa glycoprotein were resolved by microcapillary $C_{18}$ reversed-phase HPLC (45)[GET REF CITE]. Effluent was monitored by $A_{214}$ and then directly introduced into an on-line TSQ-700 triple-sector quadrapole mass spectrometer with an electrospray ionization source and collision gas as described (Swiderek, K. et al., 1995, "Trace structural analysis of proteins," p. 36. In B. Hancock et al. (eds.), *Meth. Enzymol*, Academic Press, Inc., New York). Glycopeptides were detected by scanning for a neutral loss of 162 AMU, indicative of the loss of hexose (i.e., Man) units, or 132 AMU for loss of pentose units (Huddleston, M. et al., 1993, *Anal. Chem.* 65:877–884.).

Methyl esterification of selected α-mannosidase digested peptides was performed in 0.5 N methanolic-HCl at 20° C. for 30 min. Upon drying under $N_2$, the methyl esterified peptides were N-acetylated in methanol: pyridine: acetic anhydride (50:1:5) for 30 min at 20° C.

The molecular weight of peptides, glycopeptides and α-mannosidase digested peptides was determined by FAB-MS. Individual peptides were dissolved in 5% $CH_3COOH$ (10 to 20 μl) and samples (1 μl) were added to the thioglycerol matrix. FAB-MS was conducted on a VG Autospec (Fission Instruments, Inc., Beverly, Mass.) fitted with a cesium ion gun operated at 25–30 kV. Data acquisition and processing were performed using the VG Analytical Opus software (Fission Instruments).

6. Preparation and Analysis of Oligoglycosyl Alditols

Oligosaccharides were released from purified glycopeptides by reductive β-elimination conducted as follows (Chattejee, D. et al., 1987, *J. Biol. Chem.* 262:3528–3533). Glycopeptides (320 ng-3 μg) were suspended in a solution of 0.05 M NaOH containing 1M $NaBH_4$, and maintained at 37° C. for 4 h. The reactions were neutralized and desalted by addition of Dowex 50 W×8 ($H^+$) beads (Sigma). Supernatants were collected and repeatedly evaporated to dryness under a stream of $N_2$ with the addition of 10% $CH_3COOH$ in $CH_3OH$. The released oligoglycosyl alditols were permethylated, hydrolyzed with 2 M $CF_3COOH$, reduced with $NaB[^2H]_4$, and peracetylated (McNeil, M. et al., 1989, *Meth. Enzymol.* 179:215–242.). GC-MS of the partially methylated alditol acetates was performed on a Hewlett-Packard 5890 gas chromatograph fitted with a (15 m×0.25 mm ID) DB-5 capillary column (J & W Scientific, Folsom, Calif.) and connected to a Hewlett-Packard 5790 mass detector as described (McNeil et al., supra).

7. Microsequence Analysis

Peptides isolated by reversed-phase HPLC or recovered following digestion with mannosidase were spotted directly onto PVDF membrane precoated with polybrene as described by Swiderek et al. (supra). Immobilized peptides were subjected to automated Edman degradation on a gas-phase sequencer equipped with a continuous flow reactor. The phenylthiohydantoin amino acid derivatives were identified by on-line reversed-phase chromatography.

B. Results

1. Sugar Analysis of the [$^{14}$C]-labeled 45 kDa Glycoprotein

Previous compositional analyses of the 45 kDa glycoprotein demonstrated a preponderance of Man plus significant amounts of other sugars, even though subsequent analysis of the covalently bound sugars implicated Man only. To solve this dichotomy and to establish the nature of the full array of bound sugars, *M. tuberculosis* was labeled with [U-$^{14}$C] glucose under conditions that allowed for uniformed labeling of all somatic sugars. The radiolabeled 45 kDa glycoprotein was exhaustively purified and subjected to acid hydrolysis. Analysis of the hydrolyzed sugars by high performance anion exchange chromatography demonstrated the presence of 3.19 nmol mannose, 0.98 nmol arabinose, 0.11 nmol glucose and a trace amount of galactose. However, only the Man component was radiolabeled, demonstrating that the other sugars were not of mycobacterial origin, probably arising from the various chromatographic supports used in the extensive purification steps applied to the 45 kDa glycoprotein.

2. Results of Proteolysis with Subtilisin

Previously, microcapillary liquid chromatography-MS and m/z 162 neutral loss scanning were used to identify four glycopeptides ($S_1$, $S_3$, $S_6$, and $S_{11}$) generated from a subtilisin digest of the 45 kDa glycoprotein. However, the conditions used to resolve these products allowed the $S_{11}$ peptide only to be obtained in pure enough form for structural analyses. Under present conditions, a well resolved HPLC map of the peptides from a subtilisin digestion of the 45 kDa protein was obtained. The products were then subjected to microcapillary chromatography-MS and neutral loss scanning, seeking peptides that fragmented to give a daughter ion of m/z 162 or 132, indicative of loss of hexosyl or pentosyl unit(s), respectively. The digest yielded 50 peptides ($S_2$–$S_{51}$), and, of these, only $S_7$, $S_{18}$, $S_{22}$, $S_{29}$, and $S_{41}$ produced daughter ions of m/z 162. No peptides were detected that produced daughter ions of m/z 132, results which were in agreement with the compositional analysis that indicated only mannosylation of the 45 kDa glycoprotein.

N-terminal amino acid sequence and masses of the individual peptides were established by automated Edman degradation and FAB-MS (Table 1). The (M+H)+ pseudomolecular ion of the $S_{41}$ glycopeptide was observed at m/z 1515.5. Thus, this product was identical to the $S_{11}$ glycopeptide previously described as the first bona fide glycopeptide in *M. tuberculosis* with the structure DPEPAPPVPTTA-Man-Man [SEQ ID NO:6]. N-terminal sequencing confirmed this identity (Table 1). The (M+H)+ pseudomolecular ion of the $S_{29}$ glycopeptide was established as m/z 1150.5, and the corresponding amino acid sequence was established as XPVAPPPPAAA [SEQ ID NO:7]. The amino-acid sequence of the $S_{18}$ glycopeptide (m/z 1008.6) was identical to that of the $S_{29}$ glycopeptide except for the absence of two Ala residues at the carboxyl terminus. Moreover, the difference between the (M+H)+ pseudomolecular ions of the $S_{29}$ and $S_{18}$ peptides (m/z 142) corresponded to two Ala residues. N-terminal amino acid analysis of the $S_{22}$ glycopeptide established the sequence GEVAPTPTXPTPQ [SEQ ID NO:8]. However, three individual (M+H)+ pseudomolecular ions of m/z 1781.9, 1619.8, and 1457.6 were observed by FAB-MS for this $S_{22}$ glycopeptide. The difference between these three ions was m/z 162, a result indicating differing levels of glycosylation of the same peptide. The $S_{33}$ peptide produced an N-terminal sequence of GEVAPTPTTPTPQ [SEQ ID NO:9] and an (M+H)+ pseudomolecular ion of m/z 1295.5, indicating that it was the non-glycosylated version of $S_{22}$ and that the site of glycosylation was the third Thr residue, the one that was not present in the N-terminal sequence of the $S_{22}$ glycopeptide. The final peptide demonstrating a neutral loss of m/z 162 was the $S_7$ peptide, which exhibited an (M+H)+ pseudomolecular ion of 954.4 and yielded the N-terminal sequence of ASPPSXA [SEQ ID NO:10]. For each of the glycopeptides the difference in the observed mass and predicted mass was a factor of 162 when Thr was substituted for the unidentified amino acid (Table 1), a substitution confirmed by alignment with the deduced amino acid sequence of the 45 kDa protein (Laqueyrerie et al., supra). In addition, several other non-glycosylated peptides from this digestion were identified by FAB-MS and the sequences of several of these established by automated Edman degradation (Table 4).

3. Results of Proteolysis with Chymotrypsin/Trypsin

Digestion of the 45 kDa glycoprotein with a mixture of chymotrypsin/trypsin produced a characteristic peptide map consisting of 31 individual peaks. Neutral loss scanning (m/z 162) revealed a single glycopeptide, $CT_6$. However, FAB-MS analysis of this glycopeptide yielded two (M+H)+ pseudomolecular ions of m/z 3614.9 and 3453.6 (Table 5). The difference between these two was m/z 162, indicating the same peptide with varying levels of glycosylation, like that observed for the $S_{22}$ peptide cluster. The $CT_6$ peptide was rechromatographed by RP-HPLC resulting in resolution of the two peptides. FAB-MS analysis coupled with N-terminal amino acid sequencing demonstrated identical sequences of

VAPPPAPAPAPAEPAPAPAPAGEVAPTPTTPTPQR [SEQ ID NO: 11]

but with a mono-Man unit on the m/z 3453.6 peptide, whereas the m/z 3614.9 peptide was diglycosylated. Thus, $CT_6$ represented a larger version of the $S_{22}$ glycopeptide cluster. Additionally, as with the $S_{22}$ cluster, a naturally non-glycosylated form of $CT_6$ was detected, $CT_7$ (m/z 3291.2) (Table 5). As with the peptides from the subtilisin digest, several non-glycosylated peptides from the chymotrypsin/trypsin digest were identified by FAB-MS and N-terminal amino acid sequencing (Table 5).

4. Detailed Analyses of Individual Glycopeptides

It is well known to be difficult to identify clearly amino acids at sites of glycosylation by means of N-terminal sequencing of O-glycosylated proteins or peptides. This problem was noted in the case of the glycopeptides generated by subtilisin digestion of the 45 kDa glycoprotein. Thus, the unidentifiable amino acid in each glycopeptide (Table 4) represented the site of glycosylation. The original analysis of the $S_{41}$ peptide by secondary ion-MS demonstrated that this peptide was O-glycosylated at a Thr residue (Dobos et al., supra). To confirm this earlier result and to determine whether the other glycopeptides were glycosylated in a similar manner, individual glycopeptides obtained from the subtilisin digested material were analyzed by FAB-MS before and after digestion with α-mannosidase. Additionally, the oligoglycosyl alditols released from the glycopeptides by β-elimination were analyzed by GC-MS in order to identify sugar residues and their linkages.

TABLE 4

FAB-MS and N-terminal amino acid sequence analysis of peptides generated by subtilisin digestion of 45 kDa glycoprotein from *M. tuberculosis*

| Fragment | Location | Sequence[1] Amino Acid | SEQ ID NO: | Mass[2] Predicted | Observed |
|---|---|---|---|---|---|
| $S_7$ | 13–19 | ASPPSXA | 12 | 630.3[3] | 954.4 |
| $S_8$ | 229–238 | NNPVDKGAAK | 13 | 013.5 | 1013.5 |
| $S_{10}$ | 123–128 | DTRIVL | 14 | 16.7 | 716.6 |
| $S_{12}$ | 20–26 | AAPPAPA | 15 | 94.3 | 594.2 |
| $S_{13}$ | 88–96 | GWVESDAAH | 16 | 71.4 | 972.0 |
| $S_{18}$ | 27–35 | XPVAPPPPA | 17 | 46.6[3] | 1008.6 |
| $S_{20}$ | 142–152 | TDSKAAARLGS | 18 | 076.6 | 1076.6 |
| $S_{21}$ | 100–115 | GSALLAKTTGDPPFPG | 19 | 528.8 | 1528.6 |
| $S_{22}$ | 269–281 | GEVAPTPTXPTPQ | 20 | 295.6[3] | 1781.9 |
| $S_{22}$ | 269–281 | GEVAPTPTXPTPQ | 20 | 295.6[3] | 1619.8 |
| $S_{22}$ | 269–281 | GEVAPTPTXPTPQ | 20 | 295.6[3] | 1457.6 |
| $S_{25}$ | 85–89 | LPAGW | 21 | 43.3 | 543.2 |
| $S_{26}$ | 126–130 | IVLGR | 22 | 57.4 | 557.3 |
| $S_{29}$ | 27–37 | XPVAPPPPAAA | 23 | 88.6[3] | 1150.5 |
| $S_{30}$ | 184–188 | YYEVK | 24 | 01.4 | 701.3 |
| $S_{33}$ | 269–281 | GEVAPTPTTPTPQ | 25 | 295.6 | 1295.5 |

TABLE 4-continued

FAB-MS and N-terminal amino acid sequence analysis of peptides generated by subtilisin digestion of 45 kDa glycoprotein from *M. tuberculosis*

| Fragment | Location | Sequence[1] Amino Acid | SEQ ID NO: | Mass[2] Predicted | Observed |
|---|---|---|---|---|---|
| $S_{36}$ | 36–46 | AANTPNAQPGD | 26 | 055.6 | 1055.7 |
| $S_{37}$ | 173–185 | LDANGVSGSASYY | 27 | 303.6 | 1303.5 |
| $S_{38}$ | 186–198 | EVKFSDPSKPNGQ | 28 | 432.7 | 1432.7 |
| $S_{41}$ | 1–12 | DPEPAPPVPXTA | 29 | 191.6[3] | 1515.5 |
| $S_{42}$ | 201–208 | TGVIGSPA | 30 | 01.4 | 701.4 |
| $S_{43}$ | 221–236 | FVVWLGTANNPVDKGA | 31 | 686.9 | 1686.7 |
| $S_{44}$ | 129–141 | GRLDQKLYASAEA | 32 | 421.7 | 1421.9 |
| $S_{45}$ | 158–165 | YMPYPGTR | 33 | 84.4 | 984.5 |
| $S_{46}$ | 56–65 | PNAPPPPVIA | 34 | 72.6 | 972.6 |
| $S_{47}$ | 168–173 | QETVSL | 35 | 76.4 | 676.4 |
| $S_{48}$ | 203–220 | VIGSPAANAPDAGPPQRW | 36 | 1803.9 | 1804.1 |
| $S_{49}$ | 79–84 | GGFSFA | 37 | 85.3 | 585.4 |
| $S_{50}$ | 241–247 | AESIRPL | 38 | 85.5 | 785.5 |

[1]Amino acid sequences obtained by automated Edman degradation are shown in bold face type. Amino acid sequences inferred from FAB-MS analysis and alignment with the deduced amino acid sequence of the 45 kDa protein are shown in normal face type.
[2]Monoisotopic mass of the predicted $(M + H)^+$ molecular ion.
[3]The predicted mass was calculated with Thr in the position of the unidentified amino acid.

TABLE 5

FAB-MS and N-terminal amino acid sequence analysis of peptides generated by chymotrypsin/trypsin digestion of the 45 kDa protein from *M. tuberculosis*

| Fragment | Location | N-terminal Amino Acid Sequence Analysis[1] | SEQ ID NO: | Predicted Mass[2] | Observed Mass |
|---|---|---|---|---|---|
| $CT_4{}^3$ | 176–184 | NGVSGSASY | 39 | 841.8 | 842.3 |
| | 126–130 | IVLGR | 40 | 557.4 | 557.7 |
| $CT_5$ | 201–219 | TGVIGSPAANAPDAGPPQR | 41 | 1775.9 | 1776.7 |
| $CT_6{}^3$ | 248–282 | VAPPPAPAPAPAEPAPAPAPA GEVAPTPTTPTPQR | 42 | 3290.4 | 3614.9 |
| | | VAPPPAPAPAPAEPAPAPAPA GEVAPTPTTPTPQR | 42 | 3290.4 | 3453.6 |
| $CT_7$ | 248–282 | VAPPPAPAPAPAEPAPAPAPA GEVAPTPTTPTPQR | 42 | 3290.4 | 3291.2 |
| $CT_8{}^3$ | 107–125 | TTGDPPFPGQPPPVANDTR | 43 | 1964.0 | 1964.9 |
| | 137–149 | ASAEATDSKAAAR | 44 | 1248.6 | 1248.2 |
| $CT_9{}^3$ | 126–134 | IVLGRLDQK | 45 | 1041.6 | 1042.1 |
| | 74–81 | IDNPVGGF | 46 | 818.4 | 818.6 |
| $CT_{10}$ | 201–220 | TGVIGSPAANAPDAGPPQRW | 47 | 1962.0 | 1962.6 |
| $CT_{12}$ | 186–200 | EVKFSDPSKPNGQIW | 48 | 1731.9 | 1733.0 |
| $CT_{17}{}^3$ | 225–247 | LGTANNPVDKGAAKALAES | 49 | 2307.2 | 2307.4 |
| | 90–99 | IRPLVESDAAHFDY | 50 | 1153.5 | 1153.5 |
| $CT_{19}$ | 82–89 | SFALPAGW | 51 | 848.4 | 848.3 |
| $CT_{25}$ | 84–106 | ALPAGWVESDAAHFDYGSAL LAK | 52 | 2390.2 | 2391.4 |
| $CT_{27}$ | 169–175 | ETVSLDA | 53 | 734.9 | 735.3 |

[1]Amino acid sequences obtained by automated Edman degradation are shown in bold face type. Amino acid sequences inferred from FAB-MS analysis and alignment with the deduced amino acid sequence of the 45 kDa glycoprotein are shown in normal face type.
[2]Monoisotopic mass of the predicted $(M + H)^+$ molecular ion.
Two $(M + H)^+$ molecular ions were observed by FAB-MS (a) $S_7$ Glycopeptide Initial FAB-MS of the α-mannosidase digested $S_7$ peptide did not yield a detectable pseudomolecular ion signal. However, a strong signal was observed at m/z 708.2 when the same sample was first N-acetylated and methyl esterified. The m/z difference between the undigested and core $S_7$ peptides indicated glycosylation with two α-Man residues.

Additionally, the m/z values of the pseudomolecular ions of the glycosylated and deglycosylated-N-acetylated-methyl esterified $S_7$ peptides were consistent with Thr being the unknown amino acid at position 6. Methylation analysis of the oligoglycosyl alditol released from the peptide by β-elimination demonstrated the presence of pre-reduced 2-linked and terminal Man residues (Table 6). Thus, the $S_7$ peptide possessed the amino acid sequence ASPPSTA [SEQ ID NO:54 and was O-glycosylated at the Thr residue with α1-2-linked mannobiose.

(b) $S_{22}$ Glycopeptide

As stated previously, the broad peak corresponding to the $S_{22}$ peptide was comprised of three individual peptides, all of which contained the same amino acid sequence but differed in the extent of their glycosylation. This cluster of peptides was rechromatographed by RP-HPLC, and the largest of the three peaks was selected for further FAB-MS analysis. The m/z difference between the (M+H)$^+$ pseudomolecular ions of the glycosylated and deglycosylated forms of the $S_{22}$ peptide was m/z 324, demonstrating that this component peptide of the $S_{22}$ cluster was glycosylated with two α-Man residues. N-terminal sequencing of the α-mannosidase digested form of this $S_{22}$ peptide produced a sequence identical to that obtained for the naturally occurring non-glycosylated $S_{33}$ peptide (GEVAPTPTTPTPQ; SEQ ID NO:25), confirming that the $S_{22}$ glycopeptide was O-glycosylated at the third Thr residue. Similar analyses of the two other glycopeptides of the $S_{22}$ cluster confirmed that one (m/z 1781.9) was glycosylated with three α-Man residues and the other (m/z 1457.6) with a single α-Man residue. Analysis of the (oligo)glycosyl alditols further demonstrated heterogeneous glycosylation of the peptide with α-Man, (α1-2)-mannobiose or (α1-2)-mannotriose.

(c) $S_{29}$ Glycopeptide

FAB-MS analysis of the α-mannosidase treated $S_{29}$ glycopeptide yielded two (M+H)$^+$ pseudomolecular ions of m/z 1150.5 and 988.5, indicating only partial removal of the α-Man residues. Nevertheless, the 988.5 (M+H)$^+$ pseudomolecular ion corresponded to the fully deglycosylated form of this peptide when Thr was substituted for the unknown N-terminal amino acid. Sugar analysis of the $S_{29}$ glycopeptide further demonstrated glycosylation by a single Man residue (data not shown). Together these results demonstrated that the N-terminal Thr of this peptide (TPVAPPPPAAA; SEQ ID NO:55) was glycosylated with a single α-Man residue. As expected, similar analyses of $S_{18}$ gave identical results for the nature and location of glycosylation.

(d) $S_{41}$ Glycopeptide

Previously, the $S_{41}$ glycopeptide was shown to be O-glycosylated at the position 10 Thr residue. α-Mannosidase digestion followed by N-acetylation, methyl esterification and FAB-MS analysis produced (M+H)$^+$ pseudomolecular ion of m/z 1297.6, indicating the loss of two α-Man residues. The oligoglycosylalditol released from the $S_{41}$ glycopeptide was found to be comprised of a pre-reduced 2-linked mannitol and a terminal Man (Table 6). Thus, the Thr residue at position 10 of this peptide was glycosylated with an (α1-2)-linked mannobiose.

In all, these results demonstrated that there were four sites of glycosylation on the 45 kDa MPT 32 glycoprotein and that each site of glycosylation consisted of a Thr residue O-linked to an α-mannose, α-mannobiose, or α-mannotriose. All of the glycosidic linkages were determined to be (α1-2). Of the four glycosylation sites, only one appeared to possess heterogeneity in the number of mannosyl residues present.

C-terminal regions of the mature 45 kDa glycoprotein. Specifically, Thr residues at amino acid positions 10 and 18 are O-glycosylated with the mannobiose unit α-D-Manp(1→2)-α-D-Manp, the Thr 27 is substituted with a single α-D-Manp unit, while Thr 277 (in the C-terminal region) may be linked to a α-D-Manp, α-D-Manp(1→2)-D-Manp or α-D-Manp(1→2)-α-D-Manp(1→2)-D-Manp unit. Such glycosylation microheterogeneity is consistent with other well described prokaryotic glycoproteins. Other known O-glycosylated bacterial proteins contain a GlcNAc unit O-linked to either Thr or Ser. In fact, the nature of O-glycosylation of the 45 kDa protein of *M. tuberculosis* is more reminiscent of the simpler sites of O-glycosylation found in the yeast mannoproteins/mannans (Lehle, L. et al., "Protein glycosylation in yeast," In: Montreuil J. et al. (eds). *GLYCOPROTEINS*. Elsevier, N.Y., 1995).

TABLE 6

GC-MS analysis of partially methylated alditol acetates from the permethylated oligoglycosyl alditols released by β-elimination of the glycopeptides obtained by subtilisin digestion of the 45 kDa glycoprotein MPT 32

| Peptide | Retention time (min)[1] | Fragment ions of partially methylated alditol acetates (m/z) | Sugar[2] |
|---|---|---|---|
| $S_7$ | 9.49 | 129, 145, 161, 205 | 2-linked Man[3] |
|  | 11.02 | 102, 118, 129, 145, 161, 162, 205 | terminal Man |
| $S_{22}$[4][(M + H)$^+$m/z 1619.8] | 9.49 | 129, 145, 161, 205 | 2-linked Man[3] |
|  | 11.02 | 102, 118, 129, 145, 161, 162, 205 | terminal Man |
| $S_{22}$[4][(M + H)$^+$m/z 1781.8] | 9.50 | 129, 145, 161, 205 | 2-linked Man[3] |
|  | 11.03 | 102, 118, 129, 145, 161, 162, 205 | terminal Man |
|  | 12.03 | 129, 130, 161, 190 | 2-linked Man[3] |
| $S_4$ | 9.50 | 129, 145, 161, 205 | 2-linked Man[3] |
|  | 11.03 | 102, 118, 129, 145, 161, 162, 205 | terminal Man |

[1]Retention time of the partially methylated alditol acetates separated by GC.
[2]The sugar residues were identified based on the diagnostic ions observed in the mass spectrum of the partially methylated alditol acetates and by referring to the retention time of authentic standards.
[3]pre-reduced 2-linked mannose
[4]The $S_{22}$ glycoside was rechromatographed by RP-HPLC to obtain the individual glycopeptides.

A comparison of glycosylated proteins confirms that a strict consensus sequence is not required for O-glycosylation. Nevertheless, several loose amino acid motifs for O-glycosylation are evident in these results and others' work (Gooley, A. A. et al., 1991, *Biochem. Biophys. Res. Commun.* 178:1194–120117; Gooley, A. A. et al., 1994, *Glycobiology* 4:413–417.). The most commonly observed site is a Ser or Thr residue within Pro-rich domains; the O-glycosylation of a Ser or Thr is increased significantly when a Pro residue is located at positions −1 or +3 relative to the glycosylated amino acid. Originally, we proposed that this motif applied in the case of the mycobacterial 45 kDa MPT32 glycoprotein. However, in this current study, the sequence data on individual glycopeptides illustrate a motif possessing at least two Pro residues located within a four-amino-acid stretch upstream of the glycosylated Thr.

Evaluations of the effects of O-glycosylation on the conformation of proteins indicate that the presence of sugar units in heavily clustered domains limits protein folding, leading to extended conformations of the protein in these areas. Thus, in the context of MPT 32, it is probable that the combination of glycosyl units in the vicinity of a preponderance of Pro residues will ensure a minimum of secondary or tertiary structure leading to a "stiff," extended conformation. This feature explains the dramatic difference in the predicted molecular mass of 45 kDa based on mobility in SDS-PAGE compared to the true molecular weight of 30.2 kDa (Laqueyrerie, A. et al., supra).

The present inventors hypothesize that glycosylation plays a role in the transport of the 45 kDa glycoprotein across the cellular envelope of *M. tuberculosis* analogous to the enhanced secretion observed for the O-glycosylated form of the cellulase produced by *Trichoderma reesei*. The gene sequence encoding the 45 kDa glycoprotein demonstrates the presence of a signal peptide similar to that of many other *M. tuberculosis* culture filtrate proteins (Young, D. B. et al., In: J. McFadden (ed.), *Molecular Biology of the Mycobacteria*. Surrey University Press, Surrey, U.K., 1990, pp. 1–35). However, in contrast to the 45 kDa glycoprotein, a large number of other *M. tuberculosis* culture filtrate proteins are associated with the cell wall (Anderson et al., 1991, supra). Accordingly, the extended conformation predicted for the N- and C-terminal regions of the 45 kDa protein, combined with extensive glycosylation in these regions, appear to be responsible for the exclusive targeting of this protein to the extracellular environment. Indeed, Laqueyrerie et al. (supra) suggested that this 45 kDa protein may contribute to the uptake and transport of metabolites across the mycobacterial cell wall and cytoplasmic membrane, which themselves are endowed with unusual physico-chemical attributes.

Mannosylation of mycobacterial proteins may bear similarities to that of the yeast mannoproteins. The di- and tri-mannosyl units of the 45 kDa glycoprotein are identical to the "mannose caps" of mycobacterial LAM (the so-called Man-LAM) in absolute configuration and linkage (Chatterjee, D. et al., 1992, *J. Biol. Chem.* 267:6234–6239), suggesting that the enzymatic machinery is shared by both systems. The mannosyl units of the 45 kDa protein may share a role in the phagocytosis of *M. tuberculosis*, analogous to that of the Man-LAM (Schlesinger, L. S. et al., 1994, *J. Immunol.* 152:4074–4079).

EXAMPLE IV

Isolation of Ag85 Complex Proteins

The three closely related Ag85 proteins have been extensively characterized. Because of their unique fibronectin binding capacity, their involvement in complement receptor mediated phagocytosis of *M. tuberculosis* has been suggested (P. Peake, et al., *Infect. Immun.* 61, 4834 (1993)) leading to the designation of their respective genes as fbpA, fbpB and fbpC (W. J. Philipp, et al., *Proc. Natl. Acad. Sci. USA* 93, 3137 (1996)).

Methods and Results

Figure 12:
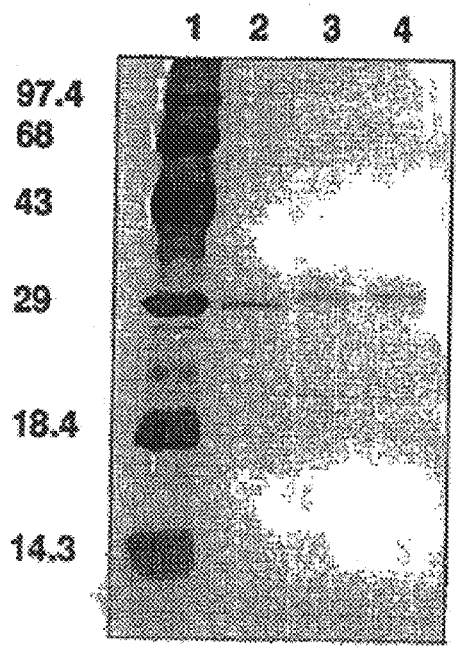
FIG. 12 shows the results of PAGE of Ag85 proteins purified by hydrophobic interaction chromatography: (lane 1) molecular weight standards (lane 2) purified 85B, (lane 3) 85C, (lane 4) 85A.
Figure 13:
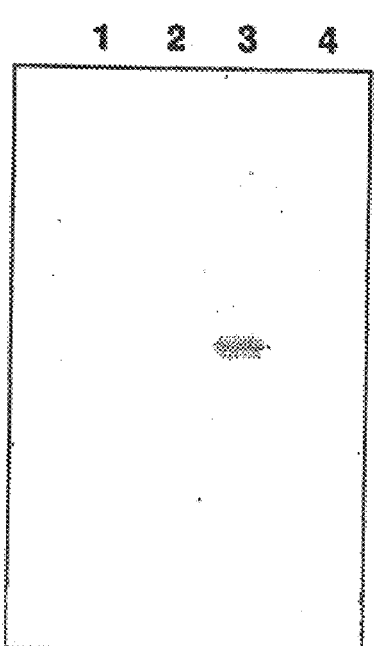
FIG. 13 shows Western blot analysis of the purified Ag85 products (from FIG. 12). Using mAb HYT-27 as the probe confirmed that each product was a member of the Ag85 complex. Lane designation is the same as in FIG. 12.

*M tuberculosis* H37Ra culture filtrate proteins (CFP) (the source of the Ag85 components in the context of their antigenicity; Wiker et al., 1992, supra) were harvested from cells in mid-logarithmic growth as described above and precipitated with 40% saturated $(NH_4)_2SO_4$, yielding a fraction with substantial transferase activity and containing the full complement of Ag85 components (FIG. 12) as confirmed by Western blot analysis (FIG. 13). Full purification of the individual Ag85 proteins was achieved by hydrophobic interaction chromatography as follows: Protein obtained by precipitation with a 40% saturated solution of $(NH_4)_2SO_4$ was dialyzed against storage buffer (10 mM $KH_2PO_4$ pH 7.5, 1 mM EDTA, 1 mM DTT) and 38 mg applied to a column (1×10 cm) of Phenyl Sepharose (Pharmacia Biotech, Uppsala, Sweden). The column was washed with 3 vol of storage buffer at a flow rate of 1 ml/min which eluted the majority of proteins while leaving the Ag85 complex bound to the Phenyl Sepharose matrix. The individual proteins of the Ag85 complex were eluted with 30 ml of buffer A (10 mM Tris HCl pH 8.6, 1 mM DTT, 1 mM EDTA) followed by a linear gradient composed of 100% buffer A to 100% buffer B (10 mM Tris HCl pH 8.6, 1 mM DTT, 1 mM EDTA, 50% ethylene glycol) over a 40 ml vol followed by 10 ml of 100% buffer B. Western blot analysis demonstrated that all were members of the Ag85 complex. Analysis by 2-D PAGE and silver-nitrate staining confirmed their purity and revealed migration patterns consistent with those previously reported (Nagai et al., supra).

Work on defining the molecular basis of bacterium-host cell interactions has dominated mycobacterial research for years with considerable effort devoted to elucidating the immunogenic and immunomodulatory characteristics of the Ag85 complex (Wiker et al., supra). These proteins are well known for their ability to stimulate a potent T-cell response (Havlir, D. et al., supra). However, until the present invention, there was no appreciation of the utility of Ag85C as an early antigen for serodiagnosis of TB. Whatever the role of Ag85C in pathogenesis, the existence of an early antibody response to this antigen as discovered by the present inventors provides a previously unappreciated utility for this protein in methods of early TB diagnosis.

EXAMPLE V

Definition of *M. tuberculosis* Culture Filtrate Proteins by 2-Dimensional Polyacrylamide Gel Electrophoresis Mapping, N-terminal Amino Acid Sequencing and Electrospray Mass Spectrometry As described above, in vitro cultivation of *M. tuberculosis* (Mt) results in the accumulation of a complex set of proteins in the extracellular milieu, collectively termed the culture filtrate proteins (CFPs). The most notable feature of this protein fraction is its immunodominance. CFP has been suggested to be a major repository of antigens involved in the protective immune response and to provide biochemical definition of this fraction. More recently, it has been contended that the dichotomous immune responses engendered by vaccination of experimental animals with live versus heat killed bacilli are attributable to the active secretion of such antigens by viable Mt. This hypothesis is supported by the demonstration of the ability of Mt CFP to induce a protective T-cell response. Attempts to define the immunologically active components within this fraction has led to the purification and characterization of several proteins including the 6 kDa ESAT6, 24 kDa MPT64, the Ag85 complex and MPT32. A strong antibody response against some of the CFPs has been noted, including the MPT32, 38 kDa PstS homologue and an 88 kDa protein. The present inventors have found these antigens and others described herein to be useful tools for early serodiagnosis of TB.

In the most extensive characterization of the Mt CFPs prior to this invention, Nagai and colleagues purified twelve major proteins, partially characterized them and mapped them by 2-D PAGE. Several other proteins, primarily those defined by mAb reactivity, have been located within culture filtrate preparations. Culture filtrates include not only actively secreted proteins but also somatic molecules that are released into the medium during replication or by autolysis. As demonstrated by Andersen et al. (supra) the protein profile of the culture filtrate is highly dependent on cultivation time. Further, the medium used and the means of incubation (static vs. shaking) may also impact on the profile of CFP. Thus, due to variations in the protocols used for CFP preparation, a clear understanding of the protein composition of this fraction is difficult to obtain from the current literature.

In this Example, the present inventors have combined 2-D PAGE, western blot analysis, N-terminal amino acid sequencing and liquid chromatography-mass spectrometry-mass spectrometry (LC-MS-MS) to develop a detailed map of culture filtrate proteins and have obtained the partial amino acid sequences for five previously undefined, relatively abundant proteins within this fraction which are found to be useful as early antigens for serodiagnosis of TB.

Additionally, a comparative analysis of 2-D PAGE maps of the CFP of three Mt laboratory strains, H37Ra, H37Rv and Erdman, demonstrated only minor differences. The results reported below provide a detailed portrait of the protein profile of this newly appreciated immunologically important fraction and a spectrum of proteins to which proteins from clinical isolates of Mt can be compared. The definition of these proteins as the major early antigens of TB recognized by circulating antibodies in TB patients early in the disease process is presented in Examples VII and VIII, below.

A. Materials and Methods

1. Growth of Mt and Preparation of Culture Filtrate Proteins

Mt strains H37Rv (ATCC 27294) and H37Ra (ATCC 25177) were obtained from American Type Culture Collection (Rockville, Md.). Mt strain Erdman (TMC 107) was obtained from the Trudeau Mycobacterial Collection. Initially, each Mt strain was inoculated from a 1 ml frozen stock into 10 ml of glycerol alanine salts (GAS) media; three such cultures were prepared for each strain. After incubation at 37° C. for 14 days with gentle agitation each 10 ml culture was passed two more times increasing the volume of media by ten times for each pass. The resulting one liter cultures were termed pass number four. For each Mt strain, three liters of pass number four cultures were used to inoculate 30 liters of GAS media. After 14 days of growth at 37° C. with gentle agitation, the culture supernatant was removed from the cells by filtration and the CFPs concentrated and processed as described. Protein content of the concentrated culture filtrate was quantitated by the bicinchoninic acid protein assay.

To establish growth curves for Mt strains H37Ra, H37Rv, and Erdman, culture tubes (13 by 100 mm) containing 3 ml of GAS media with 0.05% Tween 80 were inoculated with actively growing Mt cultures to an optical density of 0.1 at 600 nm. These cultures were incubated at 37° C. with stirring and optical densities at A600 were obtained every 12 hours for a 22 day period.

2. Antibodies

The mAbs IT-69 (HBT11) and IT-67 (L24.b4) were obtained from Dr. Ase B. Andersen, Statens Seruminstitut, Copenhagen, Denmark. The mAb A3h4 was obtained from Drs. P. K. Das and A. Rambukana, University of Amsterdam, Amsterdam, The Netherlands and mAbs F126-2 and HYB 76-8 were obtained from Dr. A. Kolk, Royal Tropical Institute, Amsterdam, The Netherlands, and Dr. I. Rosenkrands, Statens Seruminstitut, Copenhagen, Denmark, respectively. All other mAbs were supplied through the WHO Monoclonal Antibody Bank maintained by Dr. T. Shinnick, Centers for Disease Control, Atlanta, Georgia. Anti-MPT63 polyclonal serum was provided by Drs. H. Wiker and M. Harboe, University of Oslo, Oslo, Norway. Dr. S. Nagai provided polyclonal sera specific for MPT 32, MPT 35, MPT 46, MPT 53, and MPT 57.

3. SDS-PAGE and 2-D PAGE of Culture Filtrate Proteins

SDS-PAGE was performed under reducing conditions by the method of Laemmli with gels (7.5×10 cm×0.75 mm) containing a 6% stack over a 15% resolving gel. Each gel was run at 10 mA for 15 min followed by 15 mA for 1.5 h.

2-D PAGE separation of proteins was achieved by the method of O'Farrell with minor modifications. Specifically, 70 µg of CFP was dried and suspended in 30 µl of isoelectric focusing (IEF) sample buffer [9 M urea, 2% Nonidet P-40, 5% β-mercaptoethanol, and 5% Pharmalytes pH 3–10 (Pharmacia Biotech, Piscataway, N.J.)], and incubated for 3 h at 20° C. An aliquot of 25 µg of protein was applied to a 6% polyacrylamide IEF tube gel (1.5 mm by 6.5 cm) containing 5% Pharmalytes pH 3–10 and 4–6.5 in a ratio of 1:4. The proteins were focused for 3 h at 1 kV using 10 mM $H_3PO_4$ and 20 mM NaOH as the catholyte and anolyte, respectively. The tube gels were subsequently imbibed in sample transfer buffer for 30 min and placed on a preparative SDS-polyacrylamide gel (7.5×10 cm×1.5 mm) containing a 6% stack over a 15% resolving gel. Electrophoresis in the second dimension was carried out at 20 mA per gel for 0.3 h followed by 30 mA per gel for 1.8 h. Proteins were visualized by staining with silver nitrate.

4. Computer Aided Analysis of Two-Dimensional Gels

Silver stained 2-D PAGE gels were imaged using a cooled CCD digitizing camera and analyzed with MicroScan 1000 2-D Gel Analysis Software for Windows 3.x (Technology Resources, Inc., Nashville, Tenn.). Protein peak localization and analysis was conducted with the spot filter on, a minimum allowable peak height of 1.0, and minimum allowable peak area of 2.0.

5. Western Blot Analyses

Proteins, subjected to 2-D or SDS-PAGE, were transferred to nitrocellulose membranes (Schleicher and Schuell, Keene, N.H.) which were blocked with 0.1% bovine serum albumin in 0.05 M Tris-HCl, pH 7.5, 0.15 M NaCl, and 0.05% Tween 80 (TBST). These membranes were incubated for 2 h with specific antibodies diluted with TBST to the proper working concentrations (Table 7). After washing, the membranes were incubated for 1 h with goat anti-mouse or -rabbit alkaline phosphatase-conjugated antibody (Sigma) diluted in TBST. The substrates nitro-blue-tetrazolium and 5-bromo-4-chloro-3-indoyl phosphate (BCIP) were used for color development.

Mapping of proteins reactive to specific antibodies within the 2-D PAGE gel was accomplished using 0.1% India ink as a secondary stain for the total protein population after detection by immunoblotting. Alternatively, the Digoxigenin (DIG) Total Protein/Antigen Double Staining Kit (Boehringer Mannheim, Indianapolis, Ind.) was employed for those antibody-reactive proteins that could not be mapped using India ink as the secondary stain. Briefly, after electroblotting, the membranes were washed three times in 0.05 M $K_2HPO_4$, pH 8.5. The total protein population was conjugated to digoxigenin by incubating the membrane for one hour at room temperature in a solution of 0.05 M $K_2HPO_4$, pH 8.5 containing 0.3 ng/ml digoxigenin-3-0-methylcarbonyl-ϵ-amino-caproic acid N-hydroxysuccinimide ester and 0.01% Nonidet-P40. The membranes were subsequently blocked with a solution of 3% bovine serum albumin in 0.05 M Tris-HCl, pH 7.5, 0.15 M NaCl (TBS) for 1 h followed by washing with TBS. Incubation with specific antibodies was performed as described, followed by incubation of the membranes with mouse anti-DIG-Fab fragments conjugated to alkaline phosphatase diluted 1:2000 in TBS, for 1 h. The membranes were washed three times with TBS and probed with goat anti-mouse or -rabbit horse radish peroxidase-conjugated antibody. Color development for the proteins reacting to the specific anti-Mt protein antibodies was obtained with the substrates 4-(1,4,7,10-tetraoxadecyl)-1-naphthol and 1.8% $H_2O_2$. Secondary color development of the total protein population labeled with digoxigenin utilized BCIP and [2-(4-iodophenyl)-3-(4-nitrophenyl)-5-phenyl-tetrazolium chloride] as the substrates.

6. Amino Acid Sequence Analysis

To obtain N-terminal amino acid sequence for selected proteins, CFPs (200 μg) were resolved by 2-D PAGE and transferred to polyvinylidene difluoride membrane (Millipore, Milford, Mass.) by electroblotting at 50 V for 1 h, using CAPS buffer with 10% methanol. The membrane was stained with 0.1% Coomassie brilliant blue in 10% acetic acid and destained with a solution of 50% methanol and 10% acetic acid. Immobilized proteins were subjected to automated Edman degradation on a gas phase sequencer equipped with a continuous-flow reactor. The phenylthiohydantoin amino acid derivatives were identified by on-line reversed-phase chromatography as described previously.

7. LC-MS-MS Analysis

Selected CFP were subjected to LC-MS-MS to determine the sequence of internal peptide fragments. CFPs (200 mg) were resolved by 2-D PAGE and the gel stained with 0.1% Coomassie brilliant blue and destained as described for proteins immobilized to PVDF membranes. The protein of interest was excised from the gel, washed several times with distilled water to remove residual acetic acid and subjected to in-gel proteolytic digestion with trypsin. Peptides were eluted from the acrylamide and separated by C18 capillary RP-HPLC. The microcapillary RP-HPLC effluent was introduced directly into a Finnigan-MAT (San Jose, Calif.) TSQ-700 triple sector quadrupole mass spectrometer. Mass spectrometry and analysis of the data was performed as described by Blyn et al.

C. Results

1. Definition of Proteins Present in the Culture Filtrate of Mt H37Rv

Through the efforts of the World Health Organization (WHO) Scientific Working Groups (SWGs) on the Immunology of Leprosy (IMMLEP) and Immunology of Tuberculosis (IMMTUB) an extensive collection of mAbs against mycobacterial proteins has been established. This library as well as mAbs and polyclonal sera not included in these collections allowed for the identification of known mycobacterial proteins in the culture filtrate of Mt. A detailed search of the literature identified mAbs and/or polyclonal sera reactive against 35 individual Mt CFP (Table 7). Initially, the presence or absence of these proteins in the culture filtrate of Mt H37Rv, prepared for these studies, was determined by Western blot analyses. Of the antibodies and sera tested, all but one (IT-56) demonstrated reactivity to specific proteins of this preparation (Table 7). The mAb IT-56 is specific for the 65 kDa Mt GroEL homologue; a protein primarily associated with the cytosol. Additionally the mAb IT-7 reacted with a 14 kDa and not a 40 kDa CFP.

2. 2-D PAGE Mapping of known CFP of Mt H37Rv

Figure 14:
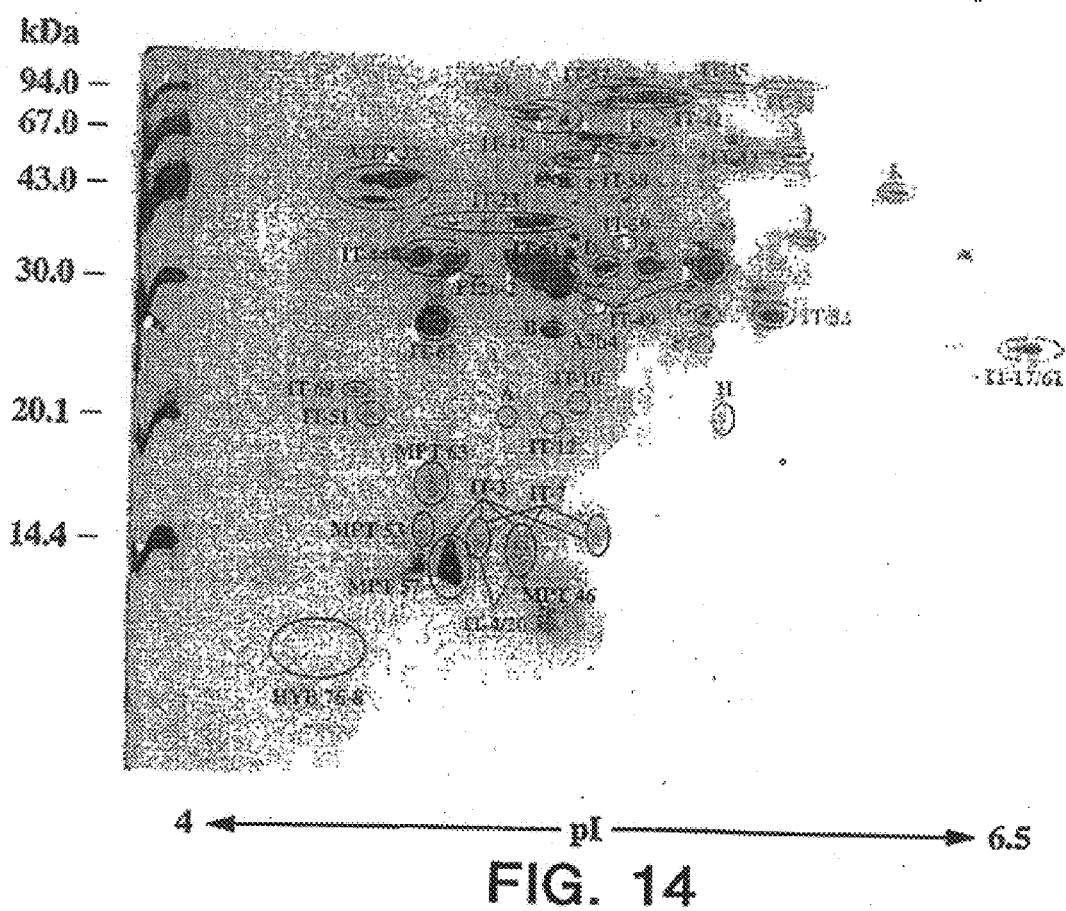
FIG. 14 shows a two dimensional PAGE of CFPs from M. tuberculosis H37Rv. Known proteins are designated by the mAb or polyclonal sera that they reacted to by 2-D western blot analysis. Unidentified proteins selected for N-terminal amino acid sequence are labeled A–K.

Using 2-D western blot analysis coupled with secondary staining (either India ink or Dig total protein/antigen double staining) the proteins reactive to specific mAbs or polyclonal sera were mapped within the 2-D PAGE profile of CFP of Mt H37Rv. In all, 32 of the reactive antibodies detected specific proteins resolved by 2-D PAGE (FIG. 14 and Table 7. However, two antibodies (IT-1 and IT-46), that were reactive by conventional western blot analysis, failed to detect any protein within the 2-D profile (FIG. 14 and Table 7). This lack of reactivity by 2-D western analysis, presumably, was due to the absence of linear epitopes exposed by the denaturing conditions used to resolve molecules for conventional Western blot analyses.

The majority of the antibodies recognized a single protein spot. However, several (IT-3, IT-4, IT-7, IT-20, IT-23, IT-41, IT-42, IT-44, IT-49, IT-57, IT-58, IT-61 and MPt 32) reacted with multiple proteins (FIG. 14). Five of these, IT-23, IT-42, IT-44, IT-57 and IT-58 reacted with protein clusters centered at 36 kDa, 85 kDa, 31 kDa, 85 kDa and 50 kDa, respectively. Additionally the proteins in each of these clusters migrated within a narrow pI range; suggesting that the antibodies were reacting with multiple isoforms of their respective proteins. In the case of the protein cluster at 85 kDa (which is the "88 kDa" early antigen of this invention) detected by IT-57, the most dominant component of this cluster was also recognized by IT-42.

Polyclonal sera against MPT 32 recognized a 45 and 42 kDa protein of relatively similar pI. While defining sites of glycosylation on MPT 32 (see above) we observed that this protein was prone to autoproteolysis and formed a 42 kDa product. Thus, the 42 kDa protein detected with the anti-MPT 32 sera was a breakdown product of the 45 kDa MPT 32 glycoprotein. The mAb (T-49 specific for the Antigen 85 (Ag85) complex clearly identified the three gene products (Ag85A, B and C) of this complex. The greatest region of antibody cross-reactivity was at molecular masses below 16 kDa. The most prominent protein in this region reacted with mAb IT-3 specific for the 14 kDa GroES homolog. This mAb also recognized several adjacent proteins at approximately 14 kDa. Interestingly, various members of this same protein cluster reacted with anti-MPT 57 and anti-MPT 46 polyclonal sera, and the mAbs IT-4, IT-7, and IT-20.

3. N-terminal Amino Acid Sequencing of Selected CFPs

The N-terminal amino acid sequences or complete gene sequences and functions of several of the CFPs of Mt, mapped with the available antibodies, are known. However, such information is lacking for the proteins that reacted with IT-42 IT-43, IT-44, IT-45, IT-51, IT-52, IT-53, IT-57, IT-59 and IT-69, as well as several dominant proteins not identified by these means. Of these, the most abundant proteins (IT-52, IT-57, IT 42, IT-58 and proteins labeled A–K) were selected and subjected to N-terminal amino acid sequencing (FIG. 14 and Table 8).

TABLE 7

Reactivity of CFPs of *M. tuberculosis* H37Rv to reported specific mAbs and polyclonal antisera

| Antibody[1] | MW (kDa) | Dilution Used | REACTIVITY 1-D | 2-D |
|---|---|---|---|---|
| IT-1 (F23-49-7) | 16 kDa | 1:2000 | + | − |
| IT-3 (SA-12) | 12 kDa | 1:8000 | + | + |
| IT-4 (F24-2-3) | 16 kDa | 1:2000 | + | + |
| IT-7 (F29-29-7) | 40 kDa | 1:1000 | + | + |

TABLE 7-continued

Reactivity of CFPs of *M. tuberculosis* H37Rv to reported specific mAbs and polyclonal antisera

| Antibody[1] | MW (kDa) | Dilution Used | REACTIVITY 1-D | 2-D |
|---|---|---|---|---|
| IT-10 (F29-47-3) | 21 kDa | 1:1000 | + | + |
| IT-12 (HYT6) | 17–19 kDa | 1:50 | + | + |
| IT-17 (D2D) | 23 kDa | 1:8000 | + | + |
| IT-20 (WTB68-A1) | 14 kDa | 1:250 | + | + |
| IT-23 (WTB71-H3) | 38 kDa | 1:250 | + | + |
| IT-40 (HAT1) | 71 kDa | 1:50 | + | + |
| IT-41 (HAT3) | 71 kDa | 1:50 | + | + |
| IT-42 (HBT1) | 82 kDa | 1:50 | + | + |
| IT-43 (HBT3) | 56 kDa | 1:50 | + | + |
| IT-44 (HBT7) | 32 kDa | 1:50 | + | + |
| IT-45 (HBT8) | 96 kDa | 1:50 | + | + |
| IT-46 (HBT10) | 40 kDa | 1:50 | + | – |
| IT-49 (HYT27) | 32–33 kDa | 1:50 | + | + |
| IT-51 (HBT2) | 17 kDa | 1:50 | + | + |
| IT-52 (HBT4) | 25 kDa | 1:50 | + | + |
| IT-53 (HBT5) | 96 kDa | 1:50 | + | + |
| IT-56 (CBA1) | 65 kDa | 1:50 | – | ND* |
| IT-57 (CBA4) | 82 kDa | 1:50 | + | + |
| IT-58 (CBA5) | 47 kDa | 1:50 | + | + |
| IT-59 (F67-1) | 33 kDa | 1:100 | + | + |
| IT-61 (F116-5) | 30 (24) kDa | 1:100 | + | + |
| IT-67 (L24.b4) | 24 kDa | 1:50 | + | + |
| IT-69 (HBT11) | 20 kDa | 1:6 | + | + |
| F126-2 | 30 kDa | 1:100 | + | + |
| A3h4 | 27 kDa | 1:50 | + | + |
| HYB 76-8 | 6 kDa | 1:100 | + | + |
| anti-MPT 32 | 50 kDa | 1:100 | + | + |
| anti-MPT 46 | 10 kDa | 1:100 | + | + |
| anti-MPT 53 | 15 kDa | 1:100 | + | + |
| anti-MPT 57 | 12 kDa | 1:100 | + | + |
| anti-MPT 63 - K64 | 18 kDa | 1:200 | + | + |

*ND: Not done
[1]Original designations for the World Health Organization cataloged Mab are given in parentheses.

Three of these proteins were found to correspond to previously defined products. The N-terminal amino acid sequence of the protein labeled D was identical to that of Ag85 B and C. This result was unexpected given that the IT-49 mAb failed to detect this protein and N-terminal amino acid analysis confirmed that those proteins reacting with IT-49 were members of the Ag85 complex. Second, the protein labeled E had an N-terminal sequence identical to that of glutamine synthetase. A third protein which reacted with IT-52 was found to be identical to MPT 51.

However, five of the proteins analyzed appeared to be novel. Three of these, those labeled B, C and IT-58 did not demonstrate significant homology to any known mycobacterial or prokaryotic sequences. The protein labeled I possessed an N-terminal sequence with 72% identity to the amino terminus of an α-hydroxysteroid dehydrogenase from a Eubacterium species, and the protein labeled F was homologous to a deduced amino acid sequence for an open reading frame identified in the Mt cosmid MTCY1A11. Repeated attempts to sequence those proteins labeled as A, G, H, J, K, IT-43, IT-44, IT-49 and IT-57 were unsuccessful.

Examples I and II show that a high molecular weight fraction of CFP of Mt reacted with a preponderance of sera from TB patients and that this fraction was distinguished from other native fractions in that it possessed the product reactive to mAb IT-57. In view of this, the protein cluster (the 88 kDa protein) defined by IT-42 and IT-57 was excised from a 2-D polyacrylamide gel, digested with trypsin and the resulting peptides analyzed by LC-MS-MS. Ten of the peptides from the digest yielded molecular masses and fragmentation patterns consistent with those predicted for tryptic fragments of the Mt KatG catalase/peroxidase (Table 8). Hence, the portion of the protein not reactive with IT 57 appears to be the KatG product. However, the IT 57-reactive part of the 88 kDa protein cluster did not have sequence homology (following LC-MS-MS analysis) to an identified Mt protein.

TABLE 8

N-terminal amino acid sequences or internal peptide fragments identified by LC-MS-MS of selected CFPs of *M. tuberculosis* $H_{37}Rv$.

| Protein | N-terminal AA Sequence | SEQ ID | Homology |
|---|---|---|---|
| A | None[1] | | |
| B | APPSCAGLD/GCTV | 56 | |
| C | XXAVXVT | 57 | |
| D | FSRPGLPVEYLQVPSP | 58 | Mt Antigen 85 A and C |
| E | TEKTPDDVFKLADDEKVEYVD | 59 | Mt Glutamine synthetase |
| F | XPVM/LVXPGXEXXQDN | 60 | Mt cosmid MTCY1A11 |
| G | None[1] | | |
| H | None[1] | | |
| I | XVYDVIMLTAGP | 61 | Eubacterium sp. VPI 12708 α-hydroxysteroid dehydrogenase |
| J | None[1] | | |
| K | None[1] | | |
| IT-43 | None[1] | | |
| IT-52 | APYENLMXP | 62 | *M. tuberculosis* MPT 51 |
| IT-58 | K/NVIRIXGXTD | 63 | |
| F126-2 | None[1] | | |

TABLE 8-continued

N-terminal amino acid sequences or internal peptide fragments
identified by LC-MS-MS of selected CFPs of *M. tuberculosis* H₃₇Rv.

| | INTERNAL PEPTIDES MAPPED | | HOMOLOGY |
|---|---|---|---|
| IT-42 | FAPLNSWPDNASLDK (129–143) | 64 | Mt. catalase/peroxidase |
| | EATWLGDER (201–209) | 65 | |
| | DAITSGIEVVWTNTPTK (311–327) | 66 | |
| | SPAGAWQYTAK (346–356) | 67 | |
| | DGAGAGTIPDPFGGPGR (357–373) | 68 | |
| | RWLEHPEELADEFAK (396–410) | 69 | |
| | TLEEIQESFNSAAPGNIK (519–536) | 70 | |
| | AGHNITVPFTPGR (556–569) | 71 | |
| | TDASQEQTDVESFAVLEPK (569–588) | 72 | |
| | GNPLPAEYMLLDK (599–611) | 73 | |
| | ANLLTLSAPEMTVLVGGLR (612–630) | 74 | |
| | VDLVFGSNSELR (692–703) | 75 | |
| | ALVEVYGADDAQPKF (704–718) | 76 | |

[1]"None" indicates that proteins were refractory to sequencing by Edman degradation.

4. Comparative CFP Profiles of Mt Strains H37Rv, H37Ra and Erdman

Figure 15A:
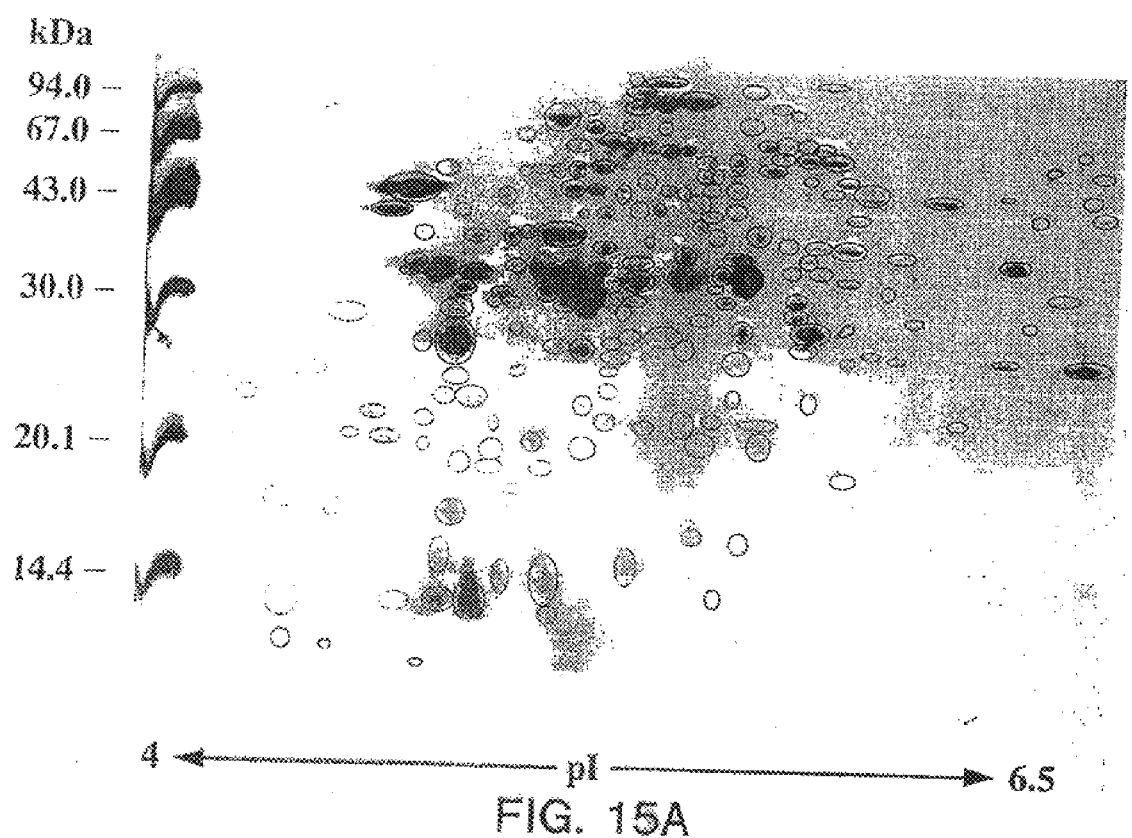
FIGS. 15A–15F show 2-D PAGE maps of CFPs of M. tuberculosis strains H37Rv, H37Ra and Erdman. Silver nitrate stained 2-D polyacrylamide gels of M. tuberculosis H37Rv (FIG. 15A), Erdman (FIG. 15C) and H37Ra (FIG. 15E) overlayed with the digitized image of proteins detected with the MicroScan 1000 2-D gel analysis software.
Figure 15B:
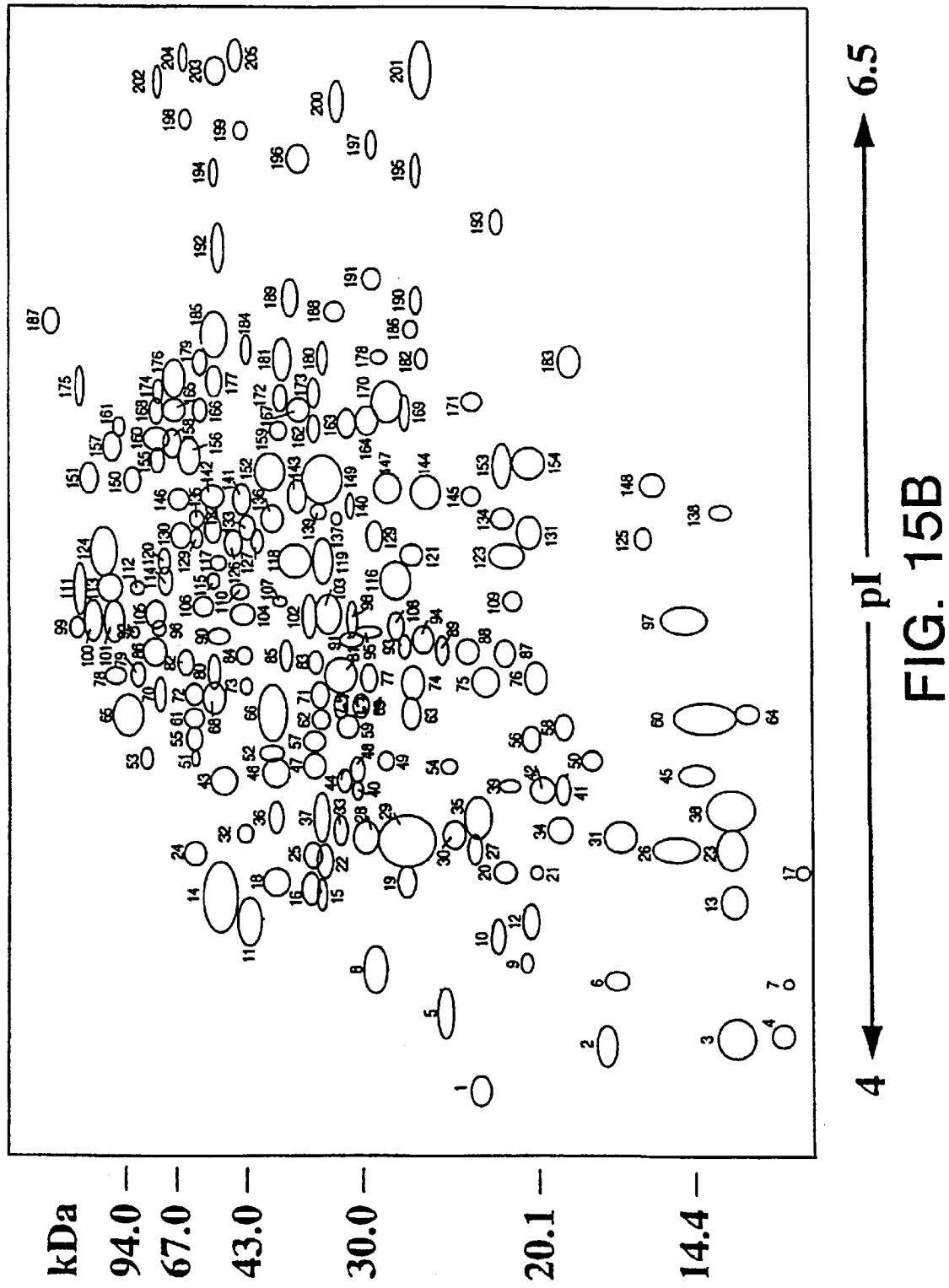
Figure 15C:
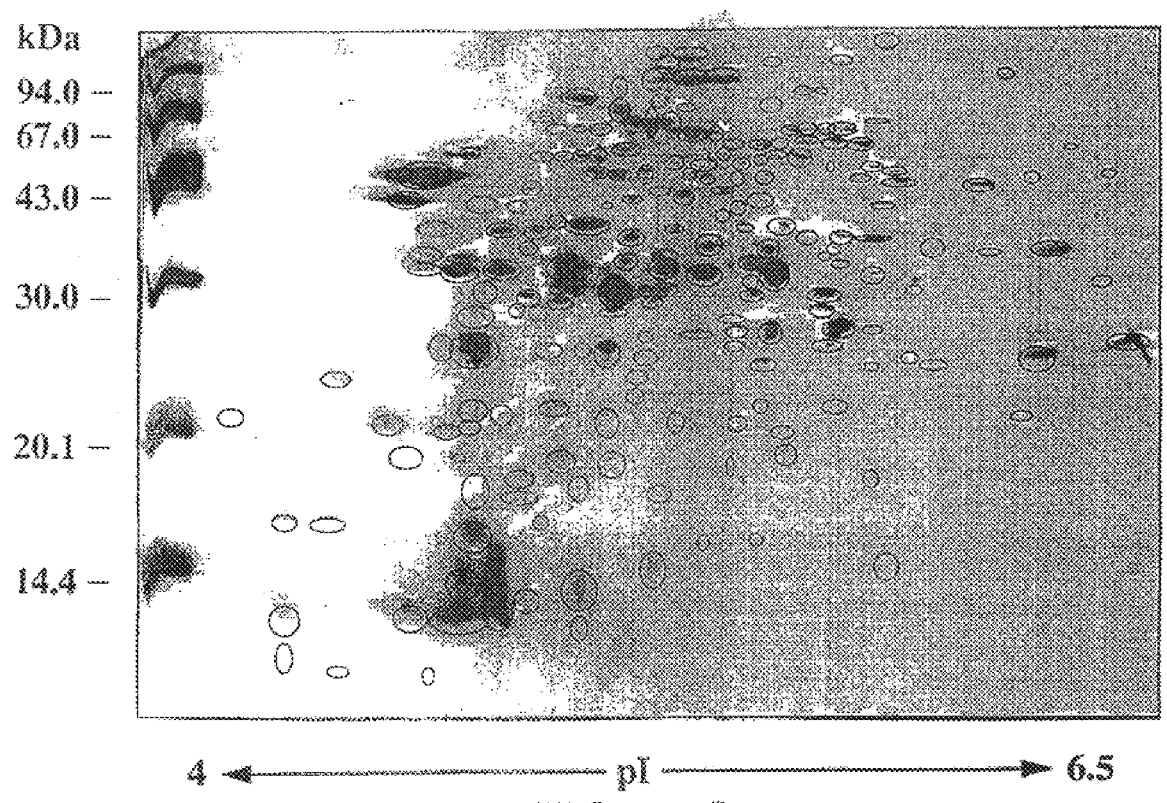
Figure 15D:
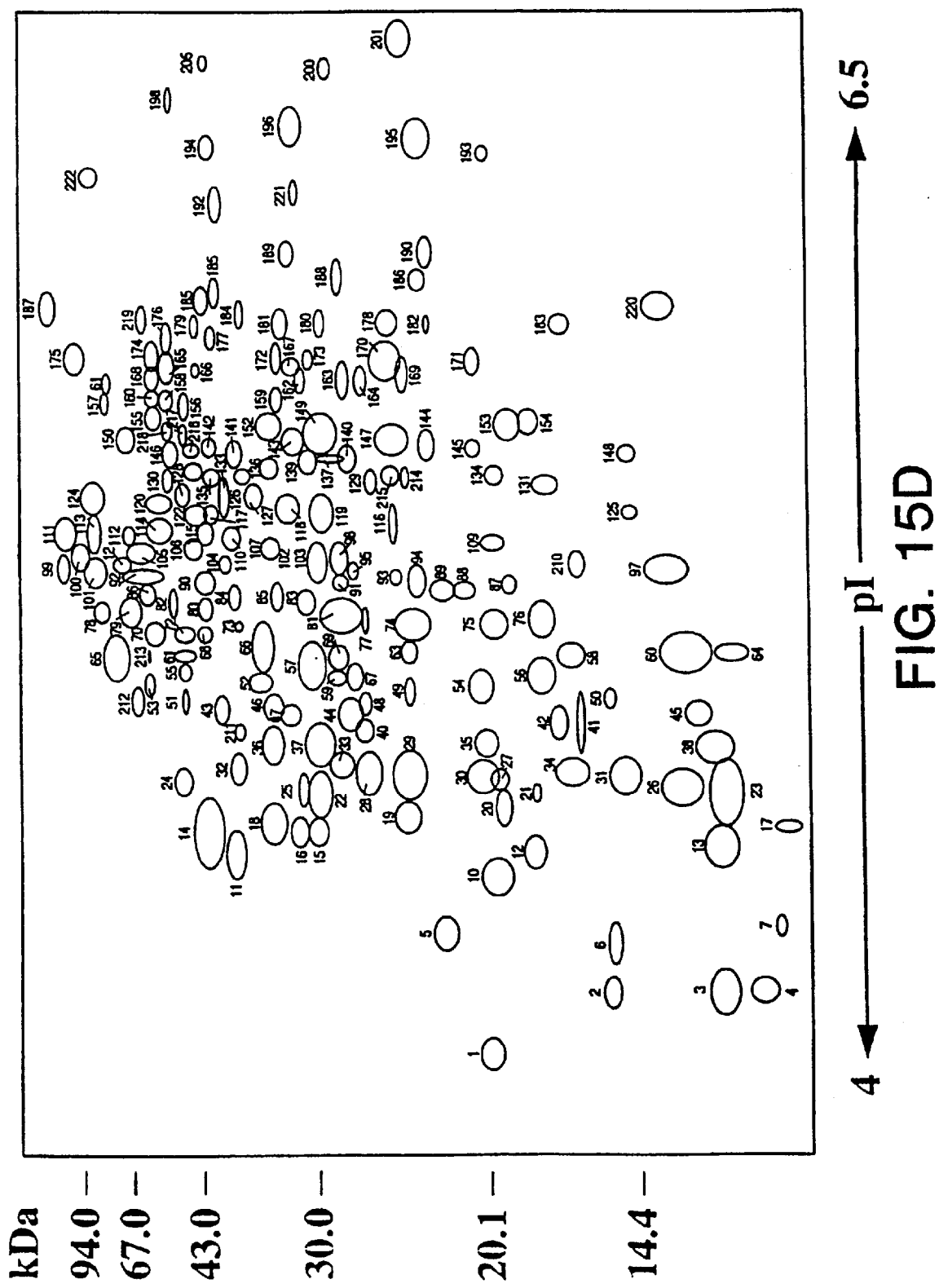

Comparative 2-D PAGE analysis of CFPs from three Mt type strains (H37Rv, H37Ra and Erdman) was performed to identify possible qualitative differences in their protein compositions. Initially, three separate lots of H37Rv CFP were pooled and resolved by 2-D PAGE. The silver stained gel was digitized and the data analyzed using the Microscan 1000 2-D gel analysis software. In all, 205 H37Rv protein spots were detected and individual proteins were numbered sequentially from acidic to basic pI and by descending molecular weight (FIGS. 15A and 15B and Table 9). Similar maps generated for the CFP of H37Ra and Erdman strains resulted in the recognition of 206 and 203 protein spots, respectively (FIGS. 15C–F and Table 9). Alignment of these three maps, using the 2-D main software, revealed a striking similarity between these three culture filtrate preparations. The protein spots of H37Ra and Erdman culture filtrate that matched those of the H37Rv culture filtrate were given identical numbers, and proteins characteristic of the H37Ra or Erdman strains were assigned original numbers (FIGS. 15A–F and Table 9).

Figure 15E:
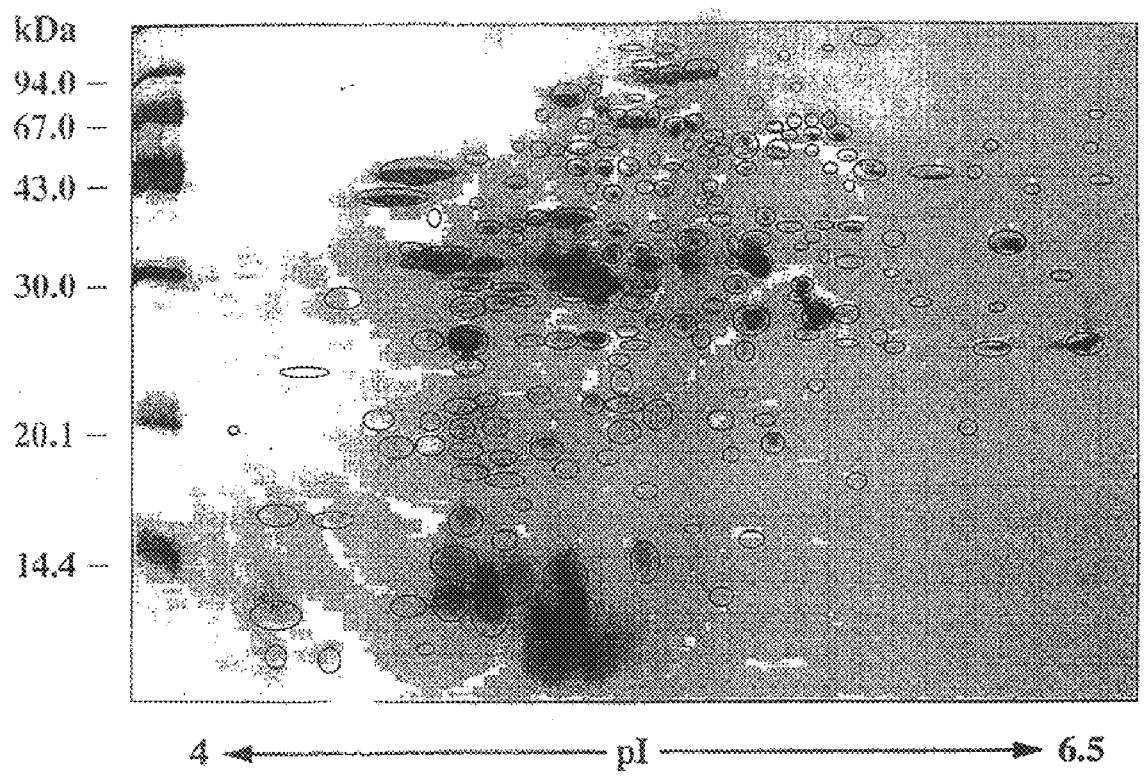
Figure 15F:
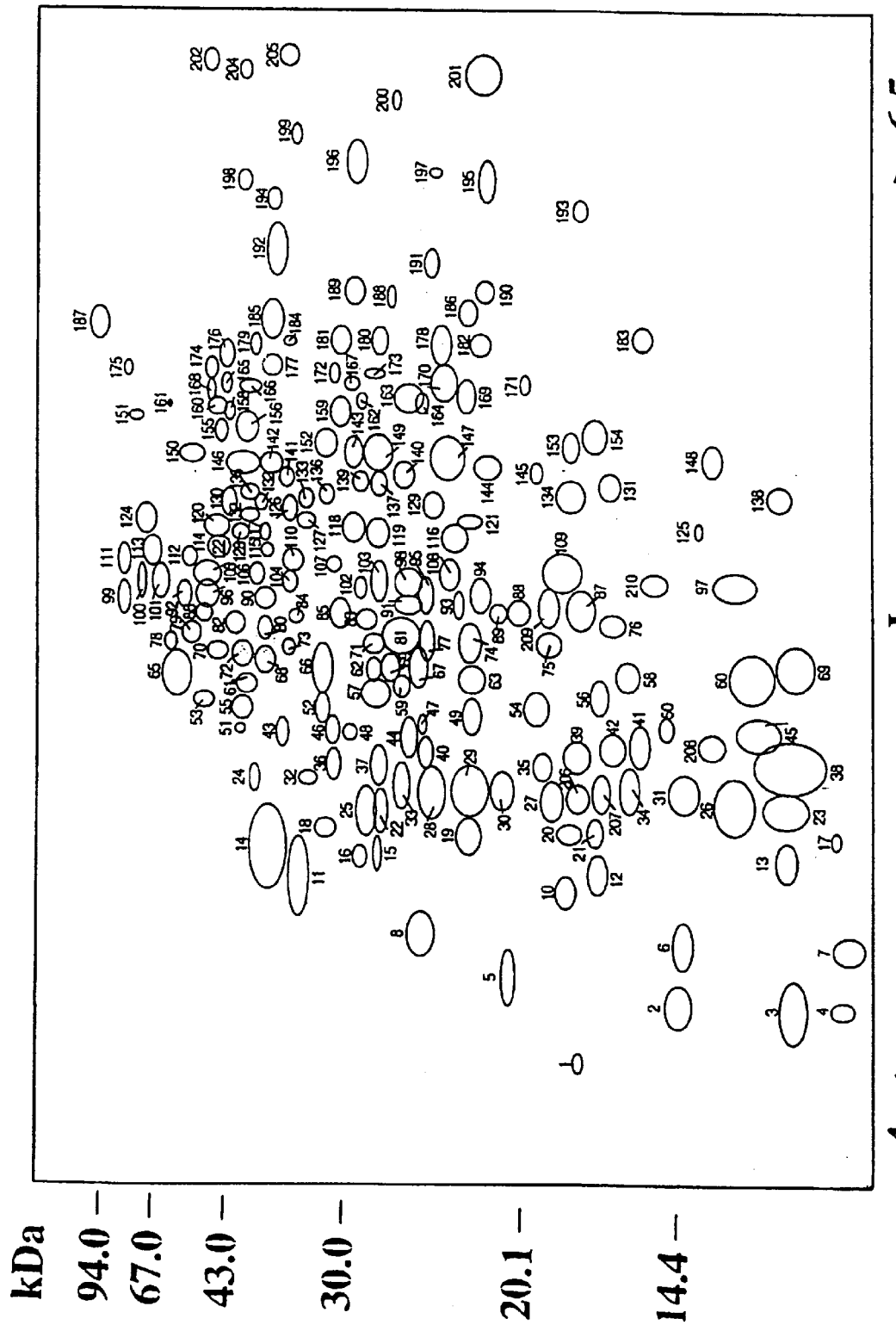

Several minor qualitative differences were identified. Strain H37Rv contained three apparently strain-specific proteins, numbered 9, 123 and 203 (FIGS. 15A and 15B and Table 9). Similarly, the proteins numbered 206, 207, 208 and 209 were apparently specific for H37Ra (FIGS. 15C and 15D and Table 9) and twelve strain specific proteins, numbered 211–222, were associated with the CFP of the Erdman strain (FIGS. 15E and 15F and Table 9). However, of the proteins apparently limited to Erdman, only 212, 210, 220, 221 and 222 were exclusive. The other seven were also present in H37Rv but at quantities below the preset software values for peak height and area detection levels. Several proteins were associated with two of the three type strains. Proteins numbered 8, 39, 62, 71, 108, 121, 138, 191, 197, 199, 202 and 204 were specific for H37Rv and H37Ra; whereas, protein 151 and 210 were present in the culture filtrate of Mt H37Rv and Erdman, and H37Ra and Erdman, respectively. Protein 151, identified by its reactivity with mAb IT-45 and its absence from H37Ra secreted proteins, was confirmed by 2-D Western blot analysis.

Figure 16:
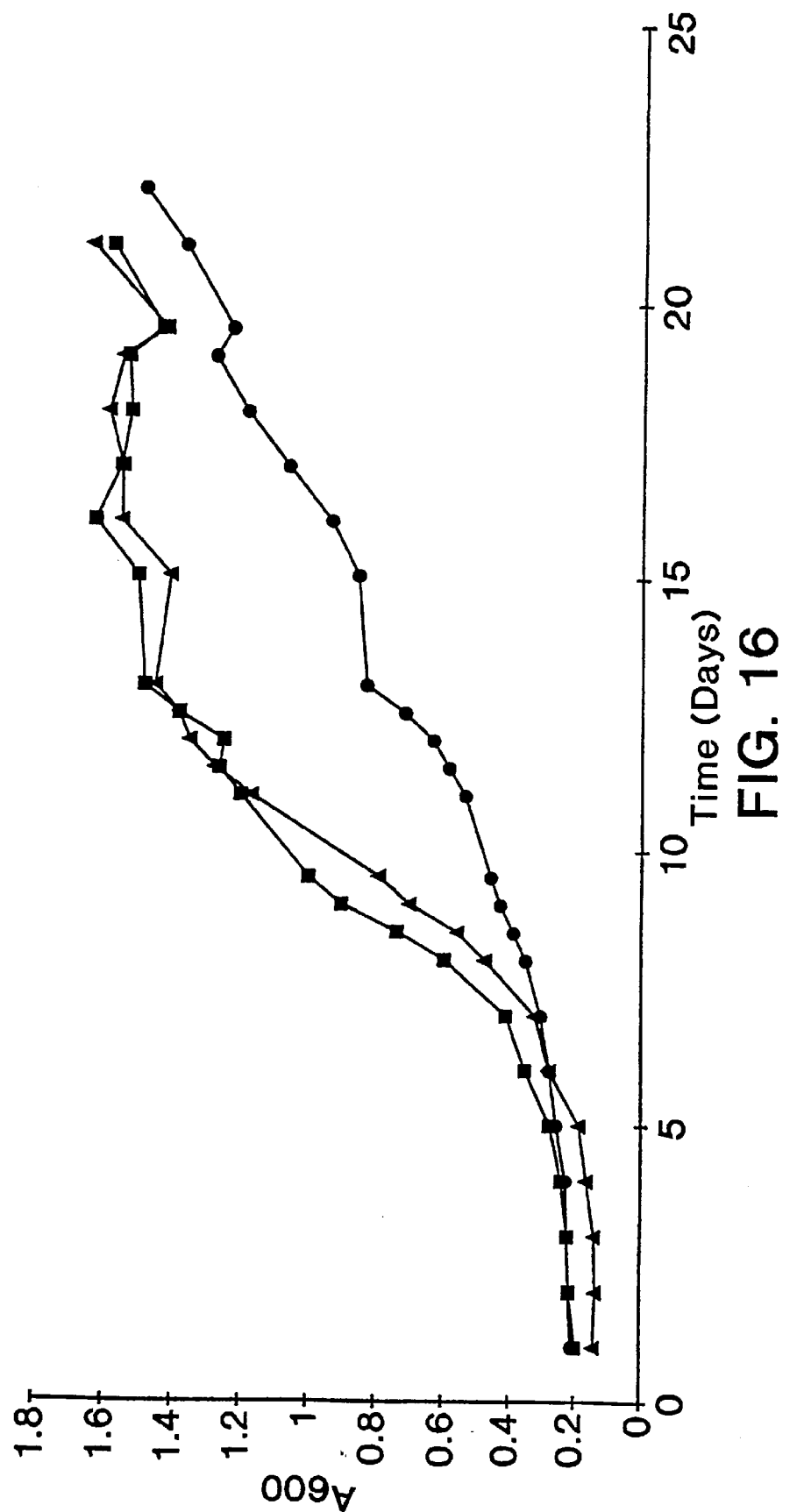
FIG. 16 shows growth curves of M. tuberculosis: strains H37Rv, H37Ra and Erdman. Data points are a mean of two or three cultures grown concurrently in GAS media.

In sum, proteins present only in one or two of the type strains were relatively minor components of the culture filtrates (FIGS. 15A–F). Their appearance and the resultant 2-D profile differences could have been caused by disparate growth rates or cellular autolysis during culture. The lack of detectable 65 kDa GroEL homologue, a marker for autolysis, in the present preparations discounted the possibility of autolysis. Analysis of growth curves showed that (a) H37Rv and Erdman had identical growth rates and (b) the 14 day CFP was harvested during the late-log growth phase (FIG. 16) In contrast the growth of H37Ra was slower and CFPs from this strain were taken during mid-log growth phase (FIG. 16). To ensure that the differences between H37Ra and the other strains was not due to differential growth rates, H37Ra culture filtrate was harvested at 21 days of growth and a 2-D PAGE map prepared and compared to that of the 14 day CFP. No differences were observed.

TABLE 9

Summary of protein spots detected by computer aided analysis of silver nitrate stained 2-D gels.

| Ref #. | H37Rv | H37Ra | Erdman | MW (kDa) | pI | Antibody Reactivity | Function/ Designation | N-terminal Sequence[1] | SEQ ID NO |
|---|---|---|---|---|---|---|---|---|---|
| 1 | 1 | 1 | 1 | 22.39 | ≦3 | | | | |
| 2 | 2 | 2 | 2 | 17.18 | ≦3 | | | | |
| 3 | 3 | 3 | 3 | 13.72 | ≦3 | | | | |
| 4 | 4 | 4 | 4 | 11.75 | ≦3 | | | | |
| 5 | 5 | 5 | 5 | 23.99 | 3.09 | | | | |
| 6 | 6 | 6 | 6 | 16.98 | 3.45 | | | | |
| 7 | 7 | 7 | 7 | 11.75 | 3.52 | HYB 76-8 | ESAT 6 | TEQQWDFAGI | 77 |
| 8 | 8 | 8 | NM | 27.23 | 3.63 | | | | |
| 9 | 9 | NM | NM | 20.30 | 3.82 | | | | |

TABLE 9-continued

Summary of protein spots detected by computer aided analysis of silver nitrate stained 2-D gels.

| Ref #. | H37Rv | H37Ra | Erdman | MW (kDa) | pI | Antibody Reactivity | Function/ Designation | N-terminal Sequence[1] | SEQ ID NO |
|---|---|---|---|---|---|---|---|---|---|
| 10 | 10 | 10 | 10 | 21.63 | 4.14 | IT-69 | | | |
| 11 | 11 | 11 | 11 | 38.90 | 4.31 | anti-MPT 32 | MPT 32 | DPAPAPPVPT | 78 |
| 12 | 12 | 12 | 12 | 20.07 | 4.31 | IT-51 | | | |
| 13 | 13 | 13 | 13 | 13.49 | 4.46 | | | | |
| 14 | 14 | 14 | 14 | 42.17 | 4.51 | anti-MPT 32 | MPT 32 | DPAPAPPVPT | 78 |
| 15 | 15 | 15 | 15 | 31.44 | 4.53 | | | | |
| 16 | 16 | 16 | 16 | 32.36 | 4.55 | | | | |
| 17 | 17 | 17 | 17 | 11.61 | 4.55 | | | | |
| 18 | 18 | 18 | 18 | 35.48 | 4.62 | | | | |
| 19 | 19 | 19 | 19 | 25.85 | 4.65 | | | | |
| 20 | 20 | 20 | 20 | 21.38 | 4.68 | | | | |
| 21 | 21 | 21 | 21 | 19.72 | 4.69 | | | | |
| 22 | 22 | 22 | 22 | 31.44 | 4.75 | IT-44 | | | |
| 23 | 23 | 23 | 23 | 13.57 | 4.76 | | | | |
| 24 | 24 | 24 | 24 | 48.70 | 4.79 | | | | |
| 25 | 25 | 25 | 25 | 32.55 | 4.79 | IT-44 | | | |
| 26 | 26 | 26 | 26 | 15.67 | 4.79 | anti-MPT 53 | MPT 53 | DECIQ | 79 |
| 27 | 27 | 27 | 27 | 22.26 | 4.81 | | | | |
| 28 | 28 | 28 | 28 | 28.35 | 4.83 | | | | |
| 29 | 29 | 29 | 29 | 26.15 | 4.83 | IT-67 | MPT 64 | FIKIF | 80 |
| 30 | 30 | 30 | 30 | 23.58 | 4.84 | | | | |
| 31 | 31 | 31 | 31 | 16.88 | 4.84 | anti-MPT 63 | MPT 63 | *AYPITGKLGSELT* | 81 |
| 32 | 32 | 32 | 32 | 38.02 | 4.87 | | | | |
| 33 | 33 | 33 | 33 | 29.85 | 4.87 | | | | |
| 34 | 34 | 34 | 34 | 19.05 | 4.88 | | | | |
| 35 | 35 | 35 | 35 | 22.26 | 4.92 | | | | |
| 36 | 36 | 36 | 36 | 35.08 | 4.93 | | | | |
| 37 | 37 | 37 | 37 | 31.44 | 4.93 | IT44/F126-2 | | | |
| 38 | 38 | 38 | 38 | 14.45 | 4.93 | anti-MPT 57 /IT-3 | GroES homolog MPT 57 | MAKVNIKPLE | 82 |
| 39 | 39 | 39 | NM | 20.87 | 4.99 | | | | |
| 40 | 40 | 40 | 40 | 28.67 | 5.00 | | | | |
| 41 | 41 | 41 | 41 | 18.62 | 5.00 | | | | |
| 42 | 42 | 42 | 42 | 19.50 | 5.00 | | | | |
| 43 | 43 | 43 | 43 | 40.74 | 5.02 | | | | |
| 44 | 44 | 44 | 44 | 29.68 | 5.02 | | | | |
| 45 | 45 | 45 | 45 | 14.96 | 5.02 | IT-3/4/7/20 | | | |
| 46 | 46 | 46 | 46 | 35.48 | 5.03 | IT-23 | PstS | CGSKPPSPET | 83 |
| 47 | 47 | 47 | 47 | 32.36 | 5.04 | | | | |
| 48 | 48 | 48 | 48 | 28.35 | 5.04 | | | | |
| 49 | 49 | 49 | 49 | 26.00 | 5.04 | | | | |
| 50 | 50 | 50 | 50 | 17.78 | 5.04 | | | | |
| 51 | 51 | 51 | 51 | 46.51 | 5.05 | | | | |
| 52 | 52 | 52 | 52 | 35.89 | 5.06 | IT-23 | PstS | CGSKPPSPET | 84 |
| 53 | 53 | 53 | 53 | 60.60 | 5.06 | | | | |
| 54 | 54 | 54 | 54 | 22.78 | 5.06 | | | | |
| 55 | 55 | 55 | 55 | 47.32 | 5.07 | | | | |
| 56 | 56 | 56 | 56 | 20.18 | 5.07 | | A | | |
| 57 | 57 | 57 | 57 | 31.62 | 5.08 | | | | |
| 58 | 58 | 58 | 58 | 18.62 | 5.08 | | | | |
| 59 | 59 | 59 | 59 | 29.68 | 5.08 | | | | |
| 60 | 60 | 60 | 60 | 14.54 | 5.09 | anti-MPT 46 IT-3/4/7/20 | MPT46 | RDSEK | 85 |
| 61 | 61 | 61 | 61 | 47.86 | 5.09 | | | | |
| 62 | 62 | 62 | NM | 31.26 | 5.09 | | | | |
| 63 | 63 | 63 | 63 | 25.56 | 5.09 | | | | |
| 64 | 64 | 64 | 64 | 13.11 | 5.09 | | | | |
| 65 | 65 | 65 | 65 | 72.86 | 5.09 | IT-40/IT-41 | DnaK homolog | MARAVGIDLG | 86 |
| 66 | 66 | 66 | 66 | 35.69 | 5.09 | IT-23 | PstS | CGSKPPSPET | 87 |
| 67 | 67 | 67 | 67 | 28.84 | 5.09 | | | | |
| 68 | 68 | 68 | 68 | 42.41 | 5.10 | | | | |
| 69 | 69 | 69 | 69 | 30.20 | 5.10 | | | | |
| 70 | 70 | 70 | 70 | 57.54 | 5.10 | | | | |
| 71 | 71 | 71 | NM | 31.62 | 5.10 | | | | |
| 72 | 72 | 72 | 72 | 47.86 | 5.10 | | | | |
| 73 | 73 | 73 | 73 | 38.46 | 5.10 | | | | |
| 74 | 74 | 74 | 74 | 25.56 | 5.10 | | B | *APPSCAGLD/GCTV* | 88 |
| 75 | 75 | 75 | 75 | 22.00 | 5.10 | | | | |
| 76 | 76 | 76 | 76 | 19.61 | 5.10 | IT-12 | 19 kDa lipoprotein | CSSNKSTTG | 89 |
| 77 | 77 | 77 | 77 | 28.18 | 5.10 | | | | |
| 78 | 78 | 78 | 78 | 79.43 | 5.10 | | | | |
| 79 | 79 | 79 | 79 | 66.83 | 5.10 | IT-41 | DnaK homolog | MARAVGIDLG | 90 |
| 80 | 80 | 80 | 80 | 42.17 | 5.10 | | C | *XXAVXVT* | 91 |

TABLE 9-continued

Summary of protein spots detected by computer aided analysis of silver nitrate stained 2-D gels.

| Ref #. | H37Rv | H37Ra | Erdman | MW (kDa) | pI | Antibody Reactivity | Function/ Designation | N-terminal Sequence[1] | SEQ ID NO |
|---|---|---|---|---|---|---|---|---|---|
| 81 | 81 | 81 | 81 | 29.85 | 5.10 | IT-49/ IT-61 | Antigen 85 B /MPT 59 | FSRPGLPVEY | 92 |
| 82 | 82 | 82 | 82 | 49.55 | 5.10 | IT-58 | | K/NVIRIXGXTD | 93 |
| 83 | 83 | 83 | 83 | 32.17 | 5.10 | | | | |
| 84 | 84 | 84 | 84 | 38.46 | 5.11 | | | | |
| 85 | 85 | 85 | 85 | 34.47 | 5.11 | | | | |
| 86 | 86 | 86 | 86 | 58.88 | 5.11 | | | | |
| 87 | 87 | 87 | 87 | 20.89 | 5.11 | IT-10 | | | |
| 88 | 88 | 88 | 88 | 23.04 | 5.11 | | | | |
| 89 | 89 | 89 | 89 | 24.27 | 5.11 | | | | |
| 90 | 90 | 90 | 90 | 42.17 | 5.11 | | | | |
| 91 | 91 | 91 | 91 | 29.17 | 5.11 | | | | |
| 92 | 92 | 92 | 92 | 69.98 | 5.11 | IT-41 | DnaK homolog | MARAVGIDLGT | 94 |
| 93 | 93 | 93 | 93 | 26.15 | 5.11 | A3h4 | | | |
| 94 | 94 | 94 | 94 | 25.12 | 5.11 | | | | |
| 95 | 95 | 95 | 95 | 27.86 | 5.11 | | | | |
| 96 | 96 | 96 | 96 | 56.23 | 5.11 | | | | |
| 97 | 97 | 97 | 97 | 15.22 | 5.11 | IT-3/7 | | | |
| 98 | 98 | 98 | 98 | 29.17 | 5.11 | | | | |
| 99 | 99 | 99 | 99 | 106.05 | 5.12 | | | | |
| 100 | 100 | 100 | 100 | 93.33 | 5.12 | | | | |
| 101 | 101 | 101 | 101 | 82.22 | 5.12 | | | | |
| 102 | 102 | 102 | 102 | 32.73 | 5.12 | IT-59 | | | |
| 103 | 103 | 103 | 103 | 31.08 | 5.12 | | D: Antigen 85 Homolog? | FSRPGLPVEYLQVPSP | 95 |
| 104 | 104 | 104 | 104 | 38.90 | 5.12 | | | | |
| 105 | 105 | 105 | 105 | 58.88 | 5.12 | | | | |
| 106 | 106 | 106 | 106 | 44.41 | 5.12 | | | | |
| 107 | 107 | 107 | 107 | 34.67 | 5.12 | | | | |
| 108 | 108 | 108 | NM | 26.61 | 5.12 | | | | |
| 109 | 109 | 109 | 109 | 20.54 | 5.12 | | | | |
| 110 | 110 | 110 | 110 | 38.90 | 5.13 | | | | |
| 111 | 111 | 111 | 111 | 104.71 | 5.13 | | | | |
| 112 | 112 | 112 | 112 | 66.83 | 5.13 | | | | |
| 113 | 113 | 113 | 113 | 85.11 | 5.14 | | | | |
| 114 | 114 | 114 | 114 | 55.59 | 5.14 | | E: Glutamine synthetase | TEKTPDDVFKLAKDEKVEYVD | 96 |
| 115 | 115 | 115 | 115 | 42.41 | 5.14 | | | | |
| 116 | 116 | 116 | 116 | 26.45 | 5.15 | | | | |
| 117 | 117 | 117 | 117 | 42.17 | 5.17 | | | | |
| 118 | 118 | 118 | 118 | 34.28 | 5.17 | | | | |
| 119 | 119 | 119 | 119 | 31.08 | 5.17 | IT-49 | Antigen 85 C /MPT 45 | FSRPGLPVEY | 97 |
| 120 | 120 | 120 | 120 | 55.59 | 5.17 | | E: Glutamine synthetase | TEKTPDDVFKLDEVE/T | 98 |
| 121 | 121 | 121 | NM | 25.70 | 5.17 | | | | |
| 122 | 122 | 122 | 122 | 45.71 | 5.18 | | | | |
| 123 | 123 | NM | NM | 20.65 | 5.18 | | | | |
| 124 | 124 | 124 | 124 | 85.11 | 5.19 | IT-42/IT-57 | Catalase/Peroxidase | MPEQHPPITE | 99 |
| 125 | 125 | 125 | 125 | 16.03 | 5.19 | | | | |
| 126 | 126 | 126 | 126 | 39.81 | 5.20 | | | | |
| 127 | 127 | 127 | 127 | 36.94 | 5.21 | | | | |
| 128 | 128 | 128 | 128 | 46.24 | 5.22 | | | | |
| 129 | 129 | 129 | 129 | 27.23 | 5.22 | | | | |
| 130 | 130 | 130 | 130 | 51.29 | 5.22 | | | | |
| 131 | 131 | 131 | 131 | 19.61 | 5.22 | | | | |
| 132 | 132 | 132 | 132 | 42.41 | 5.24 | | | | |
| 133 | 133 | 133 | 133 | 38.02 | 5.24 | | | | |
| 134 | 134 | 134 | 134 | 20.89 | 5.24 | | | | |
| 135 | 135 | 135 | 135 | 46.24 | 5.26 | | | | |
| 136 | 136 | 136 | 136 | 35.48 | 5.26 | | | | |
| 137 | 137 | 137 | 137 | 30.73 | 5.26 | | | | |
| 138 | 138 | 138 | NM | 13.49 | 5.27 | | | | |
| 139 | 139 | 139 | 139 | 31.62 | 5.28 | | | | |
| 140 | 140 | 140 | 140 | 29.17 | 5.30 | | | | |
| 141 | 141 | 141 | 141 | 38.46 | 5.33 | | | | |
| 142 | 142 | 142 | 142 | 42.41 | 5.34 | | | | |
| 143 | 143 | 143 | 143 | 33.50 | 5.34 | | | | |
| 144 | 144 | 144 | 144 | 24.97 | 5.34 | | F | XPVM/LVXPGXEXXQDN | 100 |
| 145 | 145 | 145 | 145 | 22.65 | 5.34 | | | | |
| 146 | 146 | 146 | 146 | 50.12 | 5.35 | | | | |
| 147 | 147 | 147 | 147 | 26.92 | 5.37 | | G | | |
| 148 | 148 | 148 | 148 | 15.67 | 5.37 | | | | |

TABLE 9-continued

Summary of protein spots detected by computer aided analysis of silver nitrate stained 2-D gels.

| Ref #. | H37Rv | H37Ra | Erdman | MW (kDa) | pI | Antibody Reactivity | Function/ Designation | N-terminal Sequence[1] | SEQ ID NO |
|---|---|---|---|---|---|---|---|---|---|
| 149 | 149 | 149 | 149 | 31.44 | 5.38 | IT-49 | Antigen 85 A /MPT44 | FSRPGLPVEY | 101 |
| 150 | 150 | 150 | 150 | 69.18 | 5.39 | | | | |
| 151 | 151 | NM | 151 | 94.41 | 5.40 | IT-45 | | | |
| 152 | 152 | 152 | 152 | 35.89 | 5.45 | | | | |
| 153 | 153 | 153 | 153 | 21.13 | 5.47 | | | | |
| 154 | 154 | 154 | 154 | 20.07 | 5.47 | | H | | |
| 155 | 155 | 155 | 155 | 58.88 | 5.50 | IT-43 | | | |
| 156 | 156 | 156 | 156 | 48.70 | 5.53 | | | | |
| 157 | 157 | 157 | 157 | 82.22 | 5.61 | | | | |
| 158 | 158 | 158 | 158 | 53.70 | 5.61 | | | | |
| 159 | 159 | 159 | 159 | 34.67 | 5.68 | | | | |
| 160 | 160 | 160 | 160 | 57.54 | 5.70 | | | | |
| 161 | 161 | 161 | 161 | 79.43 | 5.74 | | | | |
| 162 | 162 | 162 | 162 | 31.99 | 5.76 | | | | |
| 163 | 163 | 163 | 163 | 29.17 | 5.80 | | | | |
| 164 | 164 | 164 | 164 | 27.86 | 5.80 | | | | |
| 165 | 165 | 165 | 165 | 52.48 | 5.86 | | | | |
| 166 | 166 | 166 | 166 | 45.71 | 5.86 | | | | |
| 167 | 167 | 167 | 167 | 33.11 | 5.86 | | | | |
| 168 | 168 | 168 | 168 | 58.88 | 5.88 | | | | |
| 169 | 169 | 169 | 169 | 25.85 | 5.88 | | | | |
| 170 | 170 | 170 | 170 | 26.92 | 5.91 | IT-52 | MPT 51 | APYENLMVPSV | 102 |
| 171 | 171 | 171 | 171 | 22.13 | 5.93 | | | | |
| 172 | 172 | 172 | 172 | 34.67 | 5.98 | | | | |
| 173 | 173 | 173 | 173 | 31.81 | 5.98 | | | | |
| 174 | 174 | 174 | 174 | 56.23 | 6.02 | | | | |
| 175 | 175 | 175 | 175 | 98.86 | 6.08 | IT-53 | | | |
| 176 | 176 | 176 | 176 | 52.48 | 6.18 | | I | XVYDVIMLTAGP | 103 |
| 177 | 177 | 177 | 177 | 42.17 | 6.18 | | | | |
| 178 | 178 | 178 | 178 | 26.61 | 6.33 | | | | |
| 179 | 179 | 179 | 179 | 45.19 | 6.36 | | | | |
| 180 | 180 | 180 | 180 | 30.90 | 6.39 | | | | |
| 181 | 181 | 181 | 181 | 34.47 | 6.42 | | J | | |
| 182 | 182 | 182 | 182 | 24.83 | 6.42 | | | | |
| 183 | 183 | 183 | 183 | 18.20 | 6.49 | | | | |
| 184 | 184 | 184 | 184 | 38.02 | 6.55 | | | | |
| 185 | 185 | 185 | 185 | 41.93 | 6.73 | | | | |
| 186 | 186 | 186 | 186 | 25.41 | 6.88 | | | | |
| 187 | 187 | 187 | 187 | 133.35 | 7.00 | | | | |
| 188 | 188 | 188 | 188 | 30.20 | 7.17 | | | | |
| 189 | 189 | 189 | 189 | 33.50 | 7.30 | | | | |
| 190 | 190 | 190 | 190 | 24.97 | 7.39 | | | | |
| 191 | 191 | 191 | NM | 27.38 | 7.58 | | | | |
| 192 | 192 | 192 | 192 | 40.74 | 8.39 | | K | | |
| 193 | 193 | 193 | 193 | 20.54 | 9.64 | | | | |
| 194 | 194 | 194 | 194 | 41.93 | 10.33 | | | | |
| 195 | 195 | 195 | 195 | 24.97 | 10.41 | | | | |
| 196 | 196 | 196 | 196 | 32.73 | 10.74 | | | | |
| 197 | 197 | 197 | NM | 27.23 | 10 | | | | |
| 198 | 198 | 198 | 198 | 50.12 | 10 | | | | |
| 199 | 199 | NM | 199 | 38.90 | 10 | | | | |
| 200 | 200 | 200 | 200 | 29.68 | 10 | | | | |
| 201 | 201 | 201 | 201 | 24.83 | 10 | IT-17 /IT-61 | Superoxide dismutase /MPT 58 | MAEYTLPDLD | 104 |
| 202 | 202 | 202 | NM | 60.60 | 10 | | | | |
| 203 | 203 | NM | NM | 42.17 | 10 | | | | |
| 204 | 204 | 204 | NM | 48.70 | 10 | | | | |
| 205 | 205 | 205 | 205 | 38.90 | 10 | | | | |
| 206 | NM | 206 | NM | 20.87 | 4.83 | | | | |
| 207 | NM | 207 | NM | 20.40 | 4.79 | | | | |
| 208 | NM | 208 | NM | 15.67 | 5.02 | | | | |
| 209 | NM | 209 | NM | 22.61 | 5.11 | | | | |
| 210 | NM | 210 | 210 | 19.05 | 5.11 | | | | |
| 211 | NM | NM | 211 | 38.95 | 4.93 | | | | |
| 212 | NM | NM | 212 | 59.10 | 5.04 | | | | |
| 213 | NM | NM | 213 | 57.54 | 5.10 | | | | |
| 214 | NM | NM | 214 | 25.85 | 5.22 | | | | |
| 215 | NM | NM | 215 | 26.15 | 5.24 | | | | |
| 216 | NM | NM | 216 | 46.24 | 5.35 | | | | |
| 217 | NM | NM | 217 | 48.70 | 5.40 | | | | |
| 218 | NM | NM | 218 | 53.70 | 5.43 | | | | |
| 219 | NM | NM | 219 | 59.10 | 6.42 | | | | |
| 220 | NM | NM | 220 | 15.80 | 6.90 | | | | |

TABLE 9-continued

Summary of protein spots detected by computer aided analysis of silver nitrate stained 2-D gels.

| Ref #. | H37Rv | H37Ra | Erdman | MW (kDa) | pI | Antibody Reactivity | Function/ Designation | N-terminal Sequence[1] | SEQ ID NO |
|---|---|---|---|---|---|---|---|---|---|
| 221 | NM | NM | 221 | 32.36 | 9.00 | | | | |
| 222 | NM | NM | 222 | 94.35 | 9.30 | | | | |

[1]N-terminal sequences obtained by present inventors are in italics.

C. Discussion

In contrast to Mt cell wall, cell membrane and cytoplasmic proteins, the CFPs are well defined in terms of function, immunogenicity and composition. However, a detailed analysis of the total proteins, and the molecular definition and 2-D PAGE mapping of the majority of these CFPs has not been performed. Nagai and colleagues identified and mapped by 2-D PAGE the most abundant proteins filtrate harvested after five weeks of culture in Sauton medium. The present study used culture filtrates from mid- to late-logarithmic cultures of three Mt type strains H37Ra, H37Rv, and Erdman to provide for the first time a detailed analysis understanding of this widely studied fraction.

Computer analysis of the 2-D gels of CFP resolved 205, 203 and 206 individual protein spots from filtrates of strains H37Rv, H37Ra and Erdman, respectively. Of the total spots, 37 were identified using a collection of mAb and polyclonal sera against CFPs. Several of these antibodies recognized more than one spot; several are believed to react with multiple isoforms of the same protein or were previously shown to recognize more then a single gene product. In all, partial or complete amino acid sequences have been reported for 17 of the proteins mapped with the available antibodies (see Table 9).

While most of the antibodies used produced definitive results, one a cluster of four proteins in the 14 to 15 kDa range cross-reacted with several different mAbs that had been assigned to well characterized proteins (FIGS. 15A–F). The most dominant and acidic protein of this cluster reacted with mAb IT-3 and with the anti-MPT 57 polyclonal serum; both of which are specific for the 10 kDa GroES homologue. It was therefore concluded that the most dominant and acidic protein of this cluster is indeed the 10 kDa GroES homologue. IT-3 also bound to three adjacent protein spots, two of which were recognized by mAbs specific for the 16 kDa α-crystallin (IT-4 and IT-20). One protein reacted specifically with the anti-MPT 46 polyclonal serum (which is not specific for α-crystallin). When purified α-crystallin was added to the CFPs followed by 2-D PAGE, it did not co-migrate with the proteins in question. Thus, neither of the three proteins adjacent to the GroES homologue spot is α-crystallin; their identities await further analysis.

For greater molecular definition, a number of abundant products observed in the 2-D PAGE were subjected to N-terminal sequence analysis.

One such protein that migrated between Ag85B and Ag85C was found to have 16 residues (FSRPGLPVEYLQVPSP, [SEQ ID NO:95]) identical to the N-terminus of mature Ag85A and Ag85B, and different from Ag85C by a single residue (position 15). This protein spot was apparently merely a homologue of Ag85A or B. However, its complete lack of reactivity with an Ag85-specific mAb (IT-49), its weight greater than that of Ag85B and its shift in pI in relation to Ag85A suggested that this product may have resulted from post translational modifications. Alternatively, this protein may be a yet unrecognized fourth member of the Ag85 complex. However, members of the Ag85 complex appear to lack post-translational modifications in some reports whereas others report several bands corresponding to Ag85C after isoelectric focusing. However, no direct evidence supports the existence of a fourth Ag85 product.

A second product sequenced was a 25 kDa protein with a pI of 5.34. Its N-terminal sequence (XPVM/LVXPGXEXXQDN, [SEQ ID NO:100]) showed homology to an internal fragment (DPVLVFPGMEIRQDN, [SEQ ID NO:105]) corresponding to open reading frame 28c of the Mt cosmid MTCY1A11. Analysis of that deduced sequence revealed a signal peptidase I consensus sequence (Ala-Xaa-Ala) and an apparent signal peptide preceding the N-terminus of the 25 kDa protein sequenced above.

N-terminal sequencing of selected CFPs identified three novel products:

(1) protein with 72% identity to the N-terminus of a 42 kDa α-hydroxysteroid dehydrogenase of Eubacterium sp. VPI 12708;

(2) 27 kDa protein previously defined as MPT-51; and (3) 56 kDa protein previously identified as glutamine synthetase.

Three proteins showed no significant homology between their N-termini and any known peptides. For these proteins and for others that were refractory to N-group analysis, more advanced methods of protein sequencing (e.g., LC-MS-MS) will permit acquisition of extended sequence information.

The protein cluster which was recognized by mAbs IT-42 and IT-57 was a primary focus of this study. These proteins migrated at a molecular mass range of 82–85 kDa in one co-inventor's laboratory (or 88 kDa in another co-inventor's laboratory) and a pI range of 5.12–5.19. Results described in Examples I, II and VII referred to a CFP of approximately 88 kDa that reacted with 70% of sera from TB patients and demonstrated a specificity of 100%. Subsequent 2-D mapping coupled with 2-D western blot analysis showed these dominant antigens which induce early antibody responses in TB patients are the same as the proteins reactive with IT-57 and IT-42. As stated above, this antigen is referred to as the 88 kDa protein.

Although repeated attempts of N-terminal sequencing of the proteins of this cluster were unsuccessful, LC-MS-MS studies demonstrated the presence of one products in this cluster, the KatG catalase/peroxidase.

The generation of a detailed map of the culture filtrate of H37Rv through computer aided analysis allowed alignment and comparison of CFPs from other type strains of Mt which revealed qualitative differences. However, all differences detected were associated with proteins observed in minor quantities. One explanation for these differences was that the growth characteristics of the three strains varied significantly. Several studies have noted the length of incubation of Mt cultures has a dramatic effect on the profile of proteins released into the culture supernatant by the tubercle bacilli.

In particular, the work of Andersen et al. (supra) demonstrates that a small, well defined set of proteins are actively excreted during the first three days of incubation and that the gradual secretion of cell wall proteins occurred during the logarithmic growth phase. Further the release of cytoplasmic proteins, as monitored by the presence of isocitrate dehydrogenase and the 65 kDa GroEL homolog are not observed until the end of logarithmic growth phase.

Because this study utilized CFPs harvested during the mid- to late-logarithmic growth, and because Western blot analysis using mAb IT-56 ruled out the GroEL homologue, it is concluded that the CFP preparations used herein comprise (1) actively excreted proteins and (2) cell wall proteins secreted during logarithmic growth, but lack significant quantities of somatic proteins released by autolysis.

The generations of these 2-D protein maps of the culture filtrate of type strains of Mt now provides a baseline for the evaluation of the culture filtrates of a well defined collection of clinical isolates. Such an analysis is warranted given the recent observations that many Mt isolates lack the gene encoding MPT 40, and the loss of KatG activity in many isoniazid resistant strains of Mt is associated with the concurrent overexpression of AhpC.

This type of broad survey of virulent Mt strains has led to, and will continue to allow, the identification of immunologically important proteins and will lead to identification of novel virulence factors leading to improved approaches to chemotherapy. Thus, not only does the present invention enhance the overall knowledge in the art of the physiology of Mt, but it also provides immediate tools for early serodiagnosis.

EXAMPLE VI

Further Characterization of the 88 kDa Antigen by Recombinant Methods

A. Determination of Identity of the 88 kDa Antigen Reactive with the mAb IT-57

The 2-D Western blot analysis and the 2-D mapping of the culture filtrates of *M. tuberculosis* suggested that the serodominant 88 kDa antigen may be the same protein as is recognized by mAbs IT-42 and IT-57 (# 101, 113, 124, FIG. 15B). In order to determine the identity of these antigens, mass spectrometry of the peptides prepared from the protein cluster that reacted with both IT-57 and IT-42, was performed. The results showed that protein # 124, reactive with both mAbs, was the KatG catalase/peroxidase. Peptide analysis of protein spots # 101 and 113 that reacted with only mAb IT-57 were inconclusive. In order to obtain the protein reactive with mAb IT-57, approximately 20,000 phages of a λgt11 *M. tuberculosis* expression library were screened by plaque blotting using mAb IT-57. The λgt11 clone reactive with mAb IT-57 and encoding a protein with a molecular mass of 88 kDa is designated "λgt11 (IT-57)." The lysates from *E. coli* lysogenized with λgt11 (IT-57) and the LFCFP were separated by SDS-PAGE polyacrylamide on 10% gels, transferred to nitrocellulose filters and probed with mAb IT-57. Results are shown in FIG. 21, lanes 2–4. The mAb IT-57 recognized an 88 kDa band in the LFCFP (FIG. 21, lane 2), and in the lysate of *E. coli* lysogen of λgt11 (IT-57) (lane 3). No proteins in the lysate from the *E. coli* 1089 lysogenized with the wild type λgt11 reacted with the mAb.

B. Hybridization of the Clone Coding for the 88 kDa Antigen with the katG Gene

Since the spot on the 2-D blot reactive with mAb IT-57 showed some overlap with the spot reactive with mAb IT-42, it was important to determine if the 88 kDa protein encoded by the clone λgt11 (IT-57) was the katG gene product or if it was a different protein with a similar molecular weight and pI. The *M. tuberculosis* katG gene encoding the catalase/peroxidase enzyme cloned into the mycobacterial shuttle vector pMD31 was obtained from Dr. Sheldon Morris. See FIG. 22*a*, lane 4. The katG gene was excised from pMD31 with the enzymes KpnI and XbaI to yield an insert of 2.9 kb (FIG. 22*a*, lane 5). An insert of approximately 3.2 kb obtained after EcoRI digestion of the DNA from λgt11 (IT-57) (FIG. 22*a*, lane 3) was used for hybridization with the katG gene. FIG. 22*b* is an autoradiograph showing that the 3.2 kb insert from λgt11 (IT-57) hybridized with itself (lane 3), and with both the uncut pMD31 vector containing the katG gene (lane 4) and the katG insert DNA itself (2.9 kb, lane 5). Therefore, the 88 kDa antigen reactive with mAb IT-57 is in fact the catalase/peroxidase enzyme.

C. Sequence of the Recombinant 88 kDa Antigen Expressed in *E. coli*

To confirm that the 88 kDa protein made by λgt 11 (IT 57) was indeed the catalase/peroxidase enzyme, the insert DNA from this clone was sequenced and was found to be 99% homologous to the *M. tuberculosis* katG sequence by the NCBI BLAST search (accession number X68081).

D. Reactivity of TB sera with the Recombinant Catalase/peroxidase Protein Expressed in *E. coli*

To determine the reactivity of the 88 kDa catalase/peroxidase protein with TB patient sera, fractionated cell lysates of *E. coli-λgt*11 (IT-57) were probed with sera from 6 advanced TB patients (FIG. 21, lanes 5–10) and 4 $PPD^+$ healthy individuals (lanes 11–14). Neither the healthy control nor the TB sera reacted with the 88 kDa catalase/peroxidase protein. This lack of reactivity suggests that the 88 kDa catalase/peroxidase protein is not be the seroreactive antigen. The antibodies in the patient sera may be directed to a different 88 kDa protein. Alternatively, the 88 kDa may undergo post-translational modifications or may possess conformational epitopes that are absent from the recombinant 88 kDa catalase/peroxidase protein expressed in *E. coli*.

E. Reactivity of Tuberculosis Sera with the 88 kDa Catalase/Peroxidase Protein Expressed in *M. bovis* BCG Since TB patient sera did not react with the recombinant catalase/peroxidase expressed in *E. coli*, the katG-negative BCG strain 35747 transformed with either the pMD31:*M. tuberculosis* katG or with the control pMD31 plasmid (vector control) were tested. The LFCFPs, crude lysates from the lysogen λgt11 (IT-57), lysogenic *E. coli* 1089 infected with wild-type λgt11, katG negative BCG strain containing pMD31:*M. tuberculosis katG and the katG-negative BCG containing pMD*31, were separated by SDS-PAGE polyacrylamide on 10% gels (FIG. 23). The fractionated proteins were transferred to nitrocellulose filters and probed with an anti-catalase/peroxidase polyclonal serum (obtained from Dr. Clifton Barry, Rocky Mountain Laboratories, NIAID, Hamilton, Mont.) (FIG. 23A), mAb IT-57 (FIG. 23B), mAb IT-42 (FIG. 23C) and serum from an advanced TB patient (FIG. 23D). The anti-catalase/peroxidase polyclonal serum and the mAb IT-57 reacted strongly with an 88 kDa antigen in the LFCFP, in the *M. tuberculosis* katG containing *M. bovis* BCG and in *E. coli* λgt11 (IT-57). MAb IT-42 reacted with the same bands in the LFCFP and the *M. tuberculosis* katG BCG, but not with the 88 kDa protein expressed in *E. coli*. The control lanes containing lysates of *E. coli* 1089 (λgt11) or of the katG-negative *M. bovis* BCG (pMD31 alone) failed to react with any of the mAbs.

In contrast to the results obtained with the anti-catalase/peroxidase antibodies, the serum from the tuberculosis patient recognized an 88 kDa antigen in the lysates of the katG-negative BCG strain. This is evidence that the seroreactive 88 kDa antigen is a novel protein which has not been previously described.

F. Reactivity of Tuberculosis Sera with the *M. tuberculosis* 88 kDa Antigen

Figure 24A:
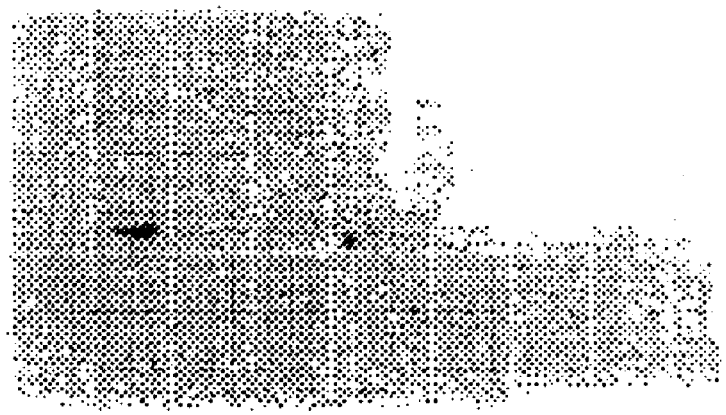
FIGS. 24A and 24B show lack of reactivity of anti-catalase/peroxidase antibodies with lysates of the katG-negative strain of M. tuberculosis (ATCC 35822).

In order to confirm that *M. tuberculosis* also contains a seroreactive 88 kDa antigen which is not the catalase/peroxidase, a katG-negative strain of *M. tuberculosis* (ATCC 35822) was tested. Lysates from this strain failed to react with any of the anti-catalase/peroxidase antibodies (FIG. 24A, lanes 3, 5, 7).

Figure 24B:
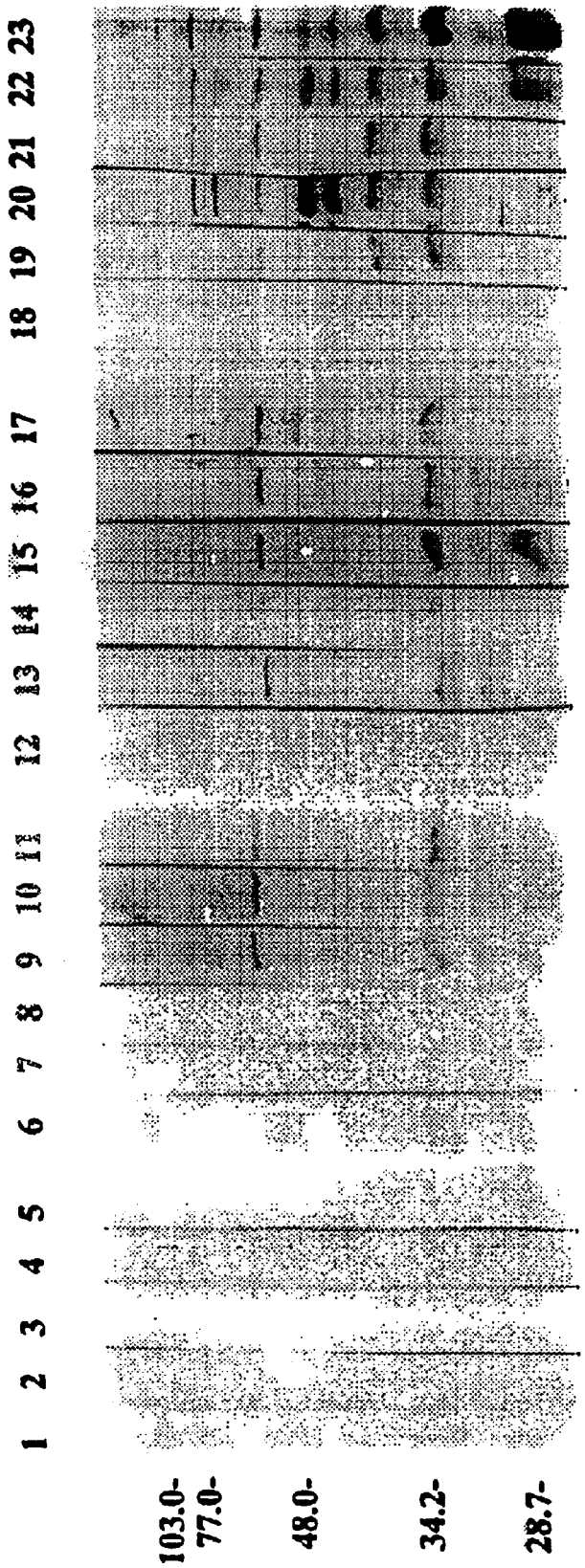

However, when individual sera from healthy controls and TB patients of all three groups were tested with the same lysates, all the group III and group IV sera reacted with the 88 kDa protein (FIG. 24B).

Identification of the Amino Acid Sequence of the Sero-Reactive 88 kDa Protein The culture filtrate protein from a katG-negative strain of *M. tuberculosis* (ATCC 35822) was resolved as above by 2-D PAGE. The protein spot ("Spot 1") corresponding to the sero-reactive 88 kDa protein was cut out of the gel and subject to an in-gel digestion with trypsin. The resulting tryptic peptides were exteracted, applied to a $C_{18}$ RP-HPLC column, and eluted with an increasing concentration of acetonitrile. The peptides eluted in this manner were introduced directly into a Finnigan LCQ Electrospray mass spectrometer. (See Materials and Methods above and Example III for further details.) The molecular mass of each peptide was determined, as was the charge state, with a zoom-scan program.

Identification of the 88 kDa protein was achieved by entering the mass spectroscopy date obtained above into the MS-Fit computer program and searching it against the *M. tuberculosis* database. The data input into the MS-Fit analysis amd the resulsts are shown below.

| Peptide Masses Input (mass tolerance: ±1.5 Da) | | | |
|---|---|---|---|
| Mass (m/z) | Charge (z) | Mass (m/z) | Charge (z) |
| 527.9 | +2 | 770.0 | +2 |
| 1054.5 |  | 948.1 | +2 |
| 559.0 | +2 | 961.8 | +2 |
| 947.5 |  | 810.7 | +2 |
| 553.4 | +2 | 720.5 | +2 |
| 560.0 | +2 | 740.5 | +2 |
| 1105.5 |  | 1209.0 | +3 |
| 696.3 | +2 | 640.8 | +2 |
| 866.0 | +2 | 933.5 | +2 |
| 1002.3 | +2 | 784.3 | +2 |
| 904.7 | +2 | 1545.7 | +2 |
| 820.6 | +2 | 1287.0 | +2 |

MS-fit Search Results

| | | |
|---|---|---|
| Sample ID (comment): | Magic Bullet digest | |
| Database searched: | NCBInr.07.09.99 | |
| Molecular weight search | (65000–97000 Da) | selects 21170 entries. |
| Full pI range: | 324311 entries. | |
| Species search | (MYCOBACTERIUM) | selects 5990 entries. |

Combined molecular weight, pI and species searches select 333 entries.
MS-Fit search selects 80 entries (results displayed for top 10 matches

| MS-FIT SEARCH DATA INPUT | | |
|---|---|---|
| Database: | NCBInr.07.09.99 | DNA Frame translation: 3 |
| Species: | Mycobacterium | |
| MW of Protein: | (from 65000 Da to 97000 Da) | |
| Protein pI: | (from 3.0 to 10.0) | All☑ |
| Digest Used: | Trypsin | Max. # Missed Cleavages: 2 |
| Cysteines Modified by: | acrylamide | |
| Peptide N terminus: | Hydrogen (H) | |
| Peptide C terminus: | Free Acid (OH) | |
| Sample ID (comment): | Magic Bullet digest | |
| Max. reported Hits: | 25 | |
| Possible Modifications Mode: | Oxidation of M | |
| Peptide Mass Shift: | ±40.1 Da | |
| Peptide Masses are: | average | |
| Min. # Peptides to Match | 9 | |
| Report MOWSE Score☑ | Pfa: 0.4 | |

Result Summary

| Rank | MOWSE Score | # (%) Masses Matched | | Protein MW (Da)/pI | Species | NCBInr. 9.7/98 Accession # | Protein Name |
|---|---|---|---|---|---|---|---|
| 1 | $6.59 \times 10^3$ | 19/26 | (73%) | 80403/5.03 | M. tuberculosis | 2497795 | (Z78020) gIcB |
| 2 | 425 | 7/26 | (26%) | 66600/5.66 | M. tuberculosis | 3261657 | (Z81368) ggtB |
| 3 | 168 | 8/26 | (30%) | 80142/5.09 | M. leprae | 2578377 | (AL008609) G |
| 4 | 52.1 | 10/26 | (38%) | 77122/5.39 | M. tuberculosis | 2501060 | (Z95387)thrS |
| 5 | 37.9 | 10/26 | (38%) | 89926/5.6 | M. tuberculosis | 1731250 | Probablycation-trans ATPase CY3 |
| 6 | 32.2 | 7/26 | (26%) | 95574/6.25 | M. leprae | 2398706 | (Z99125) hypo protein MLCL |
| 6 | 32.1 | 7/26 | (26%) | 95659/6.33 | M. leprae | 3024896 | (U00013) pps B1496_C2_18 |
| 7 | 27.3 | 7/26 | (26%) | 95033/5.37 | M. tuberculosis | 3261590 | (Z74025) ctpF |
| 8 | 26.4 | 8/26 | (30%) | 65877/5.56 | M. leprae | 2959407 | (AL022118) re Helicase DnaB |
| 9 | 21.1 | 7/26 | (26%) | 81578/5.52 | M. tuberculosis | 1817676 | (Z84724) pkn |
| 9 | 20.9 | 9/26 | (34%) | 85425/5.37 | M. tuberculosis | 1781217 | (Z83867) nuo |
| 10 | 18.5 | 7/26 | (26%) | 95486/6.93 | M. tuberculosis | 2276335 | (Z97991) hypo Protein Rv033 |

Detailed Results 1. 19/26 matches (73%) 80403.4 Da, pI=5.03. Acc#2497795. *Mycobacterium tuberculosis* (Z78020) gIcB (=malate synthase)

Figure 27:
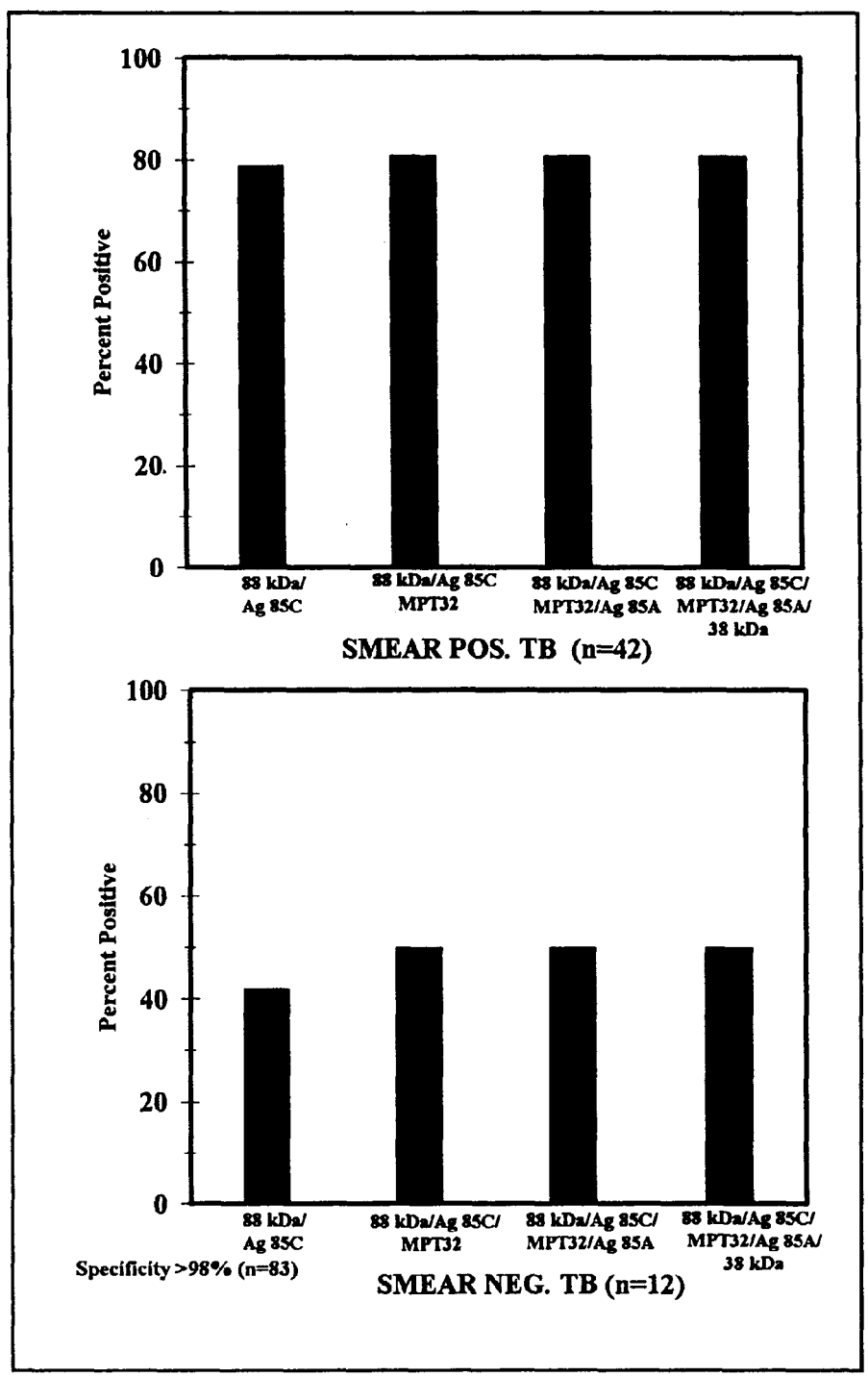
FIG. 27 shows the reactivity (% positive) of sera froma a cohort of 42 smear-positive (=late) TB patients (top panel) and 12 smear-negative TB patients (bottom panel) with various Mt antigens. Each bar represents the % of patients who were positive with at least one of the 2, 3, 4 or 5 Mt antigens indicated. For example, the height of the leftmost bar represents the % of patients whose sera reacted positively with either the 88 kDa protein, Ag 85C or both. Of the 42 late TB sera, 69% had antibodies to MPT 32, 79% to the Ag 85C and 74% to the 88 kDa protein. Taking these reactivities into account, 81% of the late TB patients had antibodies to one or more of these three antigens. In the early TB patient cohort, 33% had anti-MPT-32 antibodies, 33% had anti-Ag 85C antibodies and 33% had anti-88 kDa antibodies.
Figure 28:
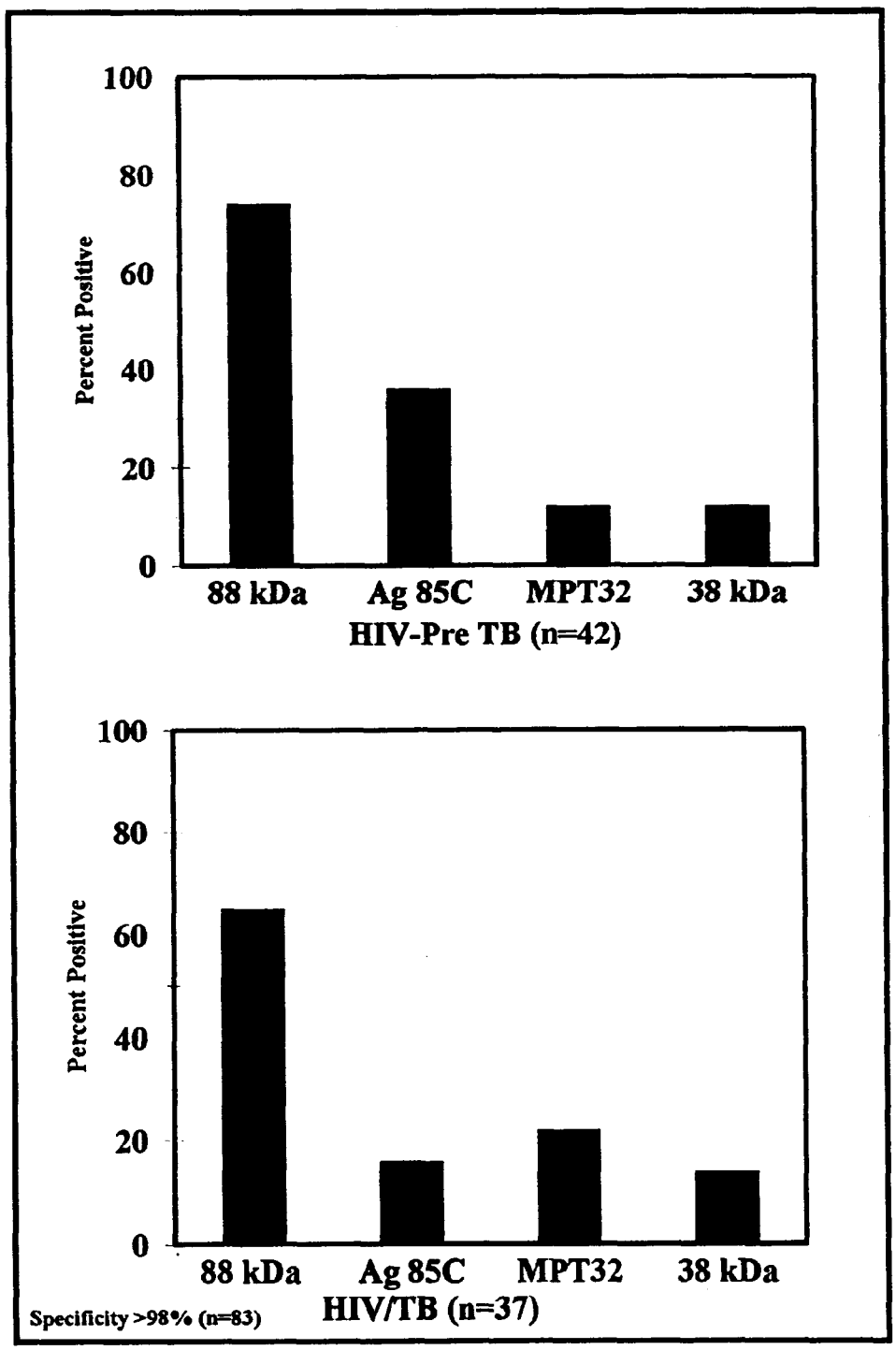
FIG. 28 shows the reactivity of sera from HIV-infected TB patients (bottom panel) and 37 HIV+ pre-TB sera with four different Mt protein antigens. The data shown here compare sera obtained at the time of clinical diagnosis of TB (HIV/TB, lower panel) with retrospective stored sera which had been obtained from the same patients during their earlier hospital visits for monitoring of their HIV infection, prior to their presenting with clinical TB (HIV pre-TB). Antibodies to the 88 kDa protein were present in the pre-TB sera of 74% of the HIV-infected individuals who went on to develop clinical TB. Although it is not possible to say whether the "pre-TB" samples represent Mt-uninfected individuals or those with early TB, the results show that the presence of anti-88 kDa antibodies is a surrogate marker in this high risk group for identifying those individuals who are at a higher risk of developing TB. The 88 kDa protein is therefor the most useful of the early antigens examined for identifying TB patients from among the HIV-infected population.
Figure 29A:
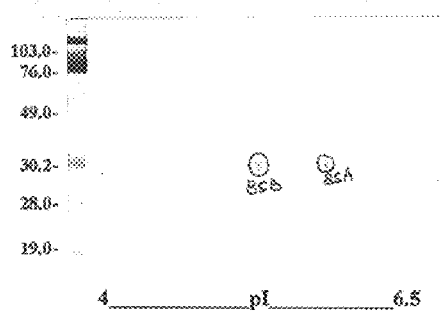
FIGS. 29A–29D are 2-dimensional immunoblots showing reactivty of sera from PPD+ healthy controls (FIG. 29A), HIV-infected pre-TB patients (FIG. 29B), non HIV-infected, smear-negative, non-cavitary (=early) TB patients (FIG. 29C) and non HIV-infected, smear-positive cavitary (=late) TB patients (FIG. 29D). PPD+ healthy controls showed weak reactivity with the components of the Ag85 complex but failed to recognize any additional antigens in the Mt culture filtrates (FIG. 29A). In contrast, the pre-TB sera from HIV-infected TB patients (FIG. 29B) showed reactivity with some of the proteins as demonstrated (Ag 85C, 88 kDa, MPT 51, and proteins marked "C," "D" and "E" (FIG. 29C and 29D), and with ~15 "protein spots" situated between the 49 kDa and the 76 kDa molecular weight markers. It cannot be determined how many proteins the latter spots represent, for some may be isomers of the same proteins. An overlapping pattern of reactivity was observed with sera from patients with early TB (FIG. 29C). The majority of these protein spots are present in very small amounts in the culture filtrate preparation. It is not possible to determine if the pre-TB and early TB sera react with the identical proteins. Sera from a majority of the late TB patients recognized the antigens that were identified by the early TB sera, and several additional proteins (FIG. 29D). MPT 51, a protein of known identityis strongly reactive with the pre-TB sera as well as sera from early TB patients. These results suggest that inclusion of MPT 51, or the other antigens that are recognized by early TB sera, will further increase the sensitivity of detection of early antibodies.
Figure 29B:
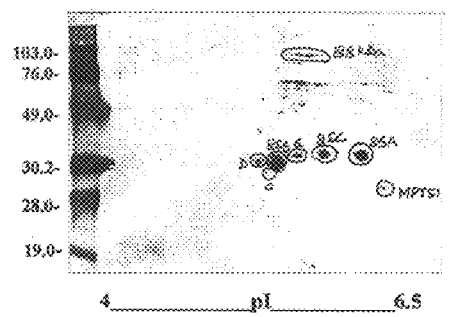
Figure 29C:
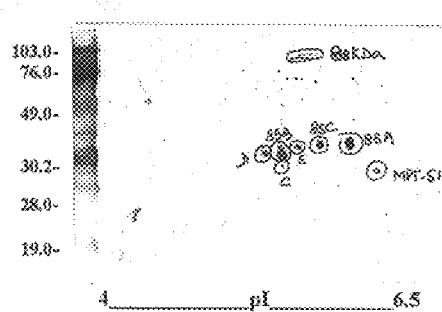
Figure 29D:
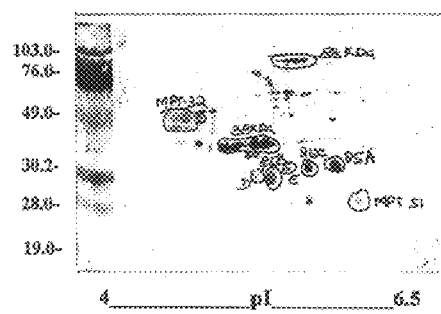

The protein was identified as GlcB (Z78020) of *M. tuberculosis*, which is believed to be the enzyme malate synthase based on sequence homology to known proteins of other bacteria. This protein has the Accession number CAB01465 on the NCBI Genbank database (based on Cole, S. T. et al., Nature 393:537–544 (1998), which describes the complete genome sequence of *M. tuberculosis*). The sequence of this protein, SEQ ID NO:106, is presented in FIG. 27.

EXAMPLE VII

Characterization of Serodominant Antigens of *M. tuberculosis*

The goal of this study was to determine the repertoire of antigens recognized by antibodies in TB patients in order to elucidate the human humoral response to Mt and to evaluate the potential of these antigens as candidates for serodiagnosis. This was accomplished by immunoblotting Mt H37Rv secreted antigens, which had been separated by 1- and 2-dimensional electrophoresis, with sera (*E. coli*-absorbed) from TB patients and healthy controls.

Of the more than 200 secreted proteins of Mt, only 26 elicited antibodies in TB patients. The identity of several of these antigens was determined based on (a) their reactivity with murine mAbs, (b) N-terminal amino acid sequencing and (c) liquid chromatography-mass spectrometry(Example V). Twelve of these 26 antigens were recognized by sera from patients with early, non-cavitary TB and by patients with advanced cavitary TB. Of these twelve antigens, five, including the 88 kDa antigen (Example I), the MPT32 and Ag 85C, reacted strongly with sera from TB; the other two antigens have yet to be identified. The present invention is directed to the development of serodiagnostic assays (as described herein) employing these antigens that elicit antibodies in both early and advanced TB patients.

Materials and Methods

Subjects (a) Advanced TB Patients

Serum samples from 33 HIV-negative individuals with confirmed pulmonary TB (advanced TB) were included in the study. Twenty of these sera were provided by Dr. J. M. Phadtare (see Example I). Nineteen of these patients were smear-positive and all had radiological evidence of moderate to advanced cavitary lesions. All these patients were bled 4–24 weeks after initiation of therapy.

(b) Early TB Patients

Thirteen TB patients from the Infectious Disease Clinic at the Manhattan VA Medical Center, New York, were culture positive, 6/13 were smear negative and 12/13 had minimal or no radiological lesions. These patients were bled either prior to, or within 1–2 weeks of, initiation of treatment.

(c) Control Groups

Twenty-three $HIV^{neg}$, $TB^{neg}$, healthy individuals were included as controls. Sixteen of these were PPD+ (skin test) and the remaining 7 were $PPD^{neg}$.

Antigens

Culture filtrates from log phase Mt $H_{37}Rv$ were used as the source of secreted antigens as described in Example I (LAM-free culture filtrate proteins or CFPs). The LFCFP preparation contained over 200 proteins (Example V, supra). Antigens were size fractionated by loading onto a preparative polyacrylamide tube gel, and proteins were separated by electrophoresis using an increasing wattage gradient (model 491 Prep Cell; Bio-Rad, Hercules, Calif.). Fractions were collected, assayed by SDS-PAGE and pooled according to molecular weights. Contaminating SDS was removed as described above. Reactivity of each fraction with human sera and an extensive panel of murine mAbs to Mt antigens are described in Example I. Fractions containing the 38 (or 35) kDa PstS and the seroreactive 88 kDa antigen were identified by reaction with anti-38 kDa mAb IT-23 and mAbs IT-57 and IT-42, respectively. Immunoadsorption of sera against *E. coli* lysates was performed as described in Example I. All ELISA assays, described in Example I, were performed using sera previously immunoadsorbed on *E. coli* lysates.

One-dimensional (1-D) SDS-PAGE and 2-D PAGE of the LFCFPs

The fractionation of the LFCFPs (8 μg/lane) was performed on mini-gels using vertical slab units (SE 250

Mighty Small II, Hoeffer Scientific, San Francisco, Calif.) with a 10% separating gel and 5% stacking gel. The gels were either stained with a silver stain (Bio-Rad Silver Stain Kit, Hercules, Calif.) or used for electrophoretic transfer for immunoblotting. The separated proteins were transferred onto nitrocellulose membranes for 1.5 hrs at a constant 100 V.

2-D PAGE was performed as described in Example V. Proteins resolved by 2-D PAGE were transferred to nitrocellulose membranes as described.

Western Blot Analysis

The 1-D and 2-D blots were blocked with 3% BSA in phosphate buffered saline (PBS) for 2 hrs, and washed for 1 hr with PBS/Tween 2% (wash buffer). Individual lanes containing fractionated LFCFPs were exposed overnight at 4° C. to individual sera (diluted 1:100 with 1% BSA in PBS). The blots containing the 2-D fractionated LFCFPs were probed with four different serum pools comprised of individual sera whose reactivity with the above antigen preparations were previously determined by ELISA. The pools included (a) 6 PPD positive healthy control sera with no specific reactivity against any of the antigens (group I), (b) 6 TB patients that lacked reactivity to all 3 antigen preparations by ELISA (group II), (c) 6 TB patients reactive with the total LFCFPs and the sized 88 kDa preparation, but not the 38 kDa antigen preparation (group III), and (d) 6 TB patients reactive with both the sized preparations (38 and 88 kDa antigens; group IV). Exposure of the blots to the individual sera or serum pools was followed by washing for 1.5 hrs with the wash buffer, after which alkaline phosphatase-conjugated anti-human IgG (diluted 1:2000, Zymed, Calif.) was added for 1.5 hrs. The blots were washed again for 2 hrs and developed with BCIP/NBT substrate (Kirkegaard & Perry Laboratories, Gaithersburg, Md.).

Results

Reactivity of Sera with Secreted Antigens of Mt

Sera were grouped according to reactivity by ELISA with total LFCFPs, or the sized fraction containing the 38 kDa PstS or the 88 kDa seroreactive protein (Table 10). Group I includes sera from 16 PPD$^+$ and 7 PPD$^{neg}$ healthy controls, none of whom were positive in ELISA with any of these antigen preparations. Group II includes 9 TB patients who tested antibody negative with all three antigen preparations; five of these patients were smear-positive and had cavitary disease. The remaining four patients lacked cavitary lesions, but two of these four were smear-positive. Group III includes thirteen patients with antibodies to both the LFCFPs and the fraction containing the 88 kDa antigen, but not the fraction containing the 38 kDa antigen. Five of these patients were smear-positive and had pulmonary cavitations. An additional four were smear-positive but lacked any cavitary lesions. The remaining four were smear negative and had no cavitations. Group IV included eleven patients, all of whom had antibodies to all three antigen preparations; 10/11 were smear-positive and all had radiological evidence of moderate to advanced cavitary disease.

TABLE 10

Classification of TB Patients

| Serum Group | n$^a$ | Smear Positivity | Radiological Cavitations | REACTIVITY WITH: LAM-free CFP | Fraction with 88 kDa Ag | Fraction with 38 kDa Ag |
|---|---|---|---|---|---|---|
| I | 23 | 0 | 0 | 0 | 0 | 0 |
| II | 9 | 7 | 5 | 0 | 0 | 0 |
| III | 13 | 9 | 5 | 11 | 13 | 0 |
| IV | 11 | 10 | 11 | 11 | 11 | 11 |

$^a$n = number of individuals in each group

Antigens in LFCFPs Recognized by Sera

Resolution of the LFCFP preparation by SDS-PAGE revealed a broad range of proteins from 14 to >112 kDa, as seen by silver staining. Sera (diluted 1:100) from individuals in all four groups were used to probe Western blots prepared from the fractionated LFCFPs. Because of the large number of individual sera tested, several blots were performed. Consequently, not all antigen bands are exactly matched when the blots are combined to show the reactivities as in FIG. 17. For standardization, the 65 kDa band was aligned. The results obtained with sera from group I individuals (PPD$^+$ and PPD$^{neg}$ healthy controls) are shown in lanes 2–16. The major antigens recognized by sera from 6 PPD$^{neg}$ healthy individuals have molecular weights of 26, 30–32 kDa and 65 kDa (lanes 2–7). The 30–32 and 65 kDa antigens were also recognized by sera of the 9 PPD$^+$ healthy controls (lanes 8–16), though only 3/9 sera in this group recognized the 26 kDa antigen (lanes 8, 13 and 14), and one serum sample recognized an additional 68 kDa antigen (lane 12).

Lanes 17–24 show the reactivity of group II tuberculous sera, which were antibody negative with all 3 antigen preparations by ELISA. Despite some variability among individual tuberculous sera, all reacted with the 30–32 kDa and 65 kDa antigens, and 5/8 (lanes 19, 21–24) contained antibodies to the 26 kDa antigen that was also recognized by the controls. Serum from one patient (lane 21) showed strong reactivity with 46, 55 and 97 kDa antigens. Four sera, including the latter patient, showed faint reactivity with antigens of 74, 76, 88, 105 and 112 kDa antigens, and with some antigens between 46–55 kDa. Sera from patients with cavitary disease (lanes 19, 22–24) and sera from patients with no cavitations (lanes 17, 18, 20 and 21) showed no significant difference in reactivity.

The reactivity of sera from 11/13 patients in group III was assessed. Group III patients had antibodies by ELISA to the LFCFPs and the 88 kDa preparation (lanes 25–35). Ten of the 11 sera (lanes 25–34) showed moderate reactivity with the 88 kDa antigen. In addition, these sera also recognized antigens of 74, 76, 105, 112 kDa, and some antigens in the region of 46–55 kDa. Although non-reactive by ELISA, 3 of 11 sera reacted with a 38 kDa antigen (lanes 26, 32 and 34). This may indicate binding to a recently described 38 kDa antigen (Bigi, F. et al., 1995, *Infect. Immun.* 63:2581–2586) which is distinct from the PstS protein. No differences were observed in the reactivity pattern between (a) sera of patients who lacked pulmonary cavitations (lanes 25–30) and (b) sera from patients with advanced cavitary lesions (lanes 31–35).

The sera of group IV patients who were reactive with all three antigen preparations by ELISA (lanes 36–43), reacted very strongly with the 38 kDa antigen and recognized a 34 kDa antigen that was not recognized by any of the group II sera. Besides these two antigens, the antigens identified by group IV sera were the same as for group III sera, although the reactivity with individual antigens was markedly stronger. The reactivity with the 88 kDa antigen was strong in 7/8 sera (lanes 37–43).

In summary, all antibody-positive TB patients (groups III and IV) reacted primarily with antigens having molecule masses >46 kDa. Antigens of 74, 76, 88, 105, 112 kDa and antigens in the 46–55 kDa region are frequent targets of human antibody responses. In contrast, the 38 kDa and 34 kDa antigens were recognized by a more restricted group of patients (group IV).

Identification of Antigens Recognized by TB Patient Sera

2D-PAGE provides enhanced resolution of complex protein mixtures. The LFCFPs preparation resolves into about 200 different proteins by this method. A complete 2-D map of the total CFPs of Mt is shown in FIG. 14 (Example V).

2D immunoblots of the fractionated LFCFPs were probed with serum pools corresponding to patient groups I–IV. The reactivity of each serum pool was compared with the reactivity of murine mAbs to identify the antigens recognized by TB patients' sera (Table 11, parts A–C).

Figure 17:
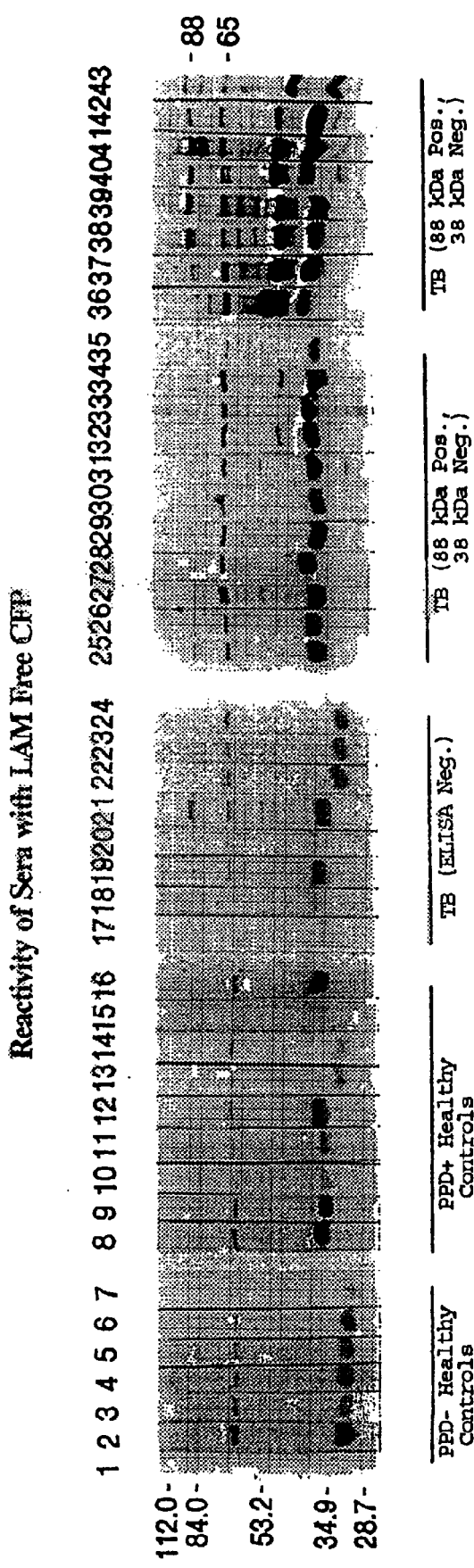
FIG. 17 shows a Western blot analysis of 1-D fractionated M. tuberculosis LFCFP with E. coli adsorbed sera. Lane 1: molecular weight markers. Lanes 2–7: PPD negative healthy individuals (Group I); lanes 8–16: PPD positive healthy controls (Group I); lanes 17–24: antibody negative TB patients (Group II); lanes 25–35: antibody positive TB patients (lacking anti-38 kDa PstS antibodies, Group III); lanes 36–43: TB patients with anti-38 kDa antibodies (Group IV).

The antigens reactive with the four serum pools are shown in FIGS. 18A–18D and described in Table 11A–C. The reference number for each antigen is that assigned in Example V, supra. All fourr serum pools reacted with 4 secreted antigens and 3 of 4 pools reacted with 2 additional secreted antigens (Table 11A). These six proteins are clearly seen in FIG. 18 (panel A reacting with pooled sera from healthy controls (group I). Reactivity with murine mAb IT-49 identified two of them to be the Ag 85B (#81, 29 kDa) and Ag 85A (#149, 31 kDa). These antigens correspond to the 30–32 kDa doublet, observed on 1-D immunoblots (FIG. 17). The other two antigens reactive with all serum groups had molecular weights of 55 kDa (#114, 120) and 58 kDa (#86, 96, 105) and failed to react with any murine mAb. The former antigen has been identified as the glutamine synthetase by N-group analysis (Example V, above). These antigens may correspond to the 65 kDa antigen that was reactive with the individual sera on 1-D blots. A 26 kDa antigen (#19, 29) and a 46 kDa (#51) were reactive with the control sera (group I) and antibody positive TB sera (group III, FIG. 18C and group IV, FIG. 18D), but failed to react with the antibody negative TB serum pool (group II, FIG. 18B). The former antigen (26 kDa, #19, 29) was identified as MPT64 based on reactivity with the murine mAb IT-67 and may be the 26 kDa antigen recognized by several control sera on the 1-D blots (FIG. 17, lanes 2–7, 8, 13 and 14).

Figure 18A:
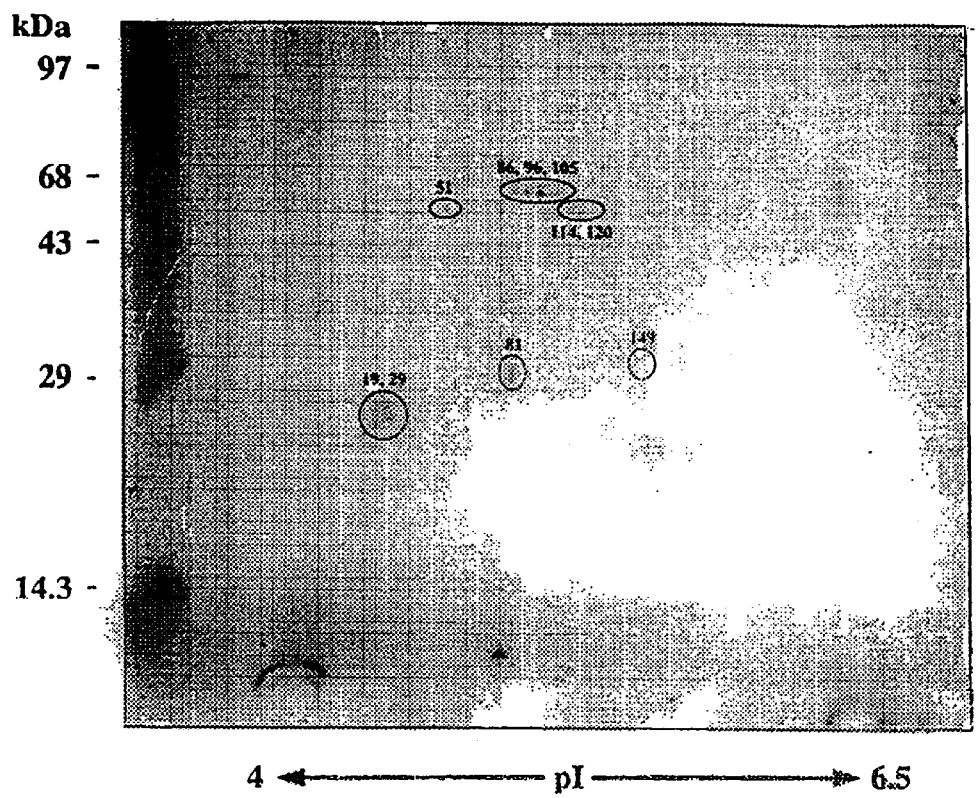
FIGS. 18A–18D shows the results of 2-dimensional fractionation and immunoblot analysis of M. tuberculosis LFCFPs with four different serum pools comprised of 6 individual sera in each pool. (panel A) group I; (panel B) group II; (panel C) group III and (panel D) group IV. The vertical axis represents molecular mass and the horizontal axis represents isoelectric point (pI).
Figure 18B:
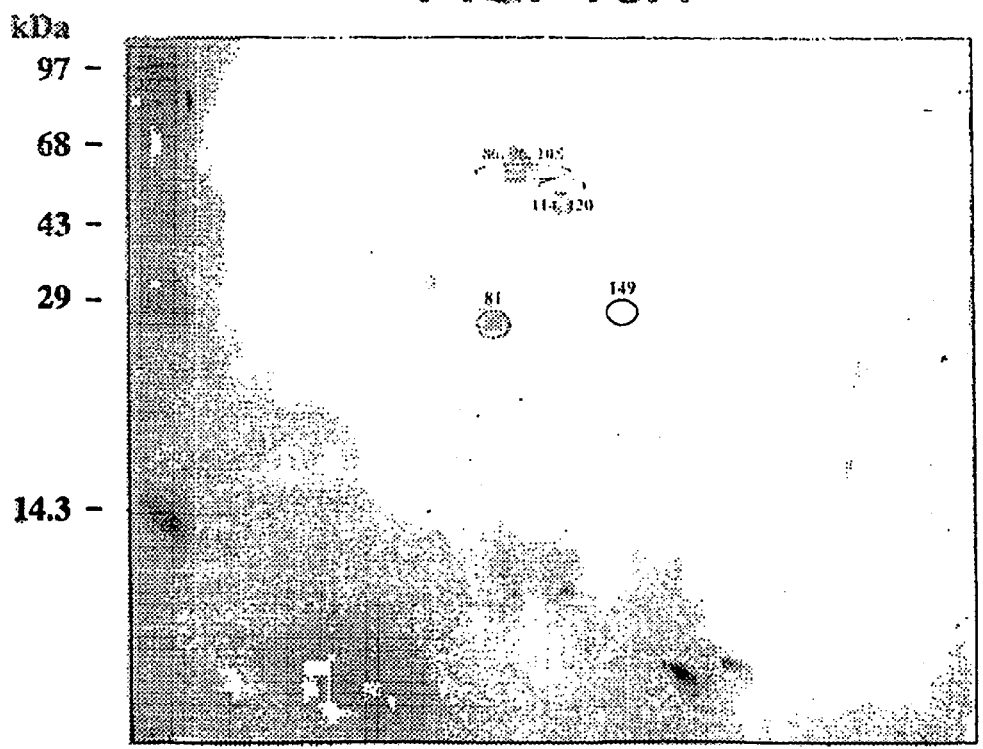

The reactivity of a serum pool of group II TB patients (which sera lack ELISA-reactive antibodies to any of the secreted antigens tested), is shown in FIG. 18B and Table 11A. This serum pool was weakly reactive with the four antigens (29, 31, 55, and 58 kDa) to which the control group (group I) reacted, but failed to show any reactivity with the 25/26 (#19, 29) and 46 kDa (#51) antigens.

Figure 18C:
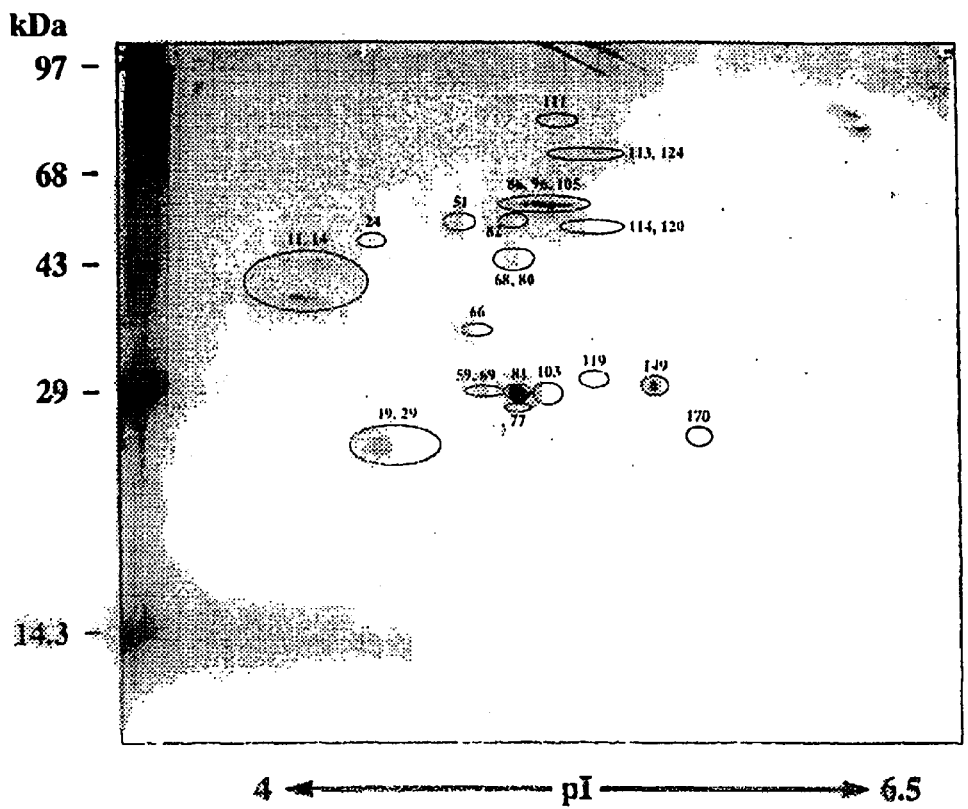

The serum pool from TB patients containing antibodies to the 88 kDa but not the 38 kDa antigen (group III), reacted with 18 secreted antigens on the 2-D blots (FIG. 18C and Table 11B). Of these, six were identical to those identified by the healthy control serum pool (group I; Table 11A). Of the remaining twelve antigens, three had molecular masses below 30 kDa: one was a 26 kDa antigen (#170, MPT51), reactive with mAb IT52 and the two others (28 kDa, #77; and 29/30 kDa, #69, 59) did not react with any of the mAbs tested. In the 30–60 kDa range, reactivity with a 31 kDa (#119, mAb IT-49, Ag 85C) and a 38/42 kDa antigen (#11, 14, MPT32) was strong, and a low level of reactivity was discernible with one isomer of the 35 kDa antigen (#66, IT-23, PstS). A 49 kDa protein (#82) was reactive with mAb IT-58). Three antigens, with molecular weights of 31 kDa, (#103), 42 kDa (#68, 80) and 48 kDa (#24) were not identified by any mAbs. These antigens correspond to the multiple bands in the 30 to 60 kDa region on the 1-D blots. In the region of 65–100 kDa, a 85 kDa protein (#113, 124, IT-42, IT-57), was reactive with this serum pool, but no antigens corresponding to the 74 and 76 kDa antigens seen on 1-D blots were discernible on the 2-D blot. The 85 kDa antigen (#113, 124) on the 2-D immunoblots corresponds to the 88 kDa antigen (Example I) and as seen in FIG. 17 and in Example V, above). This was also confirmed by checking the reactivity of the fractionated LFCFPs with mAbs IT-42 and IT-57, both of which identified the 88 kDa band. The 104 kDa protein (#111) corresponds to the 105 kDa seen on the 1-D blots. Nothing corresponding to the 112 kDa antigen on the 1-D immunoblots was observed on the 2-D immunoblots.

Figure 18D:
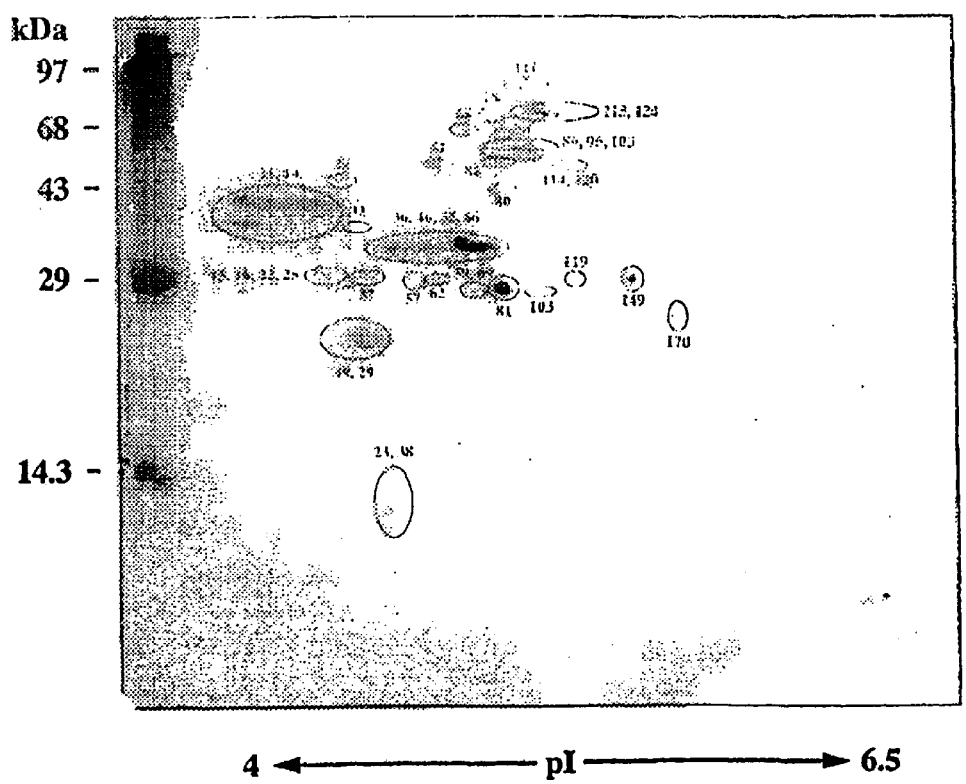

The serum pool from group IV TB patients recognized 11 of 12 antigens that were reactive with the group III serum pool (except the 28 kDa antigen, #77; Table 11B). The reactivity of the group IV serum pool however, with the 26 kDa (#170, MPT51), 31 kDa (#119, Ag 85C), 35 kDa (#66, PstS), 38/42 (#11, 14, MPT32), 49 kDa (#82; IT-58), 85 kDa (#113, 124) and the 104 kDa (#111) antigens, was stronger than with the group II serum pool. In contrast to the group III pool which showed faint reactivity with only one isomer of the 35 kDa antigen (#66, PstS; FIG. 18C), the group IV pool was reactive with all four isomers recognized by murine mAb IT-23 (FIG. 18D). Besides the 11 antigens listed to be reactive with both the group III and IV serum pools (Table 11B), the latter group also reacted with eight additional antigens (Table 11C and FIG. 18D). The antigen with a molecular weight below 30 kDa was the 13/14 kDa protein (#23, 38, IT-12 and SA12, GroES). In the 30–38 kDa region, this serum pool recognized four new antigens, with the same 31 kDa molecular weight but differing in their pI values: 31 kDa (#15, 16, 22, 25), 31 kDa (#62), 31 kDa (#57) and 31 kDa (#37), and a fifth antigen of 38 kDa (#32). Of these only the 31 kDa (#15, 16, 22, 25) was reactive with the mAb IT-44, while the remaining 4 antigens have not been previously described. In the region above 65 kDa, this pool reacted with a 66/72 kDa protein (#65, 79, mAb IT-40 and IT-41, DnaK), and an unidentified 79 kDa antigen (#78).

In summary, of the 26 antigens that are recognized by TB sera, 6 were reactive with the control sera (Table 11A). Twelve of these 26 antigens are recognized by sera from groups III and IV (Table 11B). Thus, patients both with early, non cavitary TB and advanced cavitary TB have antibodies to these antigens. Of these 12 antigens, 5 are strongly recognized and consequently, are preferred antigens for a serodiagnostic assay for early TB as described herein. These are the 85 or 88 kDa antigen (#113, 124; Example I), the 38/42 protein (#11,14, MPT32), the 31 kDa antigen (#119, Ag 85C), an uncharacterized 49 kDa antigen (#82; IT-58), and a 26 kDa antigen (#170, IT-52). In contrast, eight additional antigens listed in Table 11C, and the 38 kDa protein (#66, PstS; Table 11B) are recognized primarily by advanced TB sera and would therefore be of limited serodiagnostic value.

Discussion

The results presented above show that, of the approximately 200 proteins secreted by replicating bacteria, only a limited subset is recognized by the TB patients' immune system resulting in antibodies with appropriate specificity in the patients' sera. Even within this subset, some antigens are recognized by early and advanced (late) TB patients whereas others are recognized exclusively by late TB patients. In view of the fact that the 38 kDa PstS protein is the most "successful" serodiagnostic antigen known in the art (Bothamley et al., 1992, supra; Harboe et al., 1992, *J. Infect. Dis.*, supra), the present discovery of several antigens that are recognized by patients who lack anti-38 kDa antibodies is very important. As shown here and in the earlier Examples, removal of cross-reactive antibodies from sera by immunoadsorption with *E. coli* antigens allows definition of Mt antigens with strongly seroreactive determinants. Previous attempts to identify antigens of Mt that elicit antibodies in diseased individuals had limited success. Verbon et al. (supra), using unadsorbed sera to probe secreted Mt antigens which had been fractionated by 1-D PAGE, found no difference between reactivity of patient and control sera. Espitia et al. (supra) (also using unabsorbed sera) identified only the 38 kDa PstS protein. This antigen reacted with only 57% of TB sera. The immunoadsorption of sera with *E. coli* lysates eliminates the cross-reactive antibodies that have hindered the definition of seroreactive antigens. In addition, the 2-D analysis and mapping of each antigen as described herein has allowed precise definition of antigens that appear to be critical for rational design of serodiagnosis and at least 5 secreted proteins as useful serodiagnostic agents. Antibodies to one of these, the 85 (or 88) kDa antigen, are present in 80% of the advanced and 50% of the early TB. The 38/42 kDa antigen (#11, 14, MPT32) has also been suggested to have serodiagnostic potential (Espitia et al., 1995, supra) but not as an "early" antigen. The remaining 3 antigens, the 49 kDa (#82; IT-58), 31 kDa antigen (#119, Ag 85C), and the 26 kDa (#170, IT-52) used for assessing seroreactivity in patients until the making of the present invention.

The present inventors' laboratories have changed the Reference Number designation of some of the spots on the 2D gels shown here from a numeric to an alpha (letter) labeling. See their publication, Samanich, K. M. et al., *J. Infec. Dis.* 178:1534–1538 (1998), which is incorporated by reference in its entirety. The correspondence of some spot number to letter designations are given in the legend to FIG. 1 of that publication and reproduced below:

| New Ref (alpha) | Corresponding numeric |
|---|---|
| A | na* |
| B | 86, 96, 105 |
| C | 77 |
| D | 59, 69 |
| E | 103 |
| F | 68, 80 |
| G | 24 |
| H | na |
| I | 111 |
| J | 57 |
| K | 62 |
| L | 32 |
| M | 78 |

*na = not assigned

Ref numbers based on Sonnenberg et al., 1997, supra, as used in the present examples

TABLE 11

Antigens Recognized by Various Serum Pools

| Antigen | | | Reactive mAb | Reactivity with serum pools | | | |
|---|---|---|---|---|---|---|---|
| MW[a] | pI | Ref[b] | (Antigen Identified) | Grp I | II | III | IV |
| A. ANTIGENS RECOGNIZED BY ALL FOUR SERUM POOLS | | | | | | | |
| 25/26 | 4.65–4.83 | 19, 29 | IT-67 (MPT64) | ++ | NR | ++ | +++ |
| 29 | 5.10 | 81 | IT-49 (Ag 85B) | ++ | ++ | +++ | +++ |
| 31 | 5.38 | 149 | IT-49 (Ag 85A) | + | ++ | +++ | +++ |
| 46 | 5.05 | 51 | NONE | +/− | NR | ++ | +++ |
| 55 | 5.14–5.17 | 114, 120 | glutamine synthetase | +/− | +/− | ++ | +++ |
| 58 | 5.11–5.12 | 86, 96, 105 | NONE | ++ | ++ | ++ | +++ |
| B. ANTIGENS RECOGNIZED ONLY BY GROUP III AND IV TB PATIENTS | | | | | | | |
| 26 | 5.91 | 170 | IT-52 (MPT51) | NR | NR | ++ | +++ |
| 28 | 5.10 | 77 | NONE | | | +/− | NR |
| 29/30 | 5.08 | 69, 59 | NONE | | | + | + |
| 31 | 5.12 | 103 | NONE | | | + | + |
| 31 | 5.17 | 119 | IT-49 (Ag85C) | | | +++ | +++ |
| 35(38) | 5.09 | 66 | IT-23 (PstS) | | | +/− | +++ |
| 38/42 | 4.31–4.51 | 11, 14 | polyclonal antisera (MPT32) | | | ++ | +++ |
| 42 | 5.10 | 68, 80 | NONE | | | + | + |
| 48 | 4.79 | 24 | NONE | | | + | + |
| 49 | 5.10 | 82 | IT-58 | | | ++ | +++ |
| 85(88) | 5.14–5.19 | 113, 124 | IT-42, IT-57 | | | ++ | +++ |
| 104 | 5.13 | 111 | NONE | ↓ | ↓ | + | ++ |
| C. ANTIGENS RECOGNIZED ONLY BY GROUP IV TB PATIENTS | | | | | | | |
| 13/14 | 4.76–4.93 | 23, 38 | SA-12, IT-10(GroES) | NR | NR | NR | + |
| 31 | 4.53–4.79 | 15, 16, 22, 25 | IT-44 | | | | +++ |
| 31 | 5.09 | 62 | NONE | | | | +/− |
| 31 | 5.08 | 57 | NONE | | | | ++ |
| 31 | 4.93 | 37 | NONE | | | | + |
| 38 | 4.87 | 32 | NONE | | | | ++ |

TABLE 11-continued

Antigens Recognized by Various Serum Pools

| Antigen | | | Reactive mAb | Reactivity with serum pools | | | |
|---|---|---|---|---|---|---|---|
| MW[a] | pI | Ref[b] | (Antigen Identified) | Grp I | II | III | IV |
| 66/72 | 5.09–5.10 | 65, 79 | IT-40, IT-41 (DnaK) | | | | +++ |
| 79 | 5.10 | 78 | NONE | ↓ | ↓ | ↓ | + |

[a]Antigen molecular weight (MW) given in kDa
[b]Reference numbers correspond to the 2-D PAGE map of CFPs of Mt $H_{37}Rv$ (Example V) NR: Not reactive In addition to the five aforementioned "early" antigens, seven additional antigens showed reactivity with the group III serum pool:

(1) the 28 kDa (#77) antigen,
(2) the 29/30 kDa (#69, 59) antigen,
(3) the 31 kDa (#103) antigen,
(4) the 35 kDa (#66, IT-23) antigen,
(5) the 42 kDa (#68, 80) antigen,
(6) the 48 kDa (#24) antigen, and
(7) the 104 kDa (#111) antigen.

Hence, the presence of one or more of these antigens in an immunodiagnostic preparation in combination with one or more of the five early antigens described above enhances the sensitivity of the diagnostic assay.

Three other antigens which have apparently strong serodominant epitopes based on their significantly stronger reactivity with the antibody-positive TB sera (groups III and IV) than with sera of antibody negative TB patient sera and control sera (groups I and II; Table 11A) are: (a) the 55 kDa (#114, 120, glutamine synthetase) antigen, (b) a 46 kDa protein (#51, IT-58) antigen and (c) the 31 kDa (#149, Ag 85A) antigen. The serodiagnostic potential of Ags 85A (#149) and B (#81) has been evaluated by Van Vooren et al. (supra) by isoelectric focusing separation and immunoblot analysis. The 85A component was shown to be reactive with the TB as well as non-TB sera, whereas, 71% of the TB sera in their cohort recognized either Ag 85 B or C. Importantly, no information on reactivity in early vs. advanced disease was provided.

The present results revealed that Ag 85A and B were strongly reactive with patient sera, and less reactive with controls, although the 85B was more cross-reactive with control sera. Studies with the Ag 85 components led to the suggestion that serodiagnostic potential of these antigens will lie in their specific epitopes (Wiker et al., 1992, *Microbiol. Rev*, supra). The present invention constitutes a major step in that direction and provides a basis for the identification and detection of such epitopes.

Another protein currently being assessed as a serodiagnosis candidate is MPT64 (26 kDa, #19, 29) (Verbon et al., 1993, supra) which was reported to provide sensitivities of about 46% in active TB patients. However, the present 2-D analyses suggests that this protein, although strongly reactive with sera of advanced TB patients, fails to discriminate between the group III TB sera (lacking anti-38 kDa antibodies) and the healthy controls (group I).

The early antigens identified herein may not be the only early antigens secreted during Mt growth in vivo. These antigens may be the only ones that are distinguishable because of their strongly seroreactive antigenic determinants. Several antigens of Mt were either up- or down-regulated when the organisms were grown intracellularly in macrophages. The present inventors propose that, in vivo, Mt organisms produce only those proteins required for survival and growth under these particular conditions which may different from the requirements during growth in culture media. It is noteworthy that several of the antigens that elicit antibodies relatively early in TB (based on reactivity with group III sera), are implicated as having a role in pathogenesis in vivo. Thus, Ag 85A, Ag 85C and MPT51 all belong to the family of secreted proteins which bind to fibronectin (Wiker et al., 1992, *Scand. J. Immunol.*, supra). MPT32 is homologous to a fibronectin-binding protein of *M. leprae* (Schorey, J. S. et al., 1995, *Infect. Immun.* 63:2652–2657).

The identity of the 85 (or 88) kDa antigen (#113, 124), reported herein to be strongly seroreactive, appears to be the same protein which reacts two mAbs: IT-42 and IT-57. The protein bound by IT-42 has been identified as the KatG catalase-peroxidase enzyme (Example V, above). The identities of the adjacent protein reactive with IT-57 (#113) and with IT-58 (#82, 49kDa) have not been determined. To be targets of early antibody responses in patients, these proteins must be released by actively growing bacteria early in the disease process.

It is also noteworthy that the 28 kDa antigen (#77) reacted with the group III but not the group IV serum pools, suggesting differential expression of some antigens during different stages of disease progression (Amara, R. R. et al., 1996, *Infect. Immun.* 64:3765–3771).

Based on the foregoing discoveries, the present inventors have identified seroreactive antigens which are useful for diagnostic assays for TB patients who are relatively early in disease progression. In view of the expected homology of these antigens with similar proteins in other mycobacterial species, species-specific epitopes should now be defined for serodiagnostic uses.

Whether use of purified antigens and/or epitopes, alone or in combinations, will facilitate detection of low titers of antibodies in the antibody negative TB patients (group II) remains to be tested.

If the absence of detectable antibodies (by ELISA) is due to the formation of immune complexes in vivo (Grange, supra), the present invention provides methods to identify such complexes containing these antibodies.

In view of the large number of antigens secreted by replicating Mt in culture, it is significant that such a small number of antigens are reactive with TB patient antibodies. Extensive efforts have been expended in the art to develop serodiagnostic tools using Ag 85A and B and the 38 (or 35) kDa antigens. The present invention clearly show that at least five additional secreted antigens are recognized by a significantly larger proportion of TB patients. These antigens are targeted for design of serodiagnostic tests for TB as disclosed herein.

EXAMPLE VIII

Figure 19:
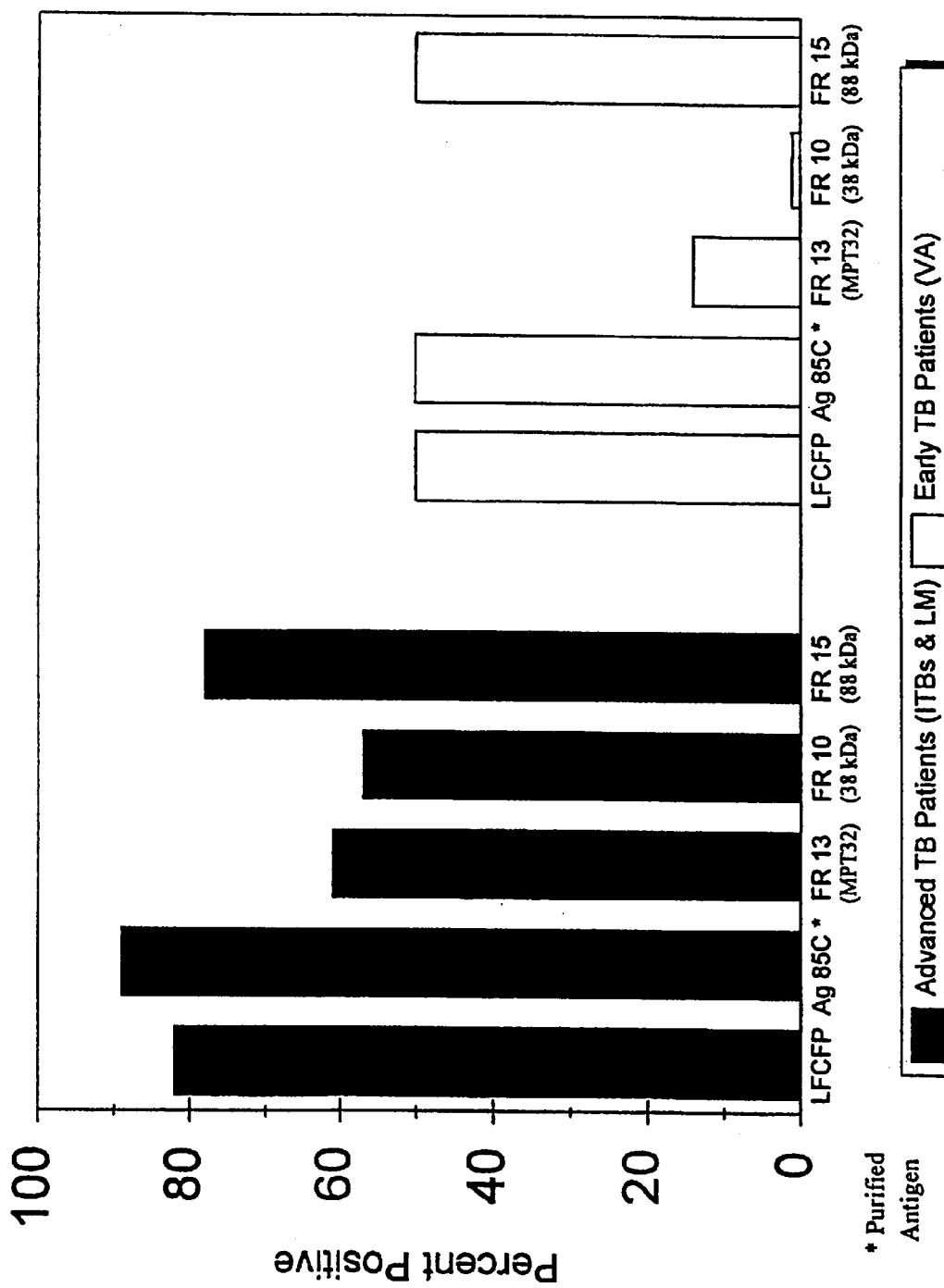
FIG. 19 is a graph showing reactivity of sera from advanced (black bars) and early (gray bars) TB patients to M. tuberculosis LFCFP, purified Ag85C or three fractions (13, 10 and 15) enriched for three early antigens (shown in parentheses below the fraction designation).
Figure 20:
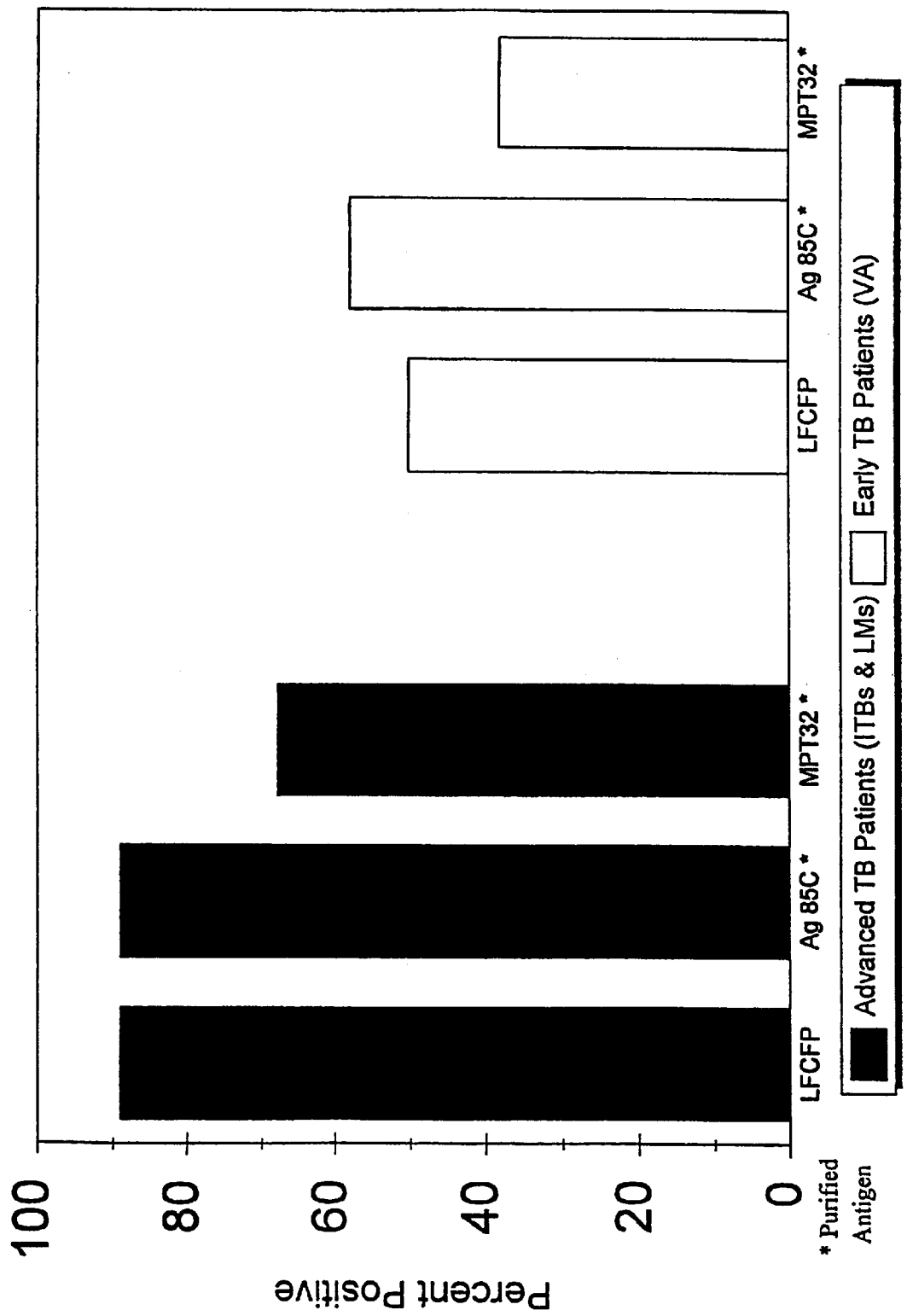
FIG. 20 is a graph showing reactivity of sera from advanced (black bars) and early (gray bars) TB patients to M. tuberculosis LFCFP, purified Ag85C or purified MPT32.

Reactivity of Sera from TB Patients with Purified Antigens and Selected Antigen Fractions The reactivity of patient and control sera with LFCFP, with fractions 10, 13 and 15, and with purified antigens Ag85C and MPT32 are summarized in FIGS. 19 and 20, and Table 12. As discussed above in Examples I and II, fraction 10 is enriched for a 38 kDa antigen, fraction 13 is enriched for MPT32 and fraction 15 is enriched for the 88 kDa antigen (also referred to as an 85 kDa antigen based on slight differences in PAGE migration between two laboratories of two of the present inventors). This 88 kDa antigen is described for the first time in the present disclosure.

The results show that all advanced TB patients who have antibodies to LFCFP can be detected by the use of Ag85C or antigen in Fraction 15. A significant proportion of these patients also have antibodies to MPT32 (Fraction 13) and the 38 kDa antigen (Fraction 10). However, Ag85C and the 88 kDa protein were recognized by most patients' immune systems resulting in antibodies.

All early TB patients who are reactive with LFCFP are also reactive with MPT32 none are reactive with the 38 kDa antigen. Reactivity with purified MPT32 is higher in the early TB group (FIG. 20) than is reactivity with a partially purified (Fraction 13) antigen (FIG. 19).

These results confirm that the reactivity of sera from early TB patients with at least three of the five early antigens described in the present invention (see, especially, Examples I and III). These findings prove that the use of purified early antigens results in enhanced assay sensitivity in patients with early TB, allowing for improved rapid detection methods.

Of these antigens, only MPT32 has received any consideration in the context of TB serodiagnosis. However, none of these antigens have ever been shown to react with early TB patient sera. Hence, this is the first suggestion of their use in methods to diagnosis TB in its early stages, which is of particular importance to immunocompromised patient such as those infected with HIV.

Reactivity of Individual Sera with Antigens

Figure 21:
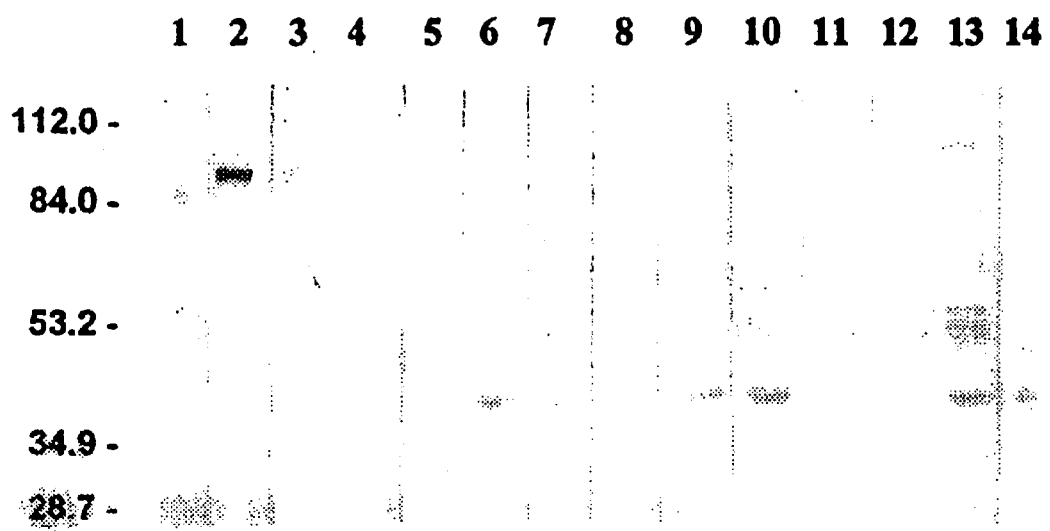
FIG. 21 shows the lack of reactivity of recombinant 88 kDa protein with the IT-57 mAb. Lane 1: molecular weight markers; lane 2 contains fractionated LFCFP probed with mAb IT-57; lanes 3 contains lysates from E. coli-λgt11 (IT-57), and lane 4 E. coli λgt11 without insert; lanes 2–4 probed with mAb IT-57. Lanes 5–14 contain lysates from E. coli-λgt11 (IT-57); lanes 5–10 probed with TB sera, lanes 11–14 probed with PPD positive healthy control sera.
Figure 22A:
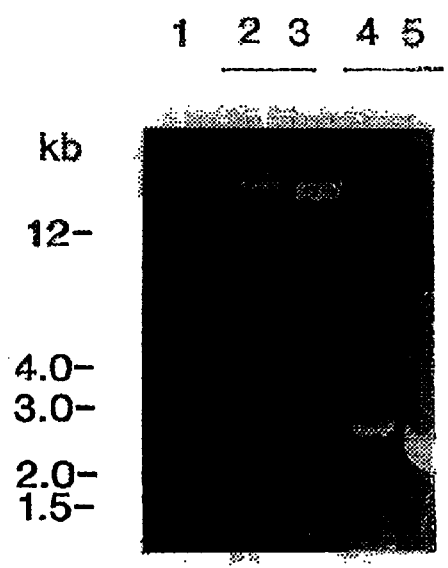
FIGS. 22A and 22B show the hybridization of a mycobacterial insert from λgt11 (IT-57) with the katG gene.
Figure 22B:
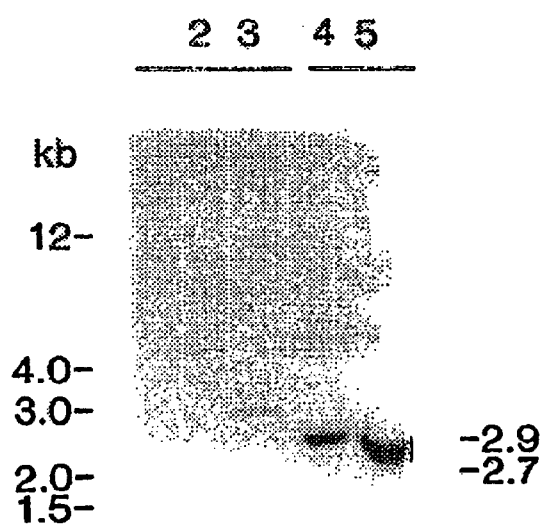
Figure 23A:
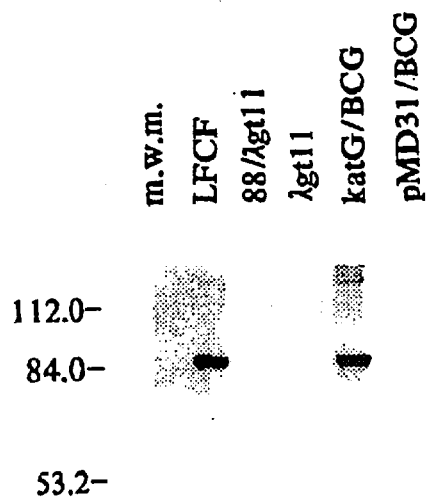
FIGS. 23A–23D show the reactivity of anti-catalase/peroxidase antibodies and TB patient sera with the catalase/peroxidase and with a novel 88 kDa antigen. The lanes in all four blots contain the same antigenic preparation. The LFCFP and lysates from E. coli 1089 lysogen λgt11 (IT-57) (lane 3, labeled 88/λgt11), λgt11 without insert (lane 4, labeled λgt11), M. bovis BCG with pMD31: katG (lane 5 labeled katG/BCG), M. bovis BCG pMD31 alone (lane 6, labeled pMD31/BCG), were probed with (FIG. 23A) mAb IT-57, (FIG. 23B) IT-42, (FIG. 23C) anti-catalase/peroxidase polyclonal antibody and (FIG. 23D) a TB patient serum. Molecular weight markers are on the left.
Figure 23B:
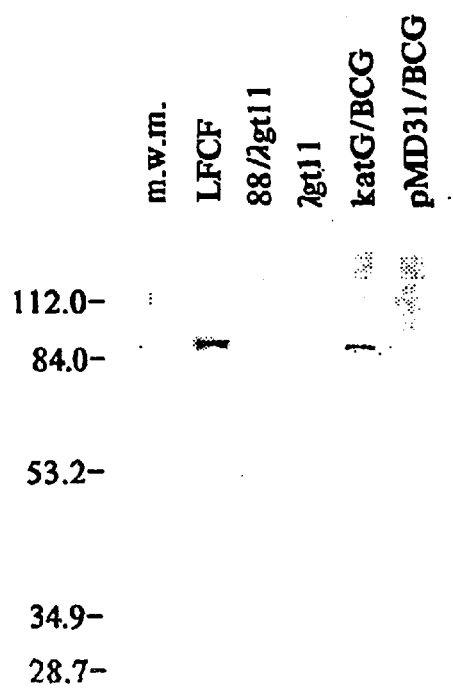
Figure 23C:
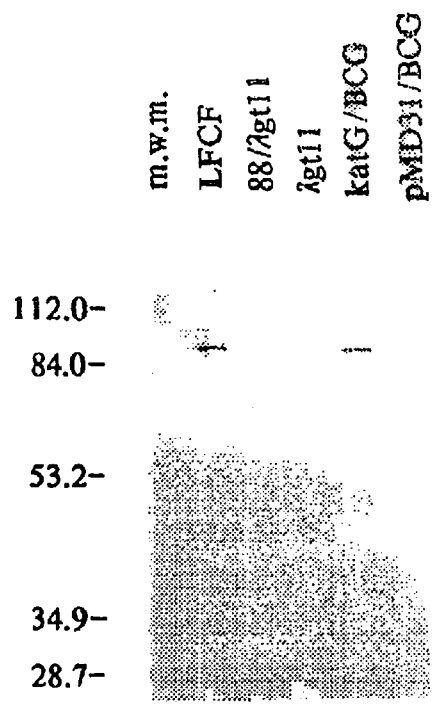
Figure 23D:
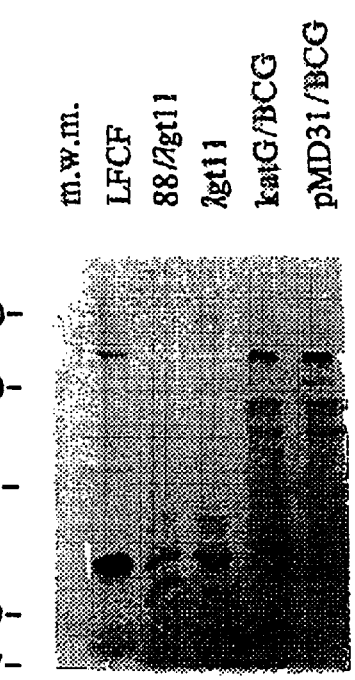
Figure 25:
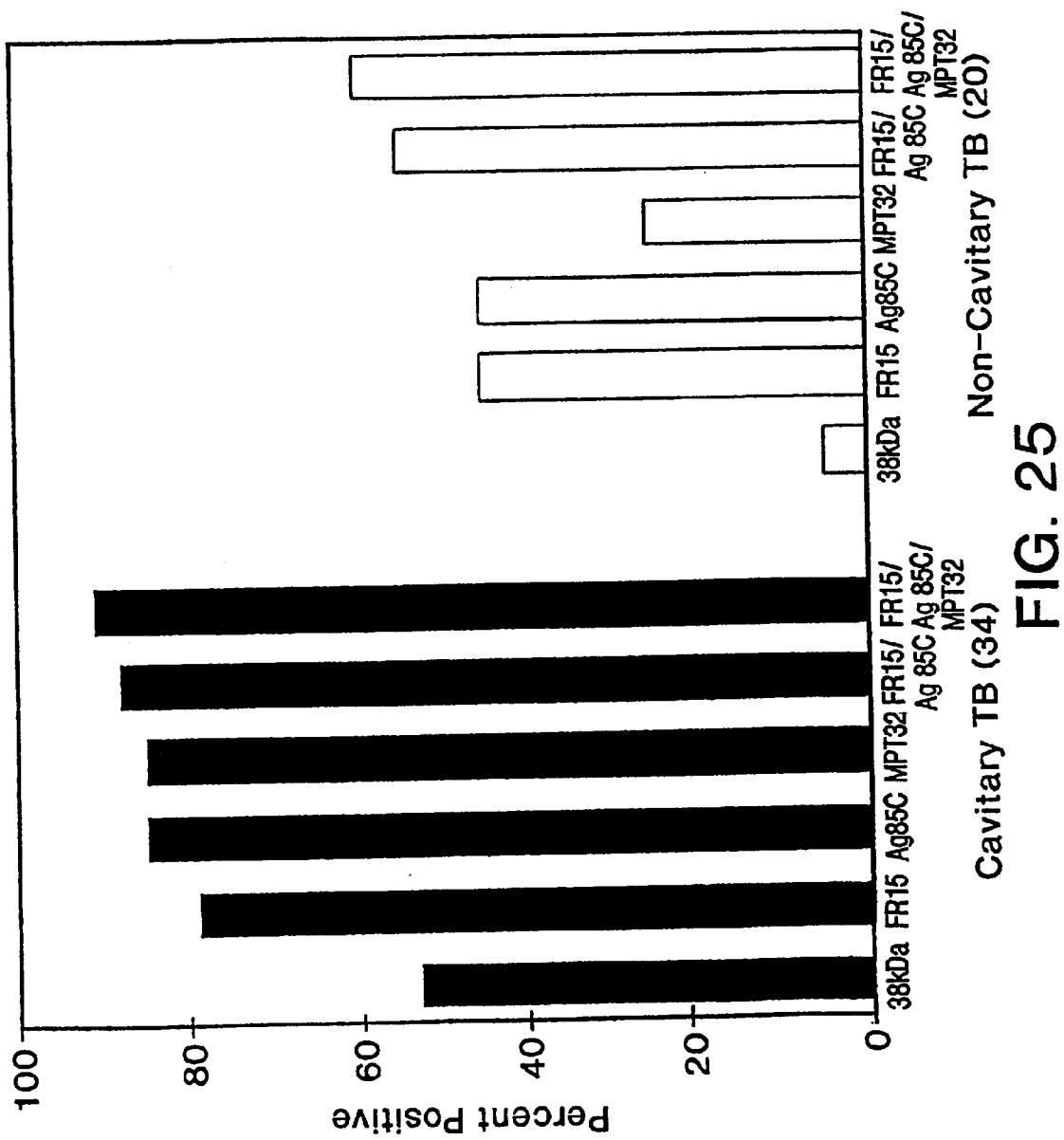
FIG. 25 is a graph showing reactivity of individual sera with different antigens of M. tuberculosis. Reactivity of sera from 34 cavitary (black bars) and 20 non cavitary (open bars) TB patients with various antigens: purified 38 kDa antigen ("38 kDa"), a sized fraction containing the 88 kDa antigen ("FR15"), purified Ag 85C ("Ag85C"), MPT32 ("MPT32")and predicted reactivity with a combination of three antigens (FR15/Ag85C or FR15/Ag85C/MPT32).

The reactivity of any single antigen on the 2-D blots with pooled sera may represent reactivity with only some of the individual sera comprising the pool. To confirm that the antigens recognized by group III serum pool are broadly reactive, individual sera were assessed for antibodies to two of the antigens identified by the group III serum pool, Ag 85C and MPT32 which the present inventors had purified. Reactivities with the purified 38 kDa PstS antigen and the 88 kDa antigen (fraction 15) was also tested. A larger cohort of TB patients than above, classified as cavitary or non-cavitary TB, was tested. Sera of 27 of the 34 (79%) cavitary and 9/20 (45%) non-cavitary patients were reactive with the 88 kDa antigen (FIG. 25 and Table 13) and 29/34 (85%) cavitary and 9/20 (45%) non-cavitary patient sera were reactive with Ag 85C (FIG. 21 and Table 6). Sera of 29 of 34 (85%) cavitary and 5/20 (25%) non-cavitary patients were reactive with the MPT32 (FIG. 25 and Table 13). In contrast, 18/34 (53%) cavitary and only 1/20 (5%) of the non-cavitary patients were reactive with the purified 38 kDa antigen (FIG. 25 and Table 13).

Analysis of these results, wherein reactivity with one or more of the 3 antigens identified herein was considered as positive reactivity, showed that antibodies were detectable in 31/34(91%) of the cavitary and 12/20 (60%) of non cavitary tuberculosis patients.

The entire cohort of TB patients was also analyzed to determine whether smear positivity and the detection of antibodies to the purified antigens tested above were comparable as methods for diagnosis of TB. Table 14 shows that 43/54 (80%) of all the TB patients are diagnosed by sputum smear and 43/54 (80%) are diagnosed by ELISA.

Although not all smear-positive patients had detectable antibodies and not all antibody-positive patients had positive smears, the combination of smear and ELISA could diagnose 50/54 (93%) of the TB patients.

When the patients were classified into cavitary and non-cavitary TB, 97% (33/34) of cavitary* and 45% (9/20) of non-cavitary TB patients were detected by smears. The sensitivity of antibody (only) detection was 91% (31/34) and 60% (12/20), respectively.

This, by using a combination of the two methods, the sensitivities were increased to 100% with cavitary TB and 80% (16/20) with non-cavitary TB patients. These results indicate that the greatest sensitivity for diagnosis of TB is attained by simultaneous use of the sputum smear and the ELISA for antibodies reactive with the antigens described herein.

TABLE 12

Reactivity of Patient Populations to Purified or Fractionated Mt Antigen

Purified Antigen or Antigen Fraction (at Serum Dilution)

| Subjects | Ag85 C (1:100) | MPT32 (1:150) | LFCFP (1:1000) | F13 (MPT32)[1] 1/200 | F15 (88 kDa) 1:200/400 | F10 (38 kDa) (1:200) |
|---|---|---|---|---|---|---|
| All TB | 36/50 | 28/52 | 30/42 | 19/50 | 29/42 | 16/42 |
|  | 72% | 54% | 72% | 38% | 69% | 38% |
| Advanced TB | 25/28 | 19/28 | 23/28 | 17/28 | 22/28 | 16/28 |
|  | 89% | 68% | 82% | 61% | 78% | 57% |
| Early TB | 11/22 | 9/24 | 7/14 | 2/14 | 7/14 | 0/14 |
|  | 50% | 38% | 50% | 14% | 50% | 0% |
| PPD[+] HC | 0/18 | 0/21 | 0/16 | 0/16 | 0/16 | 0/16 |
|  | 0% | 0% | 0% | 0% | 0% | 0% |
| PPD[neg] HC | 0/13 | 0/13 | 0/16 | 0/16 | 1/16 | 0/16 |
|  | 0% | 0% | 0% | 0% | 6% | 0% |

TABLE 12-continued

Reactivity of Patient Populations to Purified or Fractionated Mt Antigen

| | Purified Antigen or Antigen Fraction (at Serum Dilution) | | | | | |
|---|---|---|---|---|---|---|
| Subjects | Ag85 C (1:100) | MPT32 (1:150) | LFCFP (1:1000) | F13 (MPT32)[1] 1/200 | F15 (88 kDa) 1:200/400 | F10 (38 kDa) (1:200) |
| HIV+ HC | 0/39 0% | 0/34 0% | 0/21 0% | 0/16 0% | 0/21 0% | 0/21 0% |
| HIV+ TB (pre or at) | 16/52 31% | ND | 23/50 46% | ND | 37/52 71% | 34/52** 65% |

Subject designations are as in Examples I and II. HC = healthy controls. HIV+ patients with TB included those diagnosed before (pre) or at the time of (at) TB diagnosis. **Borderline values of OD

TABLE 13

Reactivity of sera with different *M. tuberculosis* antigens.

| | SENSITIVITY (%) | | | SPECIFICITY (%) |
|---|---|---|---|---|
| ANTIGEN | Total TB (n = 54) | Cavitary (n = 34) | Non Cavitary (n = 20) | (n = 83) |
| 88 kDa | 70 | 79 | 45 | 100 |
| Ag 85C | 70 | 85 | 45 | 100 |
| MPT 32 | 63 | 85 | 25 | 98 |
| 38 kDa | 35 | 53 | 5 | 100 |

TABLE 14

DIAGNOSIS OF TUBERCULOSIS

| | | Number of Patients (%) that are: | | |
|---|---|---|---|---|
| Patients | n | Smear+ | Ab+ | Smear+/Ab+ |
| Tuberculosis | 54 | 43 (80%) | 43 (80%) | 50 (93%)* |
| Cavitary TB | 34 | 33 (97%) | 31 (91%) | 34 (100%) |
| Non-Cavitary | 20 | 9 (45%) | 12 (60%) | 16 (80%) |

*8 of 12 smear-negative patients were antibody-positive.

Role of glycosylation of MPT32 in Antibody Responses

Studies described in Example III showed that MPT32 is a glycosylated protein. In order to determine if detection of antibodies to this antigen is affected by lack of glycosylation, the sized fraction 13 (see Table 3) was used for further studies. This fraction contained the MPT32 protein based on its reactivity with anti-MPT32 antiserum.

Figure 26A:
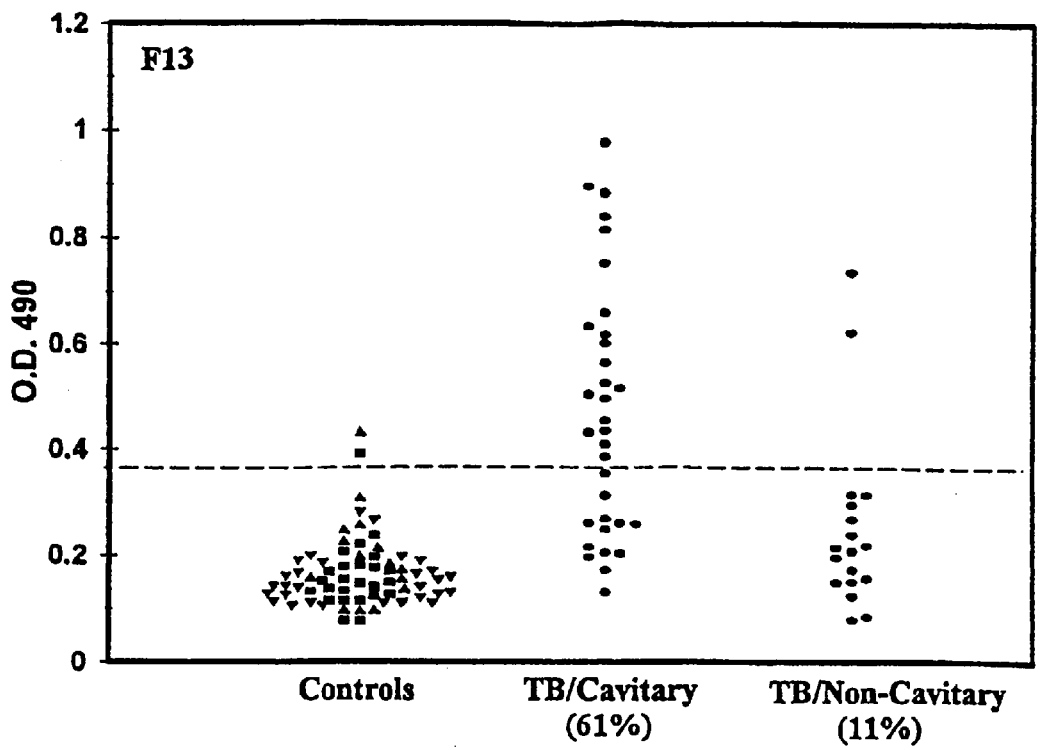
FIGS. 26A and 26B are graphs showing the reactivity of TB sera with Fraction F13, which is enriched for antigen MPT32.
Figure 26B:
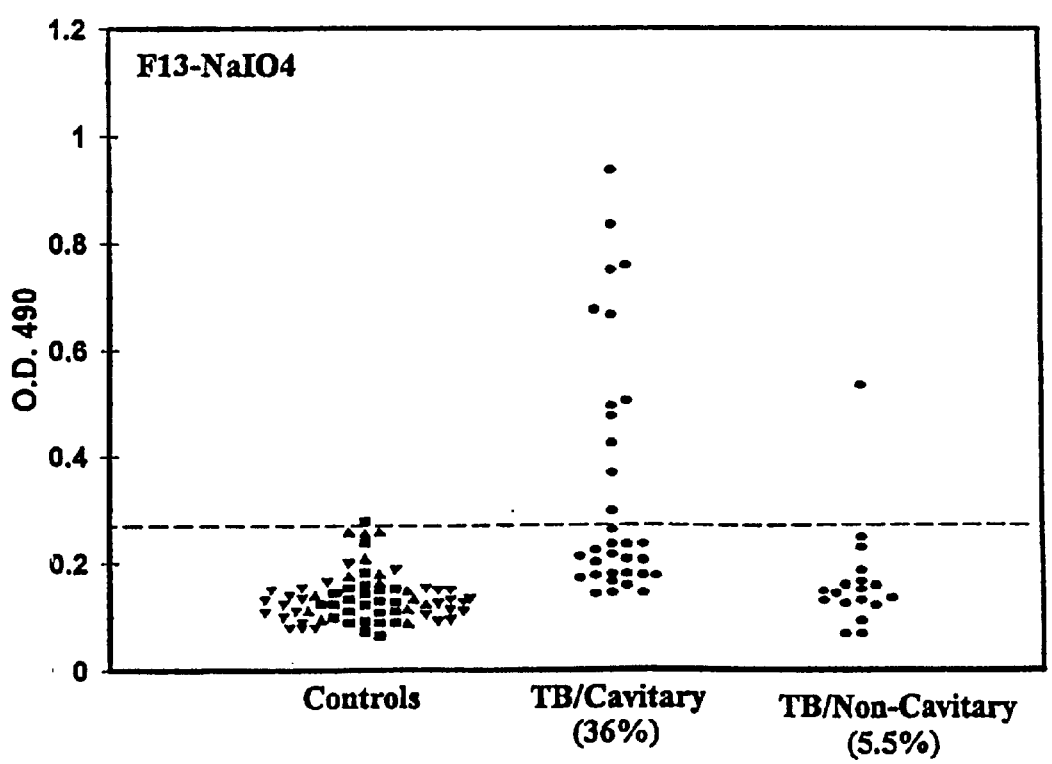

The sized fraction was treated with 100 mM sodium meta-periodate as a form of mild oxidation that denatures the carbohydrate moieties on the antigens. The reactivity of 51 TB and 69 control sera with the native and the periodate-treated antigen preparations was assessed by ELISA. The results presented in FIGS. 26A and 26B show that, whereas 20/33 (61%) of the sera of cavitary TB patients had anti-MPT32 antibodies that bound native antigen, only 13/33 (36%) of these sera were reactive with the periodate-treated antigen. Therefore, recognition of these mycobacterial proteins by antibodies of TB patients require the presence of glycosylation.

EXAMPLE IX

Anti-Mycobacterial Antibodies in Urine

Subjects

Paired serum and urine samples were obtained from 23 smear-positive, untreated (=late) TB patients attending the TB clinic at the LRS Hospital for Tuberculosis and Allied diseases at New Delhi, India. Forty-one sera and 24 urine samples obtained from PPD positive and PPD negative healthy individuals were tested as negative controls.

Determination of Anti-mycobacterial Antibodies

The reactivity of the serum samples with the culture filtrate proteins of *M. tuberculosis* was evaluated by ELISA as described above. To evaluate the presence of anti-mycobacterial antibodies in the urine samples, ELISA plates were coated overnight with 125 μl of a 4 μg/ml suspension of the culture filtrate proteins of *M. tuberculosis* at 4° C. The next morning, the plates were washed with PBS, and 125 μl of urine were added to each well. After 90 min., the plates were washed with PBS-Tween, and the bound antibody detected by anti-human IgG-Alkaline Phosphatase conjugate, and the substrate for the enzyme.

Figure 30:
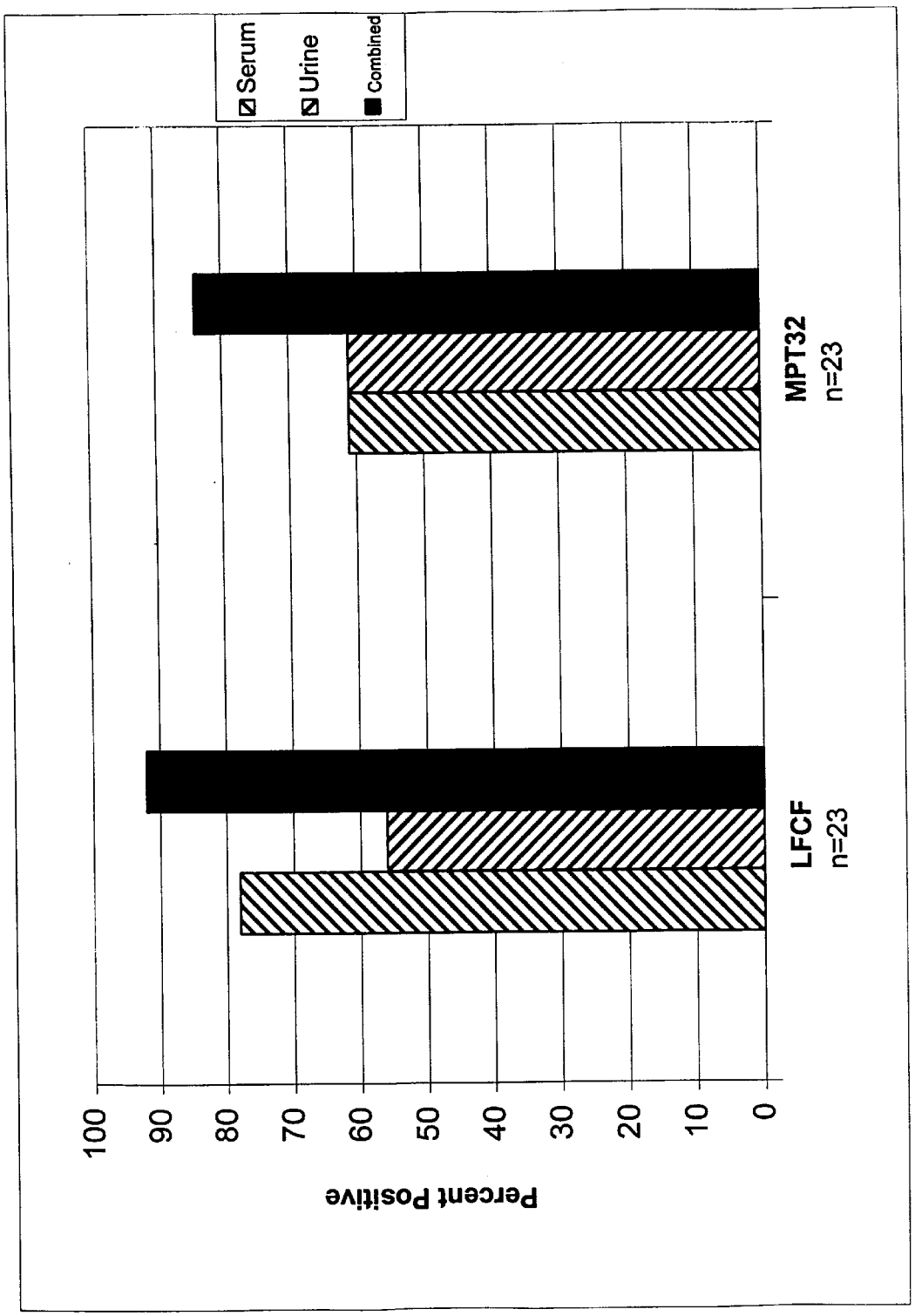
FIG. 30 is a graph showing reactivity of urine and sera from late TB patients with LFCF and MP32 protein. Results are presented as percent samples that are positive.

At specificities >98%, sera from 78% of the (=late) TB patients and urine samples from 56% had antibodies that bound to antigens in the Mt culture filtrates (FIG. 30). Taking into account the presence of antibodies in at-least one of the two body fluids (serum and/or urine), 92% of the patients had anti-mycobacterial antibodies. The same serum and urine samples were also evaluated for reactivity with purified MPT 32, which is one of the preferred antigens for the serodiagnostic test to detect early infection. In both cases, anti-MPT 32 antibodies were present in specimens from 14/23 (61%) patients (FIG. 30). Again, when considering the presence of anti-MPT 32 antibodies in at-least one of the two body fluids, 83% of the patients had anti-MPT 32 antibodies.

Figure 31:
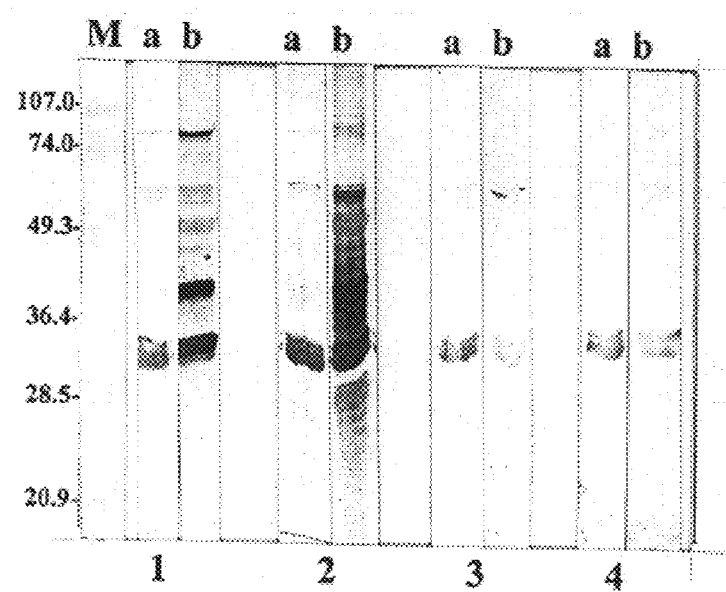
FIG. 31 shows western blots prepared from Mt culture filtrate proteins fractionated in 12% SDS-PAGE. These blots evaluate the reactivity of antibodies in urine (lanes marked "a") and serum (lanes marked "b") of smear-positive late TB patients (lanes 1 and 2) and PPD+ healthy controls (lanes 3 and 4). M: molecular weight markers.
Figure 32:
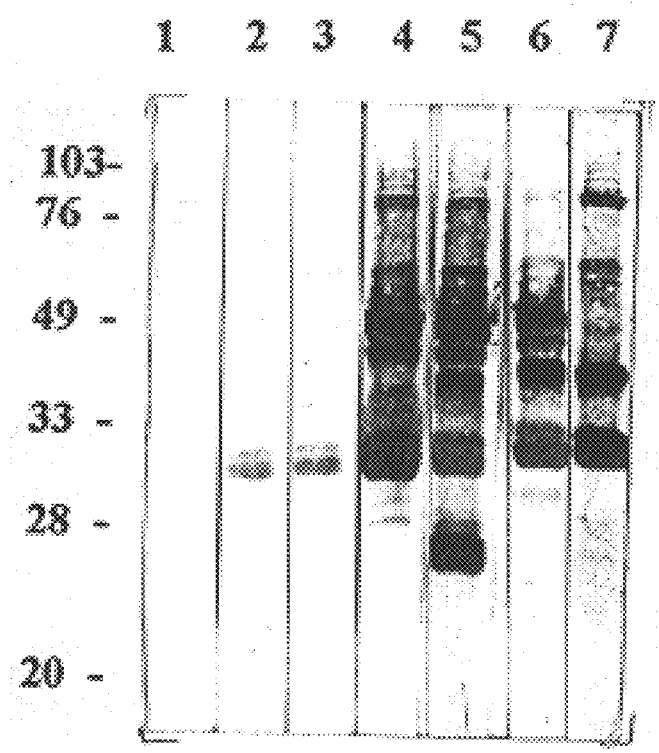
FIG. 32 shows the reactivity of animal (guinea pig) sera on western blots prepared from Mt culture filtrates fractionated in 12% SDS-PAGE. These blots evaluate the reactivity of sera fron Mt-infected guinea pigs and compare it with human TB sera. Lanes 2 and 3: negative control sera from 2 uninfected guinea-pigs. Lanes 4 and 5: sera from the M. tuberculosis infected guinea-pigs. Lanes 6 and 7: sera from 2 human TB patients.

To determine which culture filtrate antigens were recognized by these urine antibodies, Western blots were prepared from culture filtrate proteins fractionated on 10% SDS-polyacrylamide gels (FIG. 31). Individual blots were probed with sera and urine from 2 late TB patients and 2 PPD+ healthy controls. Sera and urine samples from the healthy controls showed cross-reactivity with the 30–32 and the 65 kDa proteins as discussed above. As expected, the serum samples (tested at 1:100 dilution) from the smear positive (=late) TB patients reacted strongly with several protein bands between 20–120 kDa, and reactivity with the 88 kDa band was clearly discernable. The reactivity of sera with MPT 51, MPT 32 and the Ag 85C is difficult to ascertain on 1-D blots due to the presence of several other proteins with similar molecular weights.

Urine samples from the TB patients (tested undiluted) (FIG. 31) reacted with a similar profile of antigens, albeit less well. The 88 kDa protein was recognized by antibodies in both urine samples, but the reactivity of the urine samples with MPT 32, Ag 85C and MPT 51 cannot be ascertained on 1-D blots. However, ELISA results showed that anti-MPT 32 antibodies are present in the urine (FIG. 30). This suggests that the antibodies in the urine are directed against the same antigens as are those in the serum, although antibody titers are lower. Together, these results indicate that (1) Anti-mycobacterial antibodies are present in the urine of a significant proportion of smear positive (=late)TB patients, thereby serving as the basis for a urine based diagnostic test for TB.

(2) An antibody detection based on testing both urine and serum for anti-mycobacterial antibodies significantly enhances the value of the diagnostic test. Increased sensitivity by using both body fluids is be especially important for diagnosis of early TB in smear negative (=early) subjects in whom the sensitivity of antibody detection with the current serodiagnostic test is 50% and in HIV-infected TB patients in whom the current sensitivity is 66%.

(3) A urine or urine/serum based diagnostic test for TB is performed using the same antigens of M. tuberculosis described herein (as well as others) that are defined as being seroreactive.

EXAMPLE IX

Anti-Mycobacterial Antibodies in Nonhuman Mammals

In order to determine which antigens in the culture filtrates of M. tuberculosis are recognized by non-human mammals who have TB, the following experiment was performed.

Sera were obtained from 2 guinea-pigs that had been infected by 4–5 colony forming units of aerosolized virulent *M. tuberculosis*. Guinea-pigs infected by the above protocol develop TB in 14–15 weeks. The infected animals were bled at 15 weeks post-infection, and the sera were used to probe western blots prepared from culture filtrates fractionated in 12% SDS-PAGE. Sera from 2 uninfected guinea-pigs were included as negative controls. Sera from 2 human TB patients were included for comparison. The results are shown in FIG. 32.

Sera from healthy individuals cross-react with antigens of 65 kDa and 30–32 kDa in Mt culture filtrates. Thus, sera from uninfected animals (lanes 2 and 3) also showed cross-reactivity with the 65 kDa band and the 30–32 kDa doublet.

Sera from the *M. tuberculosis* infected guinea-pigs (lanes 4 and 5) showed strong reactivity with several antigens in the culture filtrate that were not recognized by the control sera. Thus, the sera from the tuberculous animals showed strong reactivity with the 88 kDa protein described above, the 42–45 kDa protein, the 38 kDa protein, and with several other protein bands. This same antigen profile is recognized by the sera from human TB patients (lanes 6 and 7).

These results show that the antigen profile recognized by sera from mammals with TB is the same as the profile recognized by human TB patients. Therefore, the proteins that are defined herein as being useful for serodiagnosis of TB in humans can also be the basis of serodiagnostic assays for TB in other mammals. The present invention is useful in the veterinary medical setting as well.

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims.

What is claimed is:

1. A method for the early detection of active mycobacterial disease or infection in a subject, comprising assaying a biological fluid sample from a subject having symptoms of active tuberculosis, but before the onset of symptoms identifiable as advanced tuberculosis that is distinguished by (a) smear positivity of sputum for acid fast bacilli, (b) cavitary pulmonary lesions, or both (a) and (b), for the presence of early antibodies specific for a 27 kDa *M. tuberculosis* protein named MPT51 having the following properties:

(i) is present in *M. tuberculosis* culture filtrate;
(ii) has a pI of about 5.91;
(iii) is reactive with a monoclonal antibody designated IT-52;
(iv) is reactive with antibodies found in tuberculosis patients who are in a stage of disease prior to the onset of smear-positivity of sputum for acid-fast bacilli and cavitary pulmonary lesions; and
(v) is non reactive with sera from healthy control subjects or healthy subjects with latent inactive tuberculosis, wherein the presence of said early antibodies specific for said protein is indicative of the presence of said disease or infection.

2. A method for the early detection of active mycobacterial disease or infection in a subject, comprising assaying a biological fluid sample:

from a subject having symptoms of active tuberculosis, but before the onset of symptoms identifiable as advanced tuberculosis that is distinguished by (a) smear positivity of sputum for acid fast bacilli, (b) cavitary pulmonary lesions, or both (a) and (b),
for the presence of immune complexes consisting of a 27 kDa *M. tuberculosis* protein named MPT51 having the following properties:

(i) is present in *M. tuberculosis* culture filtrate;
(ii) has a pI of about 5.91;
(iii) is reactive with a monoclonal antibody designated IT-52;
(iv) is reactive with antibodies found in tuberculosis patients who are in a stage of disease prior to the onset of smear-positivity of sputum for acid-fast bacilli and cavitary pulmonary lesions; and
(v) is non reactive with sera from healthy control subjects or healthy subjects with latent inactive tuberculosis, wherein the presence of said immune complexes is indicative of the presence of said disease or infection.

3. The method of claim 1, which includes assaying said sample for antibodies specific for one or more additional early antigens of *M. tuberculosis* selected from the group consisting of:

(a) an 88 kDa *M. tuberculosis* protein having the following properties:
(1) present in *M. tuberculosis* culture filtrate;
(2) pI of about 5.2;
(3) an amino acid sequence SEQ ID NO:106:

```
MTDRVSVGNL RIARVLYDFV NNEALPGTDI DPDSFWAGVD KVVADLTPQN QALLNARDEL

QAQIDKWHRR RVIEPIDMDA YRQFLTEIGY LLPEPDDFTI TTSGVDAEIT TTAGPQLVVP

VLNARFALNA ANARWGSLYD ALYGTDVIPE TDGAEKGPTY NKVRGDKVIA YARKFLDDSV

PLSSGSFGDA TGFTVQDGQL VVALPDKSTG LANPGQFAGY TGAAESPTSV LLINHGLHIE

ILIDPESQVG TTDRAGVKDV ILESAITTIM DFEDSVAAVD AADKVLGYRN WLGLNKGDLA

AAVDKDGTAF LRVLNRDRNY TAPGGGQFTL PGRSLMFVRN VGHLMTNDAI VDTDGSEVFE

GIMDALFTGL IAIHGLKASD VNGPLINSRT GSIYIVKPKM HGPAEVAFTC ELFSRVEDVL

GLPQNTMKIG IMDEERRTTV NLKACIKAAA DRVVFINTGF LDRTGDEIHT SMEAGPMVRK

GTMKSQPWIL AYEDHNVDAG LAAGFSGRAQ VGKGMWTMTE LMADMVETKI AQPRAGASTA

WVPSPTAATL HALHYHQVDV AAVQQGLAGK RRATIEQLLT IPLAKELAWA PDEIREEVDN

NCQSILGYVV RWVDQGVGCS KVPDIHDVAL MEDRATLRIS SQLLANWLRH GVITSADVRA

SLERMAPLVD RQNAGDVAYR PMAPNFDDSI AFLAAQELIL SGAQQPNGYT EPILHRRRRE

FKARAAEKPA PSDRAGDDAA R
```

(b) a protein characterized as *M. tuberculosis* antigen 85C; and
(c) a glycoprotein characterized as *M. tuberculosis* antigen MPT32.

4. The method of claim 1, comprising, prior to said assaying step, the step of removing from said sample antibodies specific for cross-reactive epitopes or antigens of proteins present in *M. tuberculosis* and in other bacterial genera.

5. A method according to claim 4, wherein said removing is performed by immunoadsorption of said sample with *E. coli* antigens.

6. A method according to claim 1, wherein said subject is a human.

7. A method according to claim 6, wherein said subject is infected with HIV-1 or is at high risk for tuberculosis.

8. The method of claim 1, 3 or 2, comprising, before said assaying step, the step of obtaining said biological fluid sample from said subject.

9. The method of claim 4, comprising, before said assaying step, the step of obtaining said biological fluid sample from said subject.

10. The method of claim 6 comprising, before said assaying step, the step of obtaining said biological fluid sample from said subject.

11. The method of claim 7 comprising, before said assaying step, the step of obtaining said biological fluid sample from said subject.

12. The method of claim 1 or 3, wherein said biological fluid is urine.

13. The method of claim 4, wherein said biological fluid is urine.

14. The method of claim 5, wherein said biological fluid is urine.

15. The method of claim 6, wherein said biological fluid is urine.

16. The method of claim 7, wherein said biological fluid is urine.

17. The method of claim 2, wherein said biological fluid is urine.

18. The method of claim 8, wherein said biological fluid is urine.

19. The method of claim 9, wherein said biological fluid is urine.

20. The method of claim 1, 3 or 2 which further includes a test that detects mycobacterial bacilli in a sample of sputum or other body fluid of said subject.

21. The method of claim 4, which further includes a test that detects mycobacterial bacilli in a sample of sputum or other body fluid of said subject.

22. The method of claim 5, which further includes a test that detects mycobacterial bacilli in a sample of sputum or other body fluid of said subject.

23. The method of claim 6 which further includes a test that detects mycobacterial bacilli in a sample of sputum or other body fluid of said subject.

24. The method of claim 7, which further includes a test that detects mycobacterial bacilli in a sample of sputum or other body fluid of said subject.

25. The method of claim 8, which further includes a test that detects mycobacterial bacilli in a sample of sputum or other body fluid of said subject.

26. The method of claim 9, which further includes a test that detects mycobacterial bacilli in a sample of sputum or other body fluid of said subject.

27. The method of claim 12, which further includes a test that detects mycobacterial bacilli in a sample of sputum or other body fluid of said subject.

28. The method of claim 13, which further includes a test that detects mycobacterial bacilli in a sample of sputum or other body fluid of said subject.

29. The method of claim 14, which further includes a test that detects mycobacterial bacilli in a sample of sputum or other body fluid of said subject.

30. The method of claim 18, which further includes a test that detects mycobacterial bacilli in a sample of sputum or other body fluid of said subject.

31. The method of claim 19, which further includes a test that detects mycobacterial bacilli in a sample of sputum or other body fluid of said subject.

32. A kit useful for early detection of *M. tuberculosis* disease comprising:
   (a) an antigenic composition comprising a 27 kDa *M. tuberculosis* protein named MPT51 which is present in *M. tuberculosis* culture filtrate, has a pI of about 5.91, is reactive with a monoclonal antibody designated IT-52, and which is further characterized as being
      (i) reactive with antibodies found in tuberculosis patients who are in a stage of disease prior to the onset of (1) smear positivity of sputum for acid fast bacilli, (2) cavitary pulmonary lesions, or both (1) and (2), and
      (ii) non-reactive with sera from healthy control subjects or healthy subjects with latent inactive tuberculosis,
   in combination with
   (b) reagents necessary for detection of antibodies which bind to said *M. tuberculosis* protein.

33. A kit useful for early detection of *M. tuberculosis* disease comprising:
   (a) an antigenic composition consisting essentially of two or more early *M. tuberculosis* antigens each of which is characterized as being
      (i) reactive with antibodies found in tuberculosis patients who are in a stage of disease prior to the onset of (1) smear positivity of sputum for acid fast bacilli, (2) cavitary pulmonary lesions, or both (1) and (2), and
      (ii) non-reactive with sera from healthy control subjects or healthy subjects with latent inactive tuberculosis,
   which antigenic composition includes a 27 kDa *M. tuberculosis* protein named MPT51 present in *M. tuberculosis* culture filtrate which has a pI of about 5.91, and is reactive with a monoclonal antibody designated IT-52;
   in combination with
   (b) reagents necessary for detection of antibodies which bind to said early *M. tuberculosis* antigens.

34. A kit according to claim 32 or 33 wherein at least one of said early *M. tuberculosis* antigens is a recombinant protein or glycoprotein.

35. A kit according to claim 32 or 33, which further comprises at least one monoclonal antibody specific for an epitope of said early *M. tuberculosis* antigens.

36. A kit useful for early detection of *M. tuberculosis* disease, comprising:
   (a) an antigenic composition that includes:
      (i) an isolated 27 kDa *M. tuberculosis* protein named MPT51 having the following properties:
         (1) present in *M. tuberculosis* culture filtrate;
         (2) pI of about 5.91;
         (3) reactive with a monoclonal antibody designated IT-52;
         (4) reactive with antibodies found in tuberculosis patients who are in a stage of disease prior to the onset of smear-positivity of sputum for acid-fast bacilli and cavitary pulmonary lesions; and
         (5) non reactive with sera from healthy control subjects or healthy subjects with latent inactive tuberculosis
      (ii) supplemented with one or more isolated early *M. tuberculosis* antigenic proteins of a second set, characterized as in (5) and (6) above, obtainable from 14 day cultures of *M. tuberculosis* strain H37Rv grown in glycerol alanine salts medium, and selected from the group consisting of:
         (1) a 28 kDa protein having a pI of about 5.1, corresponding to the spot identified as Ref No. 77 in FIGS. 15A–F, FIG. 18, Table 9 or Table 11;
         (2) a 29/30 kDa protein having a pI of about 5.1, and corresponding to a spot identified as Ref No. 69 or 59 in FIGS. 15A–F, FIG. 18, Table 9 or Table 11;

(3) a 31 kDa protein having a pI of about 5.1 and an N-terminal amino acid sequence FSRPGLPVEY-LQVPSP (SEQ ID NO:95), and corresponding to a spot identified as Ref No. 103 in FIGS. 15A–F, FIG. 18, Table 9 or Table 11;

(4) a 35 kDa protein having a pI of about 5.1 and an N-terminal amino acid sequence CGSKPPSPET (SEQ ID NO:87), and corresponding to a spot identified as Ref. No. 66 in FIGS. 15A–F, FIG. 18, Table 9 or Table 11 and reacting with monoclonal antibody IT-23;

(5) a 42 kDa protein having a pI of about 5.1, and corresponding to a spot identified as Ref. No. 68 or 80 in FIGS. 15A–F, FIG. 18, Table 9 or Table 11;

(6) a 48 kDa protein having a pI of about 4.8, and corresponding to a spot identified as Ref. No. 24 in FIGS. 15A–F, FIG. 18, Table 9 or Table 11; and (7) a 104 kDa protein having a pI of about 5.1, and corresponding to a spot identified as Ref. No. 111 in FIGS. 15A–F, FIG. 18, Table 9 or Table 11;

which spots are obtained by 2-dimensional electrophoretic separation of *M. tuberculosis* lipoarabinomannan-free culture filtrate proteins as follows:

(A) incubating 3 hours at 20° C. in 9M urea, 2% Nonidet P-40, 5% β-mercaptoethanol, and 5% ampholytes at pH 3–10;

(B) isoelectric focusing on 6% polyacrylamide isoelectric focusing tube gel of 1.5 mm×6.5 cm, said gel containing 5% ampholytes in a 1:4 ratio of pH 3–10 ampholytes to pH 4–6.5 ampholytes for 3 hours at 1 kV using 10 mM $H_3PO_4$ as catholyte and 20 mM NaOH as anolyte, to obtain a focused gel;

(C) subjecting the focused gel to SDS PAGE in the second dimension by placement on a preparative SDS-polyacrylamide gel of 7.5×10 cm×1.5 mm containing a 6% stack over a 15% resolving gel and electrophoresing at 20 mA per gel for 0.3 hours followed by 30 mA per gel for 1.8 hours;

said antigenic composition in combination with (b) reagents necessary for detection of antibodies which bind to said early *M. tuberculosis* antigens.

37. The kit of claim 35 wherein said antigen of said second set is the 29/30 kDa protein.

38. The kit of any of claims 32, 33, 36, 37, that includes an early antigen selected from the group consisting of:

(a) an 88 kDa *M. tuberculosis* protein having the following properties:

(1) present in *M. tuberculosis* culture filtrate;

(2) pI of about 5.2;

(3) an amino acid sequence SEQ ID NO:106:

```
MTDRVSVGNL RIARVLYDFV NNEALPGTDI DPDSFWAGVD KVVADLTPQN QALLNARDEL
QAQIDKWHRR RVIEPIDMDA YRQFLTEIGY LLPEPDDFTI TTSGVDAEIT TTAGPQLVVP
VLNARFALNA ANARWGSLYD ALYGTDVIPE TDGAEKGPTY NKVRGDKVIA YARKFLDDSV
PLSSGSFGDA TGFTVQDGQL VVALPDKSTG LANPGQFAGY TGAAESPTSV LLINHGLHIE
ILIDPESQVG TTDRAGVKDV ILESAITTIM DFEDSVAAVD AADKVLGYRN WLGLNKGDLA
AAVDKDGTAF LRVLNRDRNY TAPGGGQFTL PGRSLMFVRN VGHLMTNDAI VDTDGSEVFE
GIMDALFTGL IAIHGLKASD VNGPLINSRT GSIYIVKPKM HGPAEVAFTC ELFSRVEDVL
GLPQNTMKIG IMDEERRTTV NLKACIKAAA DRVVFINTGF LDRTGDEIHT SMEAGPMVRK
GTMKSQPWIL AYEDHNVDAG LAAGFSGRAQ VGKGMWTMTE LMADMVETKI AQPRAGASTA
WVPSPTAATL HALHYHQVDV AAVQQGLAGK RRATIEQLLT IPLAKELAWA PDEIREEVDN
NCQSILGYVV RWVDQGVGCS KVPDIHDVAL MEDRATLRIS SQLLANWLRH GVITSADVRA
SLERMAPLVD RQNAGDVAYR PMAPNFDDSI AFLAAQELIL SGAQQPNGYT EPILHRRRRE
FKARAAEKPA PSDRAGDDAA R
```

(b) a protein characterized as *M. tuberculosis* antigen 85C; and (c) a glycoprotein characterized as *M. tuberculosis* antigen MPT32.

39. The kit of claim 34, that includes an early antigen selected from the group consisting of:

(a) an 88 kDa *M. tuberculosis* protein having the following properties:
   (1) present in *M. tuberculosis* culture filtrate;
   (2) pI of about 5.2;
   (3) an amino acid sequence SEQ ID NO:106.

40. The kit of claim 35 that includes an early antigen selected from the group consisting of:

(a) an 88 kDa *M. tuberculosis* protein having the following properties:
   (1) present in *M. tuberculosis* culture filtrate;
   (2) pI of about 5.2;
   (3) an amino acid sequence SEQ ID NO:106:

```
MTDRVSVGNL RIARVLYDFV NNEALPGTDI DPDSFWAGVD KVVADLTPQN QALLNARDEL
QAQIDKWHRR RVIEPIDMDA YRQFLTEIGY LLPEPDDFTI TTSGVDAEIT TTAGPQLVVP
VLNARFALNA ANARWGSLYD ALYGTDVIPE TDGAEKGPTY NKVRGDKVIA YARKFLDDSV
PLSSGSFGDA TGFTVQDGQL VVALPDKSTG LANPGQFAGY TGAAESPTSV LLINHGLHIE
ILIDPESQVG TTDRAGVKDV ILESAITTIM DFEDSVAAVD AADKVLGYRN WLGLNKGDLA
AAVDKDGTAF LRVLNRDRNY TAPGGGQFTL PGRSLMFVRN VGHLMTNDAI VDTDGSEVFE
GIMDALFTGL IAIHGLKASD VNGPLINSRT GSIYIVKPKM HGPAEVAFTC ELFSRVEDVL
GLPQNTMKIG IMDEERRTTV NLKACIKAAA DRVVFINTGF LDRTGDEIHT SMEAGPMVRK
GTMKSQPWIL AYEDHNVDAG LAAGFSGRAQ VGKGMWTMTE LMADMVETKI AQPRAGASTA
WVPSPTAATL HALHYHQVDV AAVQQGLAGK RRATIEQLLT IPLAKELAWA PDEIREEVDN
NCQSILGYVV RWVDQGVGCS KVPDIHDVAL MEDRATLRIS SQLLANWLRH GVITSADVRA
SLERMAPLVD RQNAGDVAYR PMAPNFDDSI AFLAAQELIL SGAQQPNGYT EPILHRRRRE
FKARAAEKPA PSDRAGDDAA R
```

```
MTDRVSVGNL RIARVLYDFV NNEALPGTDI DPDSFWAGVD KVVADLTPQN QALLNARDEL
QAQIDKWHRR RVIEPIDMDA YRQFLTEIGY LLPEPDDFTI TTSGVDAEIT TTAGPQLVVP
VLNARFALNA ANARWGSLYD ALYGTDVIPE TDGAEKGPTY NKVRGDKVIA YARKFLDDSV
PLSSGSFGDA TGFTVQDGQL VVALPDKSTG LANPGQFAGY TGAAESPTSV LLINHGLHIE
ILIDPESQVG TTDRAGVKDV ILESAITTIM DFEDSVAAVD AADKVLGYRN WLGLNKGDLA
AAVDKDGTAF LRVLNRDRNY TAPGGGQFTL PGRSLMFVRN VGHLMTMDAI VDTDGSEVFE
GIMDALFTGL IAIHGLKASD VNGPLINSRT GSIYIVKPKM HGPAEVAFTC ELFSRVEDVL
GLPQNTMKIG IMDEERRTTV NLKACIKAAA DRVVFINTGF LDRTGDEIHT SMEAGPMVRK
GTMKSQPWIL AYEDHNVDAG LAAGFSGRAQ VGKGMWTMTE LMADMVETKI AQPRAGASTA
WVPSPTAATL HALHYHQVDV AAVQQGLAGK RRATIEQLLT IPLAKELAWA PDEIREEVDN
NCQSILGYVV RWVDQGVGCS KVPDIHDVAL MEDRATLRIS SQLLANWLRH GVITSADVRA
SLERMAPLVD RQNAGDVAYR PMAPNFDDSI AFLAAQELIL SGAQQPNGYT EPILHRRRRE
FKARAAEKPA PSDRAGDDAA R
```

(b) a protein characterized as *M. tuberculosis* antigen 85C; and (c) a glycoprotein characterized as *M. tuberculosis* antigen MPT32.

(b) a protein characterized as *M. tuberculosis* antigen 85C; and (c) a glycoprotein characterized as *M. tuberculosis* antigen MPT32.

* * * * *